United States Patent
Donner et al.

(10) Patent No.: US 10,314,710 B2
(45) Date of Patent: Jun. 11, 2019

(54) METHODS OF FUSING A SACROILIAC JOINT

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 186 days.

(21) Appl. No.: 15/216,472

(22) Filed: Jul. 21, 2016

(65) Prior Publication Data

US 2016/0324643 A1 Nov. 10, 2016

Related U.S. Application Data

(60) Division of application No. 13/945,053, filed on Jul. 18, 2013, now Pat. No. 9,421,109, which is a
(Continued)

(51) Int. Cl.
*A61F 2/30* (2006.01)
*A61F 2/44* (2006.01)
(Continued)

(52) U.S. Cl.
CPC ...... *A61F 2/30988* (2013.01); *A61B 17/0218* (2013.01); *A61B 17/1757* (2013.01);
(Continued)

(58) Field of Classification Search
CPC .......... A61F 2/30988; A61F 2/32; A61F 2/46; A61F 2/4455; A61F 2/4611;
(Continued)

(56) References Cited

U.S. PATENT DOCUMENTS 7,935,116 B2   5/2011  Michelson
8,882,818 B1 * 11/2014 Vestgaarden .......... A61B 17/17
(Continued)

FOREIGN PATENT DOCUMENTS

WO    WO 02/085182 A2    10/2002

OTHER PUBLICATIONS

Synthes Spine. ProDisc-L Total Disc Replacement. For replacement of a diseased and/or degenerated intervertebral disc of the lumbosacral regions. Technique Guide. Copyright 2006.
(Continued)

*Primary Examiner* — Ellen C Hammond
*Assistant Examiner* — Tessa M Matthews
(74) *Attorney, Agent, or Firm* — Polsinelli PC; Joshua J. Pranckum; Samuel Wade Johnson

(57) ABSTRACT

One implementation of the present disclosure may include a method of sacroiliac joint fusion involving a joint implant and a delivery tool. The joint implant includes at least one integral anchor configured to move relative to a body of the implant when being brought into anchoring engagement with bone defining a sacroiliac joint space in which the body of the implant is located. In certain embodiments, the anchor extends distally and laterally relative to a body of the implant or the anchor rotates relative to the body of the implant via a center axle when being brought into anchoring engagement with the bone. The delivery tool may be configured to support the implant and to cause the displacement of the at least one anchor relative to the implant body so as to cause the at least one anchor to be brought into anchoring engagement with the bone.

69 Claims, 99 Drawing Sheets

Related U.S. Application Data continuation-in-part of application No. 13/475,695, filed on May 18, 2012, now Pat. No. 9,381,045, which is a continuation-in-part of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928.

(60) Provisional application No. 61/674,130, filed on Jul. 20, 2012, provisional application No. 61/335,947, filed on Jan. 13, 2010.

(51) Int. Cl.
| | |
|---|---|
| A61F 2/46 | (2006.01) |
| A61B 17/17 | (2006.01) |
| A61B 17/70 | (2006.01) |
| A61B 17/68 | (2006.01) |
| A61B 17/84 | (2006.01) |
| A61B 17/02 | (2006.01) |
| A61B 17/00 | (2006.01) |

(52) U.S. Cl.
CPC .......... *A61B 17/68* (2013.01); *A61B 17/7055* (2013.01); *A61B 17/844* (2013.01); *A61F 2/4455* (2013.01); *A61F 2/4611* (2013.01); *A61B 17/025* (2013.01); *A61B 17/7043* (2013.01); *A61B 2017/0046* (2013.01); *A61B 2017/0225* (2013.01); *A61F 2002/30163* (2013.01); *A61F 2002/30433* (2013.01); *A61F 2002/30622* (2013.01); *A61F 2002/30995* (2013.01); *A61F 2002/4622* (2013.01); *A61F 2002/4687* (2013.01); *A61F 2310/00017* (2013.01); *A61F 2310/00023* (2013.01); *A61F 2310/00179* (2013.01); *A61F 2310/00359* (2013.01)

(58) Field of Classification Search
CPC .. A61F 2002/30163; A61F 2002/30995; A61F 2002/30433; A61F 2002/30622; A61F 2002/4622; A61F 2002/4687; A61F 2310/00017; A61F 2310/00023; A61F 2310/00179; A61F 2310/00359; A61B 17/0218; A61B 17/1757; A61B 17/68; A61B 17/7055; A61B 17/844; A61B 17/025; A61B 17/7043; A61B 2017/0046; A61B 2017/0225

See application file for complete search history.

(56) References Cited

U.S. PATENT DOCUMENTS

| | | | |
|---|---|---|---|
| 9,039,765 B2 | 5/2015 | Trieu | |
| 9,044,321 B2 | 6/2015 | Mauldin | |
| 9,066,734 B2* | 6/2015 | Schoenefeld | A61B 17/1757 |
| 9,149,286 B1 | 10/2015 | Greenhalgh | |
| 9,186,155 B2 | 11/2015 | Katzman et al. | |
| 9,254,130 B2 | 2/2016 | Hollis | |
| 9,295,497 B2* | 3/2016 | Schoenefeld | A61B 17/7055 |
| 9,480,511 B2 | 11/2016 | Butters | |
| 9,486,264 B2 | 11/2016 | Reiley | |
| 9,931,212 B1 | 4/2018 | Donner et al. | |
| 9,936,983 B2* | 4/2018 | Mesiwala | A61B 17/7055 |
| 9,949,835 B2 | 4/2018 | Donner | |
| 9,949,843 B2 | 4/2018 | Reiley | |
| 10,058,430 B2 | 8/2018 | Donner et al. | |
| 10,064,727 B2 | 9/2018 | Donner et al. | |
| 10,064,728 B2 | 9/2018 | Donner et al. | |
| 10,130,477 B2 | 11/2018 | Donner et al. | |
| 10,136,995 B2 | 11/2018 | Donner et al. | |
| 2002/0068941 A1 | 6/2002 | Hanson | |
| 2002/0099376 A1* | 7/2002 | Michelson | 606/61 |
| 2002/0103487 A1* | 8/2002 | Errico | 606/61 |
| 2004/0193271 A1 | 9/2004 | Fraser | |
| 2004/0260286 A1 | 12/2004 | Ferree | |
| 2005/0261775 A1 | 11/2005 | Baum | |
| 2006/0036251 A1 | 2/2006 | Reiley | |
| 2006/0054171 A1* | 3/2006 | Dall | A61B 17/1664 128/898 |
| 2006/0106376 A1* | 5/2006 | Godara | 606/32 |
| 2007/0179610 A1 | 8/2007 | Biedermann | |
| 2007/0239278 A1 | 10/2007 | Heinz | |
| 2007/0299445 A1* | 12/2007 | Shadduck | A61B 17/7011 606/86 A |
| 2008/0021461 A1 | 1/2008 | Barker et al. | |
| 2008/0033440 A1* | 2/2008 | Moskowitz | 606/72 |
| 2008/0133016 A1 | 6/2008 | Heinz | |
| 2008/0154306 A1* | 6/2008 | Heinz | A61B 17/7055 606/256 |
| 2009/0024174 A1* | 1/2009 | Stark | 606/321 |
| 2009/0099659 A1 | 4/2009 | Oh | |
| 2009/0204215 A1 | 8/2009 | McClintock | |
| 2009/0216238 A1* | 8/2009 | Stark | 606/96 |
| 2010/0094290 A1* | 4/2010 | Vaidya | 606/60 |
| 2010/0168798 A1* | 7/2010 | Clineff | 606/279 |
| 2010/0168861 A1 | 7/2010 | Yundt | |
| 2010/0185292 A1 | 7/2010 | Hochschuler | |
| 2010/0191088 A1 | 7/2010 | Anderson | |
| 2010/0191100 A1 | 7/2010 | Anderson | |
| 2010/0204796 A1 | 8/2010 | Bae | |
| 2010/0217086 A1* | 8/2010 | Deshmukh | 600/205 |
| 2011/0087294 A1* | 4/2011 | Reiley | 606/279 |
| 2011/0160866 A1 | 6/2011 | Laurence | |
| 2011/0213221 A1 | 9/2011 | Roche | |
| 2011/0230966 A1* | 9/2011 | Trieu | A61B 17/562 623/17.12 |
| 2011/0230968 A1 | 9/2011 | Perisic | |
| 2011/0238181 A1* | 9/2011 | Trieu | A61B 17/1735 623/17.11 |
| 2012/0032808 A1 | 2/2012 | Cherubini | |
| 2012/0065548 A1 | 3/2012 | Morgan | |
| 2012/0253406 A1 | 10/2012 | Bae | |
| 2013/0035724 A1* | 2/2013 | Fitzpatrick | A61B 17/686 606/272 |
| 2013/0144393 A1 | 6/2013 | Mutchler | |
| 2013/0173004 A1 | 7/2013 | Greenhalgh | |
| 2014/0046380 A1 | 2/2014 | Asfora | |
| 2014/0135927 A1* | 5/2014 | Pavlov | A61B 17/7055 623/17.11 |
| 2014/0277165 A1* | 9/2014 | Katzman | A61B 17/1615 606/279 |
| 2014/0277460 A1* | 9/2014 | Schifano | A61F 2/4611 623/17.11 |
| 2015/0250612 A1 | 9/2015 | Schifano | |
| 2016/0120661 A1* | 5/2016 | Schell | A61F 2/4601 |
| 2016/0128838 A1* | 5/2016 | Assell | A61F 2/30988 |
| 2016/0184105 A1 | 6/2016 | Donner et al. | |
| 2016/0278818 A1 | 9/2016 | Donner et al. | |
| 2016/0278819 A1 | 9/2016 | Donner et al. | |
| 2017/0135733 A1 | 5/2017 | Donner et al. | |
| 2017/0164979 A1 | 6/2017 | Donner et al. | |
| 2017/0319240 A1 | 11/2017 | Donner et al. | |
| 2017/0325845 A1 | 11/2017 | Donner et al. | |
| 2017/0325846 A1 | 11/2017 | Donner et al. | |
| 2018/0035893 A1 | 2/2018 | Donner et al. | |
| 2018/0036017 A1 | 2/2018 | Donner et al. | |
| 2018/0055521 A1 | 3/2018 | Donner | |
| 2018/0085223 A1 | 3/2018 | Donner | |
| 2018/0092669 A1 | 4/2018 | Donner et al. | |
| 2018/0092748 A1 | 4/2018 | Donner et al. | |
| 2018/0318091 A1 | 11/2018 | Donner et al. | |
| 2018/0325675 A1 | 11/2018 | Donner | |
| 2018/0325676 A1 | 11/2018 | Donner | |

OTHER PUBLICATIONS

Amendment Under 1.312, U.S. Appl. No. 14/681,882, dated Aug. 10, 2017.

(56) References Cited

OTHER PUBLICATIONS

Australian Examination Report, AU2016204937, dated May 21, 2018.
Canadian Office Action, CA2849095, dated May 28, 2018.
China Office Action, CN201510622898.0, dated Feb. 1, 2018 (English translation).
China Office Action, CN201510622898.0, dated Sep. 1, 2017 (English translation).
Final Office Action, U.S. Appl. No. 14/344,876, dated Apr. 13, 2018.
Non-Final Office Action, U.S. Appl. No. 14/344,876, dated Jun. 2, 2017.
Non-Final Office Action, U.S. Appl. No. 14/660,784, dated Mar. 5, 2018.
Non-Final Office Action, U.S. Appl. No. 15/178,244, dated May 16, 2017.
Non-Final Office Action, U.S. Appl. No. 15/178,291, dated May 16, 2017.
Non-Final Office Action, U.S. Appl. No. 15/729,273, dated May 2, 2018.
Notice of Allowance, U.S. Appl. No. 14/344,876, dated May 18, 2018.
Notice of Allowance, U.S. Appl. No. 14/514,221, dated Jun. 16, 2017.
Notice of Allowance, U.S. Appl. No. 14/681,882, dated May 10, 2017.
Notice of Allowance, U.S. Appl. No. 14/723,384, dated Jun. 7, 2017.
Notice of Allowance, U.S. Appl. No. 15/061,524, dated Jul. 26, 2017.
Notice of Allowance, U.S. Appl. No. 15/178,244, dated Sep. 12, 2017.
Notice of Allowance, U.S. Appl. No. 15/178,291, dated Oct. 11, 2017.
Notice of Allowance, U.S. Appl. No. 15/828,556, dated Feb. 7, 2018.
Notice of Allowance, U.S. Appl. No. 15/828,677, dated Jan. 19, 2018.
Notice of Allowance, U.S. Appl. No. 15/910,753, dated May 21, 2018.
Notice of Allowance, U.S. Appl. No. 15/912,260, dated May 10, 2018.
Response to Final Office Action, U.S. Appl. No. 14/344,876, dated Apr. 27, 2018.
Response to Non-Final Office Action, U.S. Appl. No. 14/344,876, dated Sep. 5, 2017.
Response to Non-Final Office Action, U.S. Appl. No. 15/178,244, dated Aug. 15, 2017.
Response to Non-Final Office Action, U.S. Appl. No. 15/178,291, dated Aug. 16, 2017.
Response to Restriction, U.S. Appl. No. 14/660,784, dated Nov. 28, 2017.
Restriction Requirement, U.S. Appl. No. 14/660,784, dated Sep. 28, 2017.
Amendment and Response to Restriction, U.S. Appl. No. 14/447,612, dated Sep. 2, 2016.
Amendment with RCE, U.S. Appl. No. 14/567,956, dated Dec. 9, 2016.
AU Patent Examination Report No. 1, AU2012312658, dated Jul. 18, 2016.
Canadian Office Action, CA2787152, dated Jan. 25, 2017.
Chinese Office Action, CN201510622898.0, dated Dec. 23, 2016.
EP Extended Search Report, EP16191003.9, dated Feb. 6, 2017.
Final Office Action, U.S. Appl. No. 14/216,975, dated Dec. 30, 2016.
Non-Final Office Action, U.S. Appl. No. 14/127,119, dated Sep. 8, 2016.
Non-Final Office Action, U.S. Appl. No. 14/216,975, dated Jun. 20, 2016.
Non-Final Office Action, U.S. Appl. No. 14/344,876, dated Dec. 1, 2016.
Non-Final Office Action, U.S. Appl. No. 14/447,612, dated Dec. 15, 2016.
Non-Final Office Action, U.S. Appl. No. 14/681,882, dated Oct. 6, 2016.
Notice of Allowance, U.S. Appl. No. 14/127,119, dated Apr. 21, 2017.
Notice of Allowance, U.S. Appl. No. 14/216,975, dated Apr. 5, 2017.
Notice of Allowance, U.S. Appl. No. 14/413,318, dated Aug. 31, 2016.
Notice of Allowance, U.S. Appl. No. 14/447,612, dated Feb. 28, 2017.
Notice of Allowance, U.S. Appl. No. 14/514,221, dated Feb. 21, 2017.
Notice of Allowance, U.S. Appl. No. 14/567,956, dated Mar. 13, 2017.
Notice of Allowance, U.S. Appl. No. 14/567,956, dated Sep. 13, 2016.
Response to Final Office Action, U.S. Appl. No. 14/216,975, dated Feb. 27, 2017.
Response to Non-Final Office Action, U.S. Appl. No. 14/127,119, dated Dec. 29, 2016.
Response to Non-Final Office Action, U.S. Appl. No. 14/344,876, dated Mar. 1, 2017.
Response to Non-Final Office Action, U.S. Appl. No. 14/413,318, dated Aug. 3, 2016.
Response to Non-Final Office Action, U.S. Appl. No. 14/447,612, dated Jan. 25, 2017.
Response to Non-Final Office Action, U.S. Appl. No. 14/681,882, dated Jan. 5, 2017.
Response to Restriction, U.S. Appl. 14/344,876, dated Aug. 29, 2016.
Response to Restriction, U.S. Appl. No. 14/514,221, dated Oct. 24, 2016.
Response to Restriction, U.S. Appl. No. 14/723,384, dated Feb. 24, 2017.
Restriction Requirement, U.S. Appl. No. 14/447,612, dated Jul. 6, 2016.
Restriction Requirement, U.S. Appl. No. 14/514,221, dated Aug. 25, 2016.
Restriction Requirement, U.S. Appl. No. 14/723,384, dated Dec. 29, 2016.
Amendment Under 1.312, U.S. Appl. No. 15/828,622, dated Oct. 26, 2018.
Amendment Under 1.312, U.S. Appl. No. 15/992,987, dated Sep. 26, 2018.
Amendment Under 1.312, U.S. Appl. No. 15/993,170, dated Sep. 26, 2018.
Corrected Notice of Allowability, U.S. Appl. No. 15/828,622, dated Nov. 19, 2018.
Corrected Notice of Allowability, U.S. Appl. No. 15/992,987, dated Oct. 9, 2018.
Corrected Notice of Allowability, U.S. Appl. No. 15/993,170, dated Oct. 9, 2018.
European Examination Report, EP12799773.2, dated Jun. 4, 2018.
Final Office Action, U.S. Appl. No. 14/660,784, dated Jul. 20, 2018.
Final Office Action, U.S. Appl. No. 15/729,273, dated Nov. 20, 2018.
Non-Final Office Action, U.S. Appl. No. 15/385,446, dated Jul. 24, 2018.
Non-Final Office Action, U.S. Appl. No. 15/418,633, dated Aug. 7, 2018.
Non-Final Office Action, U.S. Appl. No. 15/662,045, dated Aug. 10, 2018.
Non-Final Office Action, U.S. Appl. No. 15/664,862, dated Oct. 3, 2018.
Non-Final Office Action, U.S. Appl. No. 15/785,997, dated Nov. 29, 2018.
Non-Final Office Action, U.S. Appl. No. 15/789,515, dated Oct. 29, 2018.
Non-Final Office Action, U.S. Appl. No. 15/789,602, dated Nov. 29, 2018.

(56) References Cited

OTHER PUBLICATIONS

Non-Final Office Action, U.S. Appl. No. 15/993,277, dated Nov. 26, 2018.
Notice of Allowance, U.S. Appl. No. 14/660,784, dated Nov. 15, 2018.
Notice of Allowance, U.S. Appl. No. 15/828,622, dated Aug. 9, 2018.
Notice of Allowance, U.S. Appl. No. 15/912,216, dated Jun. 20, 2018.
Notice of Allowance, U.S. Appl. No. 15/992,987, dated Aug. 16, 2018.
Notice of Allowance, U.S. Appl. No. 15/993,170, dated Aug. 8, 2018.
Notice of Allowance, U.S. Appl. No. 15/993,277, dated Dec. 4, 2018.
Preliminary Amendment, U.S. Appl. No. 15/831,589, dated Jul. 27, 2018.
Response to Final Office Action, U.S. Appl. No. 14/660,784, dated Oct. 22, 2018.
Response to Non-Final Office Action, U.S. Appl. No. 14/660,784, dated Jun. 4, 2018.
Response to Non-Final Office Action, U.S. Appl. No. 15/385,446, dated Oct. 24, 2018.
Response to Non-Final Office Action, U.S. Appl. No. 15/418,633, dated Nov. 7, 2018.
Response to Non-Final Office Action, U.S. Appl. No. 15/662,045, dated Nov. 12, 2018.
Response to Non-Final Office Action, U.S. Appl. No. 15/729,273, dated Aug. 1, 2018.
Response to Non-Final Office Action, U.S. Appl. No. 15/789,515, dated Nov. 21, 2018.
Restriction Requirement, U.S. Appl. No. 15/664,608, dated Oct. 5, 2018.

* cited by examiner

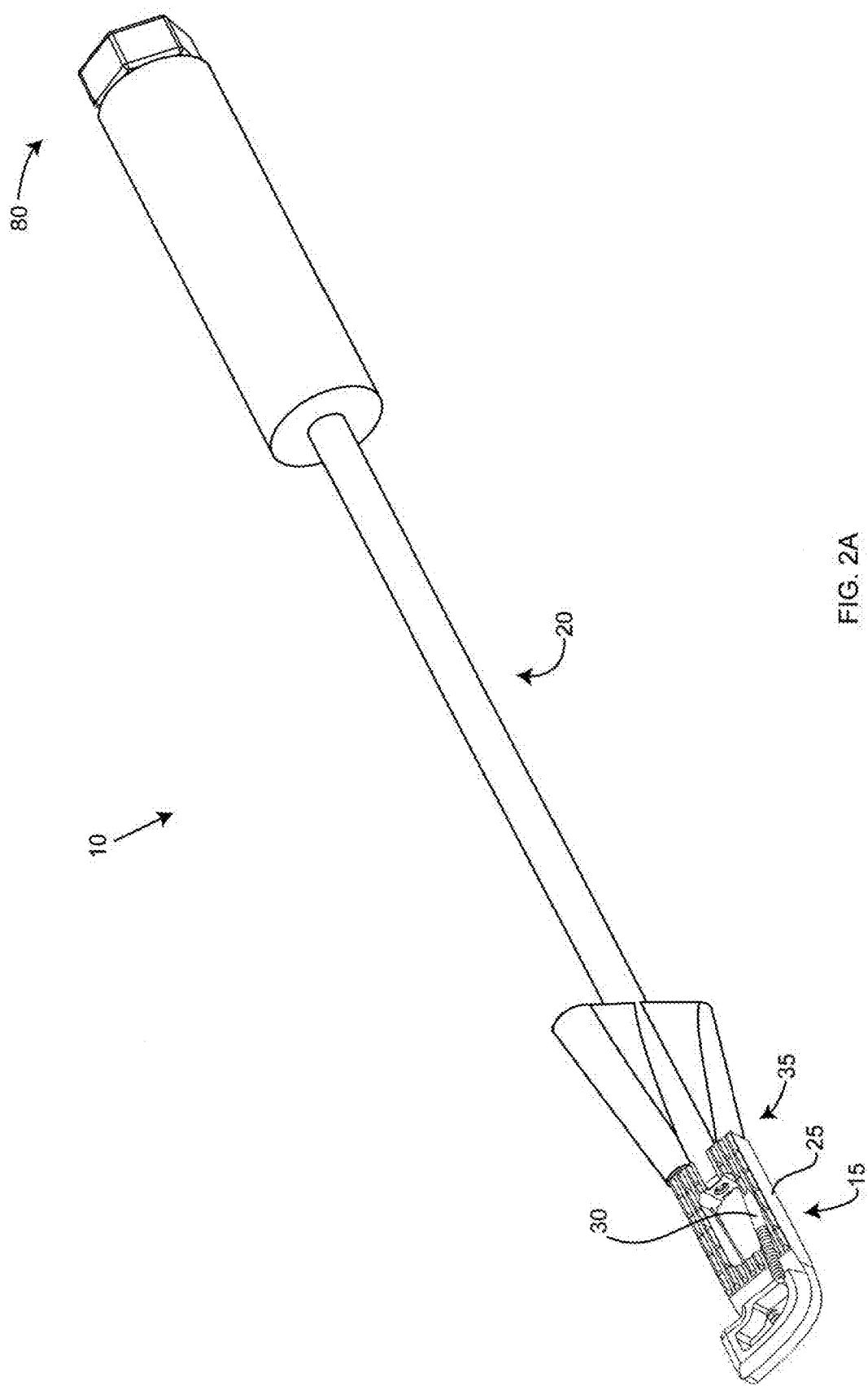

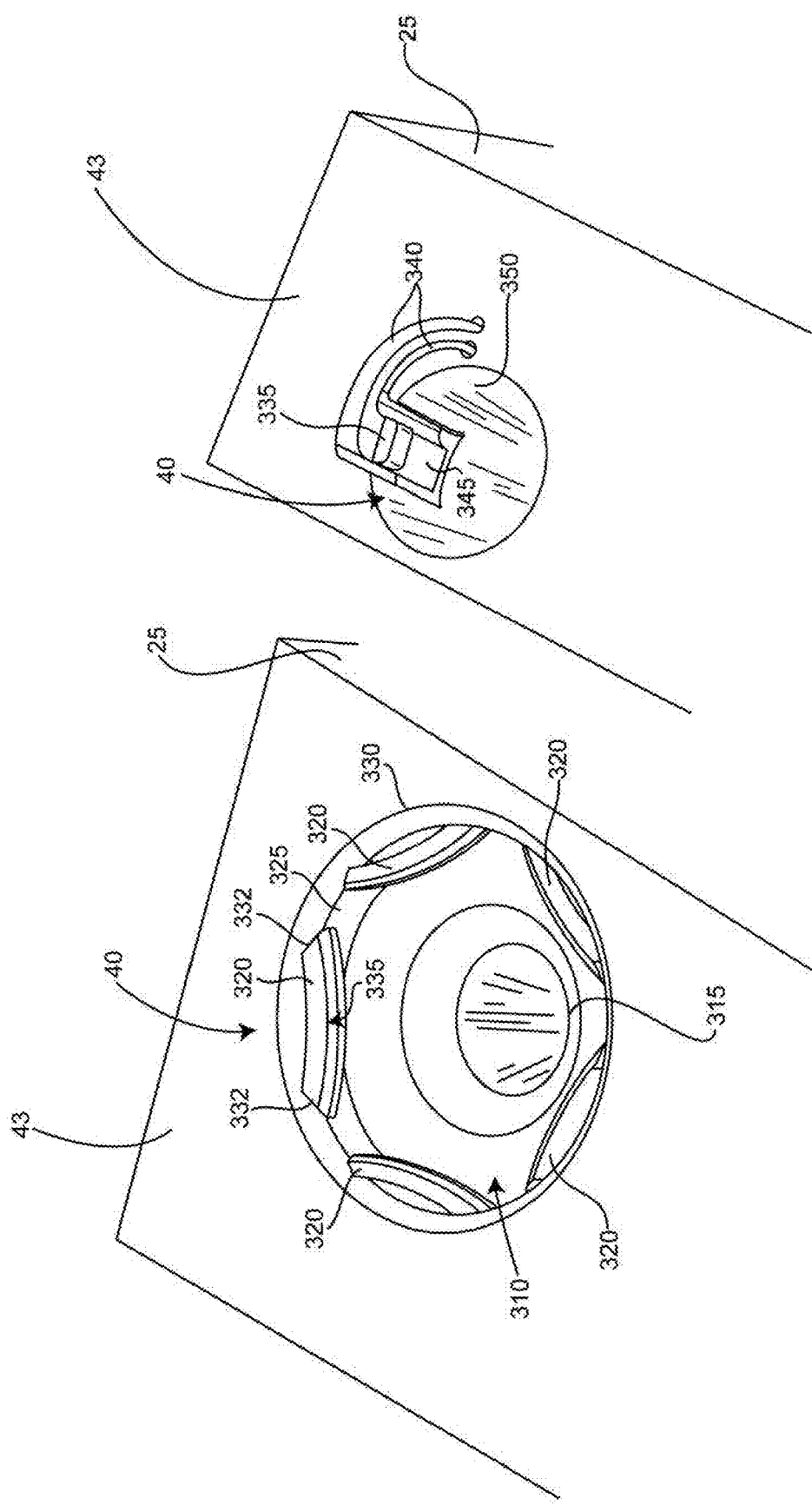

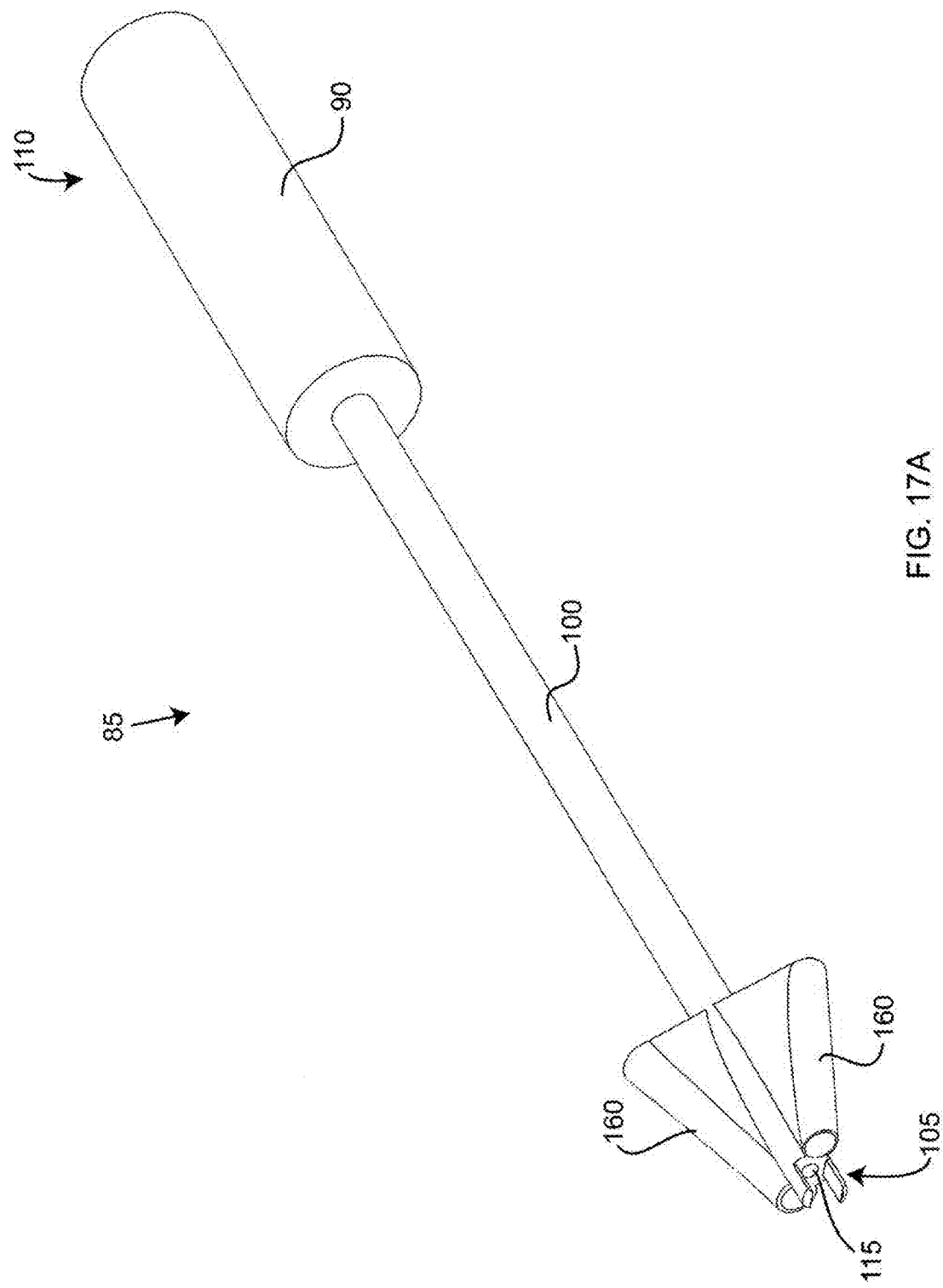

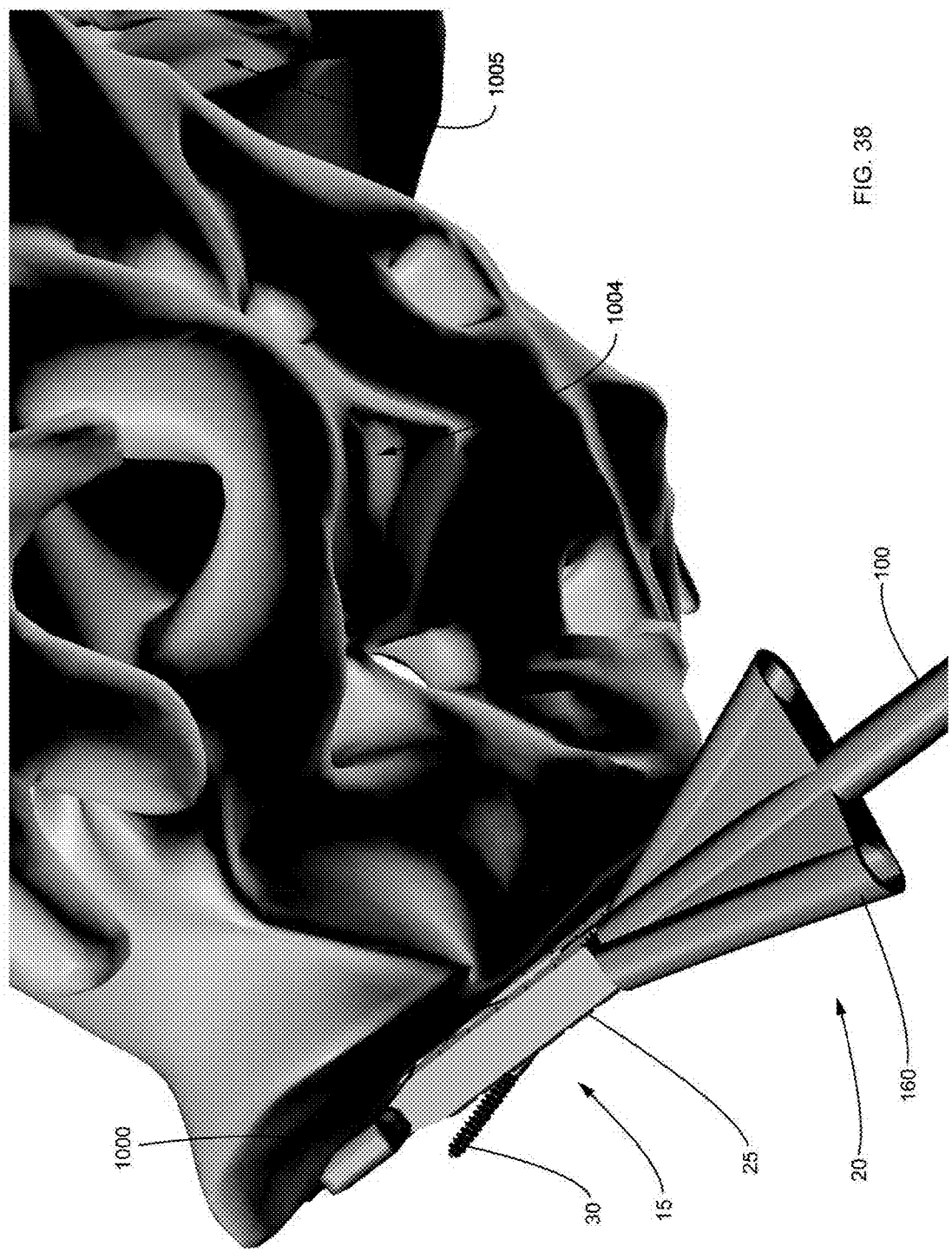

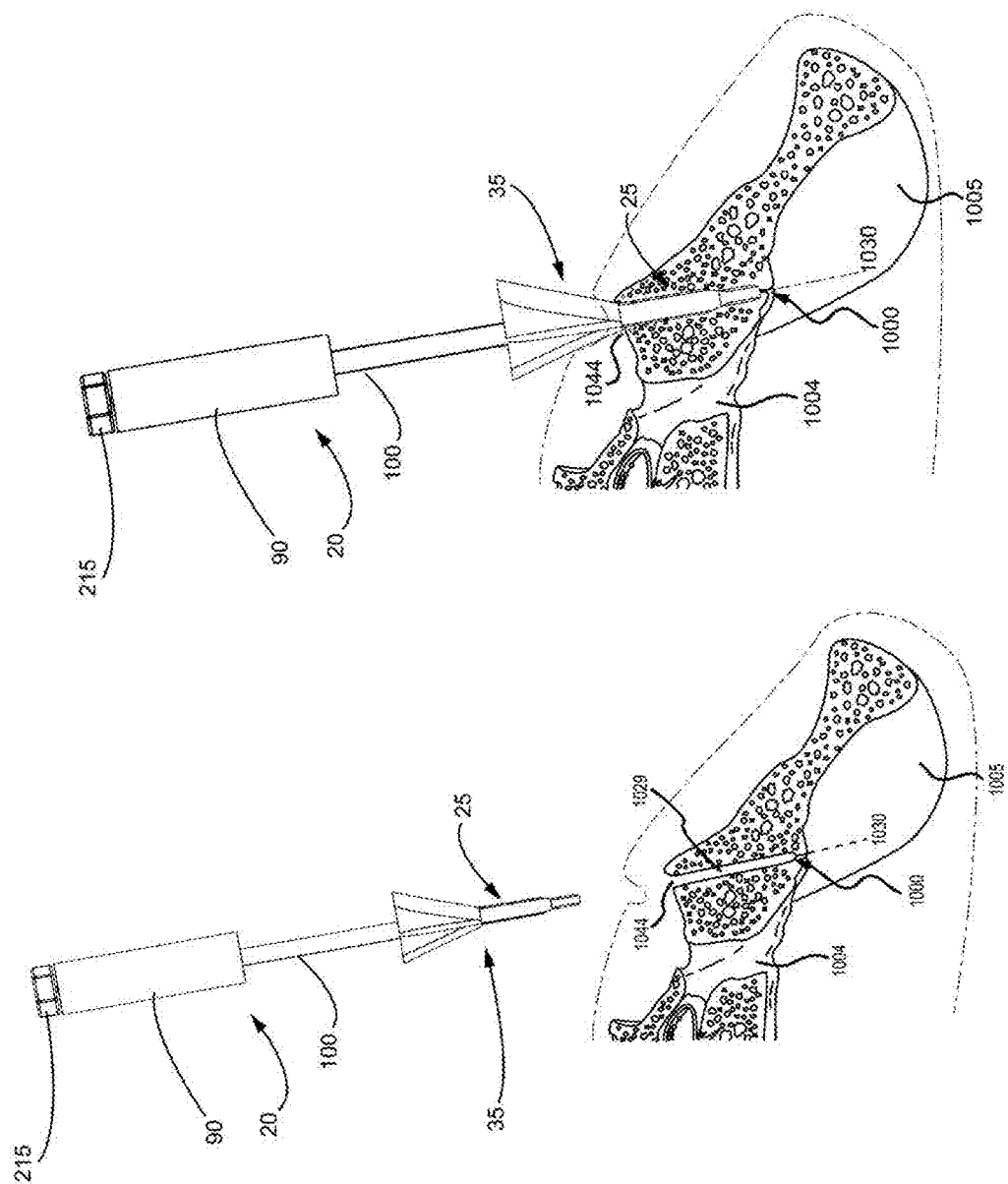

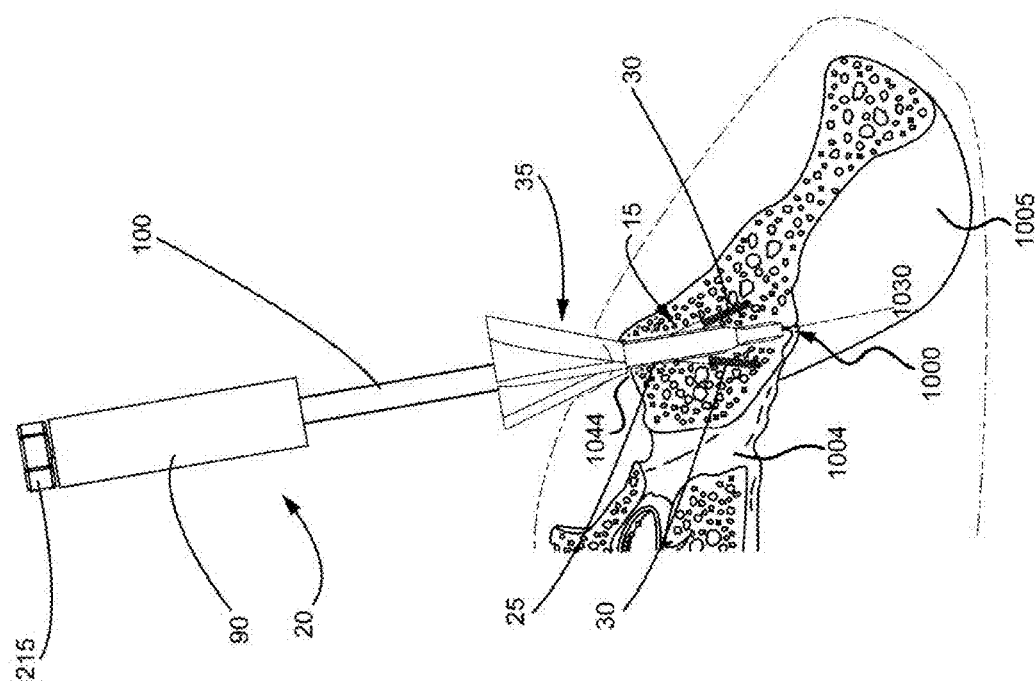
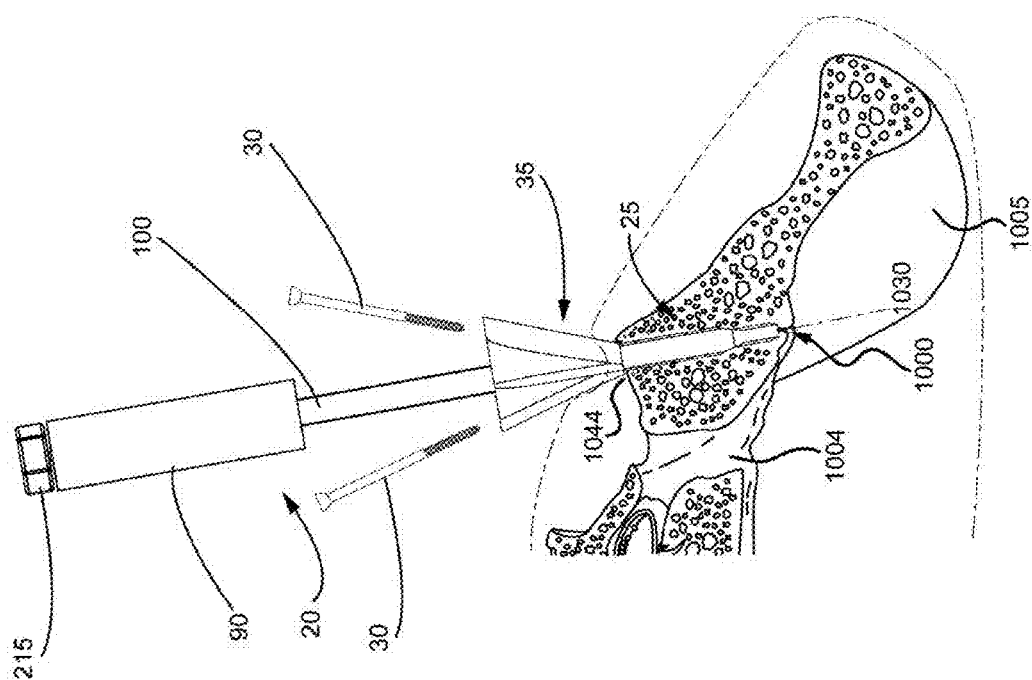

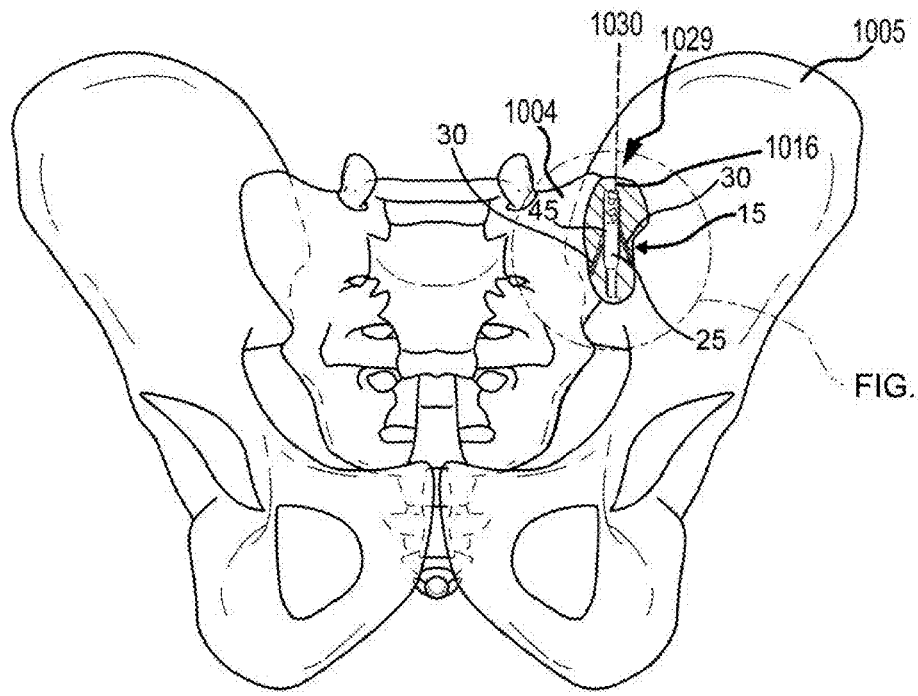
FIG. 45B
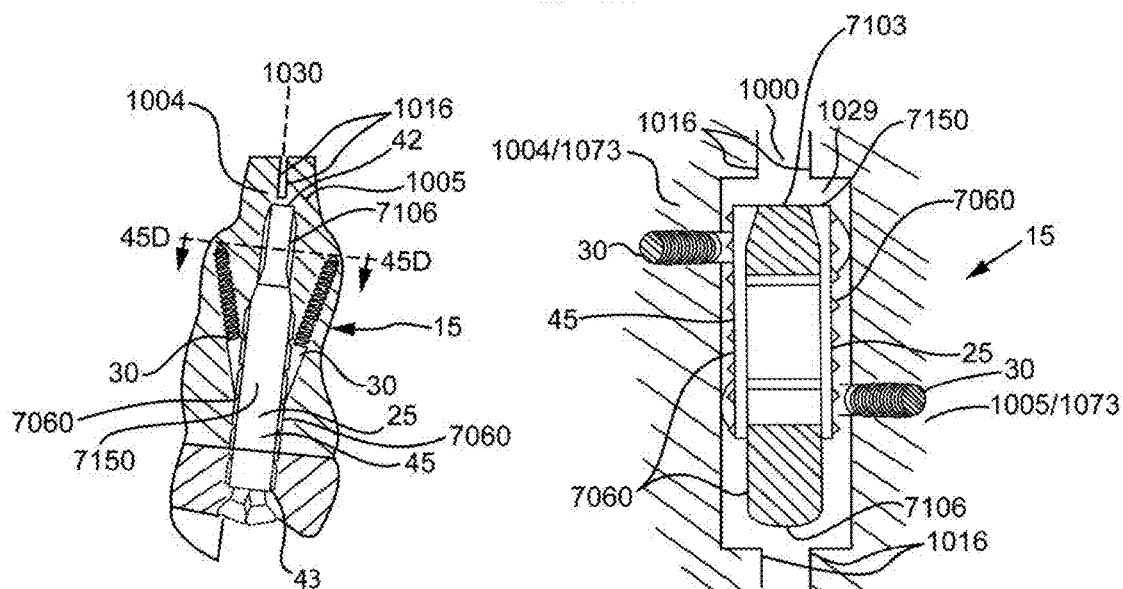
FIG. 45C
FIG. 45D

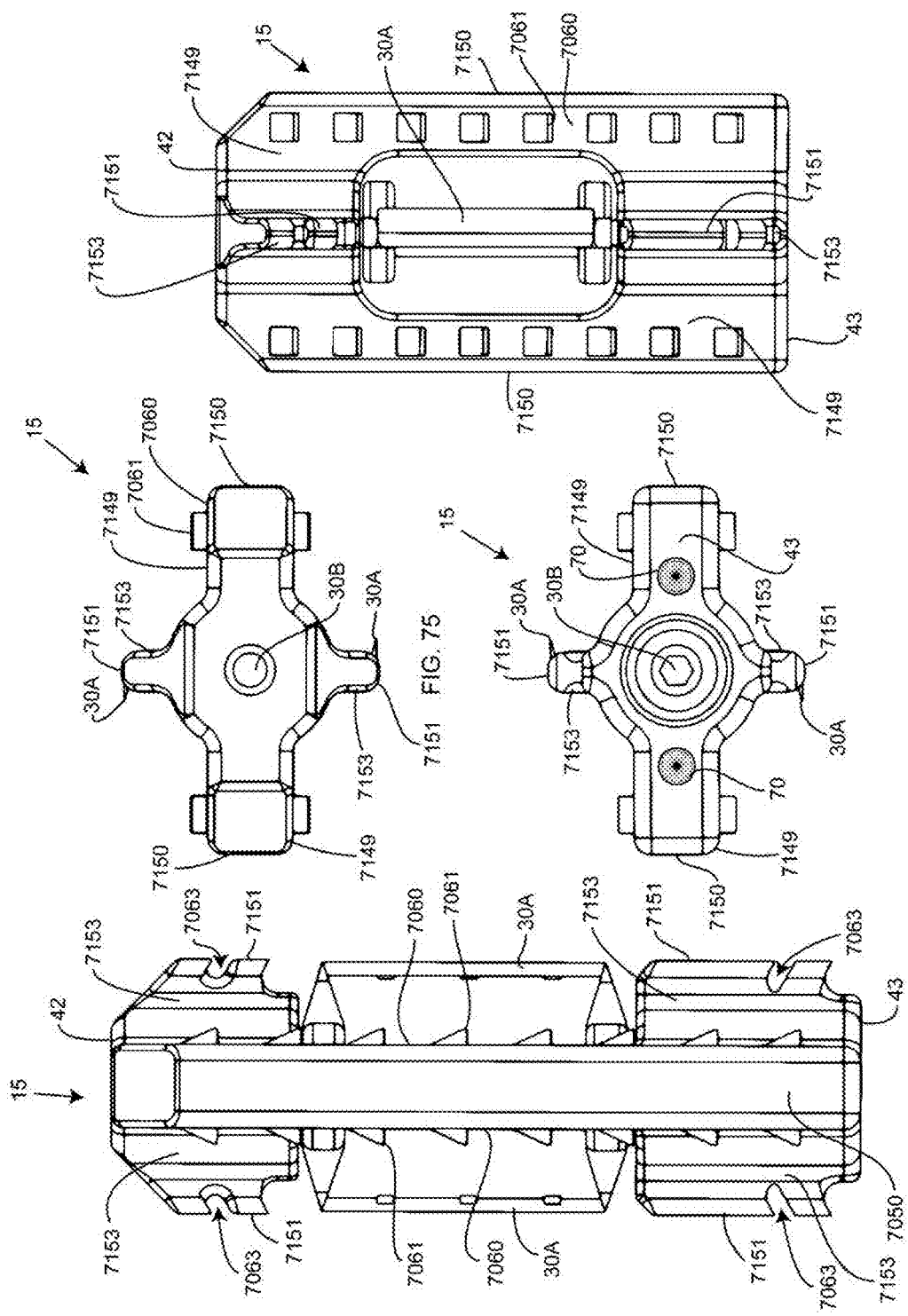

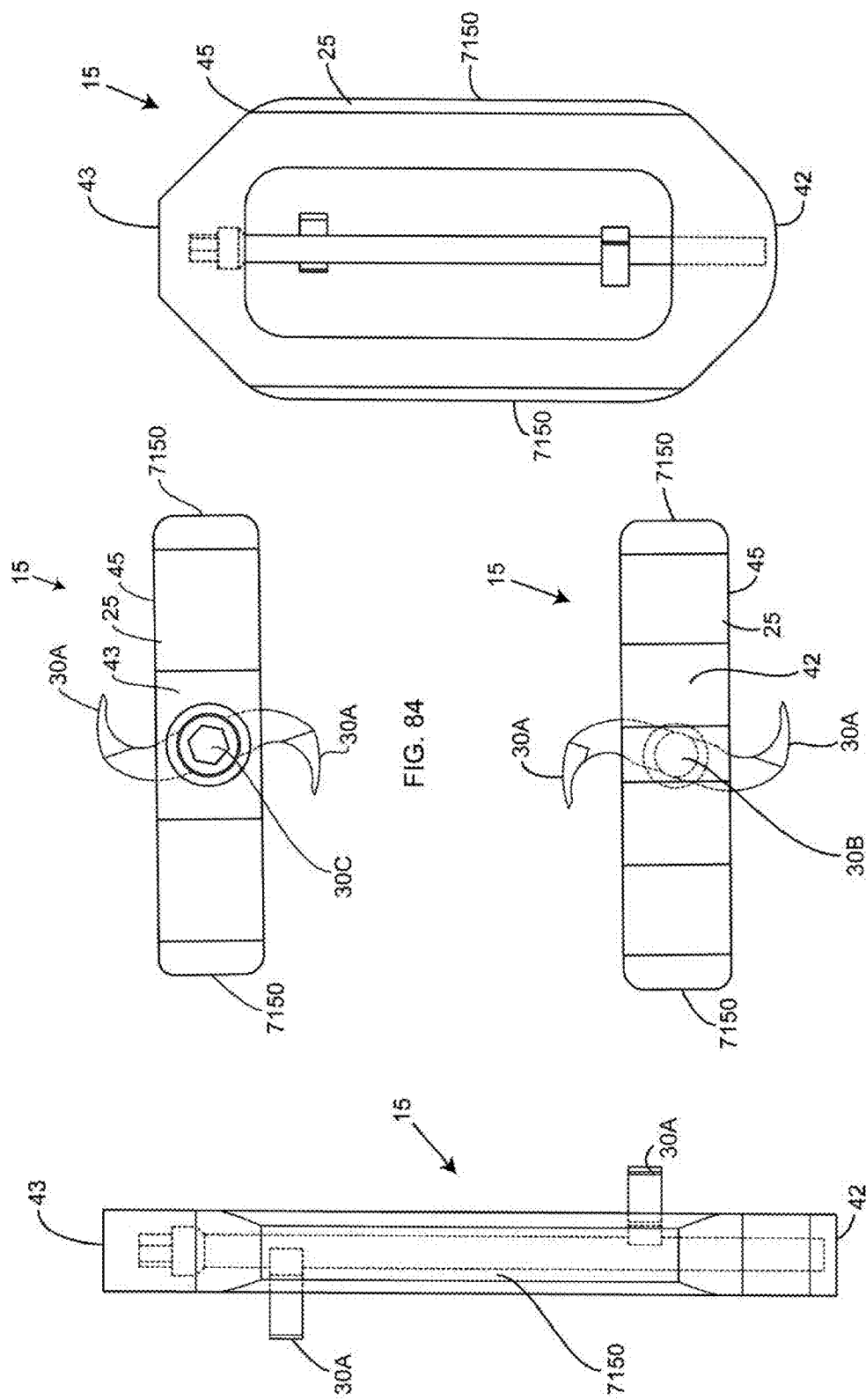

METHODS OF FUSING A SACROILIAC JOINT

CROSS REFERENCE TO RELATED APPLICATIONS

The present application is a divisional application of U.S. application Ser. No. 13/945,053 filed Jul. 18, 2013, which application claims priority to U.S. Provisional Patent Application 61/674,130, which was filed Jul. 20, 2012.

Application Ser. No. 13/945,053 is a continuation-in-part application of U.S. patent application Ser. No. 13/475,695, filed May 18, 2012, now U.S. Pat. No. 9,381,045, which application is a continuation-in-part application of U.S. patent application Ser. No. 13/236,411, filed Sep. 19, 2011, now U.S. Pat. No. 9,017,407, which application is a continuation-in-part of U.S. patent application Ser. No. 12/998,712 ("the '712 application"), which was filed May 23, 2011, now U.S. Pat. No. 8,979,928. The '712 application is the National Stage of International Patent Cooperation Treaty Patent Application PCT/US2011/000070 (the "PCT application"), which was filed Jan. 13, 2011. The PCT application claims the benefit of U.S. Provisional Patent Application 61/335,947, which was filed Jan. 13, 2010.

All of the aforementioned applications are hereby incorporated by reference in their entireties into the present application.

FIELD OF THE INVENTION

Aspects of the present invention relate to medical apparatus and methods. More specifically, the present invention relates to devices and methods for fusing a sacroiliac joint.

BACKGROUND OF THE INVENTION

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using the anterior approach can be damage to the L5 nerve root, which lies approximately two centimeters medial to the sacroiliac joint or damage to the major blood vessels. Additionally, these procedures typically involve fixation of the sacroiliac joint (immobilization of the articular surfaces of the sacroiliac joint in relation to one another) by placement of one or more screws or one or more trans-sacroiliac implants (as shown by the non-limiting example of FIG. 1) or by placement of implants into the S1 pedicle and iliac bone.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

The inventive sacroiliac fusion system described herein addresses the problems associated with conventional methods and apparatuses used in fixation and fusion of the sacroiliac joint.

BRIEF SUMMARY OF THE INVENTION

One implementation of the present disclosure may take the form of a sacroiliac joint fusion system including a joint implant and a delivery tool. The joint implant includes at least one integral anchor configured to move relative to a body of the implant when being brought into anchoring engagement with bone defining a sacroiliac joint space in which the body of the implant is located. In one embodiment, the at least one anchor extends distally and laterally relative to a body of the implant when being brought into anchoring engagement with the bone. In another embodiment, the at least one anchor rotates relative to the body of the implant when being brought into anchoring engagement with the bone. The delivery tool is configured to support the implant off of a distal portion of the tool. The delivery tool is further configured to cause the displacement of the at least one anchor relative to the implant body so as to cause the at least one anchor to be brought into anchoring engagement with the bone.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 2A is an isometric view of a first embodiment of a system for fusing a sacroiliac joint.

FIGS. 16H and 16G are enlarged isometric views of proximal ends of bores at proximal ends of any of the implant bodies disclosed herein as employing a screw type anchor arrangement.

FIGS. 17A and 17B are, respectively, distal and proximal isometric views of the shaft assembly of the delivery tool of FIGS. 2A-3.

FIG. 38 is the same view as FIG. 37, except still further enlarged and with the ilium hidden to more clearly shown the implantation of the implant system in the sacroiliac joint space.

FIGS. 42A-42M are each a step in the methodology and illustrated as the same transverse cross section taken along a plane extending medial-lateral and anterior posterior along section line 41-41 in FIG. 41B.

FIG. 45B is an anterior view of the hip region of the patient, illustrating the implant implanted in the caudal region of the sacroiliac joint space.

FIG. 45C is an enlarged view of the implant taken along the plane of the sacroiliac joint.

FIG. 45D is a transverse cross section of the implant and joint plane taken along section line 45D-45D of FIG. 45C.

FIGS. 73 and 74 are side elevation views of the implant of FIG. 72.

FIGS. 75 and 76 are, respectively, distal and proximal end views of the implant of FIG. 72.

FIGS. 81 and 82 are, respectively, side elevation and plan views of the implant of FIG. 80.

FIGS. 83 and 84 are, respectively, distal and proximal end views of the implant of FIG. 80.

DETAILED DESCRIPTION

Figure 1:
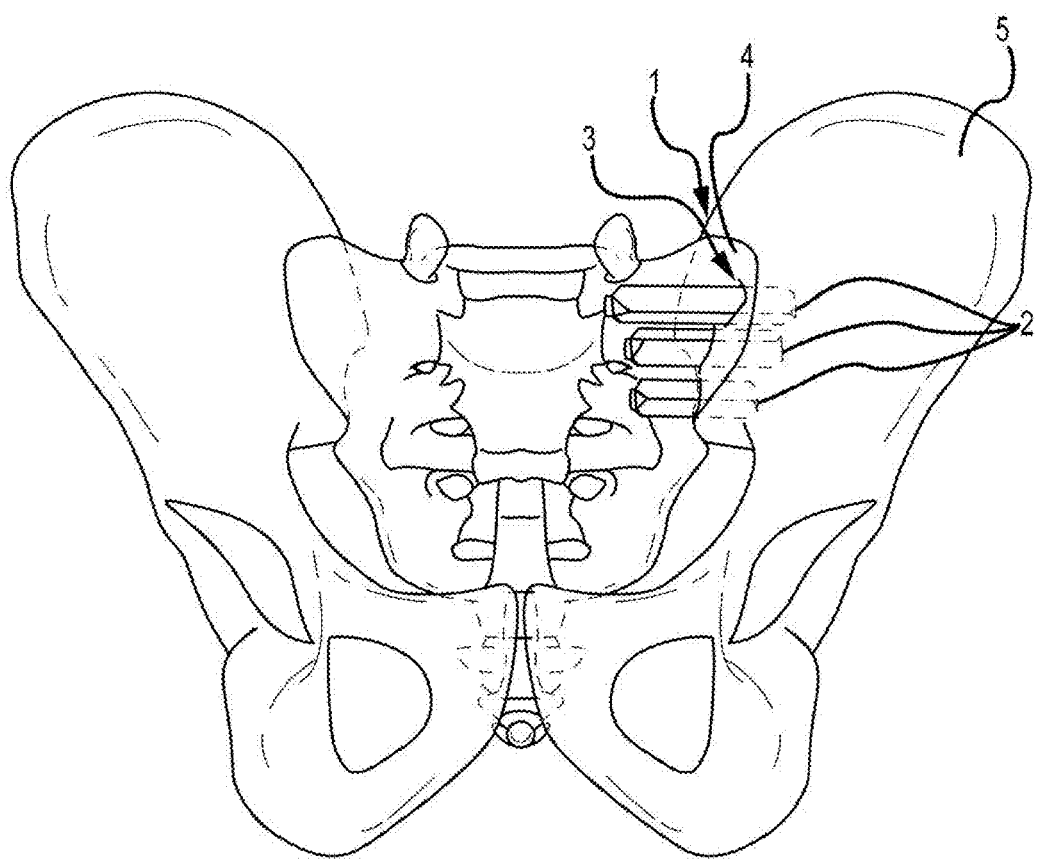
FIG. 1 is an anterior view of the pelvic region and a conventional method and device for stabilizing the sacroiliac joint.

Implementations of the present disclosure involve a system 10 for fusing a sacroiliac joint. The system 10 includes a delivery tool 20 and an implant assembly 15 for delivery to a sacroiliac joint via the delivery tool 20. The implant assembly 15, which includes an implant 25 and one or more anchors 30, is configured to fuse a sacroiliac joint once implanted at the joint. The anchors 30 are integrally supported on the implant 25 and configured to laterally project from sides of the implant. By acting on the anchors 30 or a portion of the implant at a proximal end 43 of the implant 25 (e.g., by rotational or longitudinally displacing forces actuated by a component of the delivery tool 20 or by a separate tool), the anchors may be caused to deploy from the sides of the implant so as to penetrate into bone material defining the joint space in which the implant 25 is implanted. The tool 20 is configured to support the implant 25 from a distal end 35 of the delivery tool 20 for delivery of the implant into the joint space and further configured to facilitate the deployment of the anchors from the sides of the implant. Thus, the system 10 is configured such that the implant 25 can be quickly, accurately and reliably delivered to, and anchored in, a sacroiliac joint.

Figure 2B:
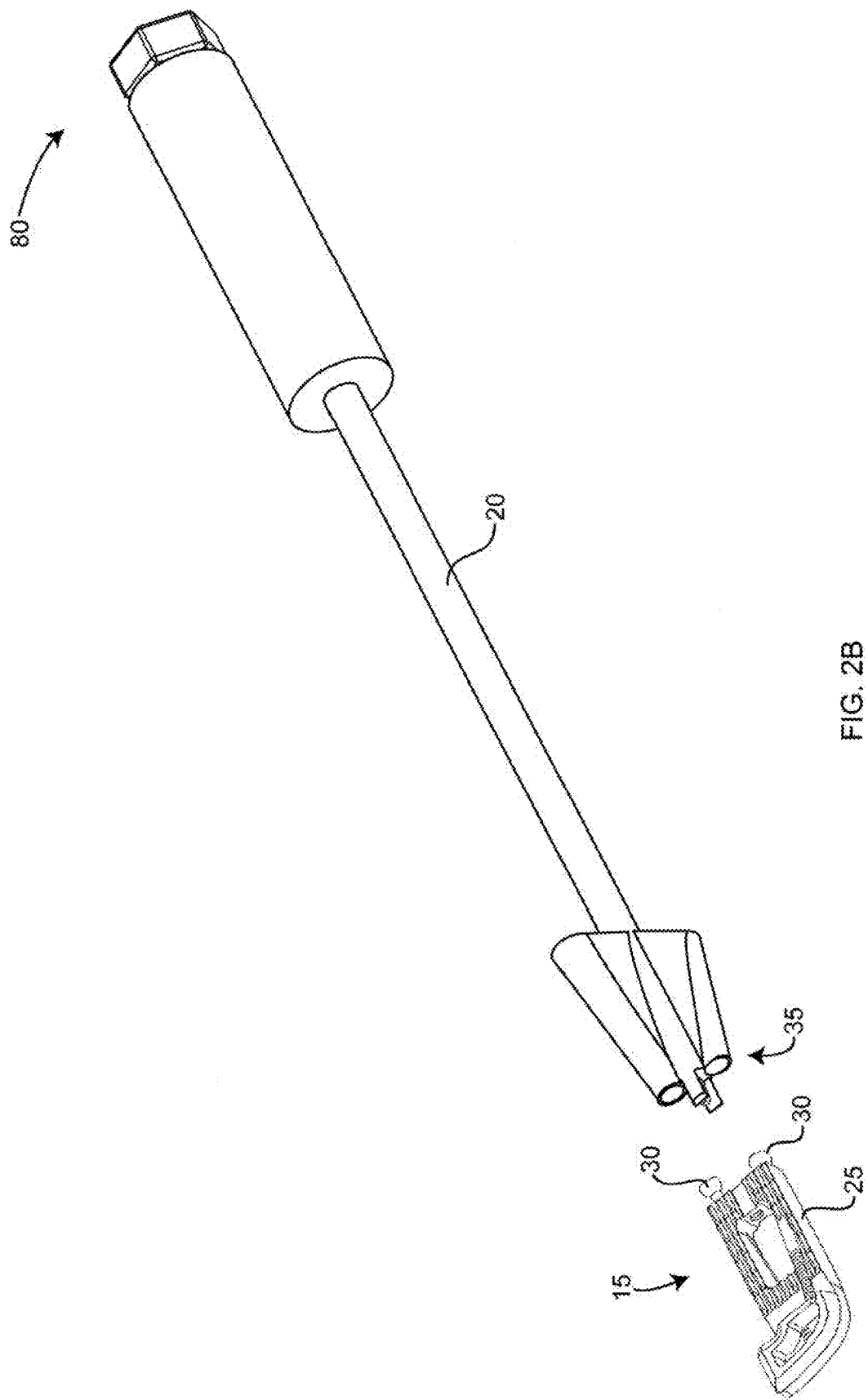
FIG. 2B is the same view as FIG. 2A, except the delivery tool and implant assembly are decoupled from each other.
Figure 3:
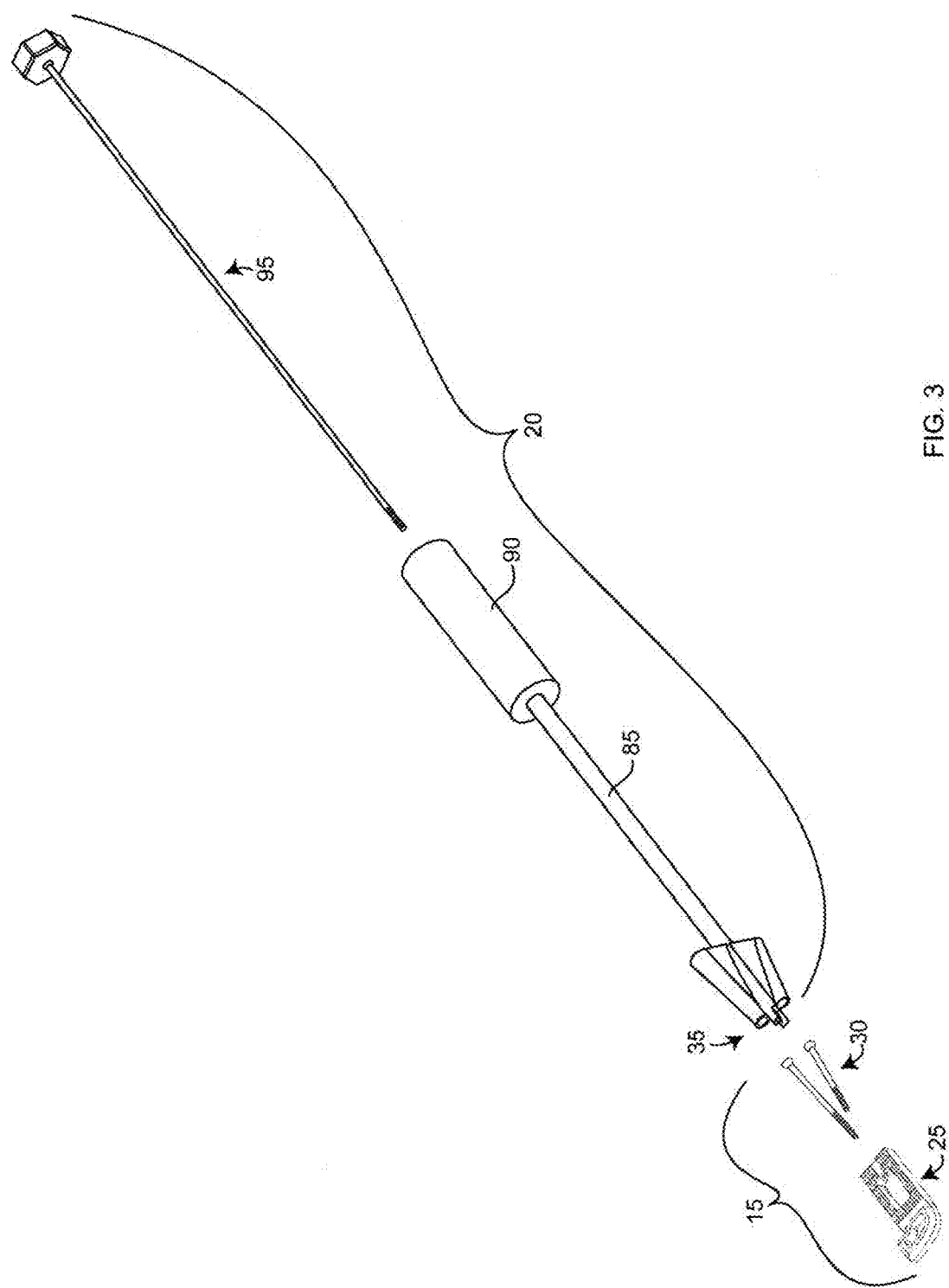
FIG. 3 is the same view as FIG. 2A, except the system is exploded to better illustrate its components.

To begin a detailed discussion of a first embodiment of the system 10, reference is made to FIGS. 2A-3. FIG. 2A is an isometric view of the system 10. FIG. 2B is the same view as FIG. 2A, except an implant assembly 15 of the system 10 is separated from a delivery tool 20 of the system 10. FIG. 3 is the same view as FIG. 2A, except the system 10 is shown exploded to better illustrate the components of the system 10.

As can be understood from FIGS. 2A and 2B, the system 10 includes a delivery tool 20 and an implant assembly 15 for implanting at the sacroiliac joint via the delivery tool 20, the implant assembly 15 being for fusing the sacroiliac joint. As indicated in FIG. 3, the implant assembly 15 includes an implant 25 and anchor elements 30 (e.g., bone screws, nails or other elongated bodies). As discussed below in greater detail, during the implantation of the implant assembly 15 at the sacroiliac joint, the implant 25 and anchor element 30 are supported by a distal end 35 of the delivery tool 20, as illustrated in FIG. 2A. In one embodiment, the distal end 35 may be fixed or non-removable from the rest of the delivery tool 20. In other embodiments, the distal end 35 of the delivery tool 20 may be removable so as to allow interchanging of different sized or shaped distal ends 35 to allow matching to particular implant embodiments without requiring the use of a different delivery tool 20. The delivery tool 20 is used to deliver the implant 25 into the sacroiliac joint space. The delivery tool 20 is then used to cause the anchor elements 30 to deploy or otherwise extend from the sides of the implant 25 and into the bone of the ilium and sacrum defining the sacroiliac joint. The delivery tool 20 is then decoupled from the implanted implant assembly 15, as can be understood from FIG. 2B.

Figure 4A:
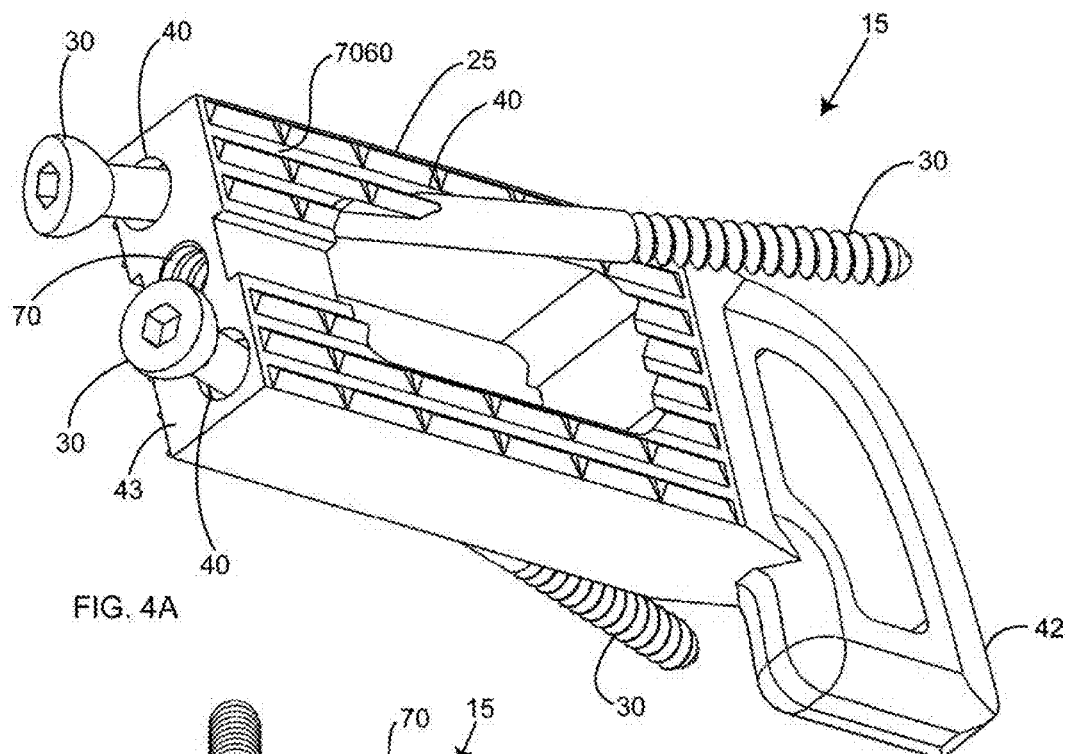
FIGS. 4A-4C are, respectively, proximal isometric, proximal end elevation and side elevation views of the implant assembly, which has a body that approximates or generally mimics a sacroiliac joint.
Figure 4B:
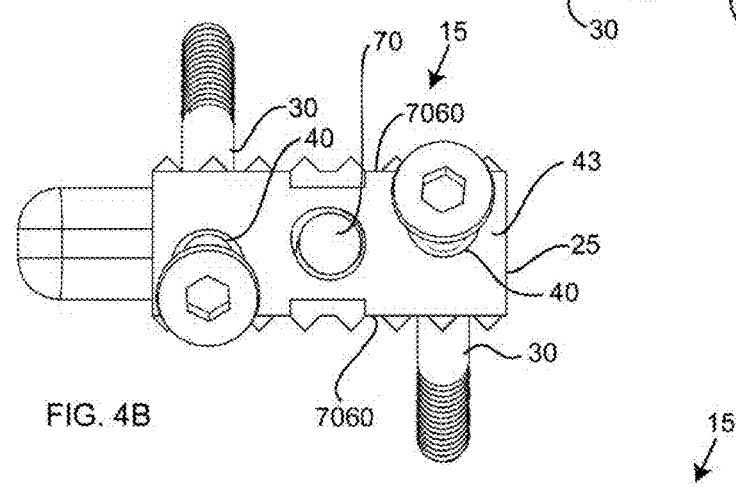
Figure 4C:
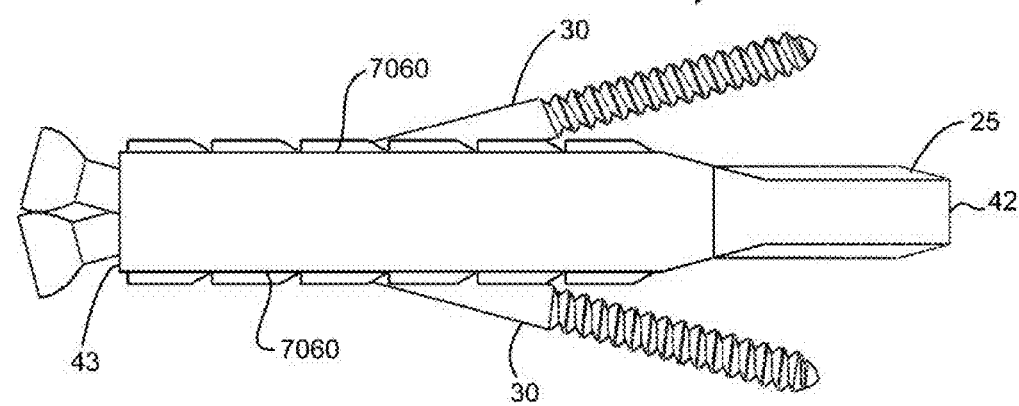
Figure 5:
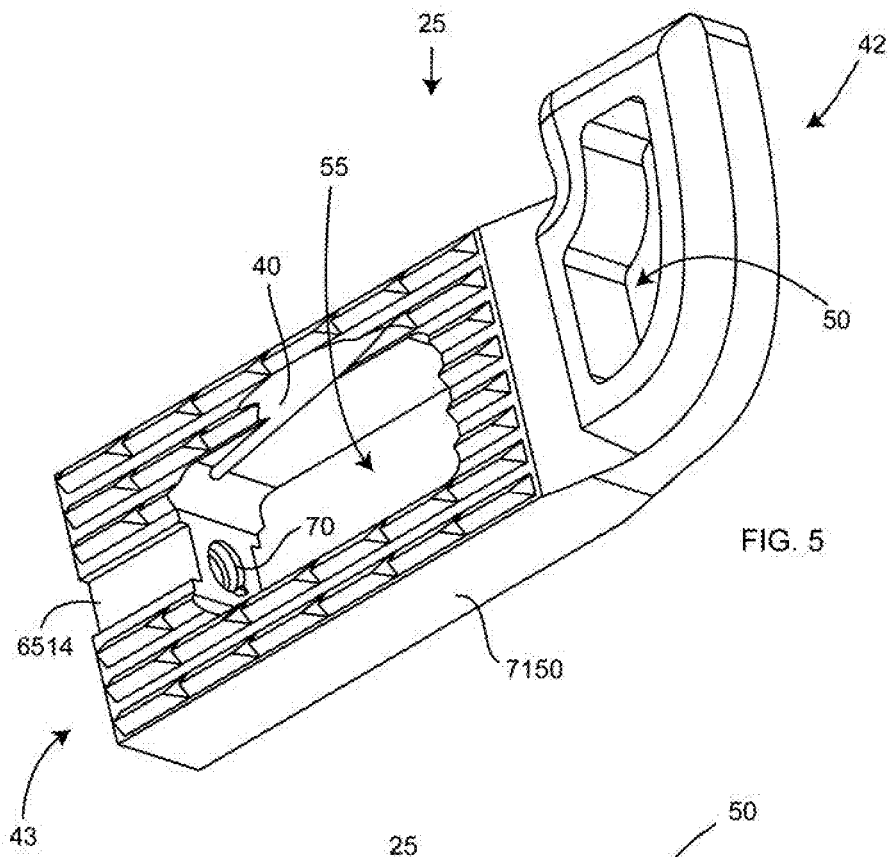
FIGS. 5 and 6 are distal end isometric views of the implant of the implant assembly of FIGS. 4A-4C.
Figure 6:
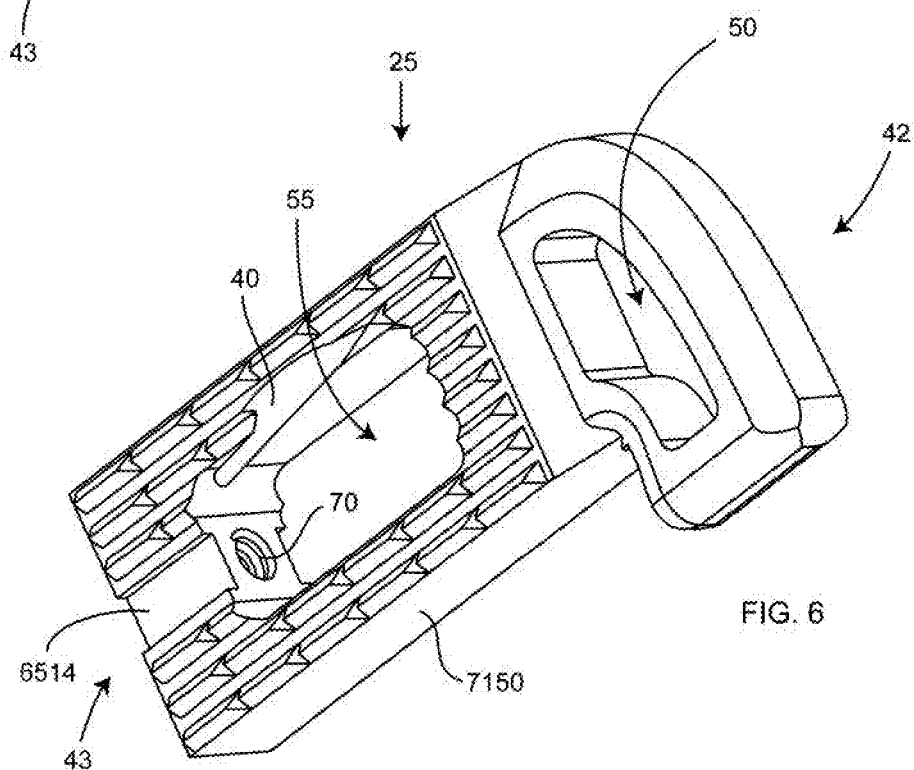

To begin a detailed discussion of components of an embodiment of the implant assembly 15, reference is made to FIGS. 4A-4C, which are, respectively, proximal isometric, proximal end elevation, and side elevation views of the implant assembly 15. As shown in FIGS. 4A-4C, the implant assembly 15 includes an implant 25 and anchor elements 30. The anchor elements 30 may be in the form of an elongated body such as, for example, a nail, rod, pin, threaded screw, etc. The anchor elements 30 are configured to be received in bores 40 defined through the implant 25. The bores 40 extend through the implant 25 distally and laterally from a proximal end 43 of the implant 25 and are sized such that the anchor elements 30 can at least project both laterally and distally from the sides of the implant 25 as illustrated in FIGS. 4A-4C.

Figure 7:
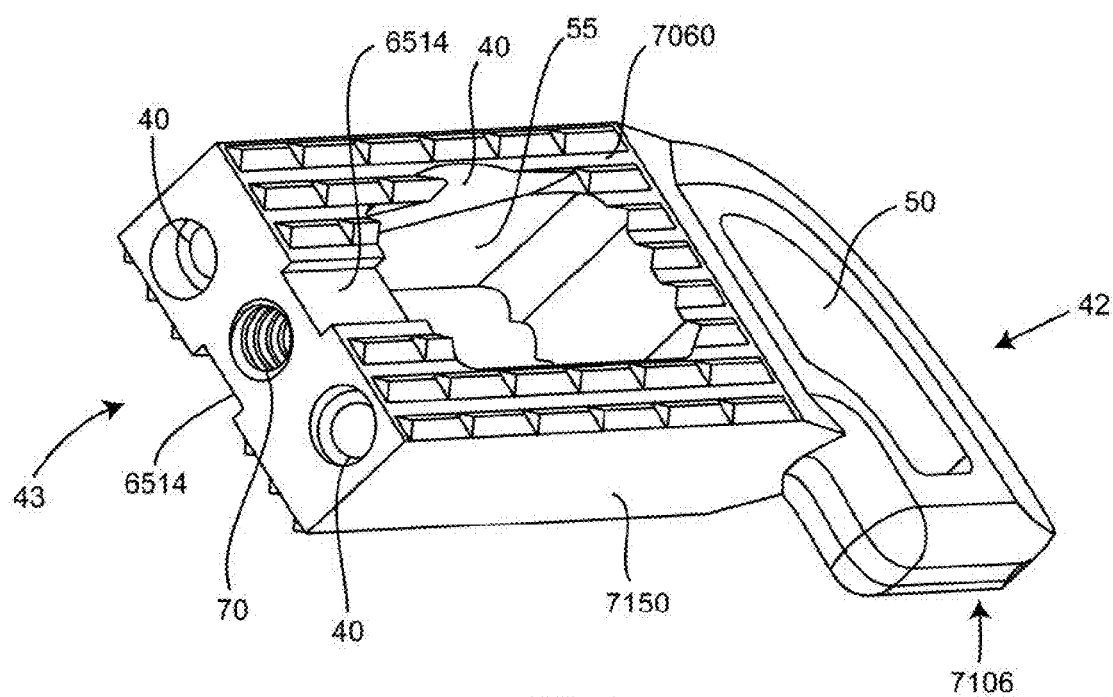
FIGS. 7 and 8 are proximal end isometric views of the implant of the implant assembly of FIGS. 4A-4C.
Figure 8:
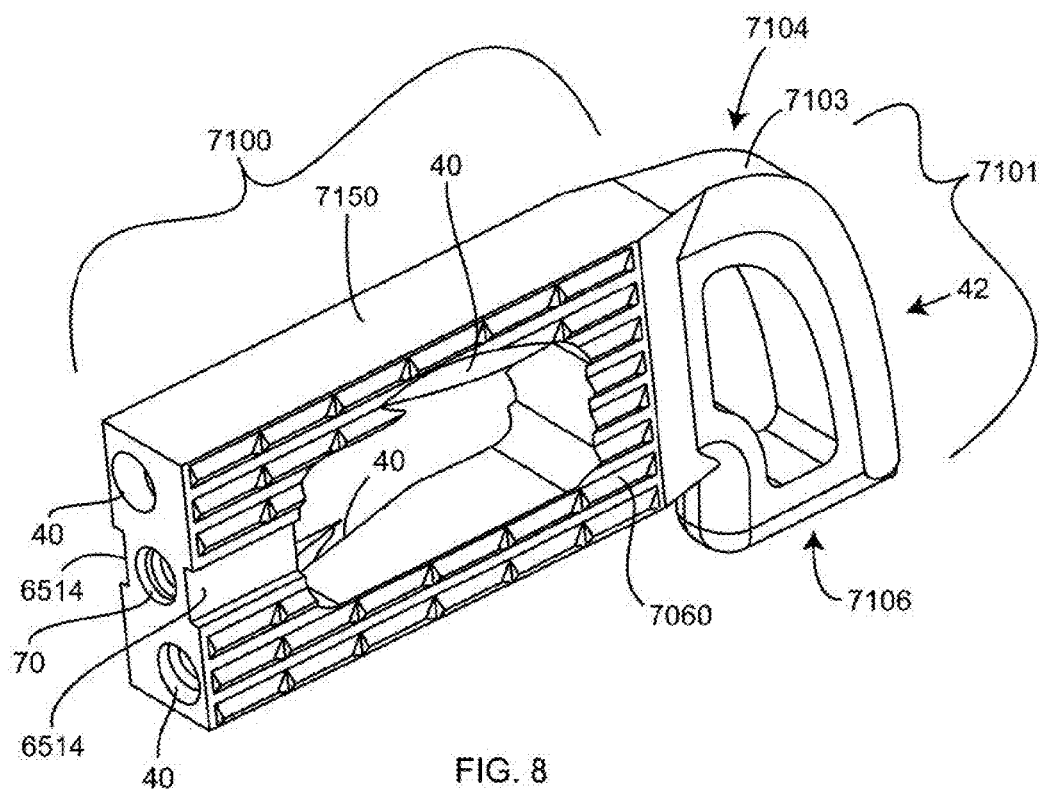
Figure 9:
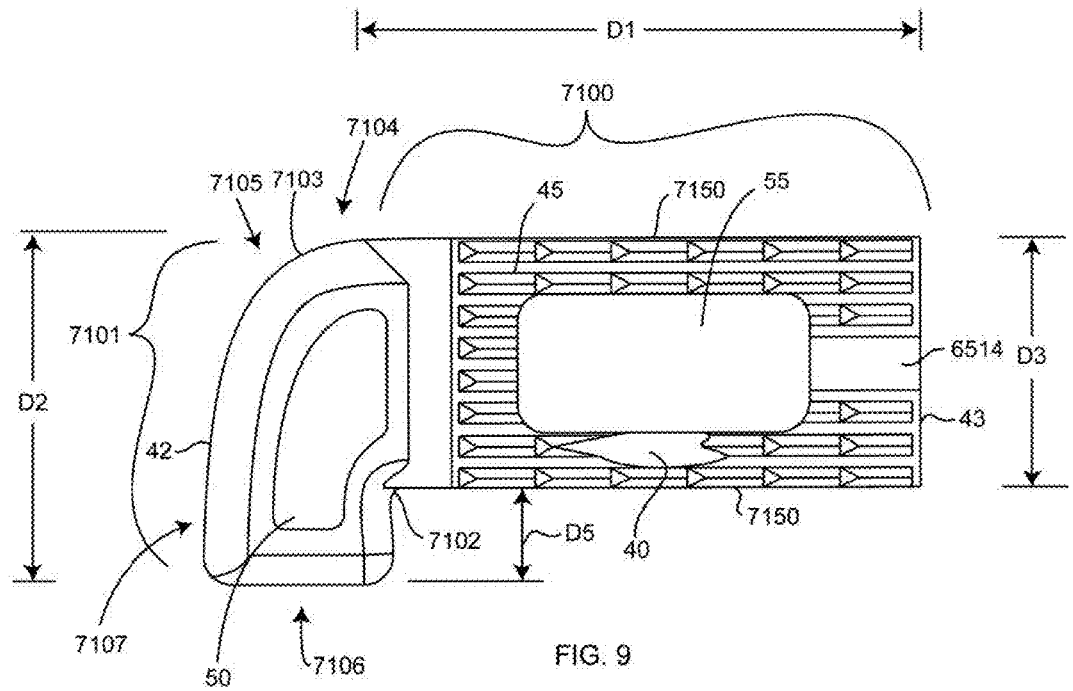
FIGS. 9 and 10 are opposite lateral side plan views of the implant of the implant assembly of FIGS. 4A-4C.
Figure 12:
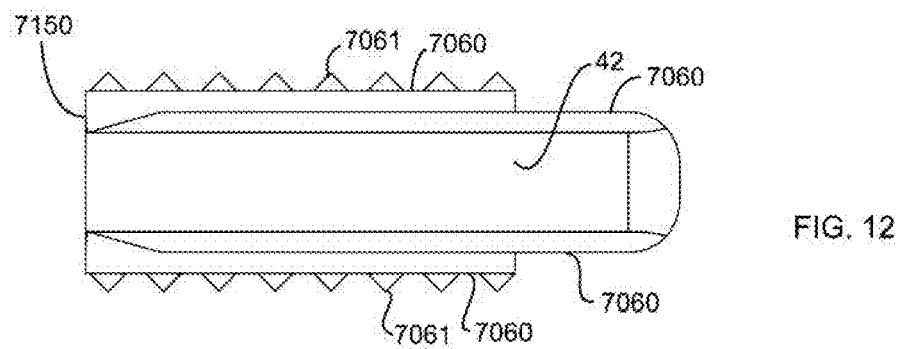
Figure 13:
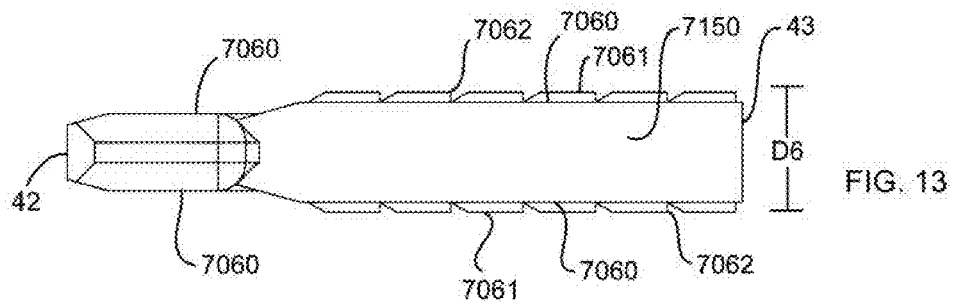
FIGS. 13 and 14 are opposite edge side elevations of the implant of the assembly of FIGS. 4A-4C.
Figure 14:
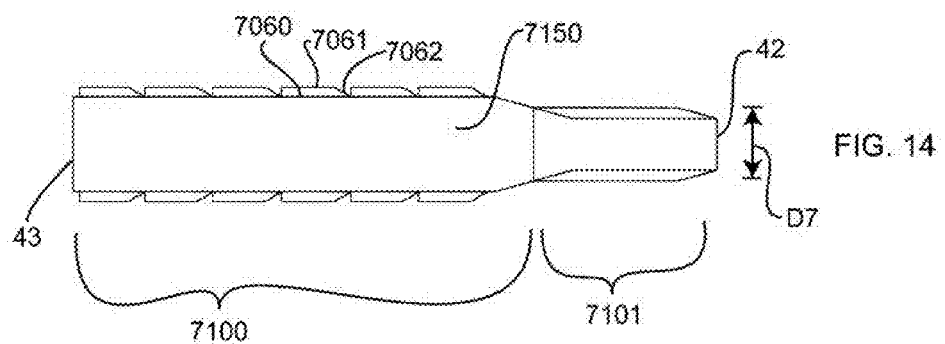
Figure 15:
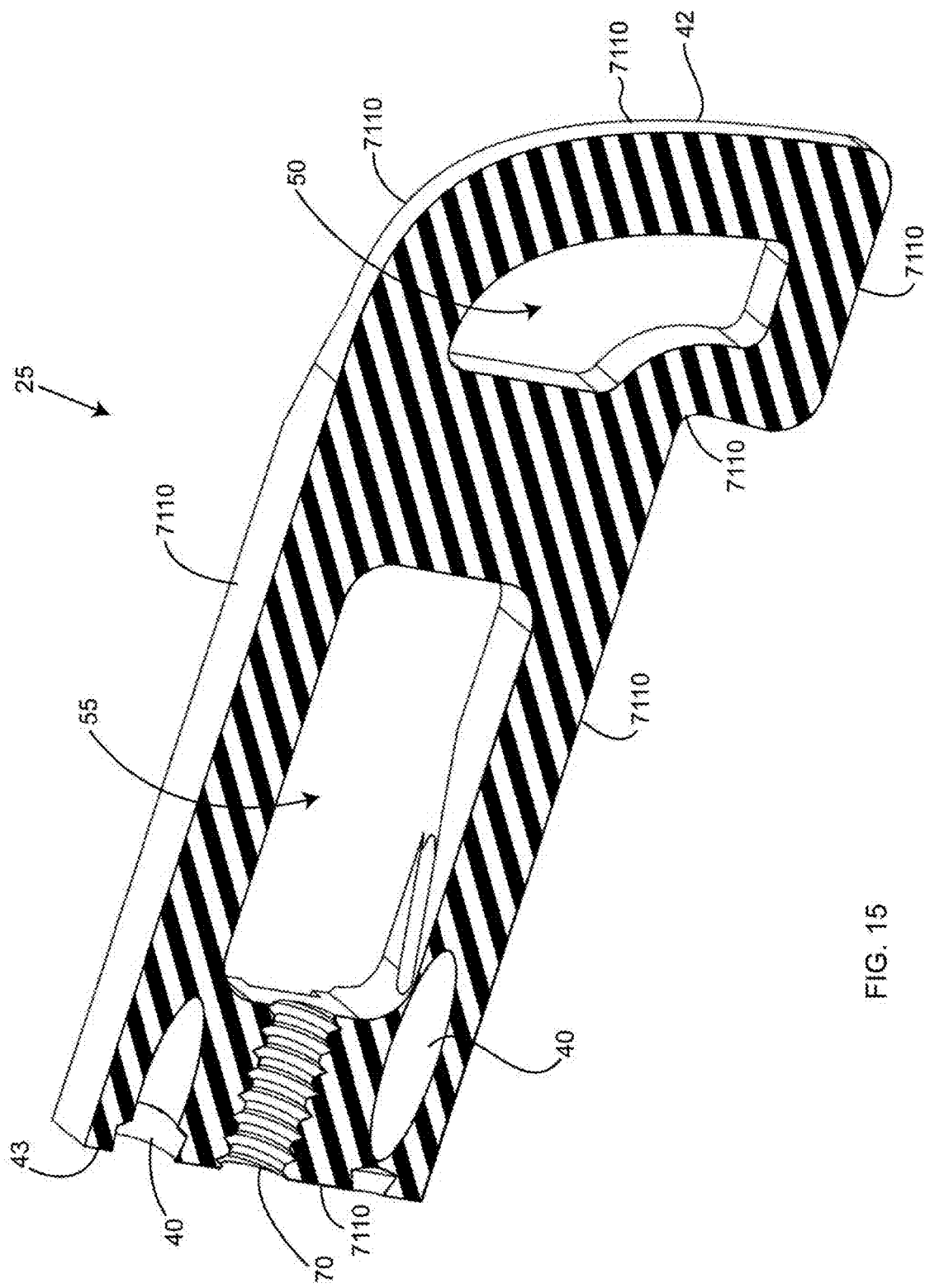
FIG. 15 is a longitudinal cross section of the implant as taken along section lines 15-15 in FIG. 11.

For a detailed discussion of the implant 25, reference is made to FIGS. 5-15. FIGS. 5-8 are various isometric views of the implant 25. FIGS. 9 and 12 are opposite plan views of the implant 25, and FIGS. 11-14 are various elevation views of the implant. FIG. 15 is an isometric longitudinal cross section of the implant 25 as taken along section lines 15-15 in FIG. 11.

Figure 10:
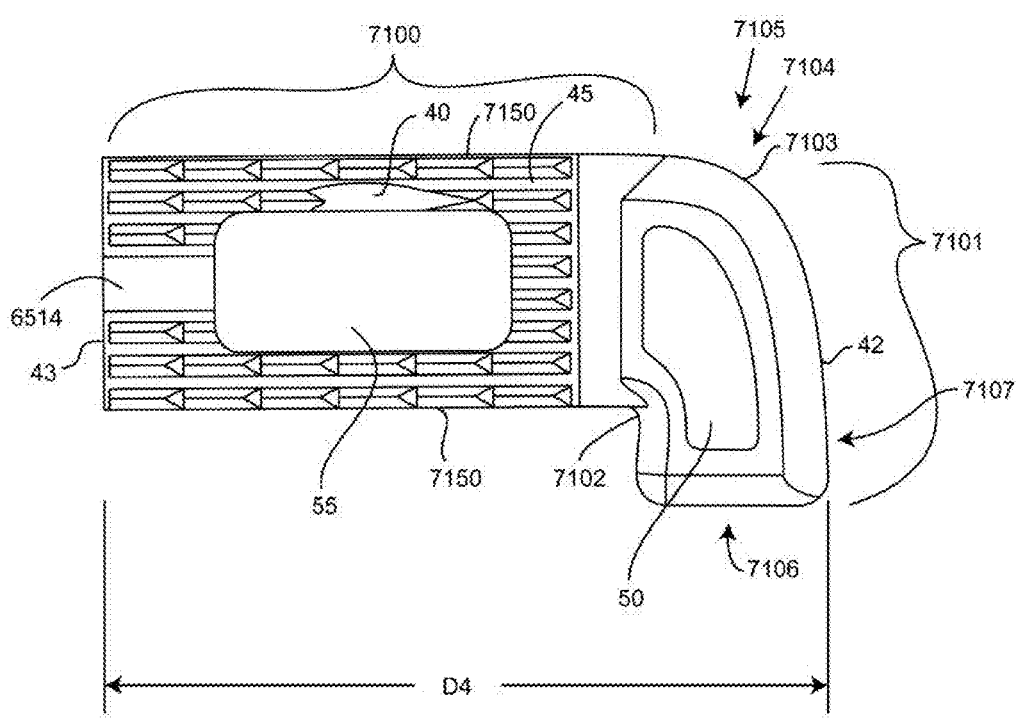
Figure 11:
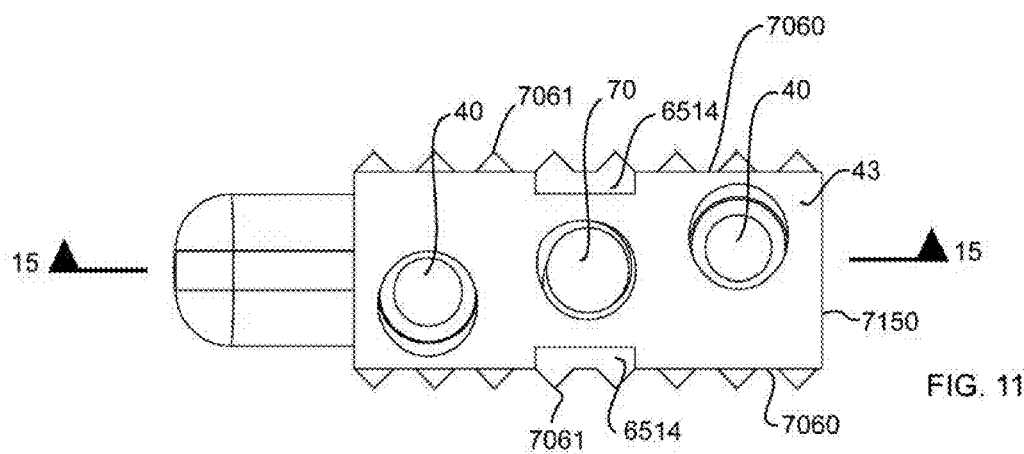
FIGS. 11 and 12 are, respectively, proximal and distal end elevations of the implant of the assembly of FIGS. 4A-4C.
Figure 45A:
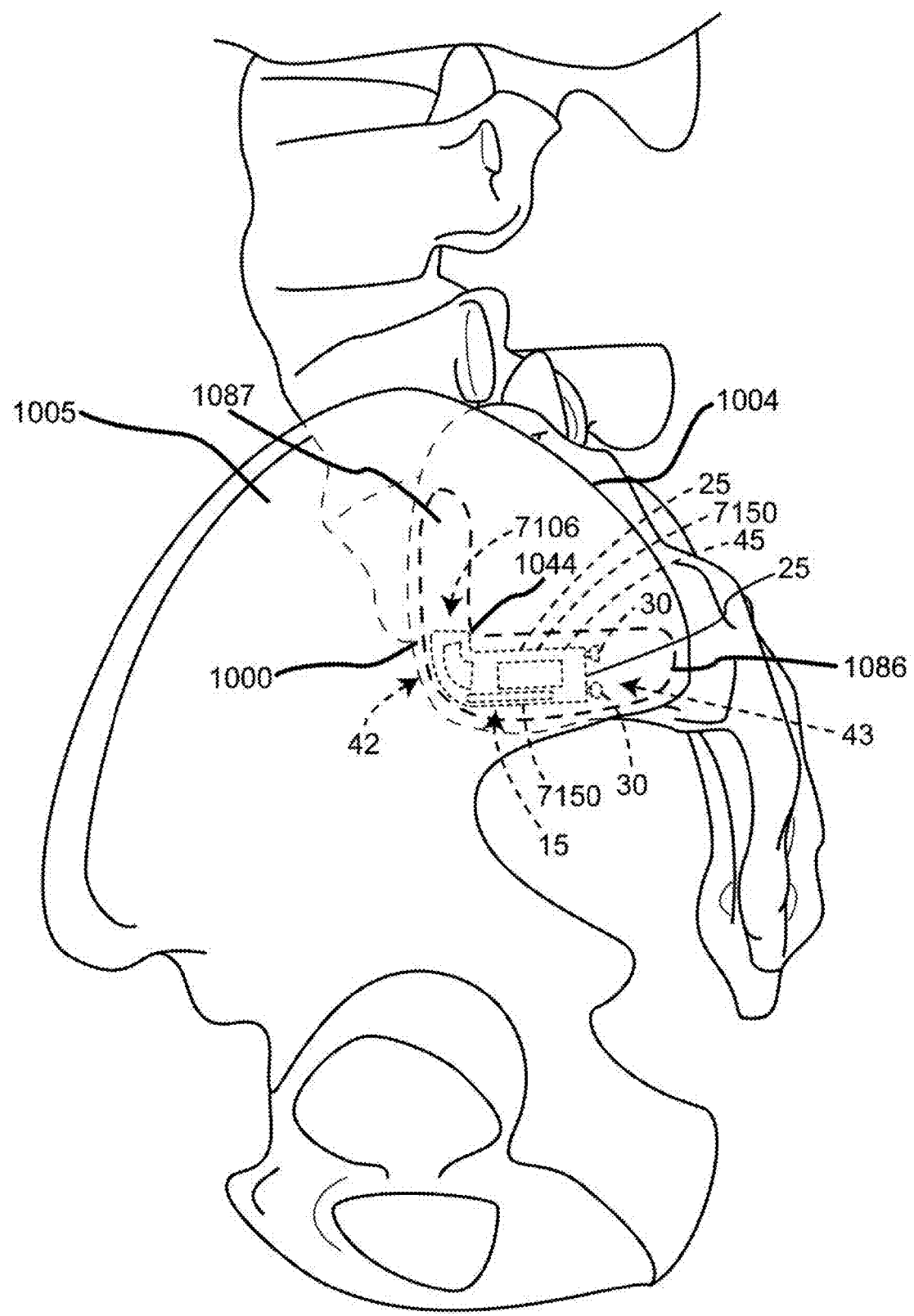
FIG. 45A is a lateral view of the hip region of the patient, illustrating the implant implanted in the caudal region of the sacroiliac joint space.

As shown in FIGS. 5-15, in one embodiment, the implant 25 includes a distal or leading end 42, a proximal or trailing end 43, a longitudinally extending body 45, bores 40 extending distally and laterally through the body from the proximal end 43, a center bore 70, a distal opening 50, and a proximal opening 55. In one embodiment, the implant 25 is configured to have a shape that generally mimics and even substantially fills a sacroiliac joint space. For example, as can be understood from a comparison of the plan views of the implant 25 as illustrated in FIGS. 9 and 10 to the shape of the sacroiliac joint articular region 1044 depicted in FIGS. 45A and 48 discussed below, the implant has an overall exterior shape that generally mimics the sacroiliac joint articular region 1044. The anatomic implant 25 can be provided from the manufacturer in the configuration generally as shown in the FIGS. 5-15.

As illustrated in FIGS. 7 and 8, the implant 25 includes a proximal end 43 for being removably coupled to the extreme distal end 35 of the delivery tool 20. Specifically, in one embodiment, the implant proximal end 43 includes a center bore 70 that extends distally through the implant from the proximal end 43. The center bore 70 may be a blind hole in that it only has a single opening, which is at the proximal end 43. Alternatively, as best understood from FIG. 15, the center bore 70 may be configured as a hole that communicates between the implant proximal end 43 and implant proximal opening 55. The center bore 70 may be threaded or otherwise configured so as to allow mechanical engagement with a distal end 220 of a retainer member 95 of the delivery tool 20, the retainer member 95 being used to secure the implant 25 off of the distal end 35 of the delivery tool 20, as described in detail below. Additionally, the center bore 70 may extend distally across void 55 and continue distally further into body 45. Accordingly, e.g., a bone graft can be placed in void 55 where the graft may have a bore similar to and in alignment with center bore 70 to allow retainer member 95 to pass there through, thereby retaining the graft in place during implantation of implant 25. Subsequently, e.g., bone marrow aspirate may be injected via center bore 70 into the bone graft material, which if substantially solid may have passages cut into it which communicate between the external surfaces of the graft and the graft's bore. In one embodiment, the center attachment bore 70 has a diameter of between approximately 2 mm and approximately 10 mm, with one embodiment having a diameter of approximately 5 mm.

As shown in FIGS. 9 and 10, the implant 25 includes a long portion 7100 and a short portion 7101 perpendicularly oriented to the long portion. The long portion transitions smoothly into the short portion via a small radius 7102 and a large radius 7103 opposite the small radius. The large radius and small radius form an elbow region 7104 of the implant. The large radius forms a heal region 7105 of the implant, and opposite the heal region is a blunt toe region 7106 forming a right angle with a base region 7107 that is generally parallel to the proximal end 43. These regions 7105-7107 form the distal end 42 of the implant 25.

As can be understood from FIGS. 9 and 10, the long portion 7100 has a length D1 of between approximately 25 mm and approximately 45 mm, and the short portion 7101 has a length D2 of between approximately 20 mm and approximately 40 mm. The small curve 7102 has a radius of between approximately 2.5 mm and approximately 16 mm, with one embodiment having a radius of approximately 8 mm, and the large curve 7103 has a radius of between approximately 8 mm and approximately 20 mm, with one embodiment having a radius of approximately 15 mm. The implant body 45 has an overall width D3 of between approximately 10 mm and approximately 20 mm and an overall length D4 of between approximately 35 mm and approximately 60 mm. The toe projects from the immediate lateral side edge 7150 of the implant body 45 by a distance D5 of between approximately 8 mm and approximately 20 mm, with one embodiment having a distance D5 of approximately 15 mm.

The implant 25 can be configured such that the body 45 of the implant is a generally continuous solid surface with the exception of the bores 40, 70 extending through portions of the body 45. However, as indicated in FIGS. 5-10 and 15, the body 45 of the implant 25 may have one or more openings or voids defined in the body 45. For example, an opening or void 50 may be defined in a distal region of the implant body 45, and another opening or void 55 may be defined in a proximal region of the implant body 45. The voids 50, 55 may be packed with bone growth material prior to the implant 25 being delivered into the sacroiliac joint space.

As indicated in FIGS. 5-15, the implant body 45 includes side edge surfaces 7150 that extend between the proximal end 43 and the distal end 42. These side edge surfaces 7150 and the similar side edge surfaces associated with the small curve 7102, the large curve 7104, the toe 7106, the distal end 42 and proximal end 43 combine to define side edge surface boundary 7110 (indicated in FIG. 15) that extends unbroken and unitary through all of the above-mentioned regions of the implant, thereby forming an outer boundary that may at least somewhat resemble the sacroiliac joint space and more fully occupy the joint space than more linearly shaped rectangle and cylindrical implant embodiments.

As illustrated in FIGS. 5-15, in one embodiment, the implant body 45 includes generally planar lateral side surfaces 7060. In some embodiments, the lateral side surfaces 7060 may be generally spaced apart by a distance or body thickness that is generally continuous over the entirety of the surfaces 7060. However, as can be understood from FIGS. 13 and 14, in some embodiments, the distance or body thickness may taper from a greater thickness D4 in the long portion 7100 and a lesser thickness D5 in the short portion 7101. In one embodiment, the greater thickness D6 may be between approximately 3 mm and approximately 10 mm, and the lesser thickness D7 may be between approximately 3 mm and approximately 6 mm.

In one embodiment, the planar lateral side surfaces 7060 may be substantially smooth. However, in other embodiments, as indicated in FIGS. 9-14, the planar lateral side surfaces 7060 may have multiple parallel ridges 7061 that extend longitudinally along the long portion 7100 and may be serrated with notches 7062 oriented so as to prevent proximal migration of the implant 25 once implanted in the sacroiliac joint. The anti-migration features 7062 are generally evenly distributed along the planar surfaces 7060. While the anti-migration features 7062 are depicted as being notches 7062 defined in the longitudinally extending ribs or ridges 7061, in other embodiments the anti-migration features 7062 may be in the form of other types of surface texturing or protrusions in the form of cylinders, trapezoids, squares, rectangles, etc. Further, although the anti-migration features 7062 are depicted in the form of unidirectional serrated notches 7062 in ridges 7061 on the planar lateral side surfaces 7060 the implant 25, the invention is not so limited and, as to particular embodiments, can be configured to have said features 7062 arranged in multiple directions, unidirectional, or a combination of multiple direction on some surfaces of the implant and unidirectional on other surfaces of the implant. Accordingly, the features 7062 can be so arranged on the various surfaces of the implant so as to prevent undesired migration in particular directions due to the forces present at the sacroiliac joint 1000.

As indicated in FIGS. 7 and 8, longitudinally extending rectangular notches 6514 may be defined in the planar lateral side surfaces 7060. As described below, such notches 6514 may interact with members 140 forming part of the delivery tool distal end 35 so as to help retain the implant 25 on the distal end 35 and to prevent the implant from rotating relative to the distal end 35 when the retaining rod threaded distal end 220 is being threaded into or out of the center bore 70.

As can be understood from FIGS. 4A and 5-10, in one embodiment, the bores 40 extend distally and laterally from a proximal end 43 of the implant 25 to begin day lighting distally in the proximal void 55 and eventually exit the implant body 45 laterally as grooves or portions of bores defined in the planar lateral side surface 7060. Since the bores 40 are oriented so as to extend distally and laterally from the proximal end 43 and, further, since the anchors 30 have sufficient length, the anchors 30 project both laterally and distally from the planar lateral side surfaces 7060 of the implant 25, as illustrated in FIGS. 4A-4C.

In summary, as can be understood from FIGS. 5-15, in one embodiment, a sacroiliac joint fusion implant 25 includes a proximal end 43, a distal end 42 generally opposite the proximal end, and side edge surfaces 7150 extending between the proximal and distal ends and defining a long portion of the implant 7100 and a short portion 7101 of the implant. The long portion is longer than the short portion and the two portions extend in directions generally perpendicular to each other. The proximal end terminates proximally in a generally blunt end and the distal end terminates distally in a generally blunt end 7106 facing in a direction generally perpendicular of the direction faced by the generally blunt end of the proximal end. The generally blunt end of the proximal end is configured to releasably couple to an implant delivery system. An offset distance between the side edge surfaces 7150 is substantially greater than a thickness of the implant as defined by an offset distance between the planar lateral side surfaces 7060. One side edge surface 7150 transitions between the long and short portions 7100, 7101 via a first curved portion 7103 and the another side edge surface 7150 transitions between the long and short portions via a second curved portion 7102 having a radius smaller than the first curved portion. The cumulative exterior side edge border surface 7110 defines a shape resembling a shape of an adult human sacroiliac joint as viewed in a direction perpendicular a plane of the sacroiliac joint. For example, the cumulative exterior side edge border surface 7110 defines a shape resembling a boot for a human foot.

In one embodiment, the implant 25 may be machined, molded, formed, or otherwise manufactured from stainless steel, titanium, ceramic, polymer, composite, bone or other biocompatible materials. The anchor member 30 may be machined, molded, formed or otherwise manufactured from similar biocompatible materials.

In some embodiments, the implant 25 may be substantially as described above with respect to FIGS. 4-15, except the implant 25 may have an overall shape that is something other than shaped to mimic the sacroiliac joint. For example, as shown in FIGS. 16A-16F, which are various isometric, plan, and elevational views of an alternative embodiment of an implant assembly 15 that may be employed with the delivery tool 20 of FIGS. 2A-3, the implant 25 may have a rectangular shape. Other than the overall shape of the implant 25 of the implant assembly 15 of FIGS. 16A-16F being different than the overall shape of the implant 25 of the implant assembly 15 of FIGS. 4A-4C and the implant 25 of FIGS. 16A-16F having only a single void 50 as opposed to two voids 50, 55, all other features of the implant assemblies 15 are essentially the same for both implant assemblies 15. While the implant 25 are shown herein to have a joint-shaped configuration and a rectangular shape, in other embodiments the implant 25 may have other shapes such as cylindrical, trapezoidal, triangular, etc. and still be useable with the delivery tool 20 of FIGS. 2A-3 and have anchors oriented and deployable as described above with respect to FIGS. 4A-16F.

As illustrated in FIGS. 16H and 16G, which are enlarged isometric views of proximal ends of bores 40 at proximal ends 43 of any of the implant bodies 25 disclosed herein as employing a screw type anchor 30, the bores 40 may be configured to have a retainer arrangement that acts against the anchors 30 when in the bores 40 to prevent the anchors 30 from backing out of the bores 40.

As indicated in FIG. 16H, in one embodiment, the proximal end of a bore 40 may have a disk-shaped seat 310 having a center hole 315 that forms the remainder of the extent of the bore 40. The disk-shaped seat 310 has a plurality of arcuate members 320 distributed along an inner circumferential boundary 325 of a rim 330 of the disk-shaped seat 310. There may be five or more or less arcuate members 320 distributed generally evenly about the inner circumferential surface 325 of the rim 330.

In one embodiment, each arcuate member 320 has ends 332 that intersect the inner circumferential surface 325 of the rim 330, with a center point 335 of the arcuate member 320 that is offset or spaced apart from inner circumferential surface 325 of the rim 330. Thus, in one embodiment, the arcuate members 320 may be deflectable so as to allow the head of the anchor member 30 to pass between the center points 335 of the members 330 as the head of the anchor member 30 is seated in the seat 310. As a result, the arcuate members 320 can act against the head of the anchor member 30 to prevent the anchor member from working its way out of the bore 40 and opening 315 of the implant 25, thereby serving as an anchor member locking mechanism.

Other anchor member locking mechanisms may be employed. For example, as illustrated in FIG. 16H, the bore 40 includes a cantilevered abutment arm 335 defined proximal end 43 of the implant body 25 via a series of parallel arcuate slots 340. In one embodiment, a face 345 of the abutment arm 335 is deflectable and biased radially inward of the inner circumferential surface 350 of the bore 40 such that when the anchor member 30 is extended through the bore 40, the face 345 abuts against the anchor member to prevent the anchor member from working its way out of the bore 40 of the implant 25, thereby serving as an anchor member locking mechanism.

In other embodiments of the implant, other anchor member locking mechanisms may be employed including, for example, set screws supported off of the implant body to engage the anchor 30 when received in a bore 40.

Figure 16A:
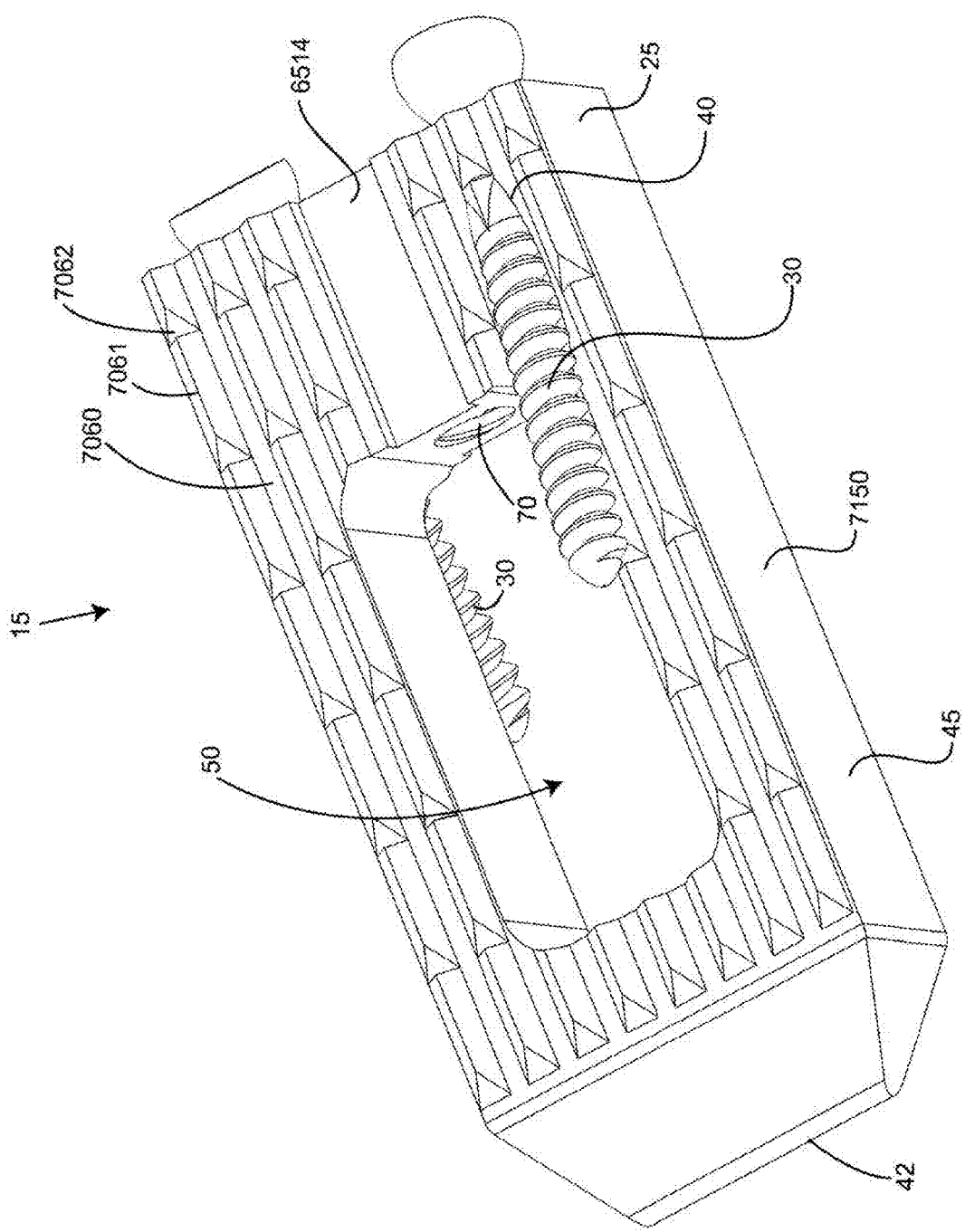
FIGS. 16A-16B are, respectively, distal isometric and proximal isometric views of an implant assembly similar to that of FIGS. 4A-15, except having a rectangular body.
Figure 16B:
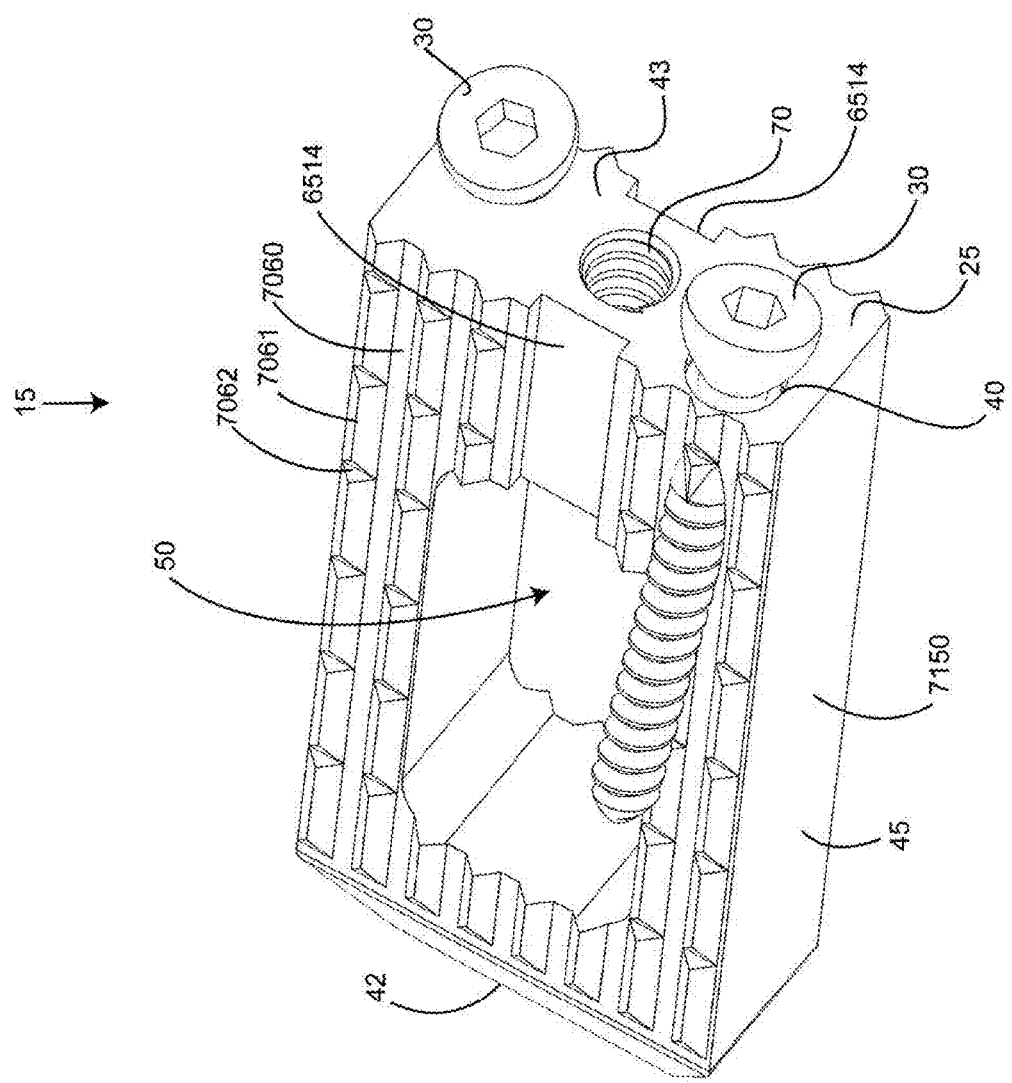
Figure 16C:
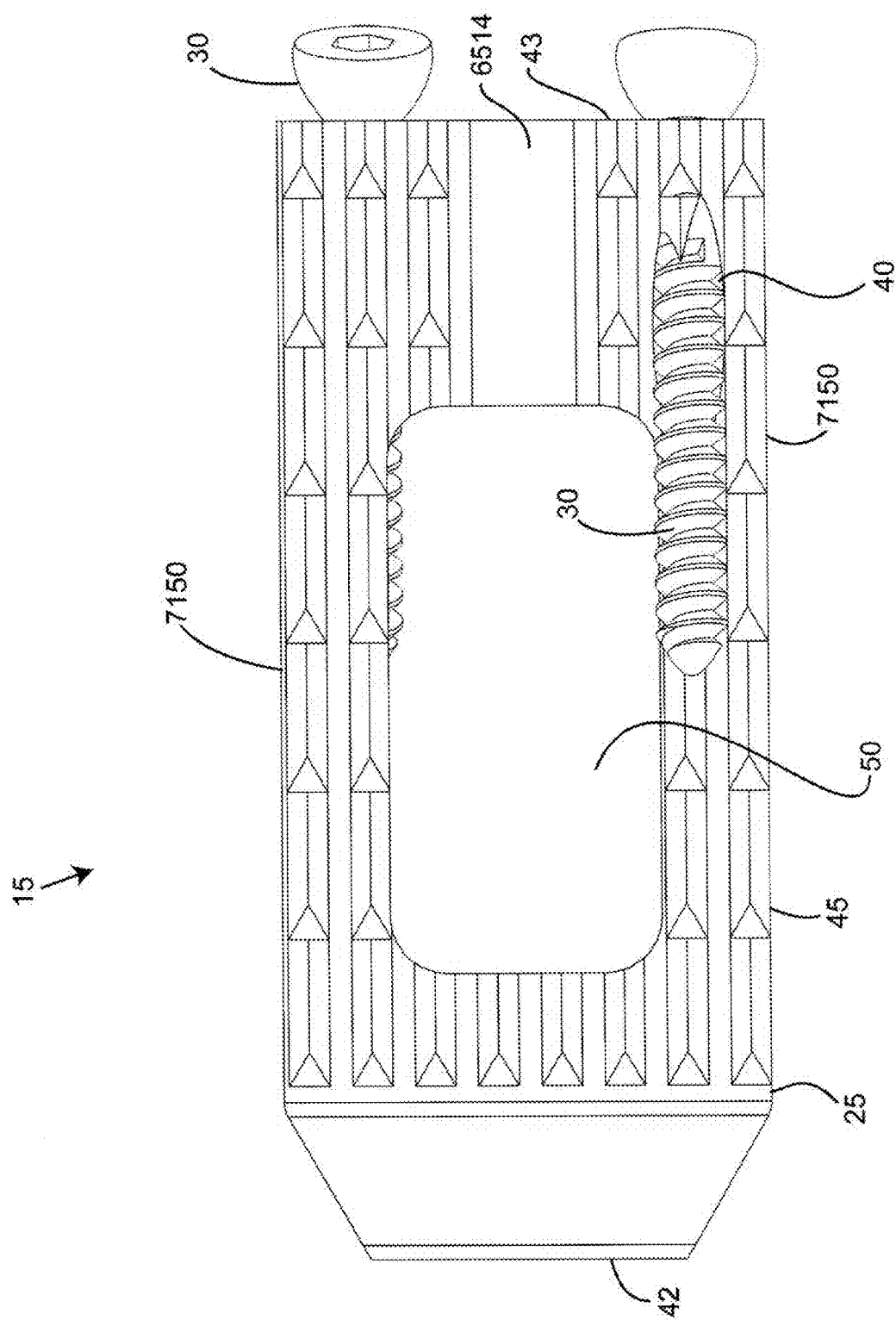
FIG. 16C is a lateral side plan view of the rectangular implant assembly.
Figure 16D:
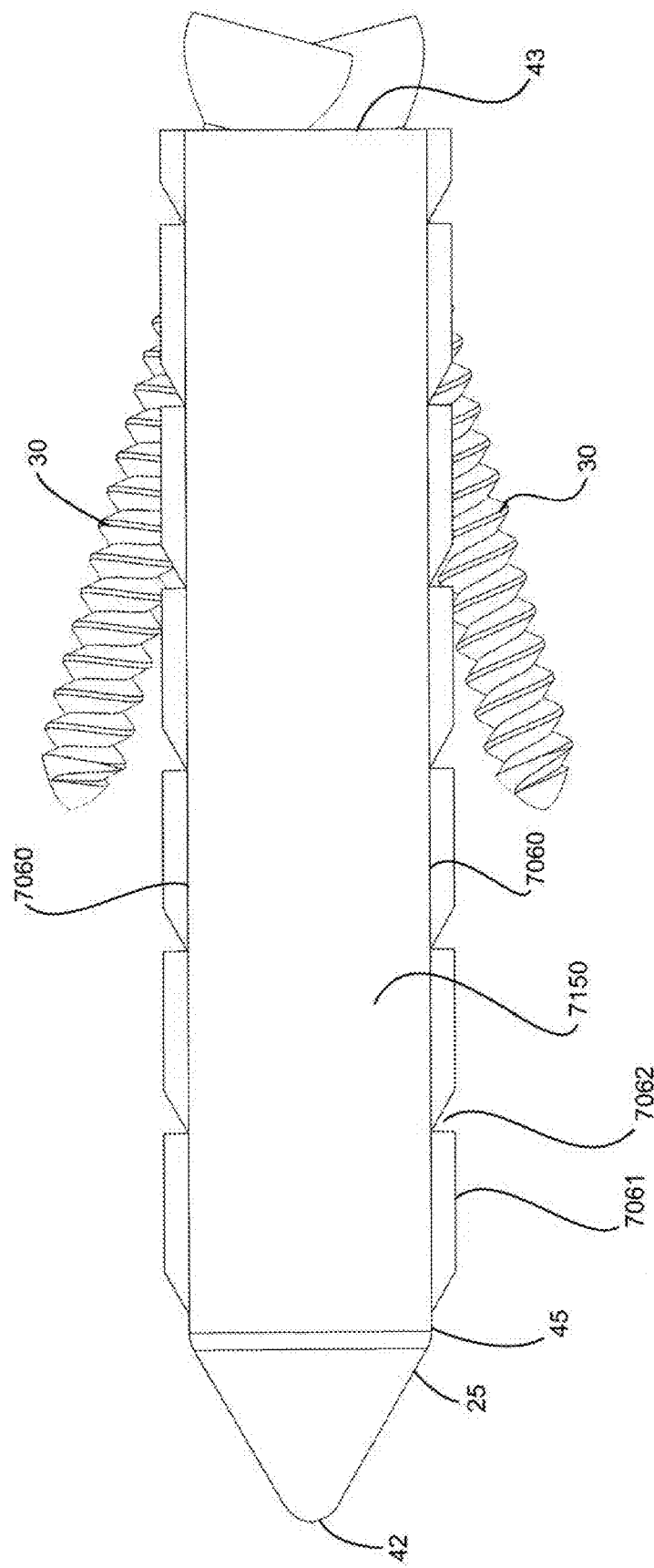
FIG. 16D is an edge side elevation of the rectangular implant assembly.
Figure 16E:
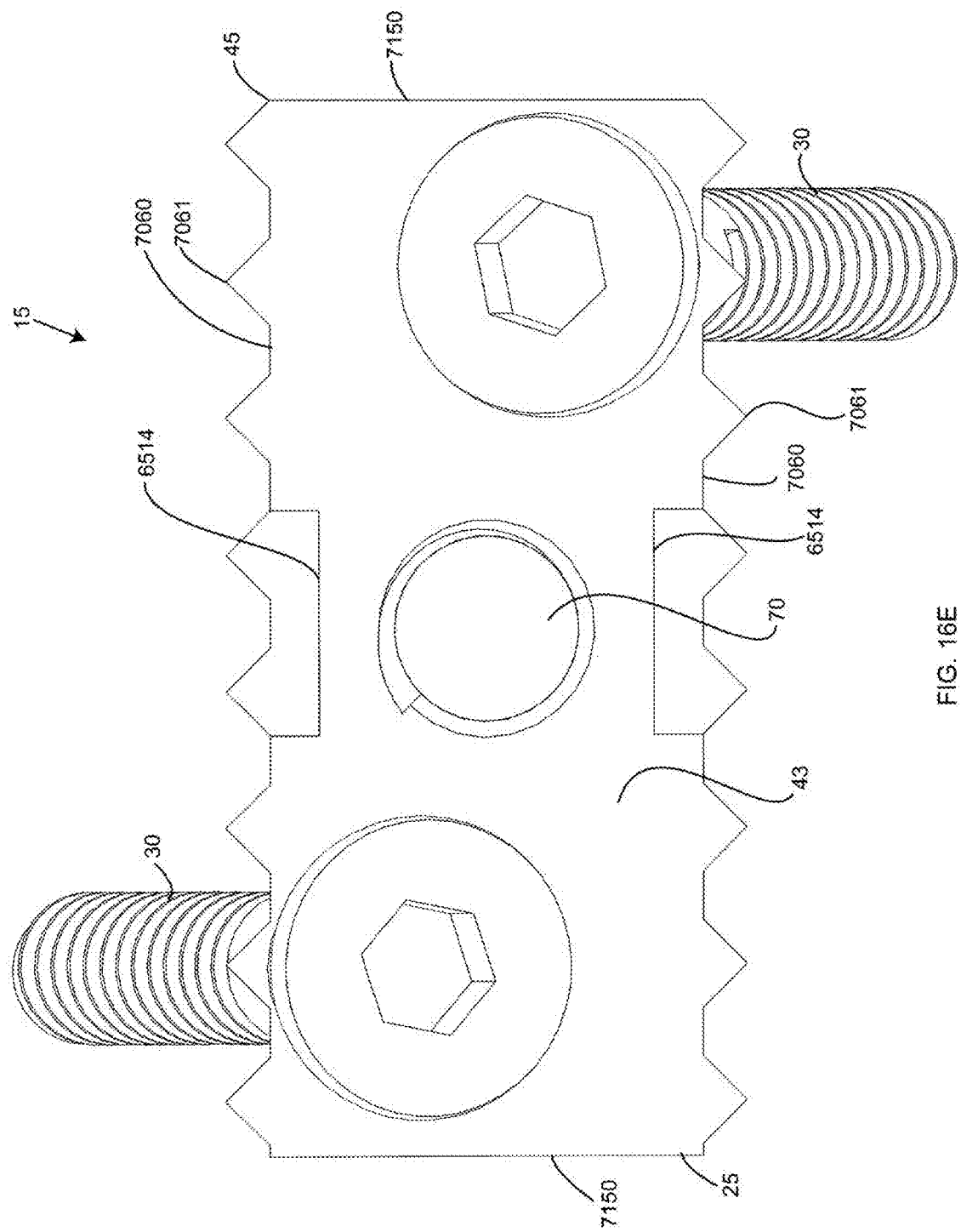
FIGS. 16E and 16F are, respectively, proximal and distal end elevations of the rectangular implant assembly.
Figure 16F:
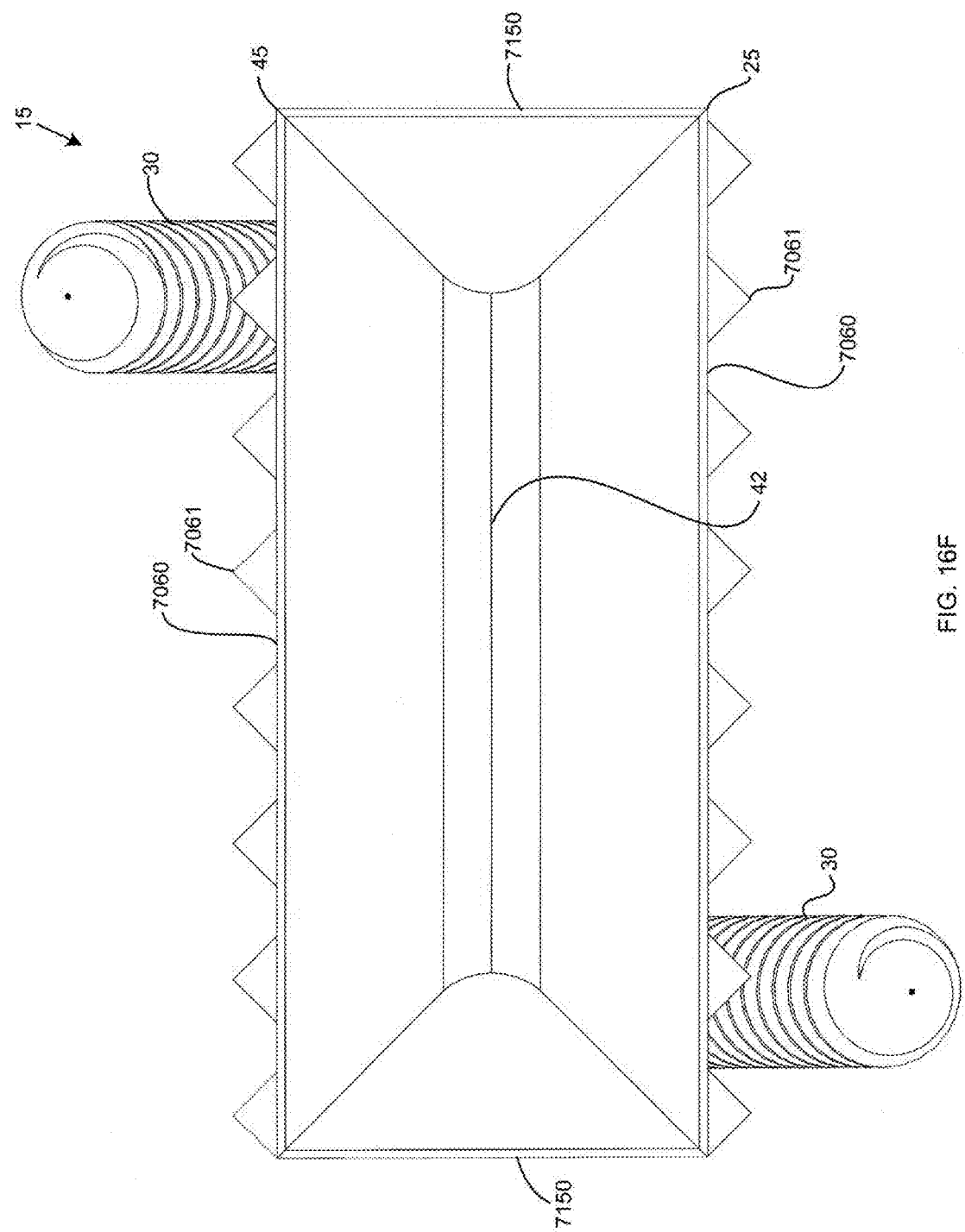
Figure 16I:
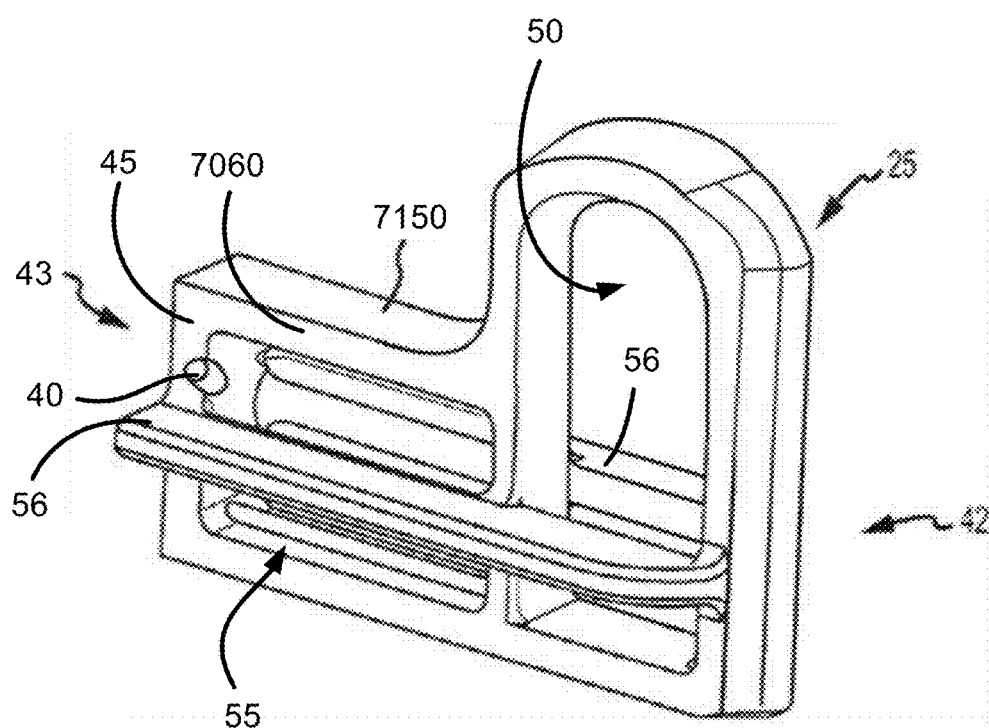
FIG. 16I is a distal end isometric view of an implant having a body that approximates or generally mimics a sacroiliac joint and includes a pair of keels extending from opposite lateral side surfaces.

The particular embodiments of FIGS. 4A-16F depict implant assemblies 15 having an implant 25 with a generally planar body 45 such that the width and length of the body 45 are substantially greater than the thickness of the body 45 and the planar body 45 is generally free of any substantial features of the body extending away from the planar lateral side surfaces 7060. However, in other embodiments, the implant body 45 of the present disclosure may have the anchoring arrangement illustrated in FIGS. 4A-16F and further be configured to have a shape and/or radially extending wings as described with respect to any of the many implant body embodiments described in U.S. patent application Ser. No. 13/475,695, which was filed May 18, 2012 and is hereby incorporated by reference in its entirety. For example, as seen in FIG. 16I, which is a distal end isometric view of the implant 25, the body 45 is similar to the implant 25 of FIGS. 5-15, except the body 45 includes a pair of keels, fins, planar members, or wing members 56 extending generally perpendicularly outward from the planar lateral side surfaces 7060. The body 45 may include voids 50, 55 as in other embodiments of the implant 25. As seen in the figure, the keels 56 may extend along a longitudinal axis of the body 45 of the implant and may extend from opposite planar lateral side surfaces 7060 such that the keels 56 are generally coplanar with each other. For example, the keels 56 opposite each other generally exist in the same plane. More specifically, planar faces of a first keel 56 are generally coplanar with the planar faces of a second keel 56 opposite the first keel 56. As seen in the figure, the keels 56 are generally positioned centrally on the respective planar lateral side surfaces 7060 so as to be generally equidistant between a top and bottom side edge surface 7150. A width of the keels 56 may be smaller than a width of the body 45 of the implant 25 between the opposite planar lateral side surfaces 7060.

The particular embodiments of FIGS. 4A-16F depict implant assemblies 15 having an implant 25 with a generally planar body 45 such that the width and length of the body 45 are substantially greater than the thickness of the body 45 and the planar body 45 is generally free of any substantial features of the body extending away from the planar lateral side surfaces 7060. However, in other embodiments, the implant body 45 of the present disclosure may have the anchoring arrangement illustrated in FIGS. 4A-16F and further be configured to have a shape and/or radially extending wings as described with respect to any of the many implant body embodiments described in U.S. patent application Ser. No. 13/475,695, which was filed May 18, 2012 and is hereby incorporated by reference in its entirety.

Alternatively, the implant may be configured as disclosed in U.S. Provisional Patent Application 61/520,956 which is entitled "Sacroiliac Joint Implant System," which was filed Jun. 17, 2011 and the corresponding Patent Cooperation Treaty patent application PCT/US12/42823.

To begin a detailed discussion of components of an embodiment of the delivery tool 20, reference is again made to FIGS. 2A-3. As shown in FIG. 2A, the delivery tool 20 includes a distal end 35 and a proximal end 80. The distal end 35 supports the components 25, 30 of the implant assembly 15, and the proximal end 80 is configured to be grasped and manipulated to facilitate the implantation of the implant assembly 15 in the sacroiliac joint.

Figure 17B:
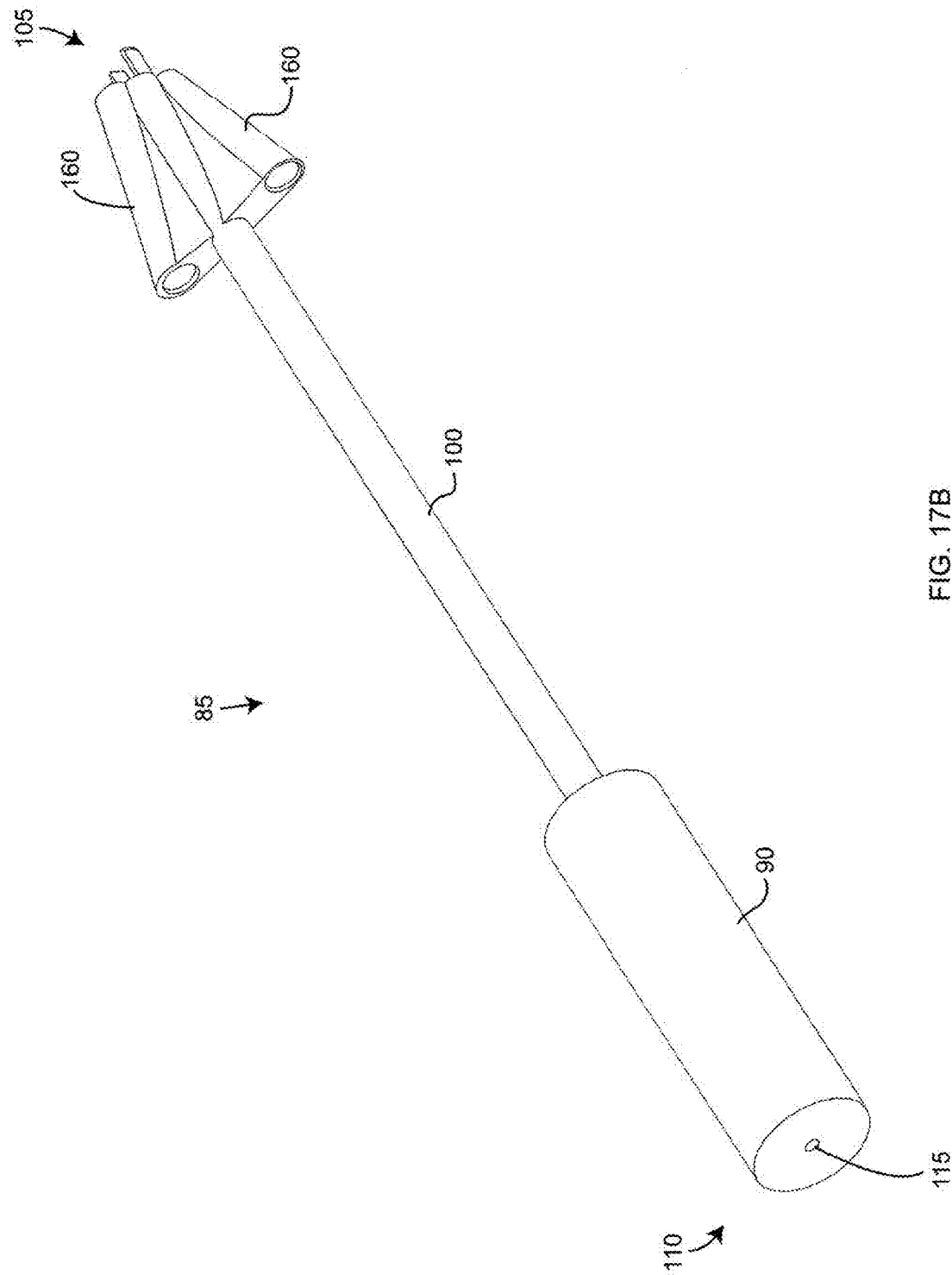

As illustrated in FIG. 3, the delivery tool 20 further includes a shaft assembly 85, a handle 90, an implant retainer 95. As shown in FIGS. 17A and 17B, which are, respectively, distal and proximal isometric views of the shaft assembly 85, the shaft assembly 85 includes the handle, 90, a tubular elongated body 100, a distal implant engagement end 105, and anchor guides 160. The handle 90 is coupled on a proximal end 110 of the tubular elongated body 100. The tubular elongated body 100 includes a lumen 115 through which the implant retainer 95 extends, as described below. The anchor guides 160 are tubular structures mounted on opposite sides of the distal implant engagement end 105. The anchor guides 160 may have other shapes that are complementary with the shape of anchors 30 having shapes. For example, anchor guides 160 may have a rectangular in cross section in order to correctly align an anchor which is rectangular in cross section with an implant bore 40 which is also rectangular in cross section.

Figure 17C:
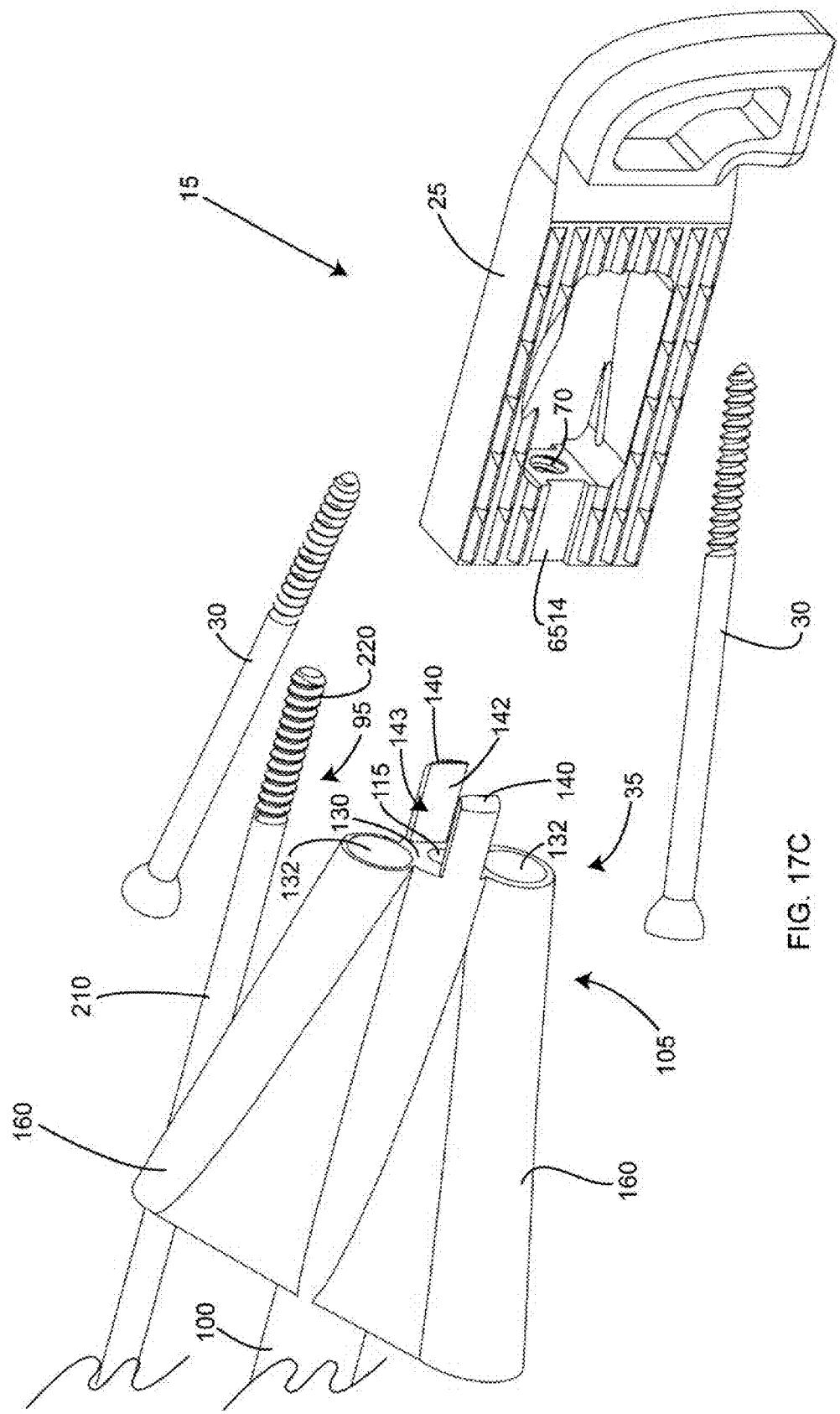
FIG. 17C is an enlarged isometric view of the delivery tool distal end and implant assembly all shown exploded.

As shown in FIG. 17C, which is an enlarged isometric view of the delivery tool distal end 35 and implant assembly 15 all shown exploded, the distal implant engagement end 105 includes a distal face 130 that is located between the distal openings of the lumens 132 of the anchor guides 160 and offset distally extending members 140. The members 140 have opposed planar faces 142 that are each configured to be matingly received by the respective notches 6514 of the implant 25 when the proximal end 43 of the implant 25 is received in an implant receiving space 143 defined by the distal face 130 and opposed planar faces 142.

Figure 18:
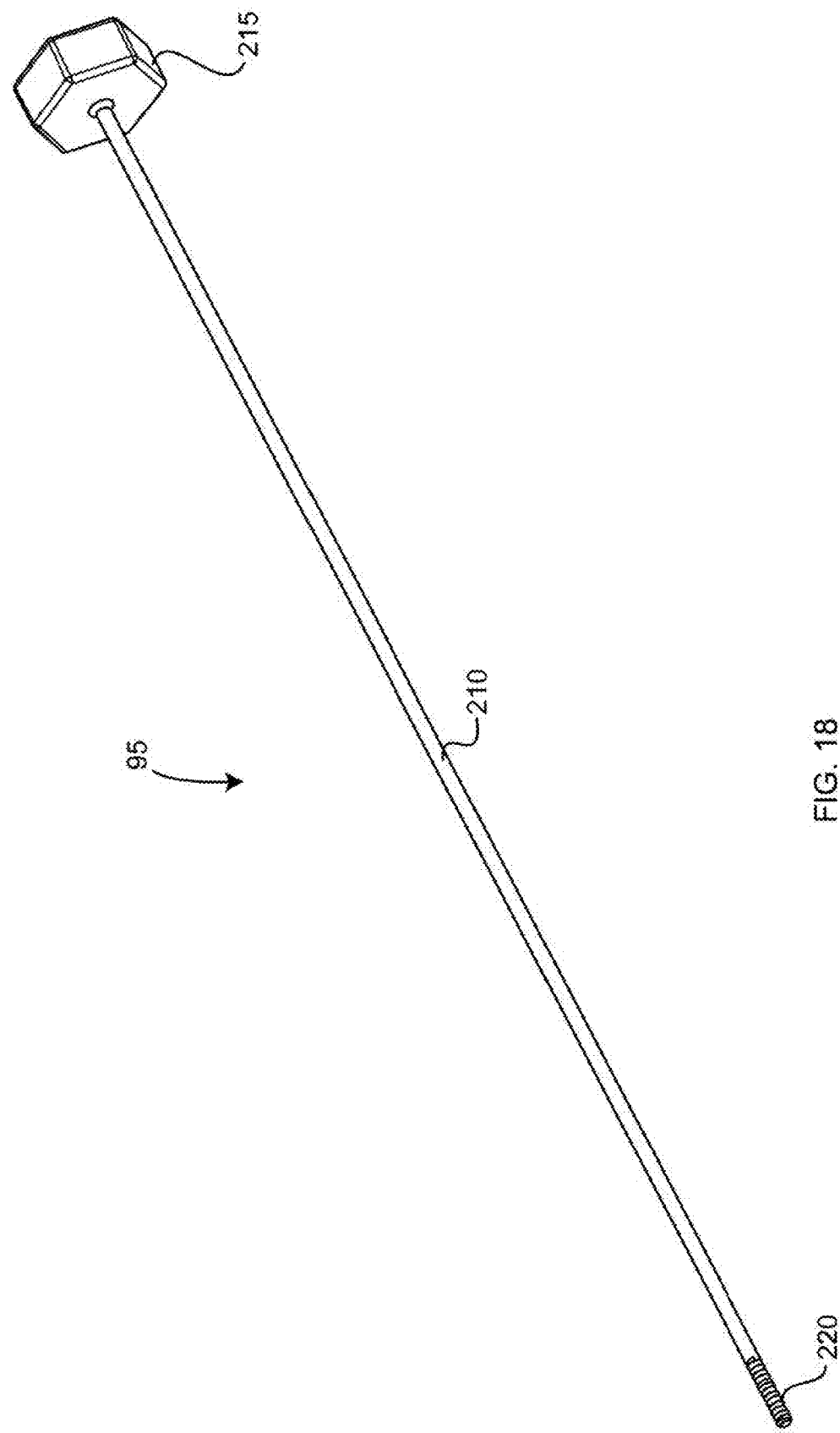
FIG. 18 is a distal isometric view of the implant retainer of the delivery tool of FIGS. 2A-3.
Figure 19:
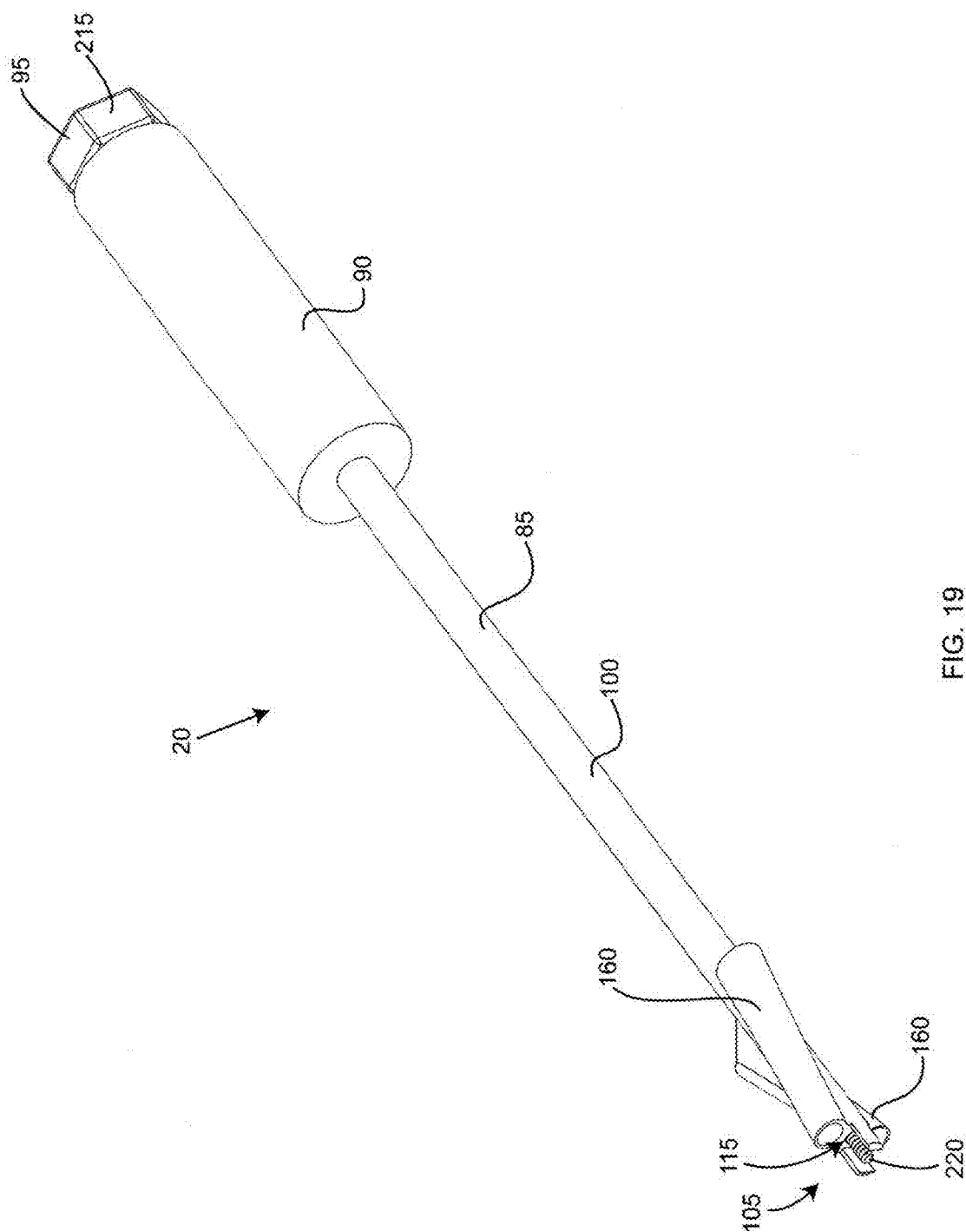
FIG. 19 is a distal isometric view of the delivery tool.

As illustrated in FIG. 18, which is a distal isometric view of the implant retainer 95, the implant retainer 95 includes a longitudinal cylindrical member 210, a handle 215 on a proximal end of the longitudinal cylindrical member 210, and an implant engagement feature 220 on a distal end the longitudinal cylindrical member 210. As can be understood from FIG. 19, which is a distal isometric view of the delivery tool 20, the member 210 of the implant retainer 95 extends through the lumen 115 of the body 100, the engagement feature 220 distally extending from the lumen 115 when a distal face of the retainer handle 215 is abutting against a proximal face of the shaft assembly handle 90.

Figure 20:
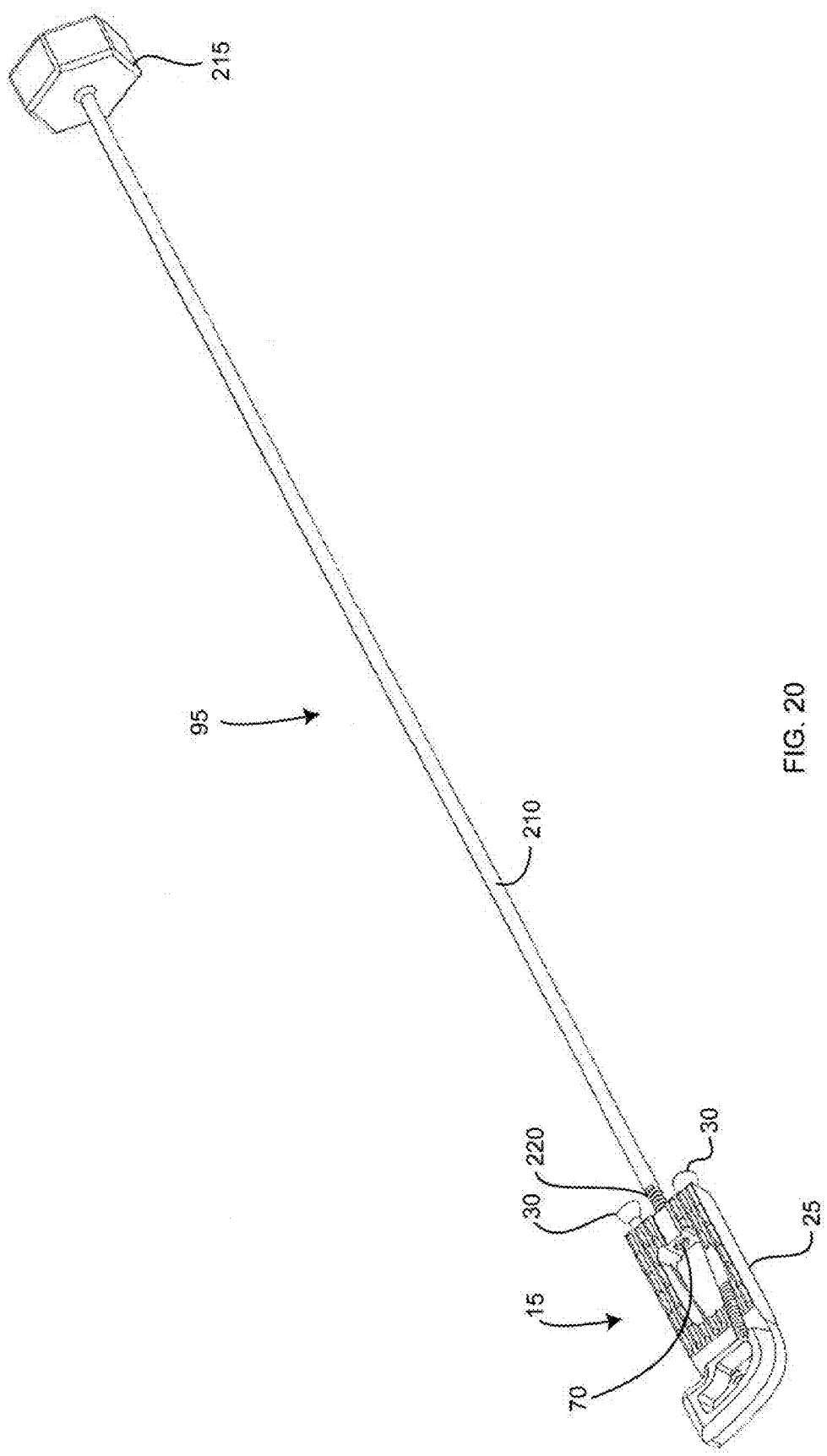
FIG. 20 is an isometric view of the implant assembly coupled to the implant retainer with the rest of the delivery tool hidden for clarity purposes.

As can be understood from FIG. 20, which is an isometric view of the implant assembly 15 coupled to the implant retainer 95 with the rest of the delivery tool 20 hidden for clarity purposes, in one embodiment, the implant engagement feature 220 is in the form of a threaded shaft for engaging complementary threads in the center bore 70, thereby securing the implant proximal face 43 against the distal face 130 of the distal implant engagement end 105, the members 140 being received in the notches 6514, as can be understood from FIG. 2A.

Figure 21:
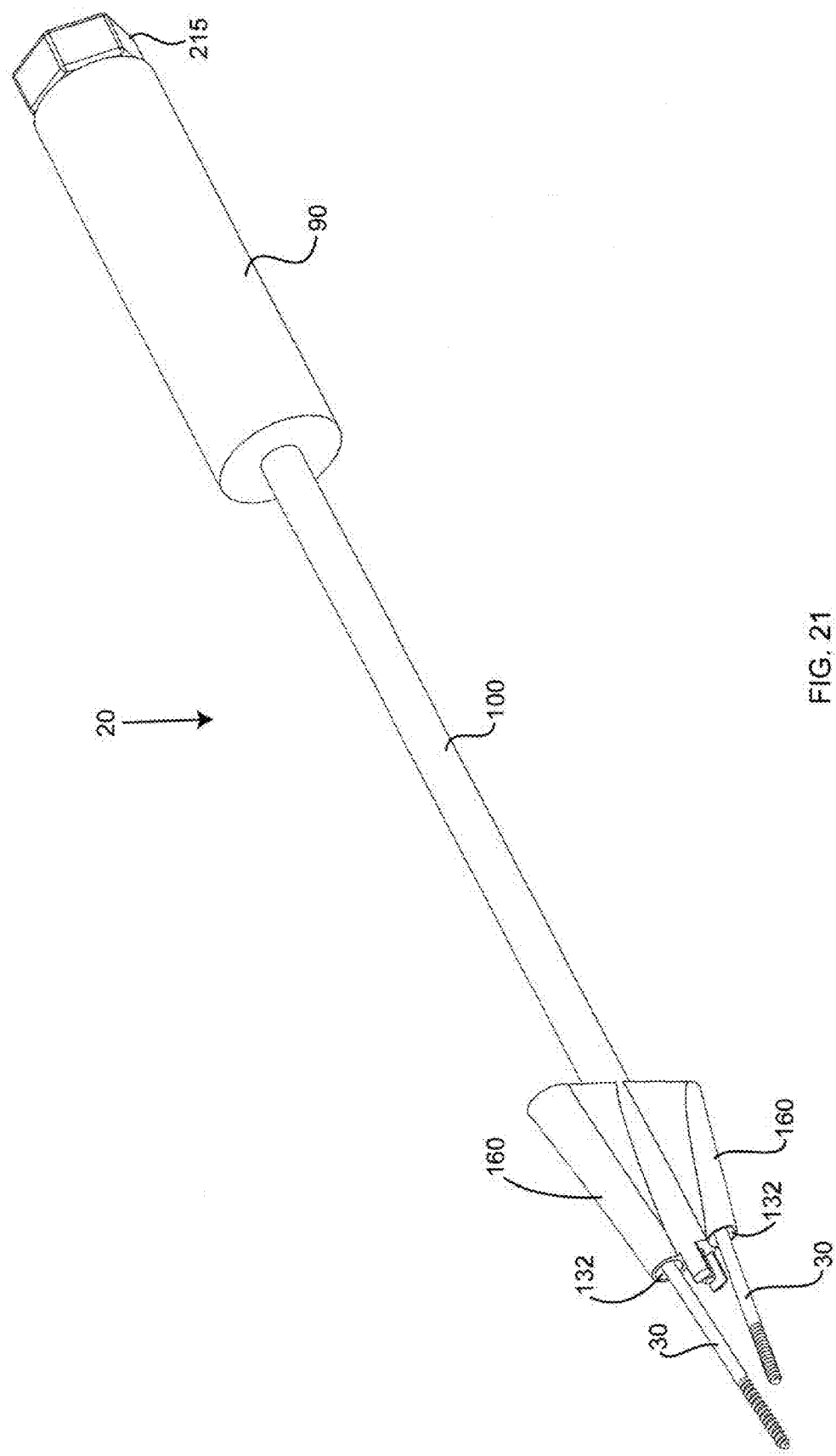
FIG. 21 is an isometric view of the delivery tool and anchors with the implant hidden for clarity purposes.

As illustrated in FIG. 21, which is a distal isometric view of the delivery tool 20 with the anchors 30 loaded in the anchor guides 160 of the delivery tool 20, the anchor guides 160 are oriented such that the longitudinal axes of the anchor guide lumens 132 extend both distally and laterally. Thus, anchors 30 loaded in the anchor guide lumens 132 are oriented so as to be guided along a trajectory that is both distal and laterally outward relative to a longitudinal axis of the tubular member 100.

Figure 22:
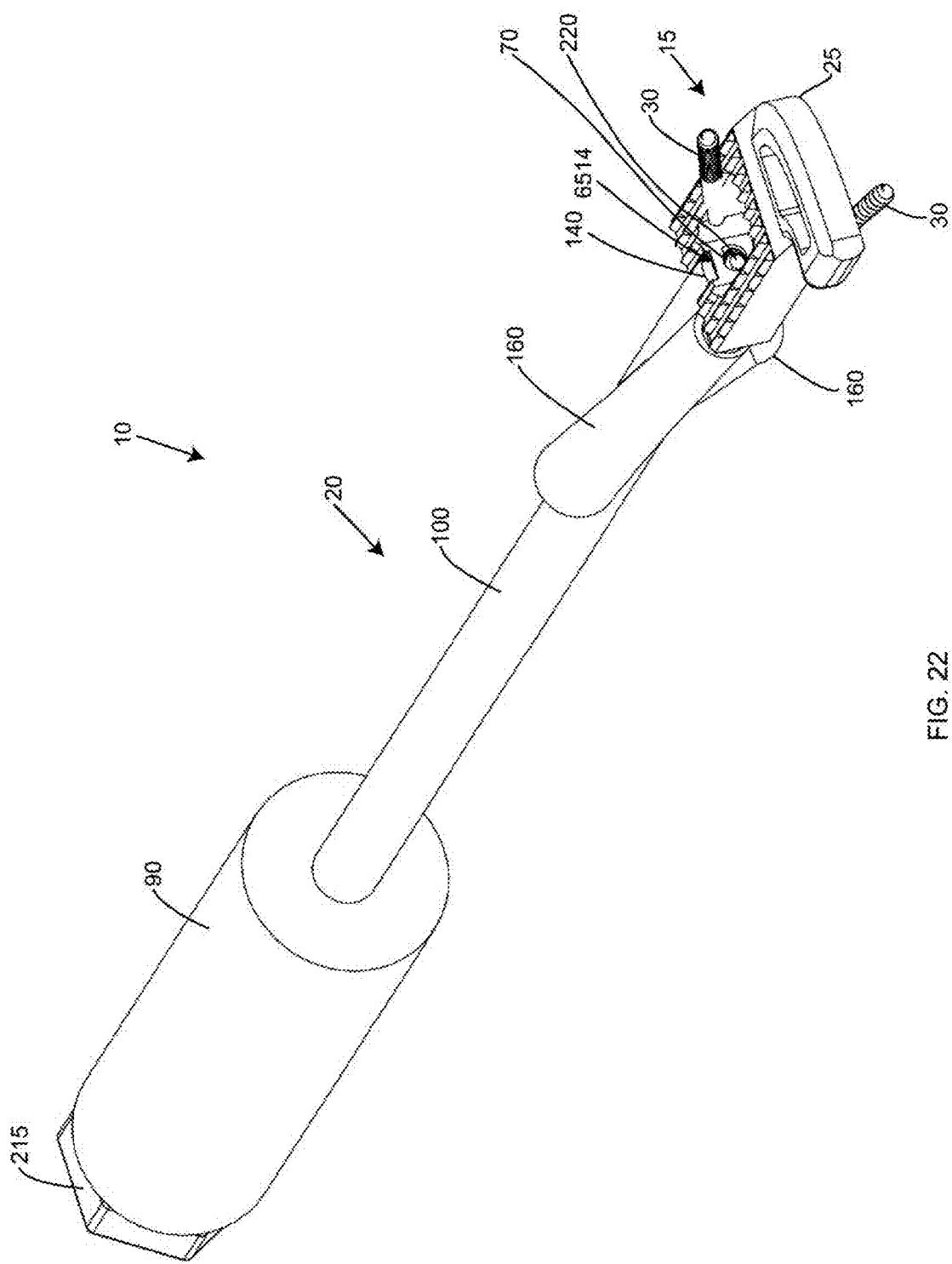
FIGS. 22 and 23 are, respectively, distal and proximal isometric views of the implant assembly supported off of the delivery tool distal end.
Figure 23:
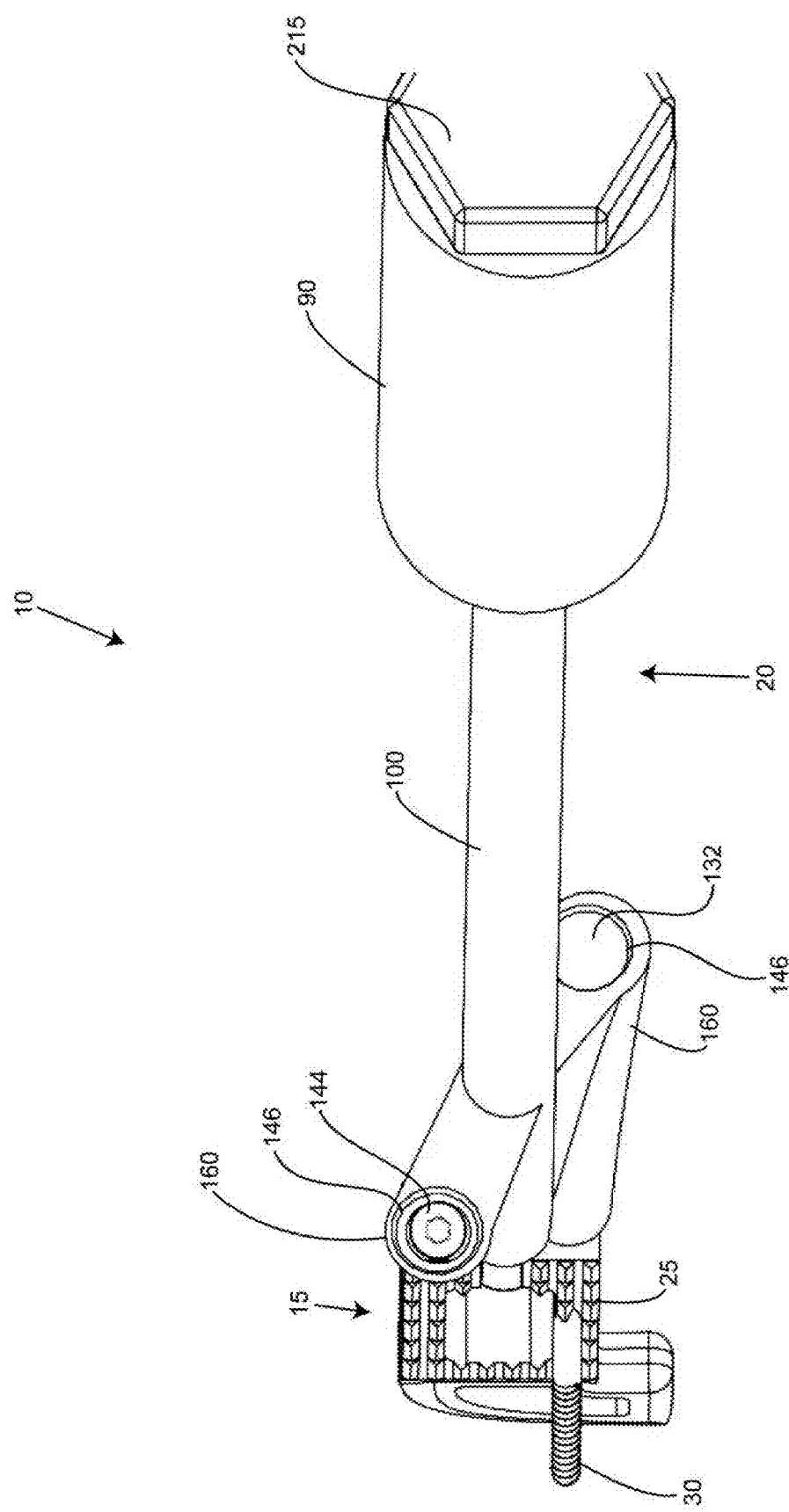
Figure 24:
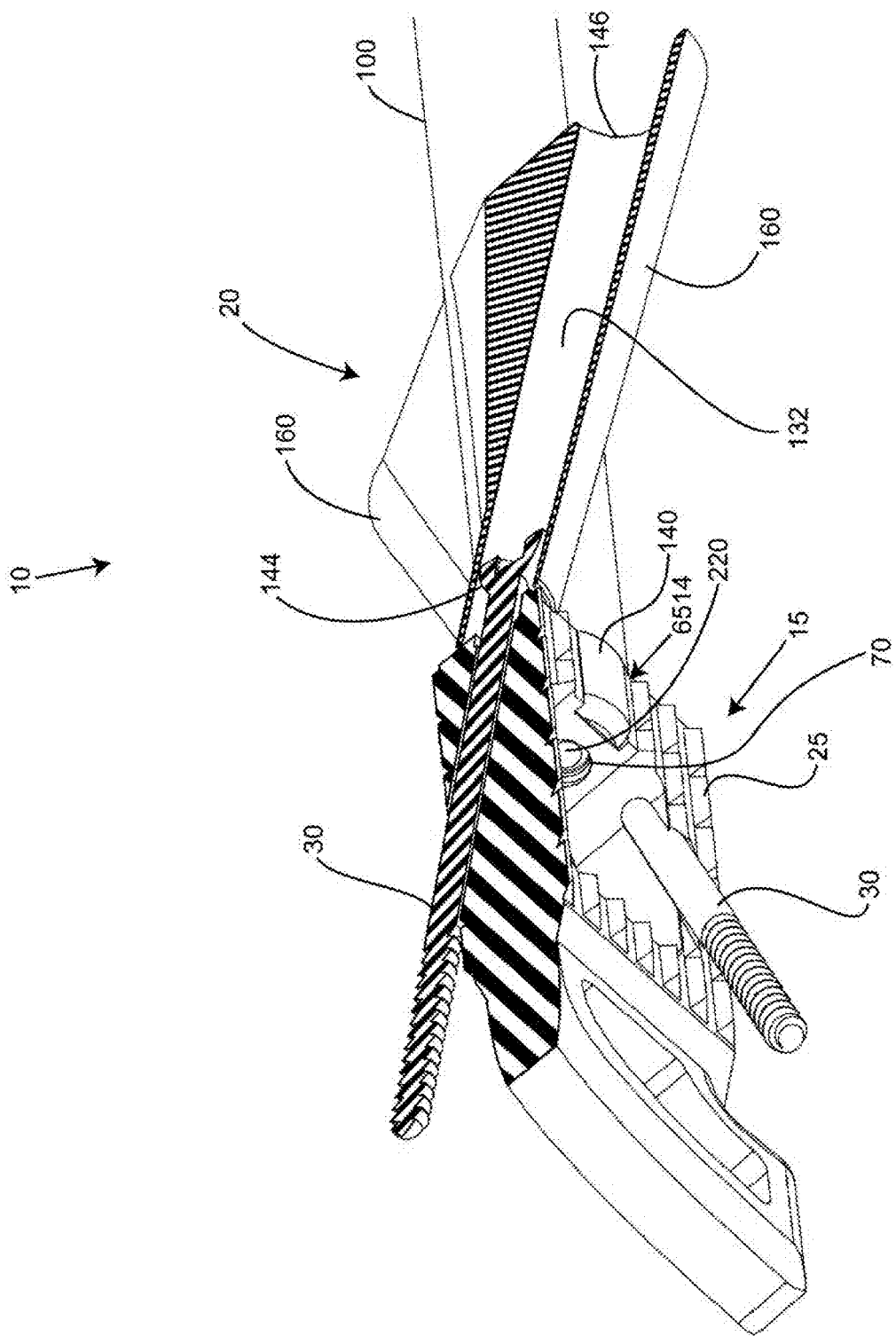
FIG. 24 is a cross section through an anchor arm, anchor and implant bore when the implant assembly is supported off of the delivery tool distal end.

FIGS. 22 and 23 are, respectively, distal and proximal isometric views of the implant assembly 15 supported off of the delivery tool distal end 35. FIG. 24 is a cross section through an anchor arm 160, anchor 30 and implant bore 40 when the implant assembly 15 is supported off of the delivery tool distal end 35. As can be understood from FIGS. 22-24, when the implant 25 is coupled to the delivery tool distal end 35, the longitudinal axes of the anchor guide lumens 132 and the respective bores 40 are coaxially aligned such that the trajectory of an anchor 30 positioned in an anchor guide lumen 132 extends through the respective bore 40. Thus, as indicated in FIG. 24, the anchor 40 automatically tracks into the respective bore 40 upon a wrench or other tool being applied to the distal or head end 144 of the anchor screw 30 via the proximal anchor lumen opening 146, as can be understood from FIG. 23.

For a general overview of a method of implanting the above-described implant system 15 in a caudal region 1086 of the sacroiliac joint articular region 1044 of a patient 1001 via the above-described delivery tool 20 through a caudal access, reference is now made to FIGS. 25-38. FIGS. 25, 29, 33 and 36 are, respectively, inferior-posterior, lateral, superior-anterior-lateral, and superior-posterior-lateral views of the patient 1001. As shown in FIGS. 25, 29, 33 and 36, the delivery tool 20 penetrates the soft tissue 1003 of the patient 1001 to extend into the patient's hip region 1002 via a tissue penetration in a superior region of one of the patient's buttocks. In doing so, the delivery tool 20 can be seen to be oriented such that a longitudinal axis of the shaft 100 of the delivery tool 20 has a generally anterior trajectory.

Figure 25:
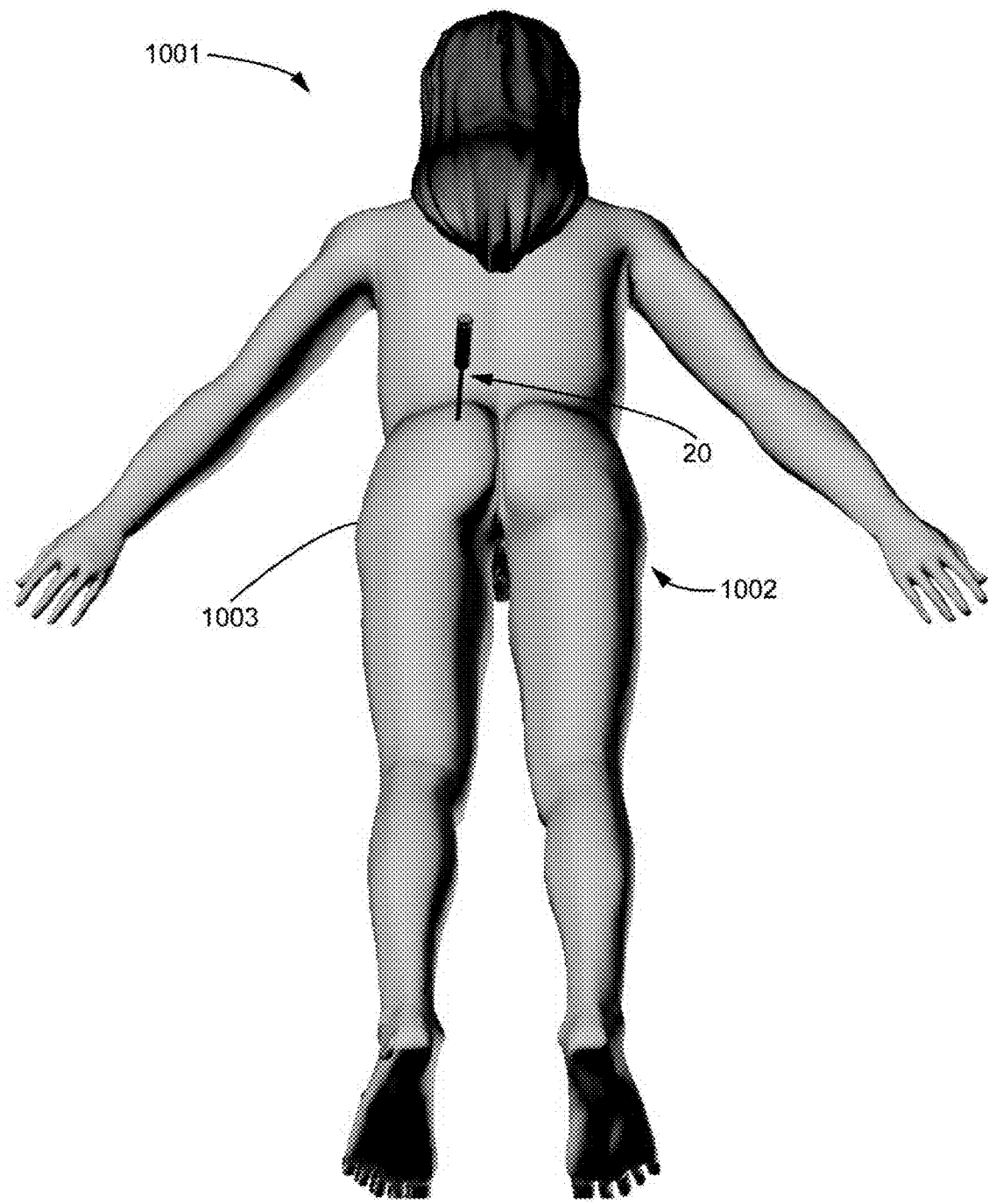
FIG. 25 is an inferior-posterior view of a patient wherein the delivery tool has penetrated the soft tissue to deliver the implant system into the sacroiliac joint in the hip region of the patient.
Figure 26:
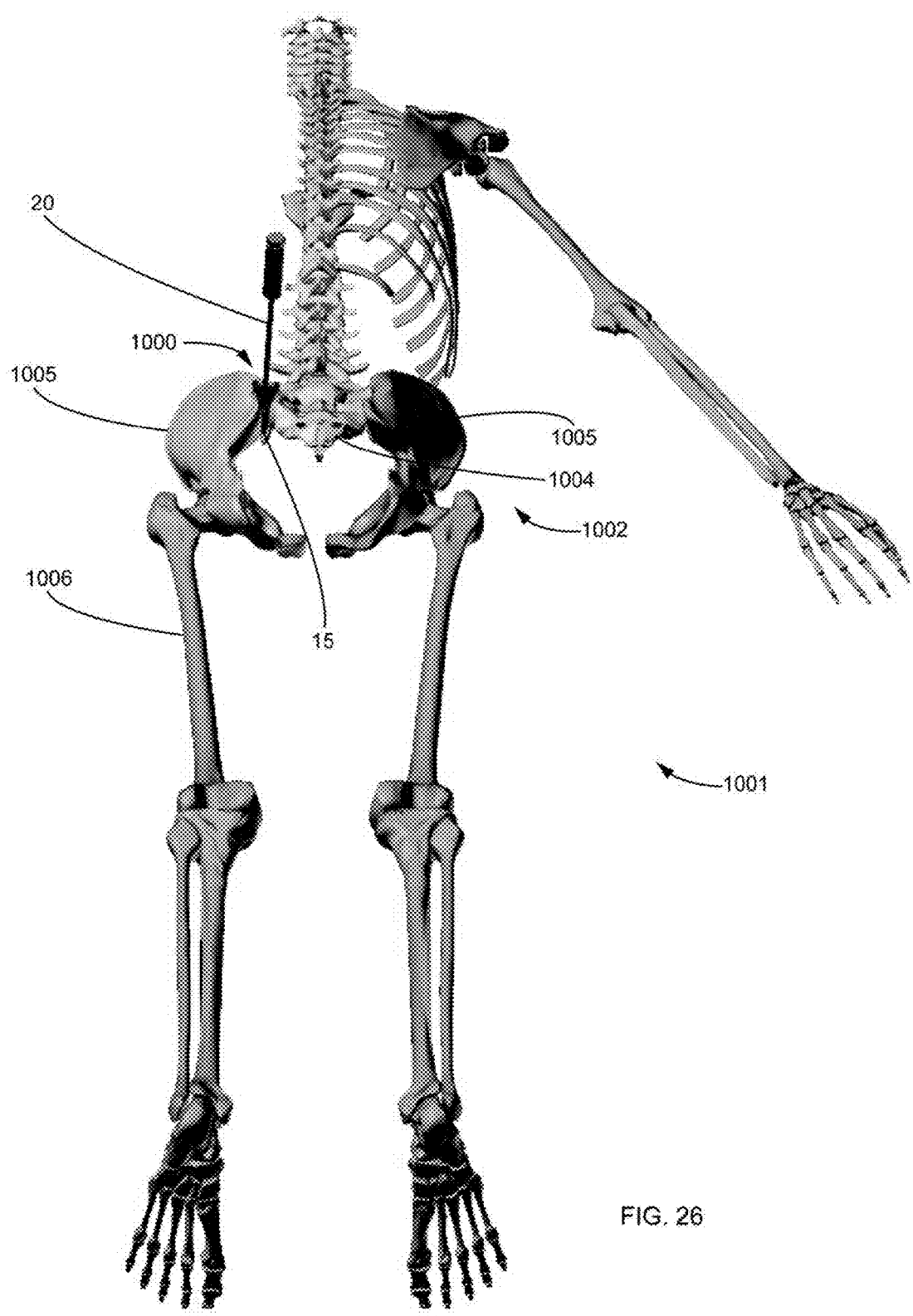
FIG. 26 is the same view as FIG. 25, except the soft tissue has been hidden to reveal only the patient's skeletal structure and the delivery tool delivering the implant system into the sacroiliac joint.
Figure 27:
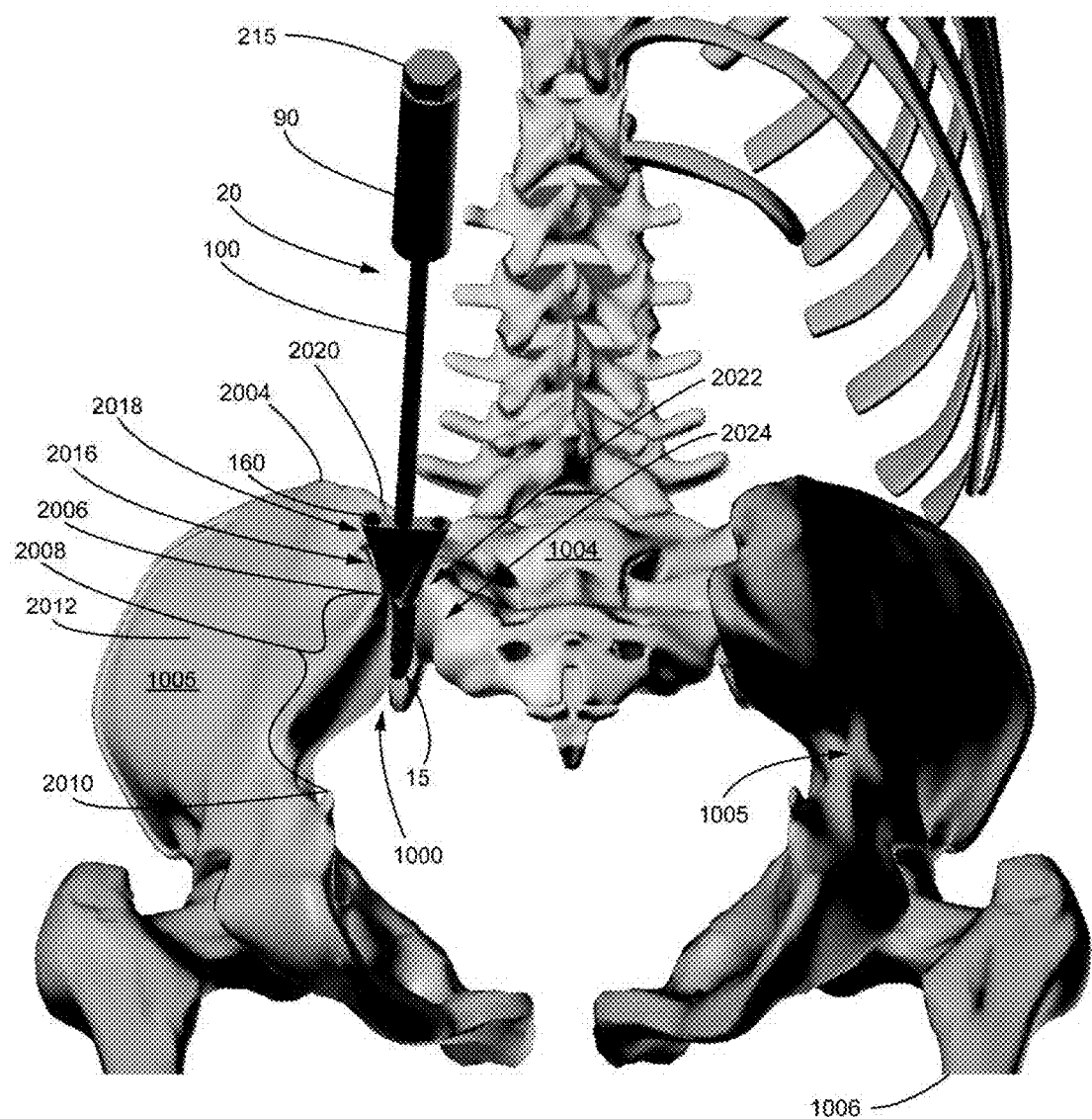
FIG. 27 is the same view as FIG. 26, except substantially enlarged to show the detail of the hip region of the patient.

FIG. 26 is the same view as FIG. 25, except the soft tissue 1003 has been hidden to reveal only the patient's skeletal structure 1006, and FIG. 27 is the same view as FIG. 26, except substantially enlarged to show the detail of the hip region 1002 of the patient. As illustrated in FIGS. 26 and 27, the position and orientation of the implant system 15 deployed in the sacroiliac joint 1000 can be understood with respect to common anatomical features of the sacrum 1004 and ilium 1005, such anatomical features including the posterior superior iliac spine 2004, posterior inferior iliac spine 2006, greater sciatic notch 2008, ischial spine 2010, and tubercle of iliac crest 2012. Other anatomical features shown include the posterior inferior access region 2016 of the sacroiliac joint articular region, the superior end 2018 on the sacroiliac joint line, the posterior inferior overhang 2020 of the posterior superior iliac spine, the inferior end 2022 on the sacroiliac joint line that is at approximately the superior beginning of the greater sciatic notch, and the lateral anterior curved boundary 2024 of the sacrum 1004.

Figure 29:
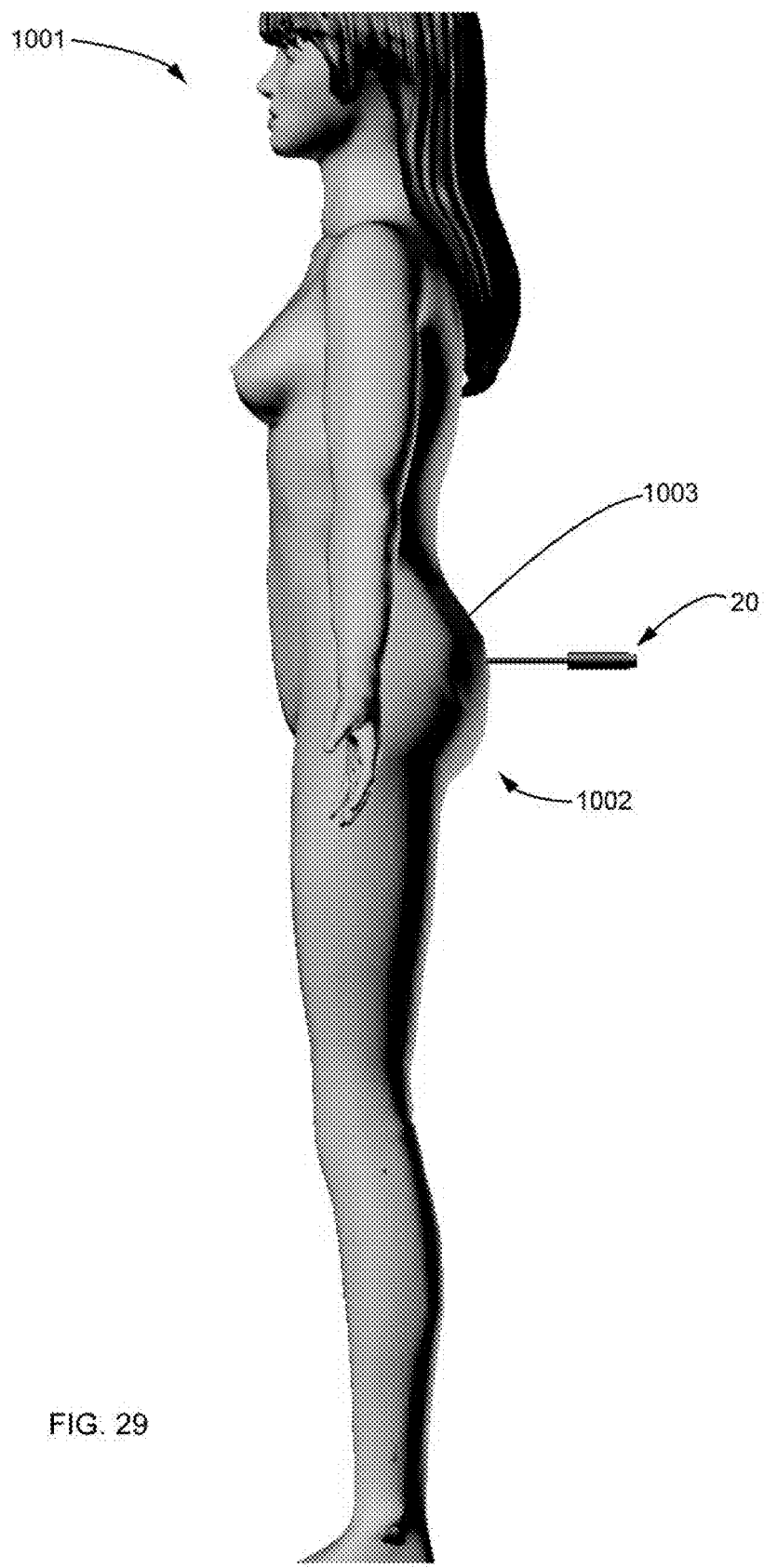
FIG. 29 is a lateral view of a patient wherein the delivery tool has penetrated the soft tissue to deliver the implant system into the sacroiliac joint in the hip region of the patient.
Figure 30:
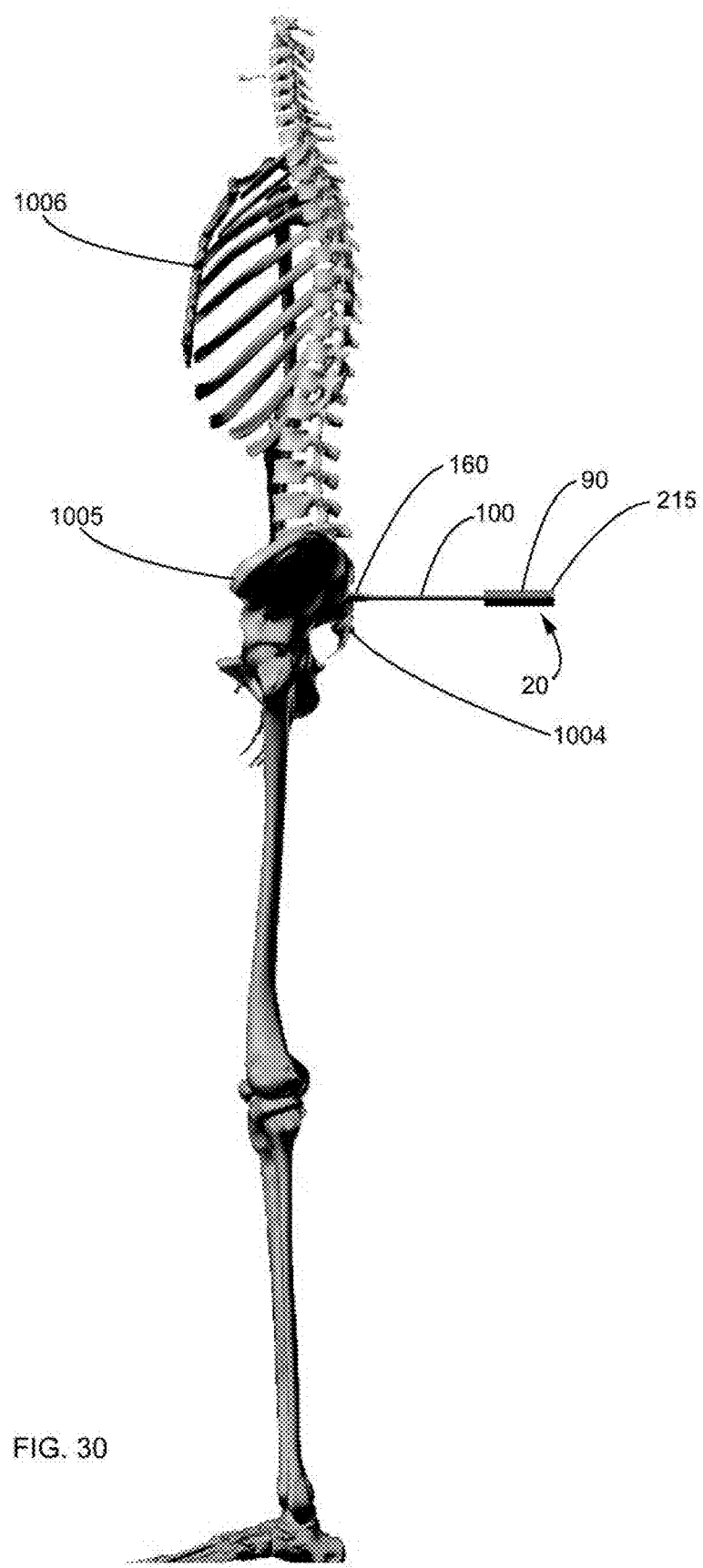
FIG. 30 is the same view as FIG. 29, except the soft tissue has been hidden to reveal only the patient's skeletal structure and the delivery tool delivering the implant system into the sacroiliac joint.
Figure 33:
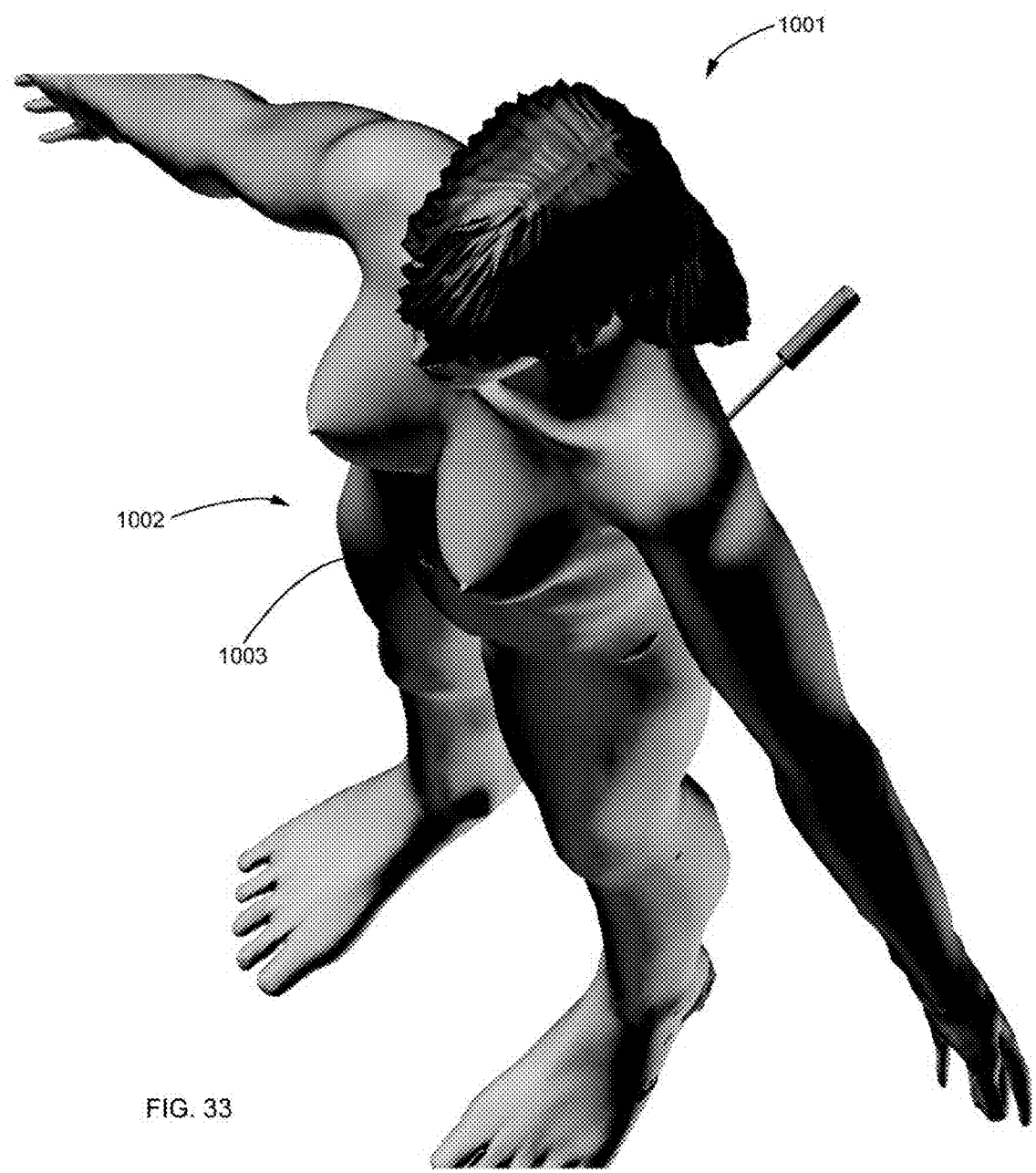
FIG. 33 is a superior-anterior-lateral view of a patient wherein the delivery tool has penetrated the soft tissue to deliver the implant system into the sacroiliac joint in the hip region of the patient.
Figure 34:
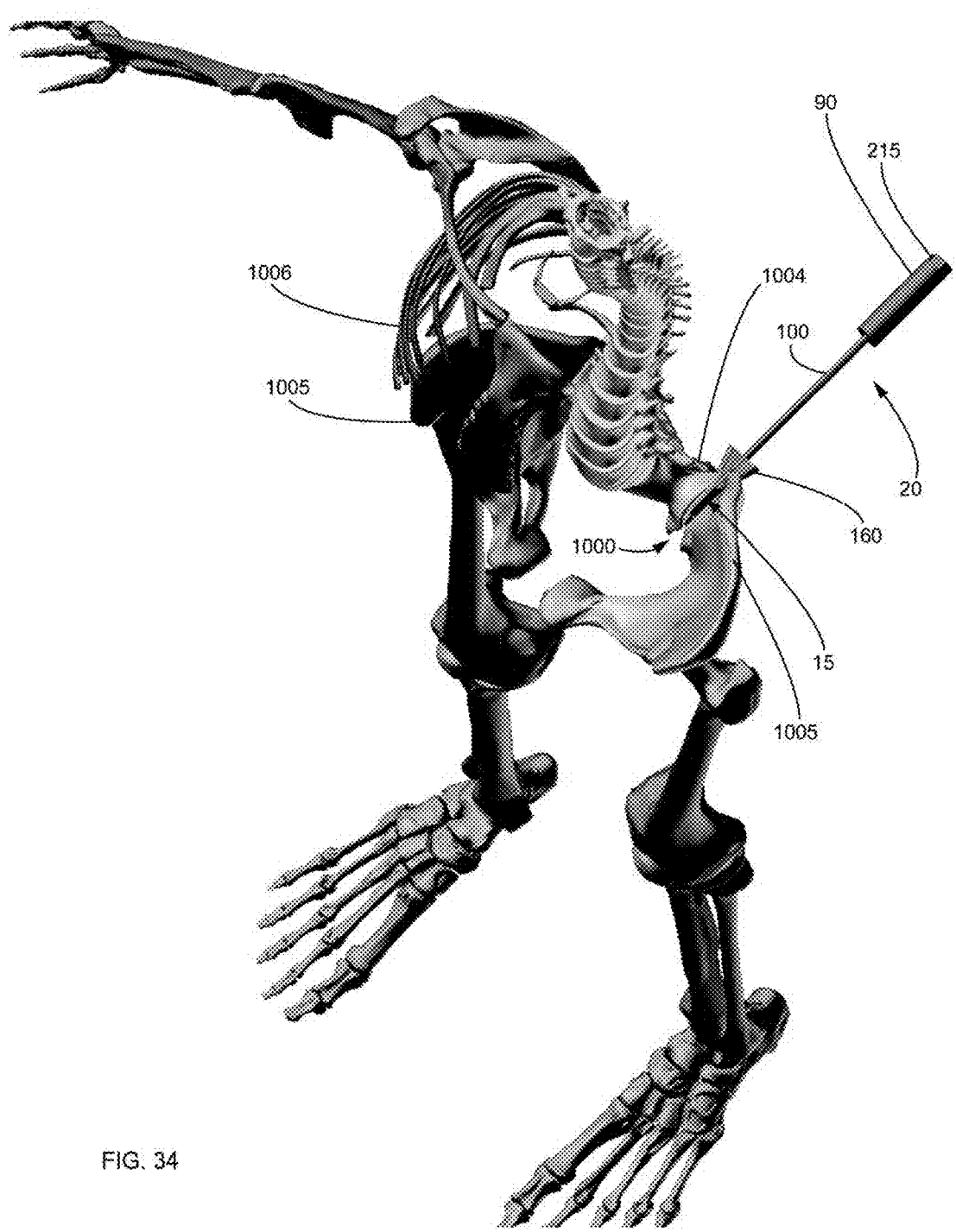
FIG. 34 is the same view as FIG. 33, except the soft tissue has been hidden to reveal only the patient's skeletal structure and the delivery tool delivering the implant system into the sacroiliac joint.
Figure 35:
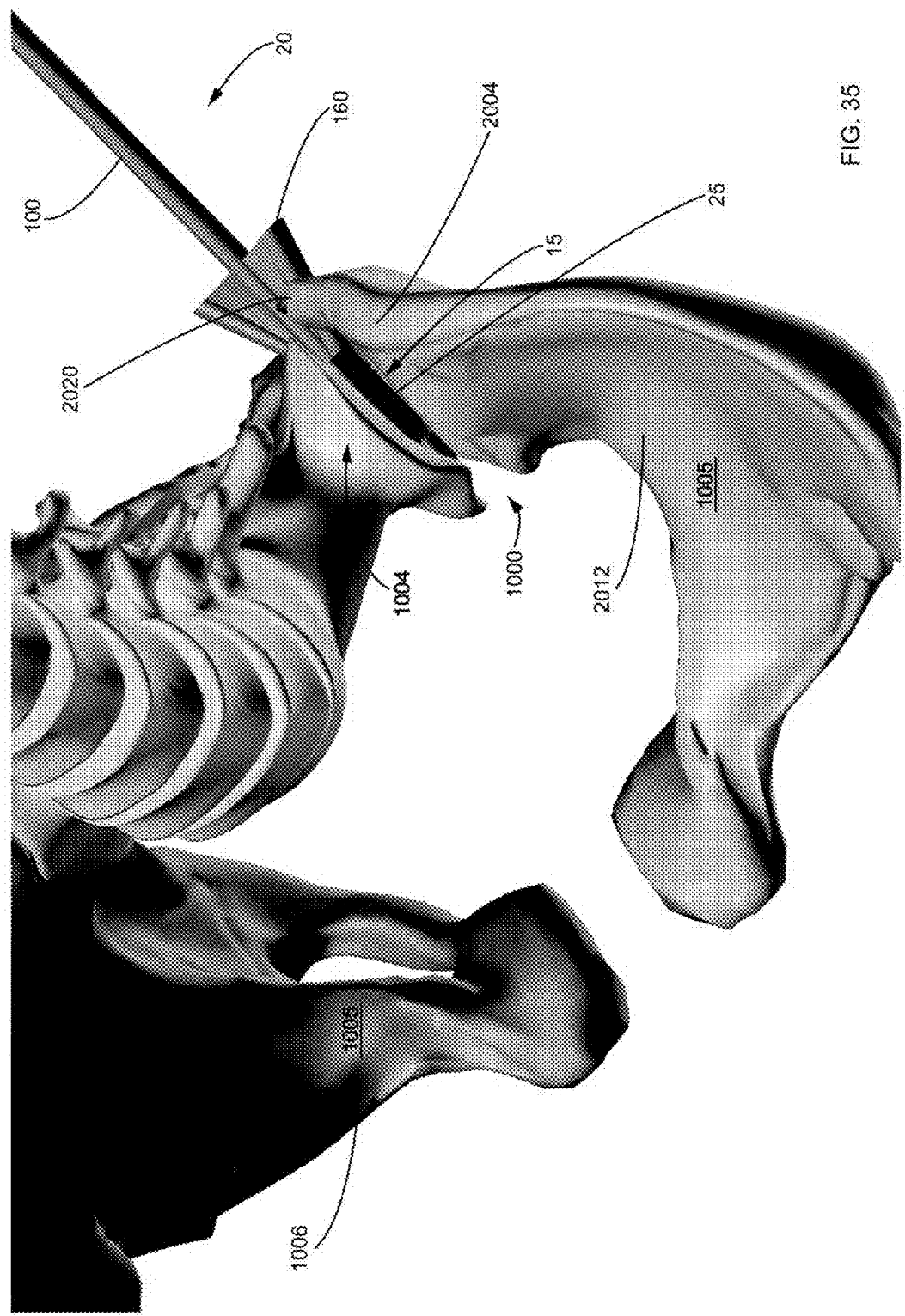
FIG. 35 is the same view as FIG. 34, except substantially enlarged to show the detail of the hip region of the patient.
Figure 36:
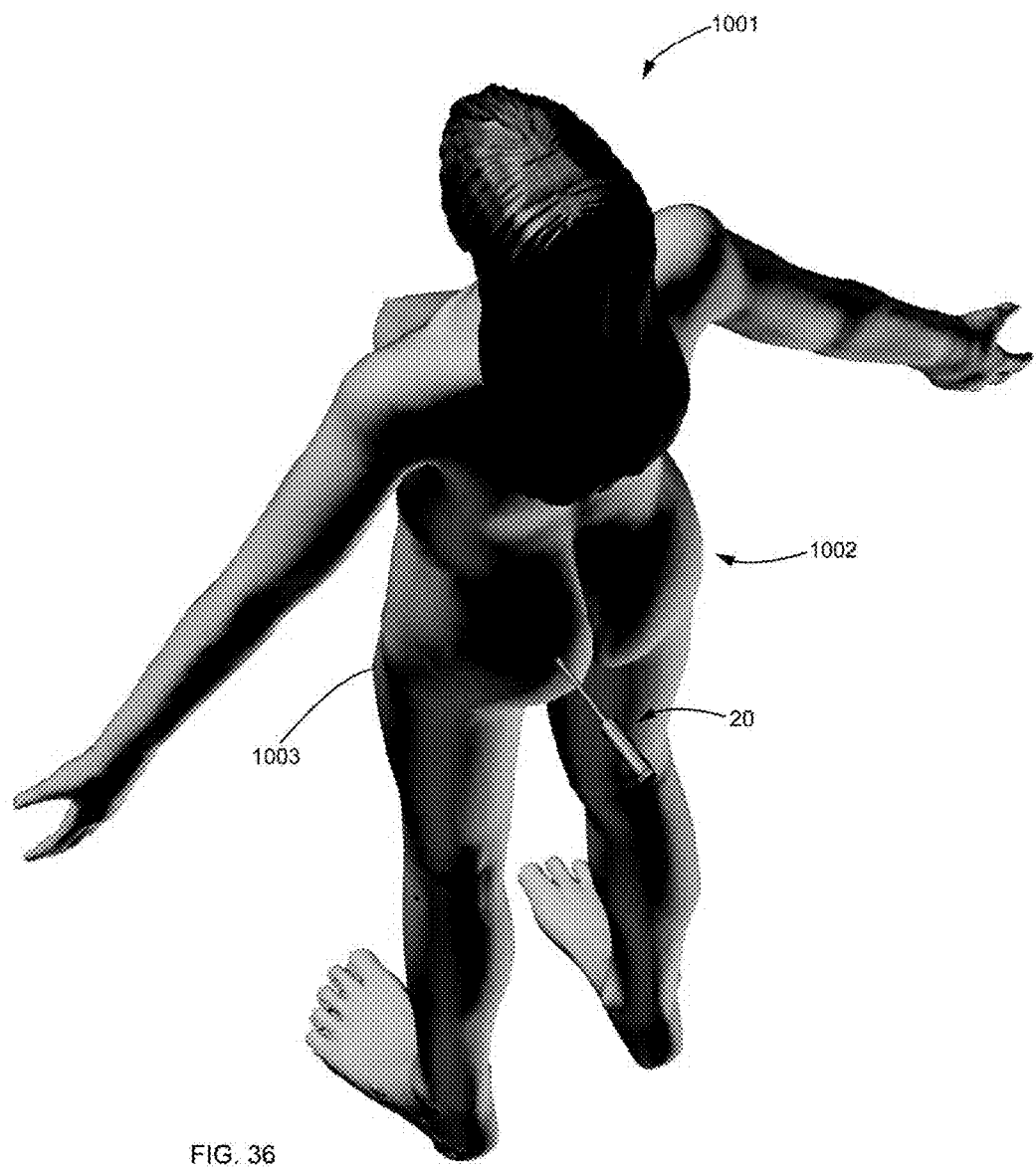
FIG. 36 is a superior-posterior-lateral view of a patient wherein the delivery tool has penetrated the soft tissue to deliver the implant system into the sacroiliac joint in the hip region of the patient.
Figure 37:
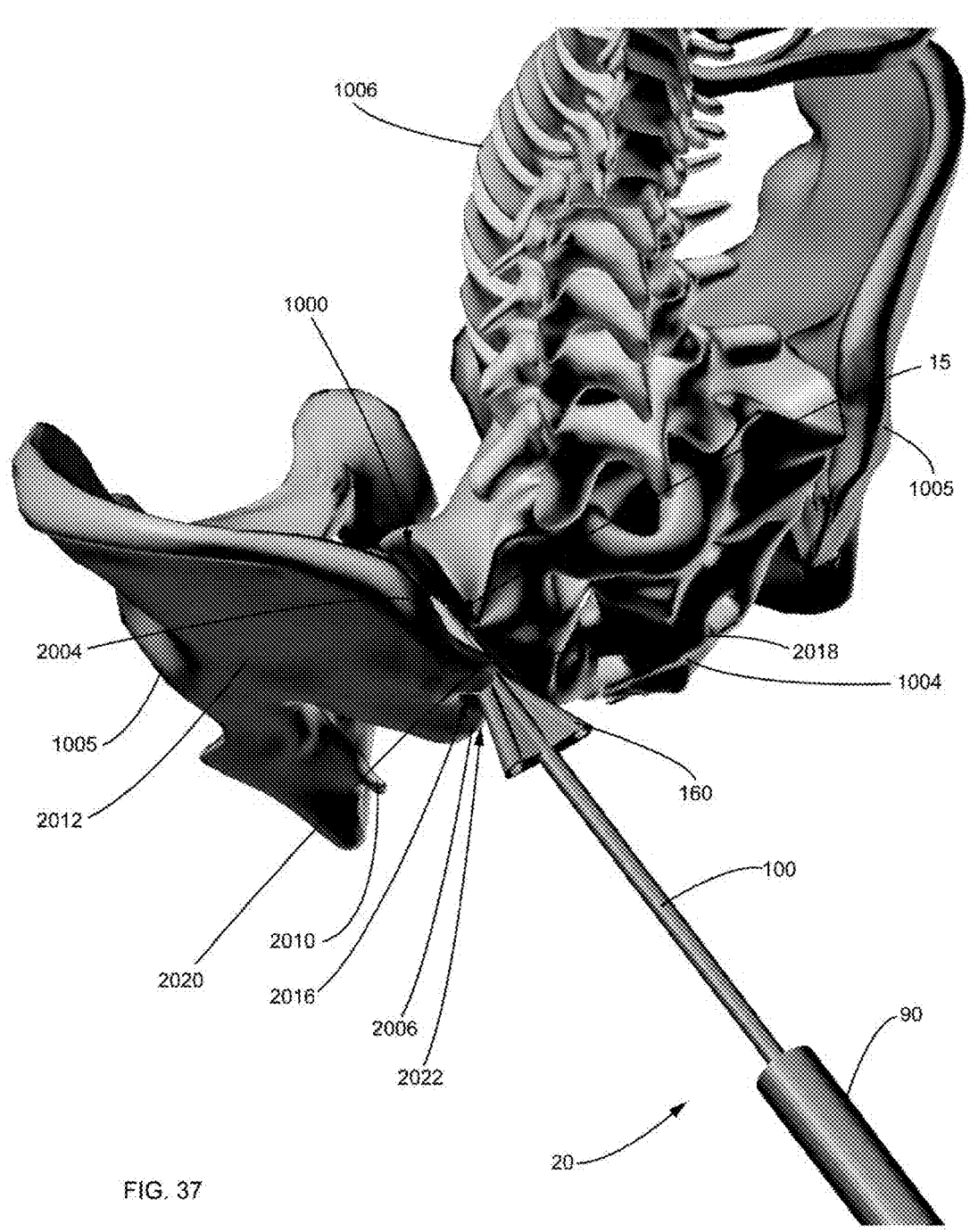
FIG. 37 is an enlarged view of the patient's hip region as viewed from the same perspective as FIG. 36, the soft tissue having been hidden to reveal only the patient's skeletal structure and the delivery tool delivering the implant system into the sacroiliac joint.

Additional understanding regarding the position and orientation of the implant system 15 deployed in the sacroiliac joint 1000 can be gained from a review of FIGS. 30 and 34, which are, respectively, the same views as FIGS. 29 and 33, except the soft tissue 1003 has been hidden to reveal only the patient's skeletal structure 1006. Still further understanding can be obtained from FIGS. 31 and 35, which are the same respective views as FIGS. 30 and 34, except substantially enlarged to show the detail of the hip region 1002 of the patient. FIG. 37 is a substantially enlarged view showing the detail of the hip region of the patient, except correlating to the view of the patient depicted in FIG. 36.

FIGS. 26 and 27 make it possible to understand the position and orientation of the delivery tool elements when the delivery tool distal end 35 is coupled to the proximal end of the implant 25 when the implant is positioned in the sacroiliac joint 1000. For example, the position and location of delivery tool elements such as the handle 90, shaft 100, implant retainer handle 215 and anchor guide 160 can be understood from FIGS. 26 and 27. FIGS. 30, 31, 34, 35 and 37 also provide understanding regarding the position and orientation of the delivery tool elements when the delivery tool distal end 35 is coupled to the proximal end of the implant 25 when the implant is positioned in the sacroiliac joint 1000.

Figure 28:
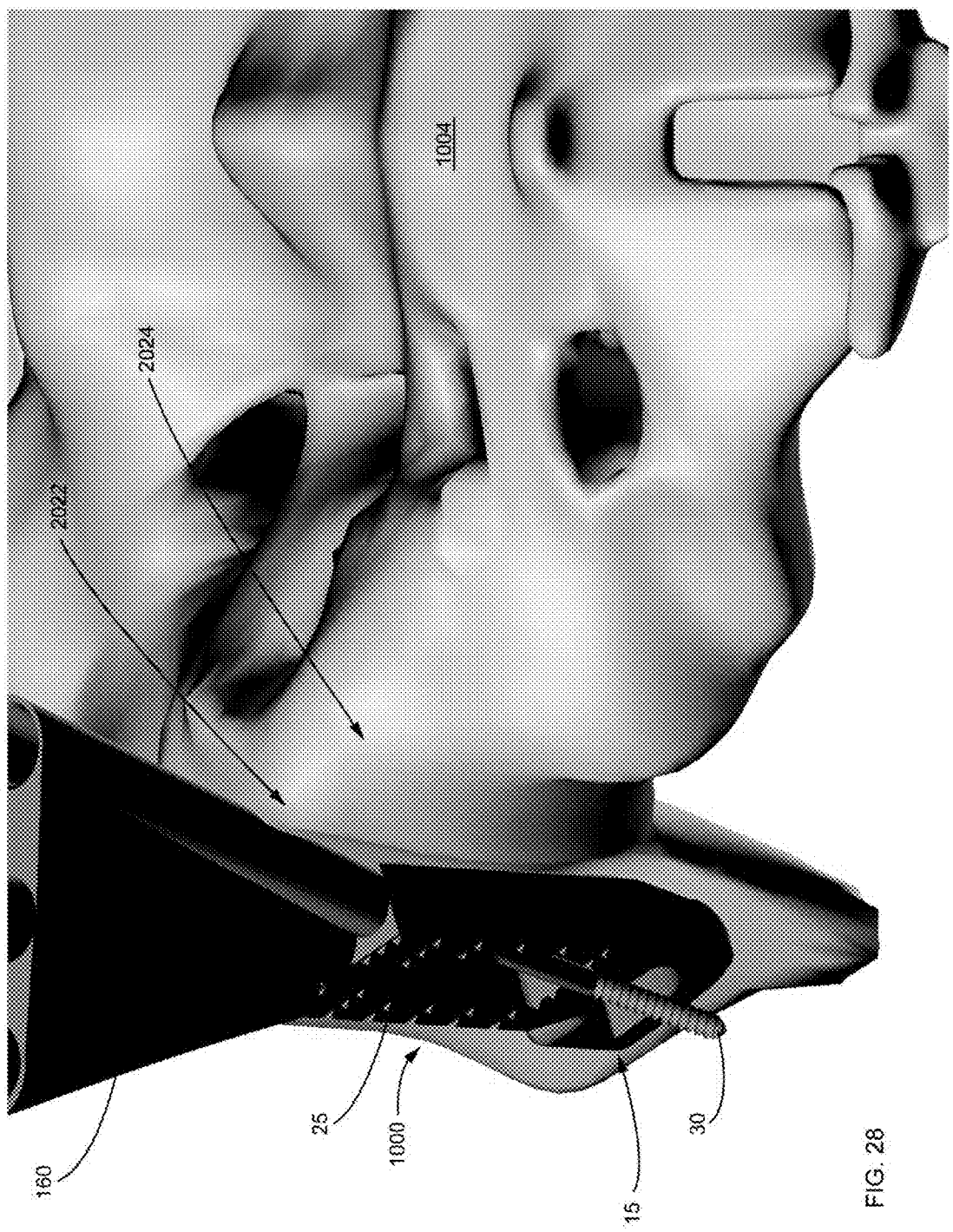
FIG. 28 is the same view as FIG. 27, except still further enlarged and with the ilium hidden to more clearly shown the implantation of the implant system in the sacroiliac joint space.
Figure 31:
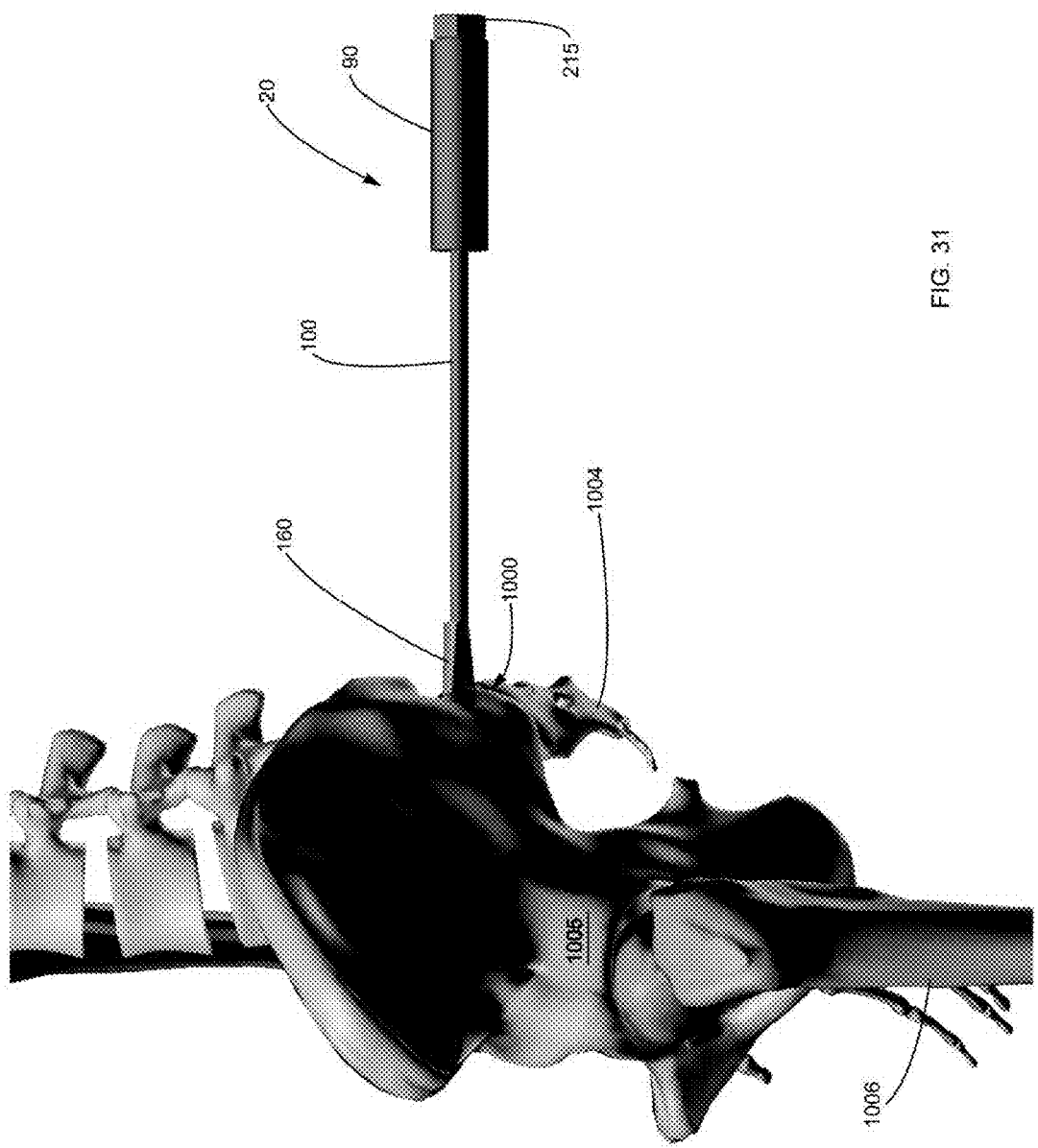
FIG. 31 is the same view as FIG. 30, except substantially enlarged to show the detail of the hip region of the patient.
Figure 32:
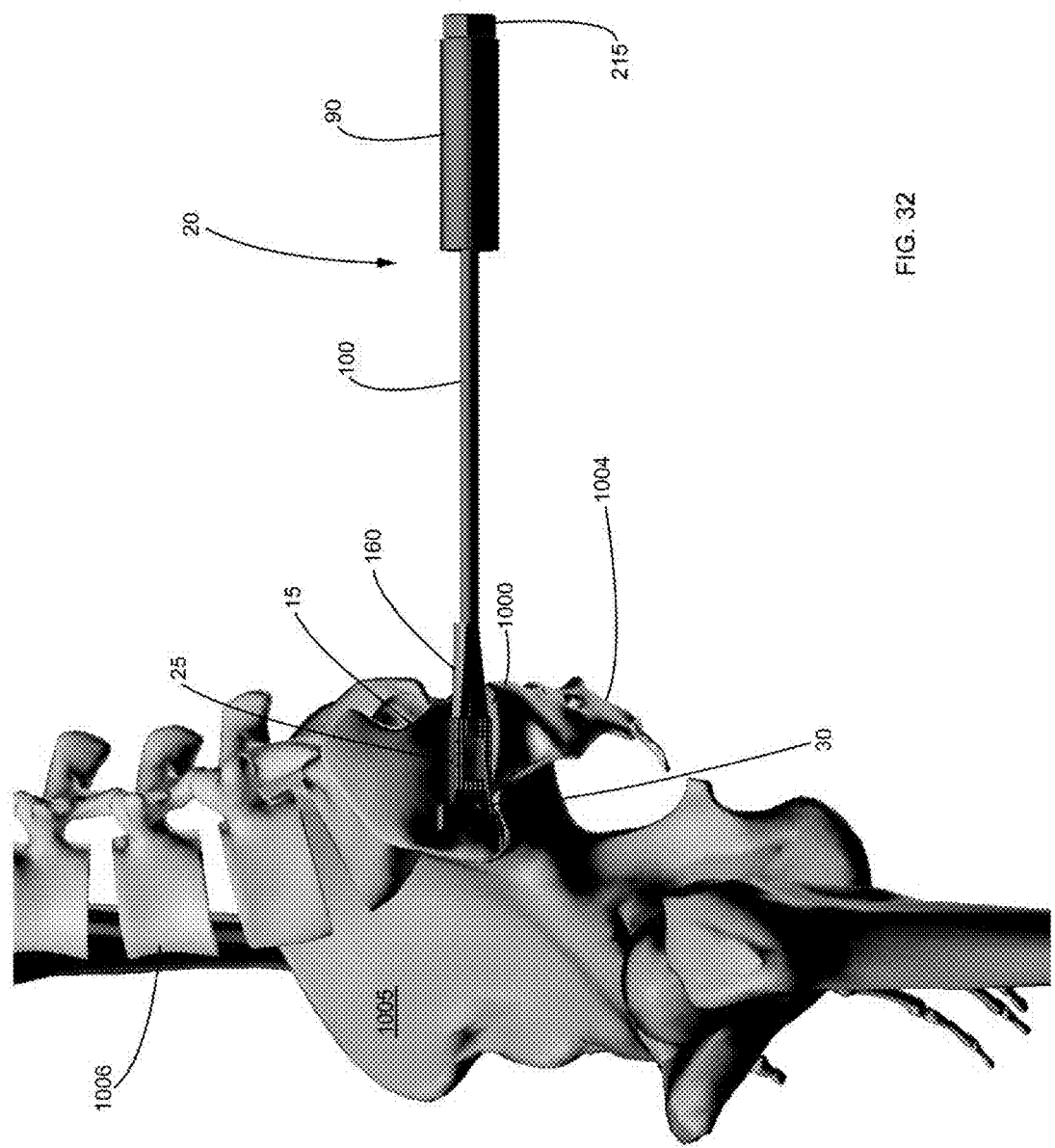
FIG. 32 is the same view as FIG. 31, except with the ilium hidden to more clearly shown the implantation of the implant system in the sacroiliac joint space.

FIGS. 28, 32 and 38 are the same respective views as FIGS. 27, 31 and 37, except still further enlarged and with the ilium hidden to more clearly shown the implantation of the implant system 15 in the sacroiliac joint 1000. The distal and lateral projection of the lateral anchor 30 from the implant 25 is clearly indicated in each of FIGS. 28, 32 and 38. The coupling of the proximal end of the implant 25 to the distal end of the delivery tool guide portion 160 can also be clearly seen in FIGS. 28, 32 and 38.

Figure 39A:
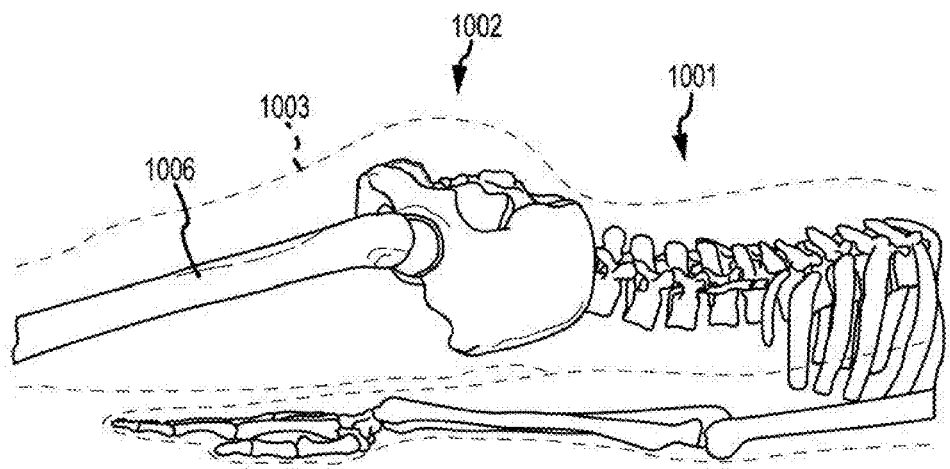
FIG. 39A is a right lateral side view of a hip region of a patient lying prone, wherein the soft tissue surrounding the skeletal structure of the patient is shown in dashed lines.

To begin a more detailed discussion regarding the step-by-step methodology associated with employing the above-described delivery tool 20 in implanting the above-described implant 25 in the sacroiliac joint 1000 of a patient 1001, reference is first made to FIGS. 39A-41B to identify the bone landmarks adjacent, and defining, the sacroiliac joint 1000. FIG. 39A is a right lateral side view of a hip region 1002 of a patient 1001 lying prone, wherein the soft tissue 1003 surrounding the skeletal structure 1006 of the patient 1001 is shown in dashed lines. FIG. 39B is an enlarged view of the hip region 1002 of FIG. 39A. As illustrated in FIGS. 39A and 39B, a lateral view of the patient's hip region 1002 reveals certain features of the ilium 1005, including the anterior superior iliac spine 2000, the iliac crest 2002, the posterior superior iliac spine 2004, the posterior inferior iliac spine 2006, the greater sciatic notch 2008 extending from the posterior inferior iliac spine 2006 to the ischial spine 2010, and the tubercle of iliac crest 2012. The sacroiliac joint articular region 1044 is shown in dashed lines. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Figure 40A:
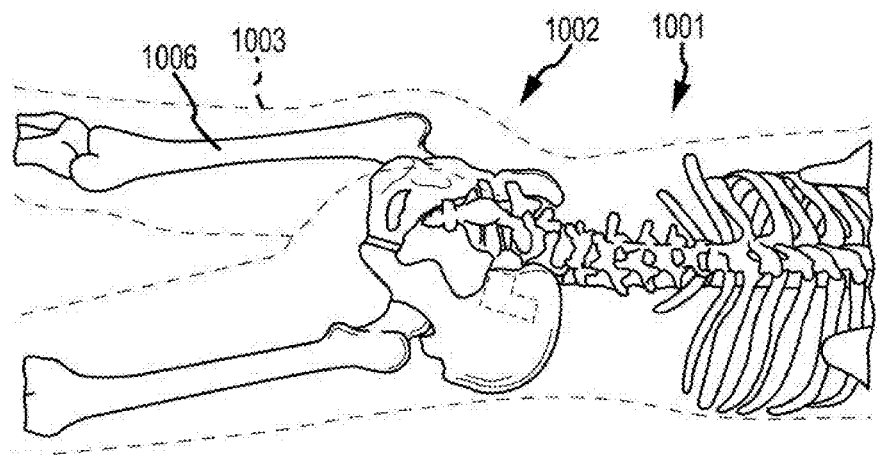
FIG. 40A is a lateral-posterior view of the hip region of the patient of FIG. 39A, wherein the patient is lying prone and the soft tissue surrounding the skeletal structure of the patient is shown in dashed lines.
Figure 40B:
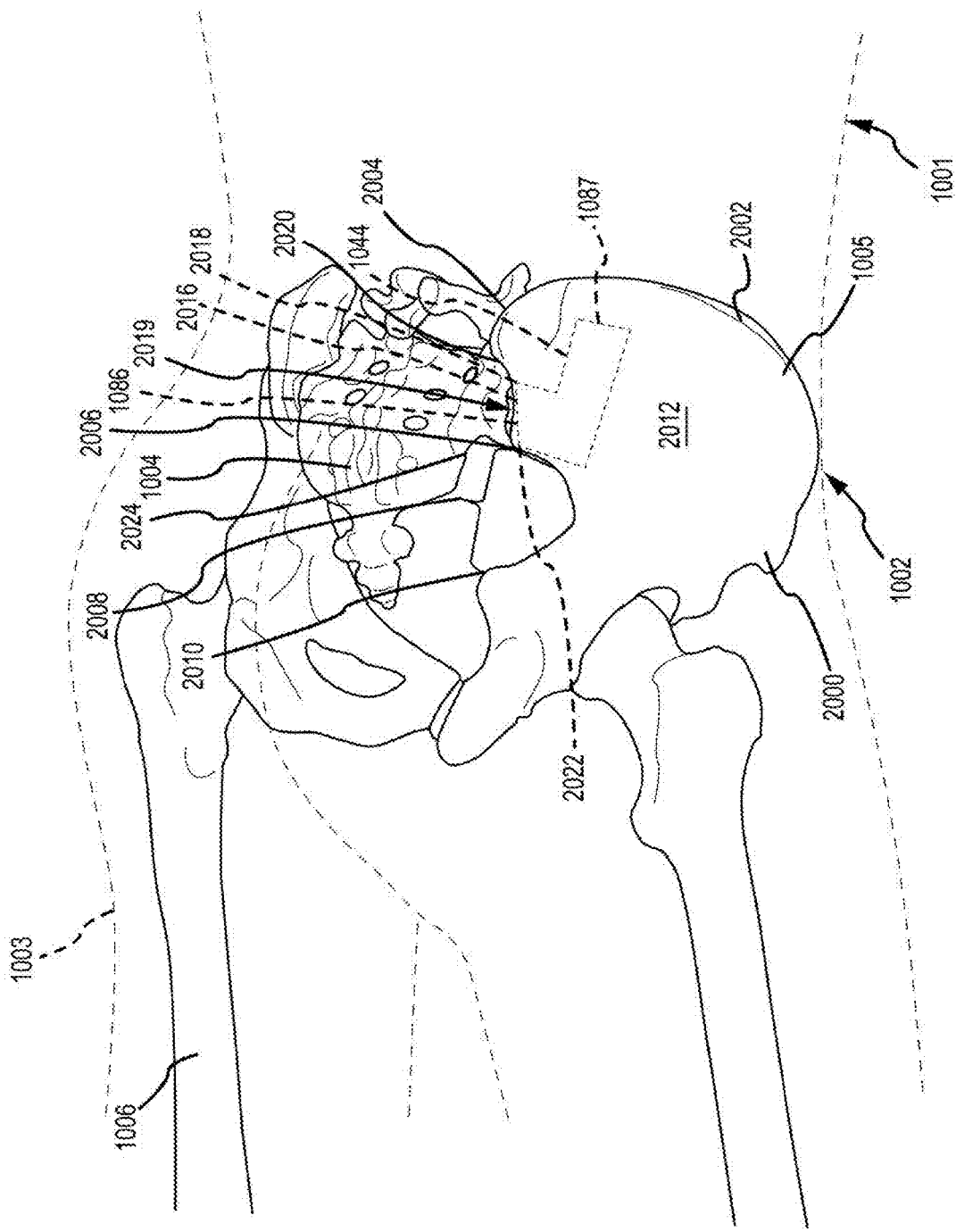
FIG. 40B is an enlarged view of the hip region of FIG. 40A.

FIG. 40A is a lateral-posterior view of the hip region 1002 of the patient 1001 of FIG. 39A, wherein the patient 1001 is lying prone and the soft tissue 1003 surrounding the skeletal structure 1006 of the patient 1001 is shown in dashed lines. FIG. 40B is an enlarged view of the hip region 1002 of FIG. 40A. As shown in FIGS. 40A and 40B, a lateral-posterior view of the patient's hip region 1002 reveals the same features of the sacrum 1004 and ilium 1005 as discussed above with respect to FIGS. 39A and 396B, except from another vantage point. The vantage point provided via FIGS. 40A and 40B provides further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Figure 41A:
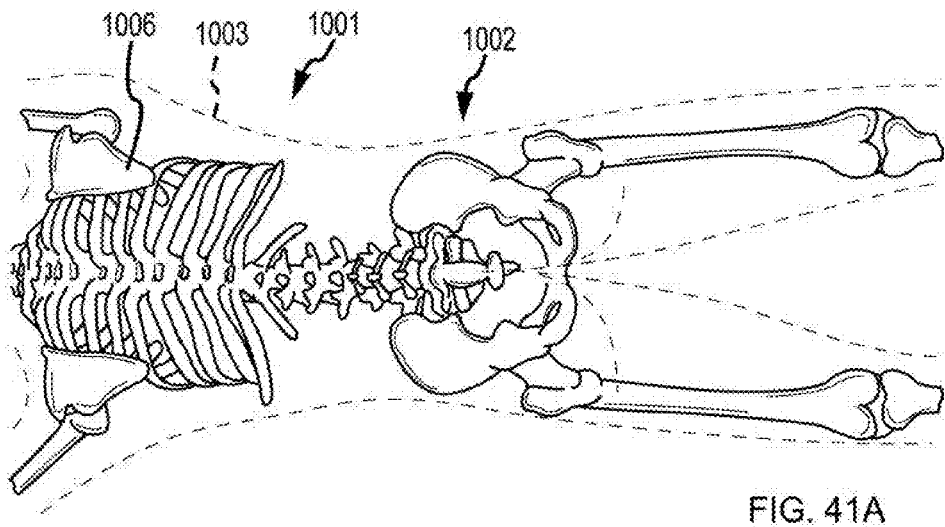
FIG. 41A is a posterior view of the hip region of the patient of FIG. 39A, wherein the patient is lying prone and the soft tissue surrounding the skeletal structure of the patient is shown in dashed lines.
Figure 39B:
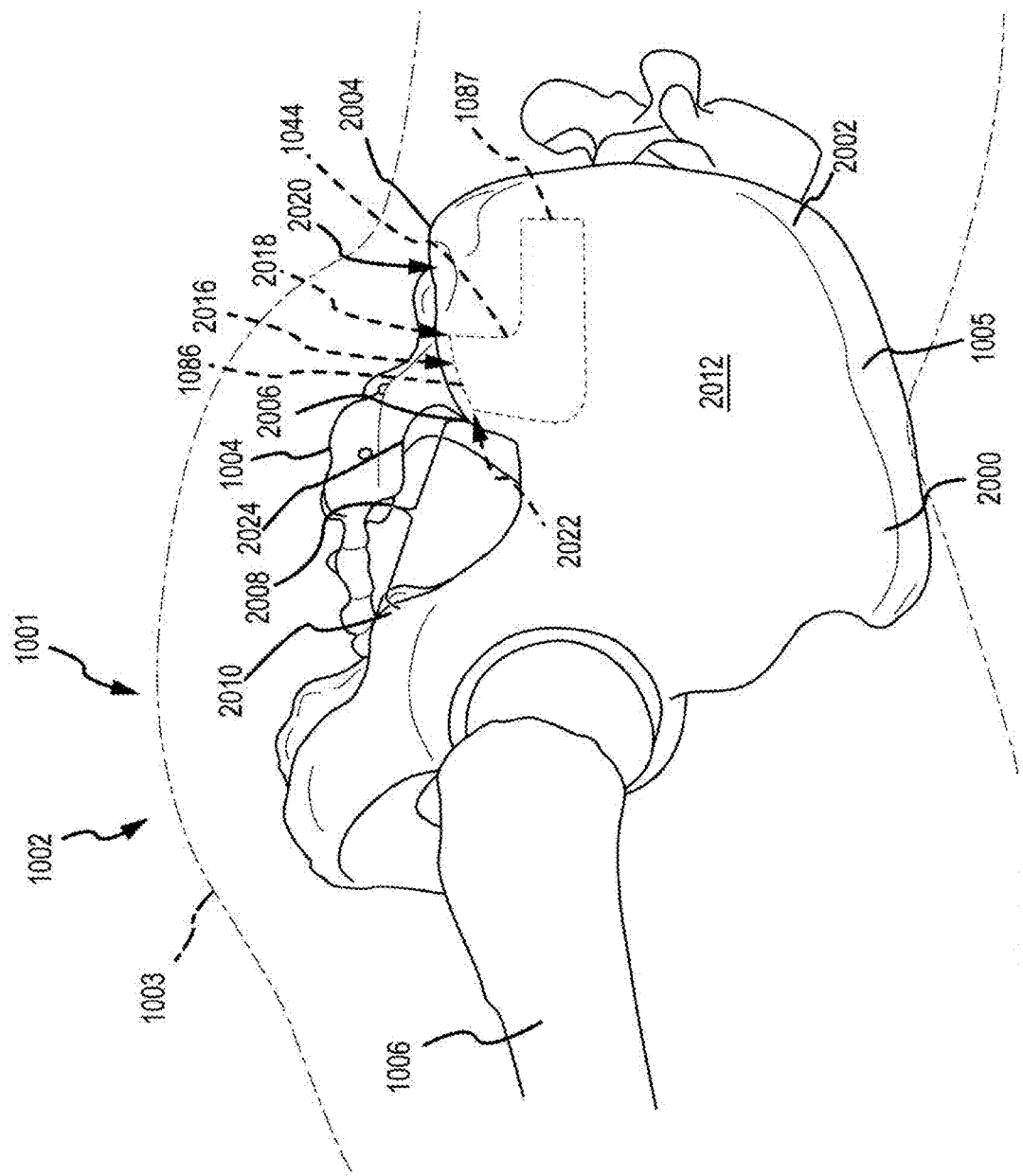
FIG. 39B is an enlarged view of the hip region of FIG. 39A.
Figure 41B:
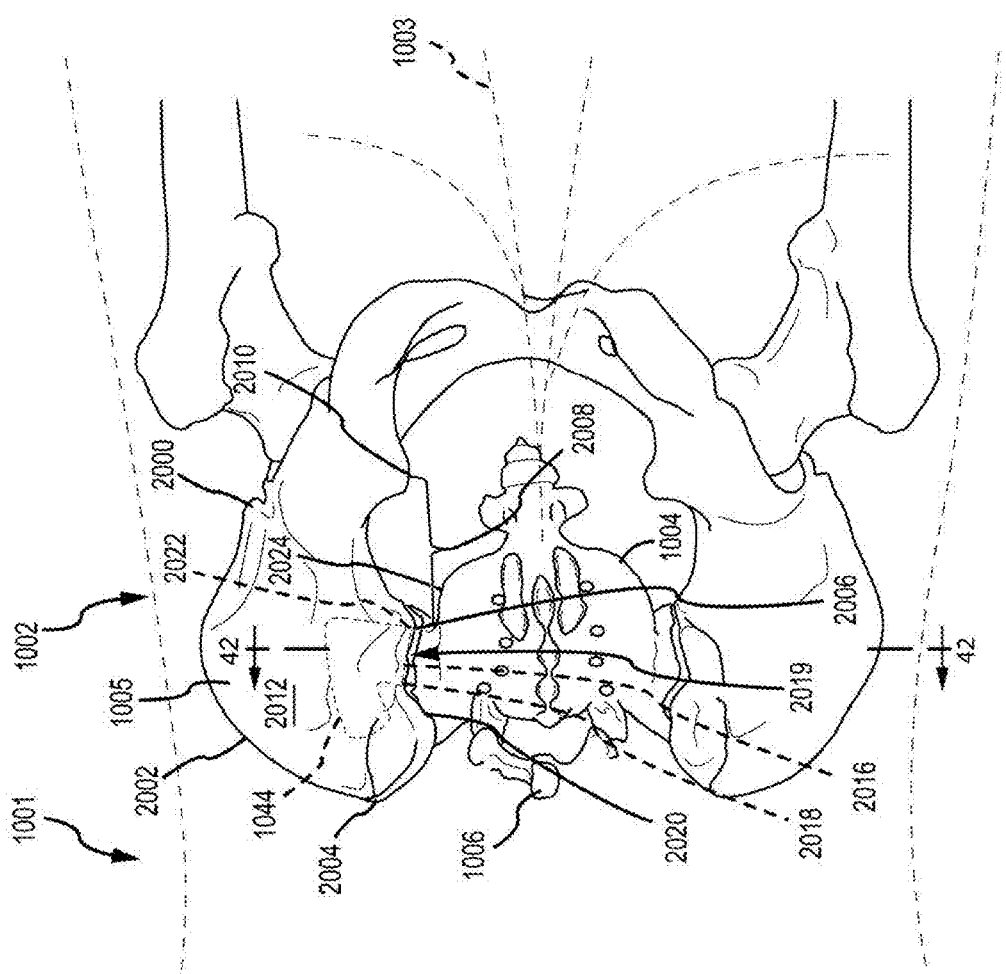
FIG. 41B is an enlarged view of the hip region of FIG. 41A.

FIG. 41A is a posterior view of the hip region 1002 of the patient 1001 of FIG. 39A, wherein the patient 1001 is lying prone and the soft tissue 1003 surrounding the skeletal structure 1006 of the patient 1001 is shown in dashed lines. FIG. 41B is an enlarged view of the hip region 1002 of FIG. 41A. As shown in FIGS. 41A and 41B, a posterior view of the patient's hip region 1002 reveals the same features of the sacrum 1004 and ilium 1005 as discussed above with respect to FIGS. 39A and 39B, except from yet another vantage point. The vantage point provided via FIGS. 41A and 41B provides yet further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Now that the relevant anatomical landmarks have been identified with respect to FIGS. 39A-41B, the methodology associated with employing any of the above-described delivery tools 20 in implanting any of the above-described implants 25 in the sacroiliac joint 1000 of a patient 1001 can be discussed. In doing so, reference will be made to FIGS. 42A-42M, which are each a step in the methodology and illustrated as the same transverse cross section taken in along a plane extending medial-lateral and anterior posterior along section line 42-42 in FIG. 41B. In this cross section, articular surfaces 1016 are covered by a thick layer of articular cartilage with a joint space existing between them, the FIGS. 42A-42M are simplified for illustrative purposes and do not show these features to scale. Now referring primarily to FIG. 42A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, Isoview 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047)(such as a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 (or other device to contain and deliver an amount of radiographic contrast 1046). In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Figure 42B:
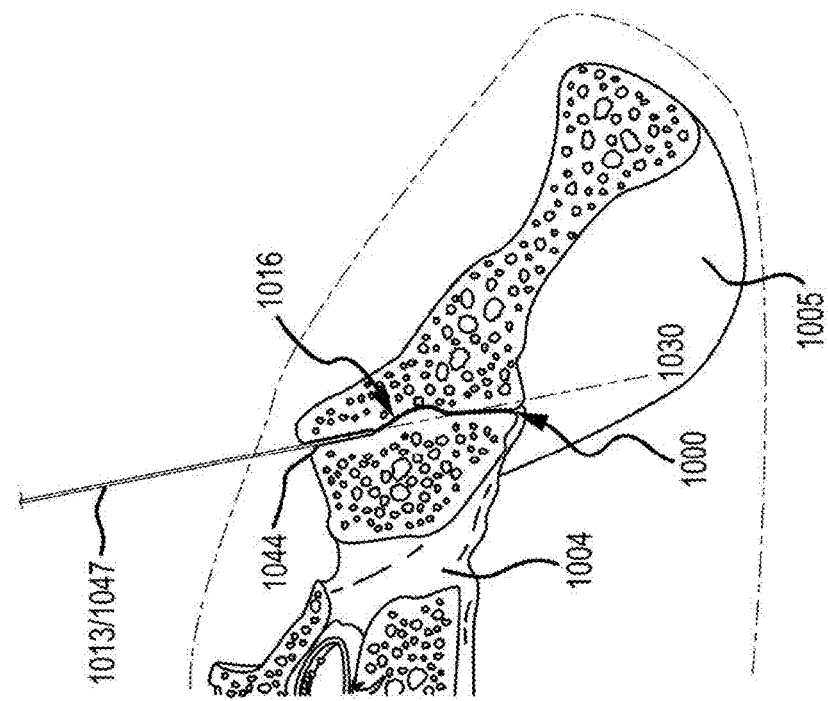
Figure 42A:
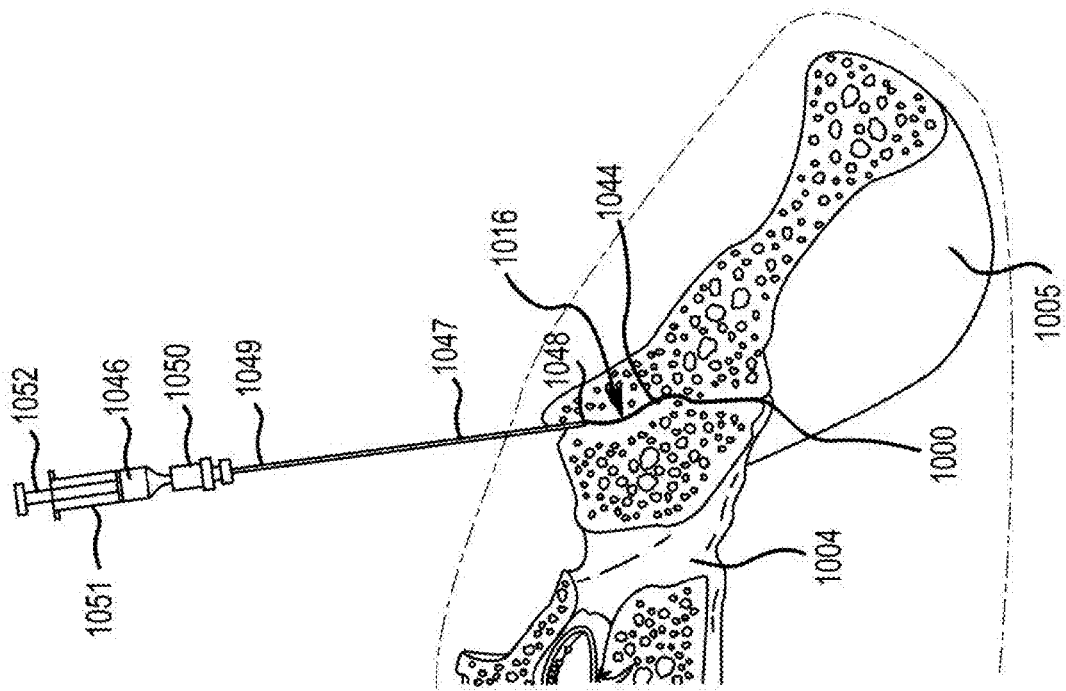
Figure 42D:
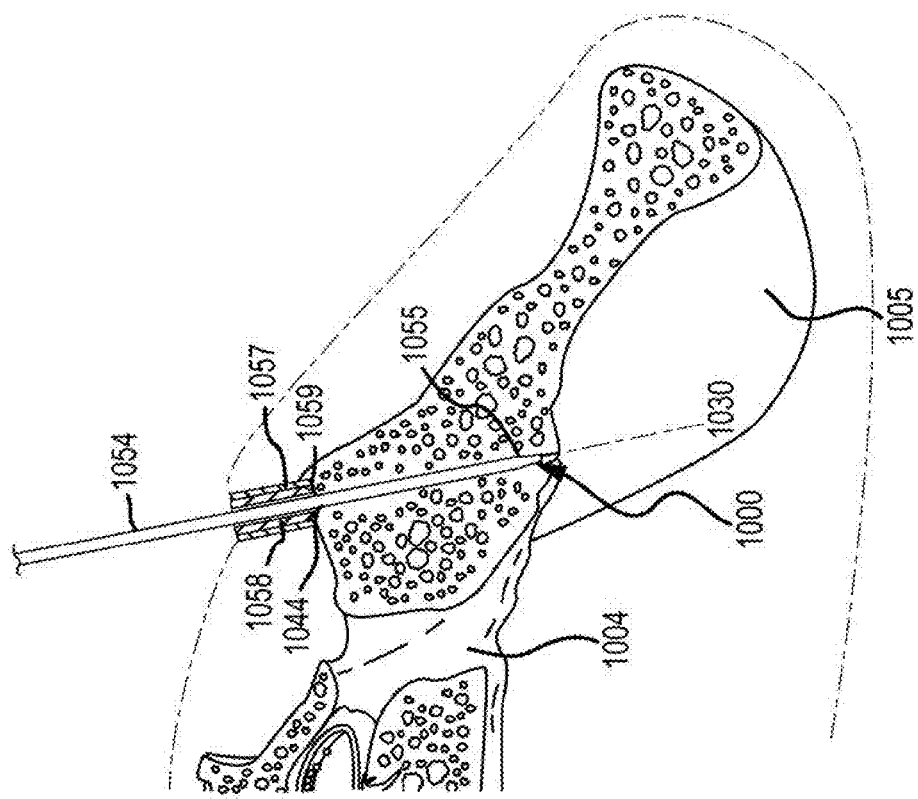

Now referring primarily to FIG. 42B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the sacroiliac joint implant 25 non-transversely between the articulating surfaces 1016 of the sacroiliac joint 1000 (e.g., locate the implant 25 non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029 (see FIG. 42H). Alternately, one or more guide pins 1013 can be inserted along substantially the same path of the tubular member 1047 for fixed engagement within the sacroiliac joint 1000 and used in subsequent steps as a guide(s).

Figure 42C:
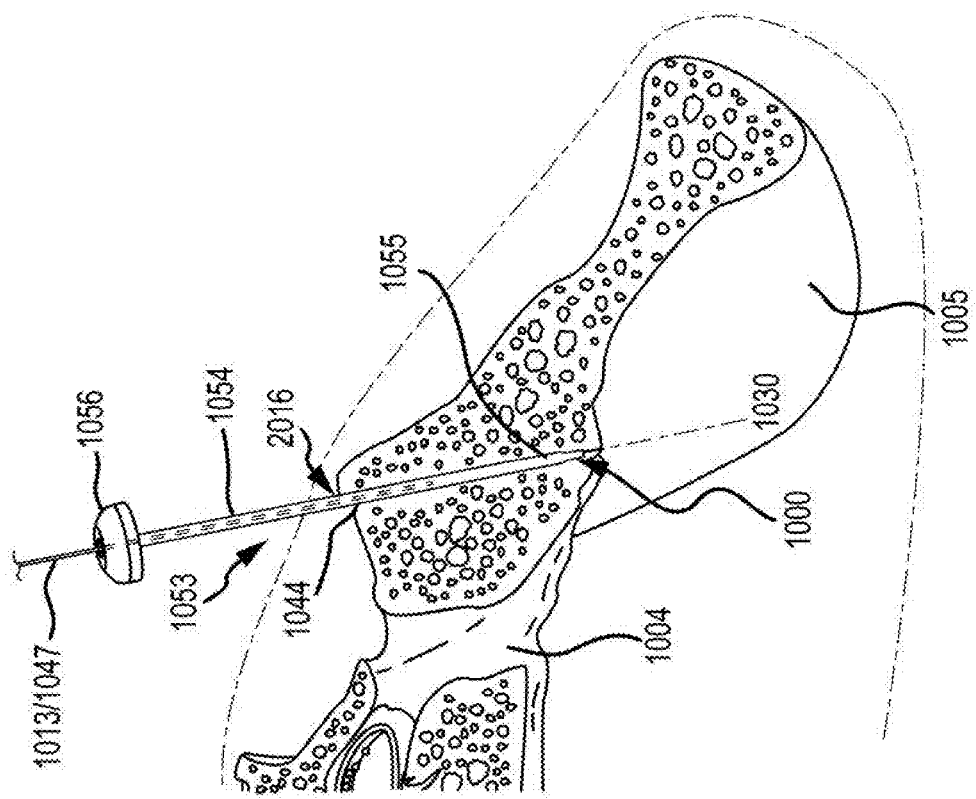
Figure 42F:
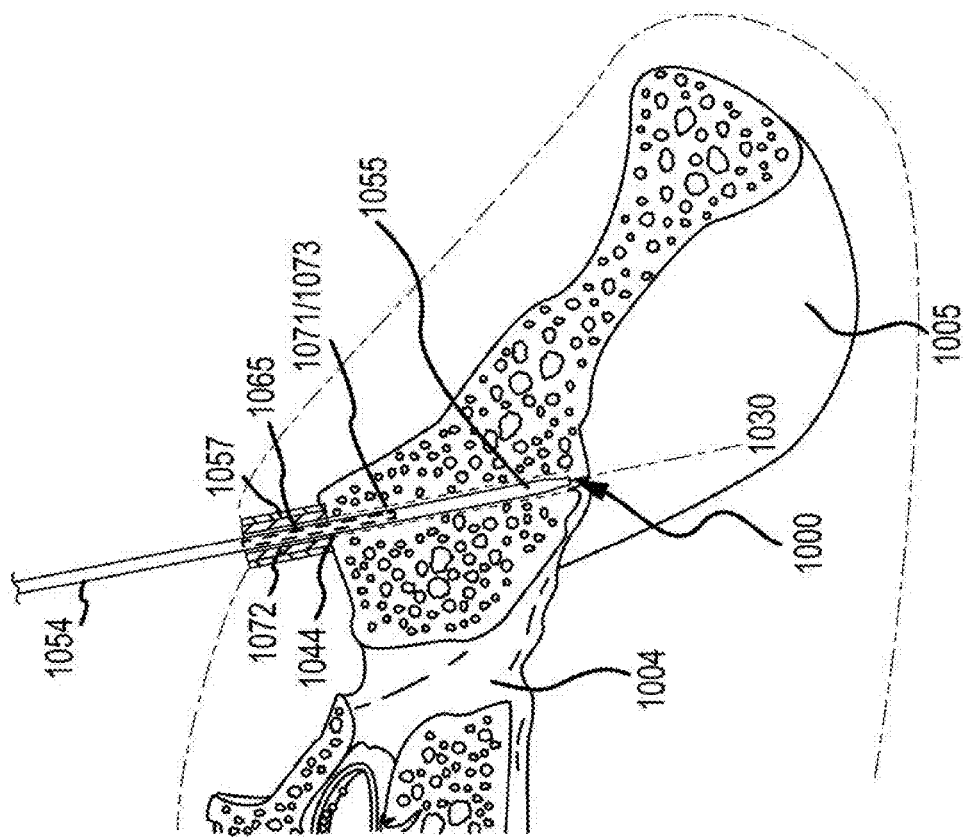

Now referring primarily to FIG. 42C, a small incision 1053 can be made in the skin at the posterior superior (or as to certain embodiments inferior) aspect of the sacroiliac joint 1000, extending proximal and distal to the tubular member 1047 along the line of the sacroiliac joint 1000 to provide a passage to access the interarticular space between the articulating surfaces 1016 (see FIG. 42B) of the sacroiliac joint 1000. More specifically, as can be understood from FIGS. 39A-41B, in one embodiment, the small incision 1053 can be made along the joint line 2019 of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin.

Alternatively, probe 1054 can be used to guide, advance or place a needle, guide wire or other instrument up to, near, or into the joint.

Additionally, in particular embodiments, probe handle 1056 or the opposed end of the probe body 1054, or both, can be configured to have an interference fit or a luer lock hub to communicate with a syringe barrel 1051 in order to advance contrast, in situ curable biocompatible materials, stem cells, or etc. through the cannulated probe 1054 or cannulated probe handle 1056.

Now referring primarily to FIG. 42D, a passage from the incision 1053 (see FIG. 42C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, as can be understood from FIGS. 39A-41B, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue locate with in the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiber optic or a LED light source to assist in visualization of the working area. Also, in some embodiments, irrigation and suction tubing may communicate with the inside passage of cannula 1057.

Figure 43A:
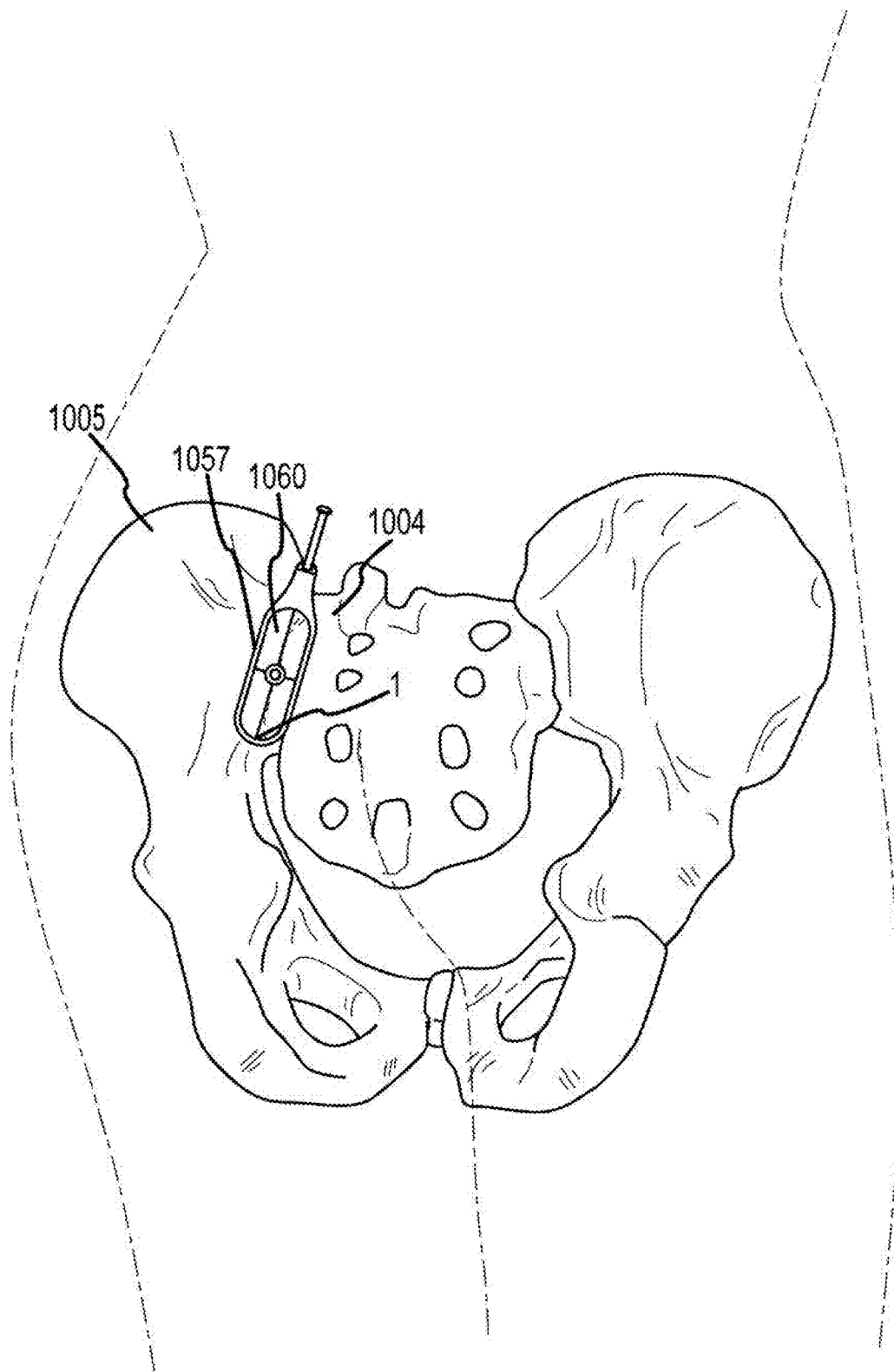
FIG. 43A is a posterior-lateral view of the hip region of the patient, illustrating the placement of a cannula alignment jig.
Figure 43B:
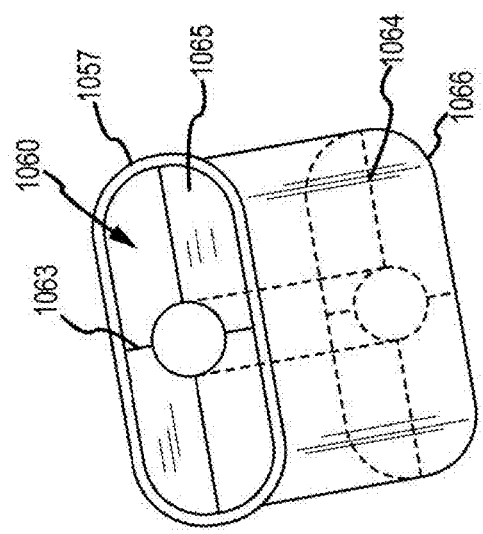
FIGS. 43B-43C are different isometric views of the cannula alignment jig.
Figure 43C:
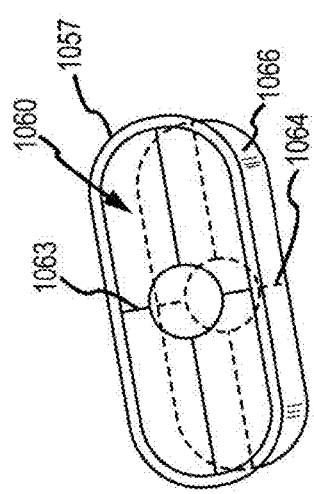

Now referring primarily to FIGS. 43A-43C, a cannula alignment jig 1060 can be advanced over the probe body 1054 (or guide pins 1013) and received within the cannula 1057. Substantially, identical cross hairs 1063, 1064 can be disposed on the upper jig surface 1065 and the lower jig surface 1066. Alignment of the cross hairs 1063, 1064 under x-ray with the sacroiliac joint 1000 can confirm that the cannula 1057 has proper orientation in relation to the paired articular surfaces 1016 of the sacroiliac joint 1000. The cannula 1057 properly oriented with the paired articular surfaces 1016 can then be disposed in fixed relation to the sacroiliac joint by placement of fasteners through the cannula 1057 into the sacrum 1004 or the ilium 1005. A handle extending from a part of the cannula may be configured to allow fixturing to an operating table.

Figure 44B:
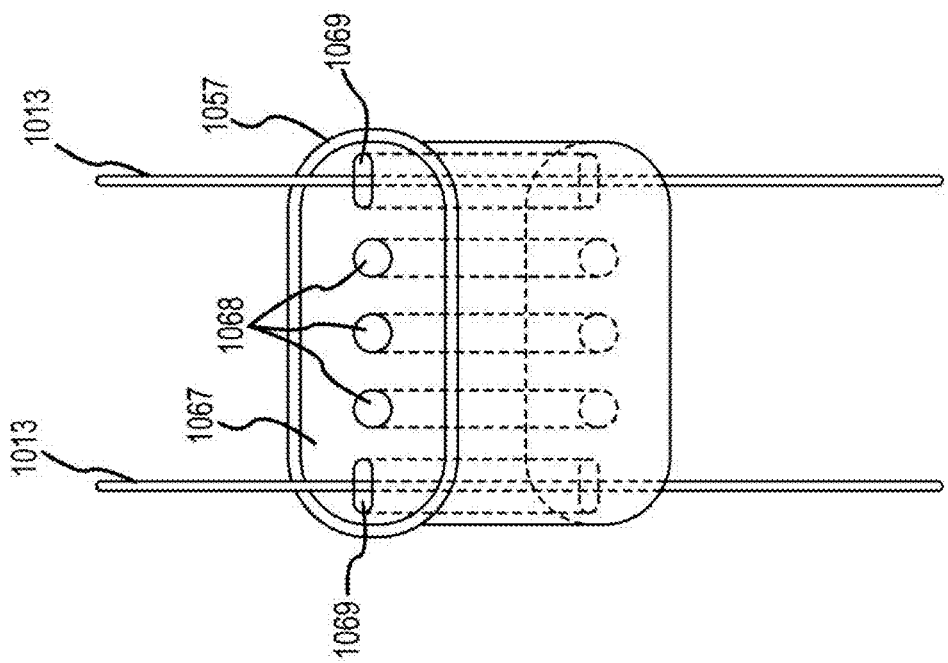
FIG. 44B is an isometric view of the drill jig.
Figure 44A:
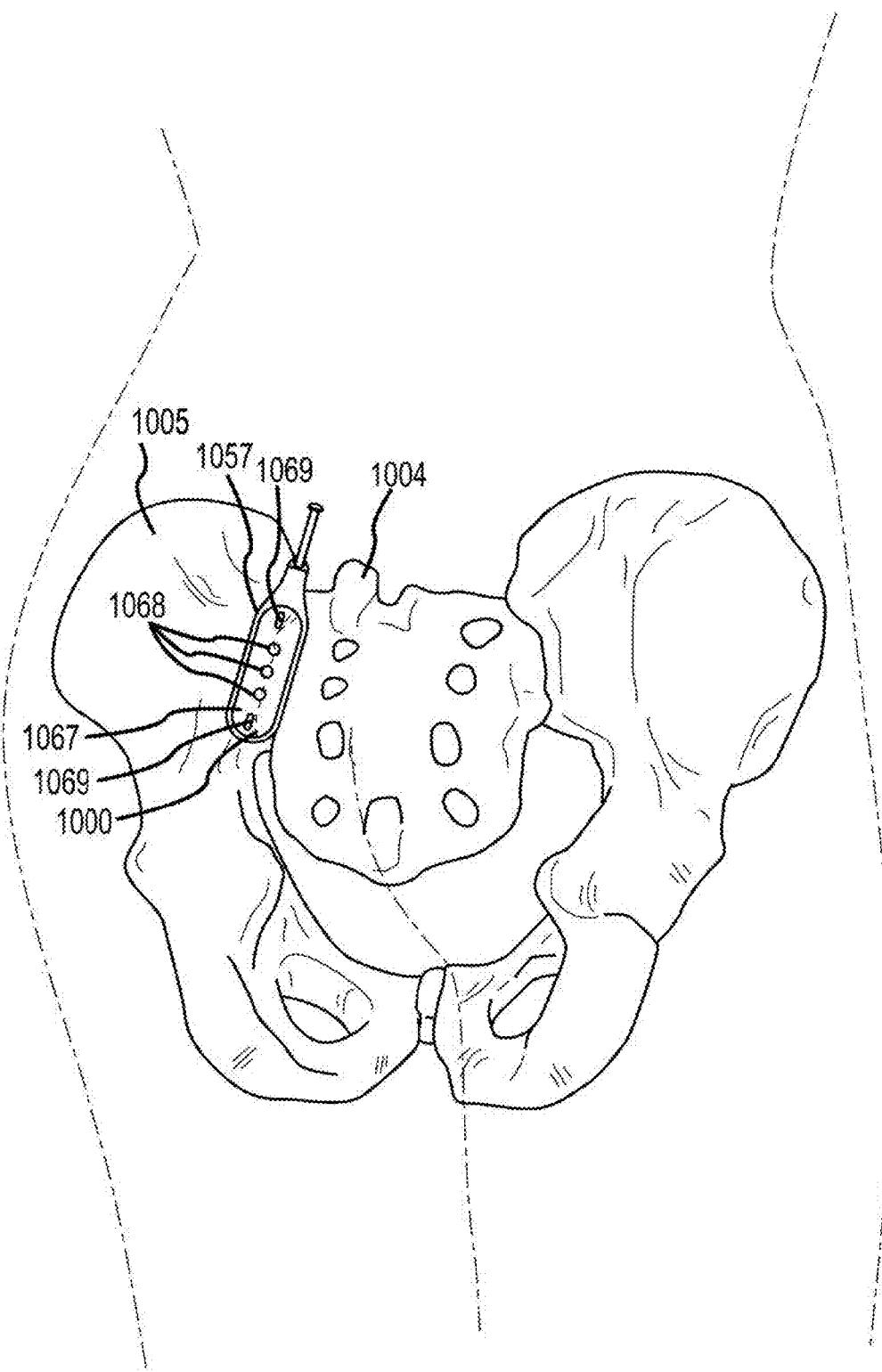
FIG. 44A is a posterior-lateral view of the hip region of the patient, illustrating the placement of a drill jig.

Now referring to FIGS. 44A and 44B, a first drill jig 1067 can be advanced over the probe body 1054 (or guide pins 1013) and received within the cannula 1057. The probe body 1054 (or guide pins 1013) extending outwardly from the sacroiliac joint 1000 passes through a drill guide hole 1068 of the first drill jig 1067 (or a plurality of guide pins 1013 can extend through a corresponding plurality of guide pin holes 1069). The drill guide hole 1068 can take the form of a circular hole as shown in the Figures, a slot, or other configuration to restrict the movement of the drill bit 1062 (see FIG. 42E) within the drill jig 1060 and provide a guide for a drill bit 1062 in relation to the sacroiliac joint 1000. Guide pin holes 1069 can receive guide pins which can be positioned between the articular surfaces 1016 of the sacroiliac joint 1000 to demarcate the zone of desired treatment or safe working zones while using, for example, lateral fluoroscopy. As a non-limiting example, a first guide pin 1013 can be advanced through a first guide pin hole 1069, or alternatively a guide pin 1013 is first inserted into the sacroiliac joint 1000 and subsequently a guide jig 1067 is advanced over the guide pin 1013, the first guide pin 1013 can enter near inferior end 2022 of the posterior inferior access region 2016 of the sacroiliac joint articular region 1044 via the sacroiliac joint line 2019 to border a portion of the greater sciatic notch 2008 thereby allowing a medical person, computer guided surgical system, or other observer to more easily highlight under x-ray a border which should not be crossed during the procedure due to the presence of nerve and other structures. Additionally, as a non-limiting example, first guide pin 1013 can configured as an electrode, insulated from the operator and the patient's soft tissues, and may be connected to a monitor to signal to an operator or surgeon when implant 25, configured with a stimulating electrode (NM), as discussed below, comes into contact with first guide pin. Similarly, a second guide pin 1013 can be placed in another guide pin hole 1069 to demarcate a second limit to a desired zone of treatment, or safe working zone. For example, a second guide pin 1013 can enter near the superior end 2018 of the posterior inferior access region 2016 of the sacroiliac joint articular region 1044 via the sacroiliac joint line 2019 to be positioned to border an area of the sacroiliac joint 1000 such as a transition zone between the extra-articular 3007 (see FIG. 48) and the interarticular region 1044 which, for example, has been highlighted by contrast material as above described.

Figure 42E:
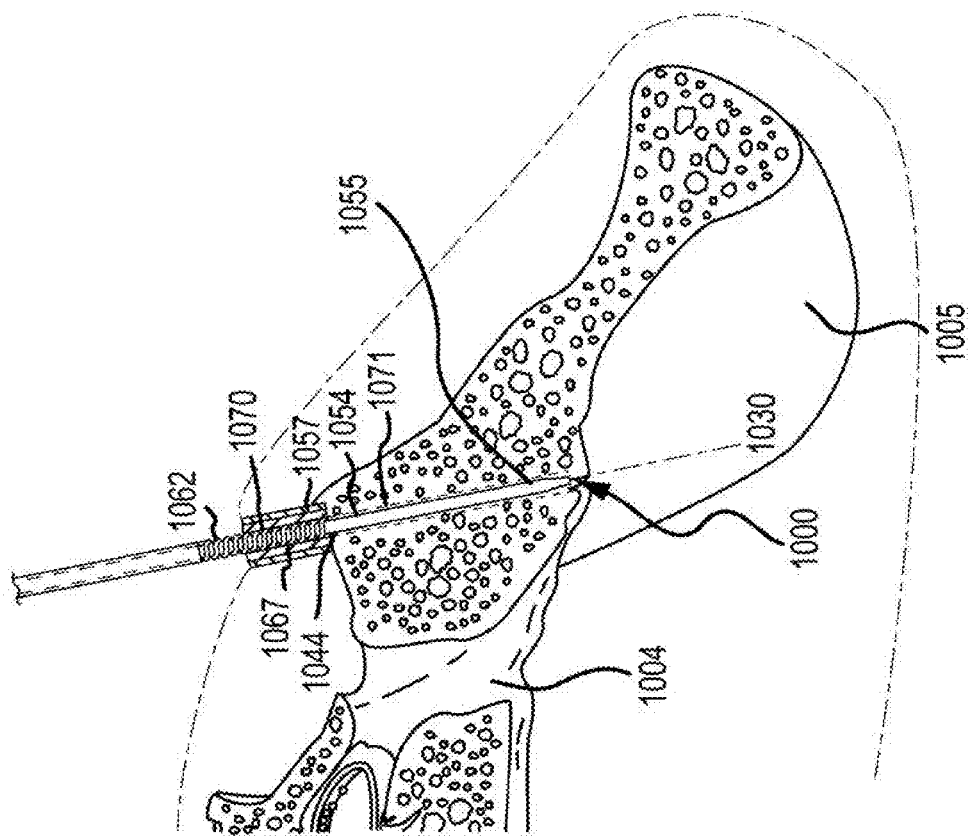
Figure 42H:
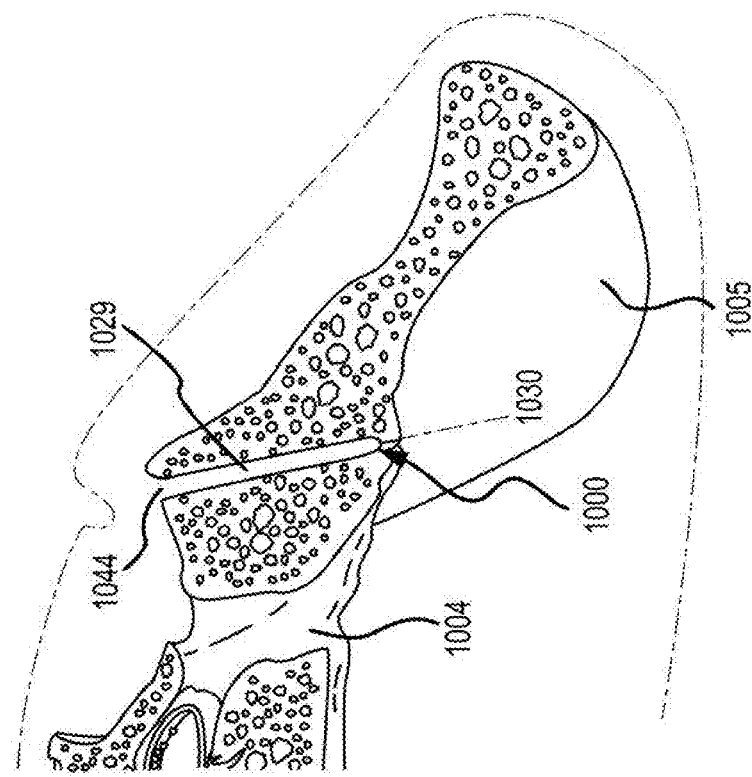

Now referring to FIG. 42E, a cannulated drill bit 1070 can be advanced over the probe body 1054 and within a drill guide hole 1068 (see FIGS. 44A and 44B) of the first drill jig 1067. The cannulated drill bit 1070 under fluoroscopic guidance can be advanced into the interarticular region 1044 between the articulating surfaces 1016 of the sacroiliac joint 1000 to produce a first bore 1071 (shown in broken line) to a determined depth. As to certain embodiments of the method, an amount of articular cartilage or other tissues from between the articular surfaces 1016 of the sacroiliac joint 1000 can be removed sufficient to allow embodiments of the sacroiliac joint implant 25 to be implanted in replacement of the removed articular cartilage or tissue. Because the method removes the degenerative articular cartilage or tissue between the articular surfaces 1016 of the sacroiliac joint 1000, the articular surfaces 1016 of the sacroiliac joint 1000 can remain intact or substantially intact allowing the sacroiliac joint implant 25 to be non-transversely located between the articular surfaces 1016 of the sacroiliac joint 1000. Understandably, other instruments can be utilized separately or in combination with a cannulated drill bit 1062 for the removal of articular cartilage or tissue between articular surfaces 1016 such as: endoscopy tools, box chisels, side cutting router bits, burs, flexible burs and bits, hole saws, curettes, lasers (such as C02, Neodymium/Y AG (yttrium-aluminum-garnet), argon, and ruby), electrosurgical equipment employing electromagnetic energy (the cutting or heating electrode can be a fine micro-needle, a lancet, a knife, a wire or band loop, a snare, an energized scalpel, or the like) where, e.g., the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

Now referring to FIG. 42F, as to certain embodiments of the invention, the first drill jig 1067 can be removed from within the cannula 1057 and a second drill jig 1072 can be advanced over the probe body 1054 and received within the cannula 1057; however, the invention is not limited to any particular number of drill jigs and as to certain embodiments of the method the first drill jig 1067 can include all the required drill guide hole(s) 1068 (or slots or other configurations of the drill guide) and as to other embodiments of the method a plurality of drill jigs can be utilized in serial order to provide all the drill guide holes 1068. As to the particular embodiment of the invention shown by the Figures, the first drill jig 1067 can provide one or more additional drill guide holes 1068 which guide in relation to the first bore 1071 a second or more cannulated drills 1062 of the same or different configuration to be inserted within and advanced into the sacroiliac joint 1000 to produce a second bore 1073 (generally shown in broken line as 1071/1073) or a plurality of bores within the sacroiliac joint 1000 spaced apart in predetermined pattern to allow removal of sufficient articular cartilage 1016 or other tissue from the interarticular space of sacroiliac joint 1000 for placement of embodiments of the sacroiliac joint implant 25 within the region defined by and between the paired articular surfaces 1016 of the sacroiliac joint 1000. As to certain methods of the invention, the first drill jig 1067 or the second drill jig 1072 or a plurality of drill jigs can be utilized in serial order to remove a portion of the sacroiliac joint 1000 for generation of an implant receiving space 1029 (see, for example, FIG. 42H). As these embodiments of the method, articular cartilage or other tissues and sufficient subchondral bone can be removed from between the articular surfaces 1016 of the sacroiliac joint 1000 sufficient to allow placement of certain embodiments of the sacroiliac joint implant 25 and one or more radial member receiving channels 1074 can be cut into at least one of the articular surfaces 1016 of said sacroiliac joint 1000 sufficient to receive other embodiments of the sacroiliac implant 25. The one or more radial member receiving channels 1074 can be cut a depth into the subchondral, cortical bone or cancellous bone of the sacrum 1004 or ilium 1005.

Figure 42G:
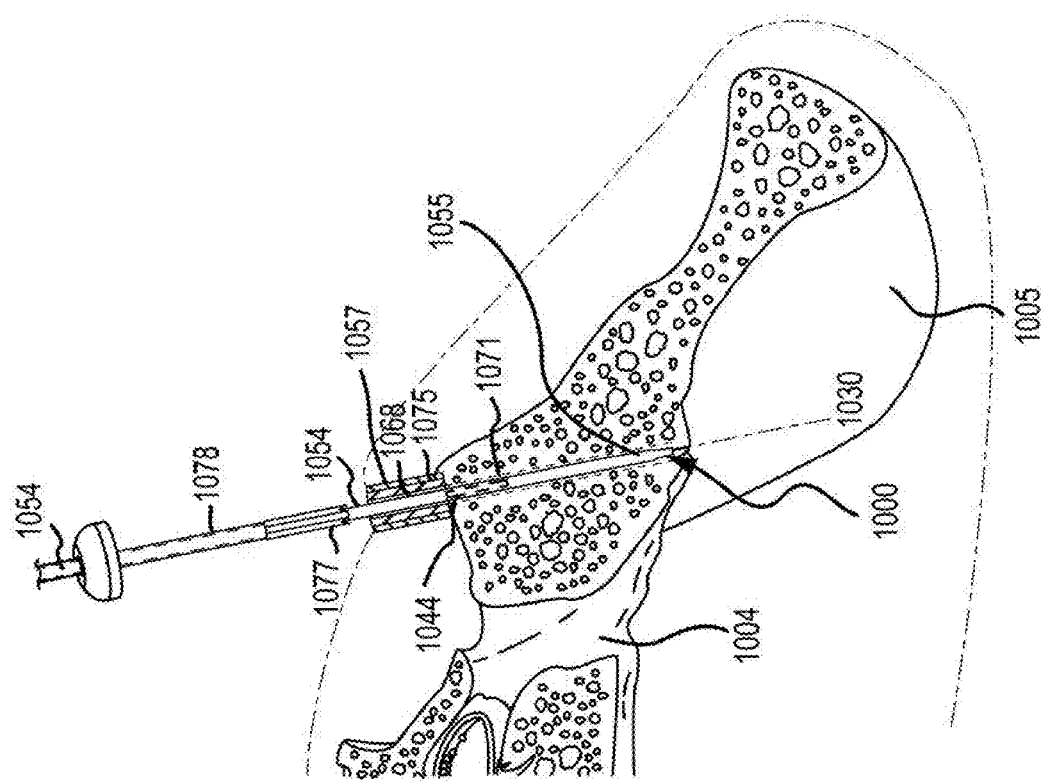

Now referring primarily to FIG. 42G, in a subsequent step, the last in the serial presentation of drill jigs 1067, 1072 can be removed from within the cannula 1057 and a broach jig 1075 can be advanced over the probe body 1054 to locate within the cannula 1057. The broach jig 1075 can include a broach guide hole 1076 which receives a first broach end 1077 of a cannulated broach 1078 advanced over the probe body 1054. The first broach end 1077 can have a configuration which can be advanced into the sacroiliac joint 1000. As to certain embodiments of the method, the first broach end 1077 can be adapted to remove an amount of articular cartilage and other tissue from between the articular surfaces 1016 within the articular region 1044 of the sacroiliac joint 1000 for non-transverse placement of a sacroiliac joint implant 25 having an elongate body 45, or having an elongate body 45 and other features (e.g., members radially extending from the body 45) between the articular surfaces 1016 of the sacroiliac joint 1000. As to other embodiments of the method, the cannulated broach 1078 can remove a sufficient portion of the sacroiliac joint 1000 to generate an implant receiving space 1029 to receive embodiments of the sacroiliac joint implant 25 having an elongate body 45 or an elongate body 45 and one or more radial members adapted for non-transverse placement between the articular surfaces 1016 or adapted to extend into the bone of the sacrum 1004 or the ilium 1005.

As a non-limiting example, FIG. 42G shows a broach 1078 configured to remove a portion of the sacroiliac joint 1000 to produce an implant receiving space 1029 (shown in FIG. 42H) to receive embodiments of the sacroiliac joint implant 25 having an elongate body 45 that extends between the articular surfaces 1016 of the sacroiliac joint 1000 and one or more anchors 30 that extend from the implant body 45 into the adjacent sacrum 1004 and ilium 1005.

Now referring primarily to FIGS. 45A-45D, the implant receiving space 1029 and the sacroiliac joint implant 25 can be configured having related dimension relations such that placement of the sacroiliac joint implant 25 within the implant receiving space 1029 disposes the sacrum 1004 and the ilium 1005 in substantially immobilized relation and substantially avoids alteration of the positional relation of the sacrum 1004 and the ilium 1005 from the normal condition, or avoids driving together or driving apart the sacrum 1004 from the ilium 1005 outside of or substantially outside of the normal positional relation. An intention in selecting configurations of the sacroiliac joint implant 25 and the implant receiving space 1029 being immobilization of the sacrum 1004 in relation to the ilium 1005 while maintaining the sacroiliac joint 1000 in substantially normal or substantially normal positional relation, or returning the sacroiliac joint 1000 to a substantially normal positional relation to correct a degenerative condition of the sacroiliac joint 1000.

As a non-limiting example, configurations of an implant receiving space 1029 allow embodiments of the sacroiliac joint implant 25 to be placed non-transversely between the caudal portion 1086 of the articular surfaces 1016 of the sacroiliac joint 1000. In one embodiment of the sacroiliac joint implant 25, the implant body 45 is located within a correspondingly configured implant receiving space 1029 to engage at least a portion of the bone of the ilium 1005 or sacrum 1004. In some embodiments, members may radially extend from the implant body 45 to extend into a portion of the bone 1073 of the sacrum 1004 and the ilium 1005. As to those embodiments of the sacroiliac joint implant 25 which having such radial members, the implant receiving space 1029 can further include one or more radial member receiving channels, which correspondingly allow the radial members to extend into the bone 1073 of the sacrum 1004 or the ilium 1005 (whether subchondral, cortical, cancellous, or the like), or impact of the sacroiliac joint implant 25 into the implant receiving space 1029 without the radial member receiving channels can forcibly urge such radial members into the bone 1073 of the sacrum 1004 and the ilium 1005. While not depicted in the accompanying figures of the present application, such radial members and radial member receiving channels are discussed in detail in U.S. patent application Ser. No. 12/998,712 (which is incorporated herein in its entirety) and can be readily employed with any of the implant embodiments disclosed herein.

As indicated in FIGS. 45B-45D, anchor members 30 (such as threaded members) can be inserted through the bores 40 in the implant 25 and into the sacrum 1004 and ilium 1005 to fix the location of the fixation fusion implant 25 within the implant receiving space 1029.

While the preceding discussion is given in the context of the implant 25 being implanted non-transversely in the caudal portion 1086 of the sacroiliac joint 1000, in other embodiments, the implant 25 may be implanted in other locations within the sacroiliac joint. For example, as disclosed in U.S. patent application Ser. No. 12/998,712, which is incorporated herein by reference, in some embodiments, the implant 25 may be implanted non-transversely in the cranial portion 1087 (see FIG. 45A) of the sacroiliac joint 1000 by the similar procedures or steps as above described with the incision and generation of the passage to the superior articular portion of the sacroiliac joint 1000. The implant may also be implanted in the sacroiliac joint in such a manner so as to extend between the cranial and caudal portions, as also disclosed in U.S. patent application Ser. No. 12/998,712.

Figure 46:
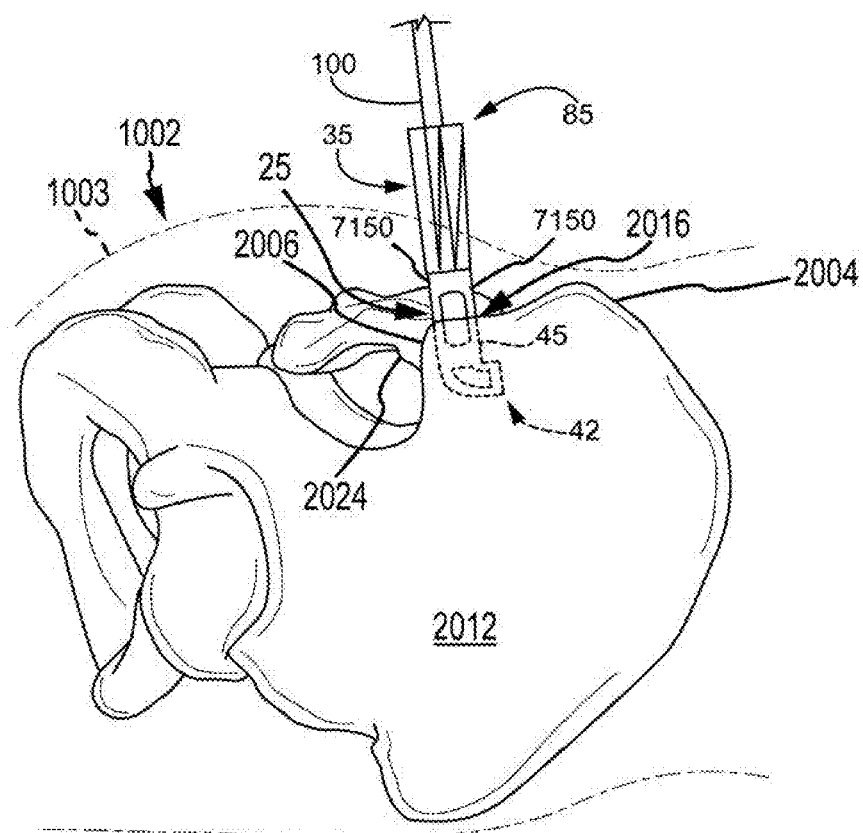
FIG. 46 is generally the same enlarged view as FIG. 39B, except illustrating the delivery tool being used to deliver the implant to the sacroiliac joint space.

To begin a discussion of employing the delivery tool 20 to implant the implant 25 in the sacroiliac joint 1000 once the implant receiving space 1029 has been created, reference is made to FIGS. 42I, and 46. FIG. 46 is generally the same enlarged view as FIG. 39B. As shown in FIGS. FIGS. 42I and 46, once the implant receiving space 1029 has been created as discussed above with respect to FIGS. 42A-42H, the implant 25 can be supported off of the distal end 35 of the delivery tool 20 and positioned such that the distal end 42 of the implant 25 begins to enter the sacroiliac joint articular region 1044 via the posterior inferior access region 2016, which is described in detail above with respect to FIGS. 39A-41B. As can be understood from FIG. 46, in entering the sacroiliac joint space, the implant 25 is oriented such that its body 45 is oriented generally parallel to, and aligned with, the sacroiliac joint line 2019. In other words, the body 45 is generally located within the joint plane 1030 such that its faces 7060 are generally parallel to the joint plane 1030 and its side edge faces 7150 project in a directions that extends along the joint plane 1030 (see, e.g., FIGS. 45C and 45D). The longitudinal axis of the shaft 100 of the delivery tool 20 has a generally anterior trajectory that is located within the joint plane 1030. Alternatively, according to particular embodiments, as a non-limiting example, the longitudinal axis of the shaft 100 of the delivery tool 20 can have a trajectory which can be defined as being generally lateral or, in particular embodiments, generally posterior. In some embodiments, when the implant 25 is being delivered into the joint space, the shaft 100 can be said to be at least one of generally superior or cephald the sciatic notch.

Figure 47:
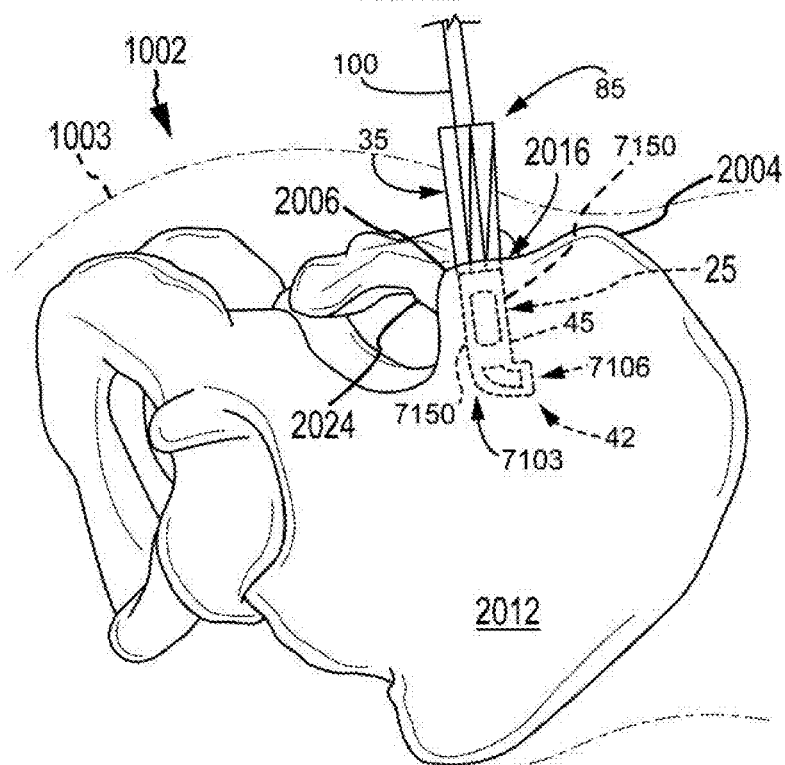
FIG. 47 is the same view as FIG. 46, except the implant has now been fully inserted into the prepared space in the sacroiliac joint.

FIG. 47 is the same view as FIG. 46, except the implant 25 has now been fully inserted into the prepared space 1029 in the sacroiliac joint 1000. As illustrated in FIGS. 42J and 47, the implant 25 is fully received in the prepared sacroiliac space 1029 such that the body 45 is oriented generally parallel to, and aligned with, the sacroiliac joint line 1030 such that its faces 7060 are generally parallel to the joint plane 1030 and its side edge faces 7150 project in a directions that extends along the joint plane 1030 (see, e.g., FIGS. 45C and 45D). As can be understood from FIG. 42J, the longitudinal axis of the implant 25 and the longitudinal axis of the shaft 100 of the delivery tool 20 may be coaxially aligned with each other and generally located in the sacroiliac joint plane 1030.

Figure 48:
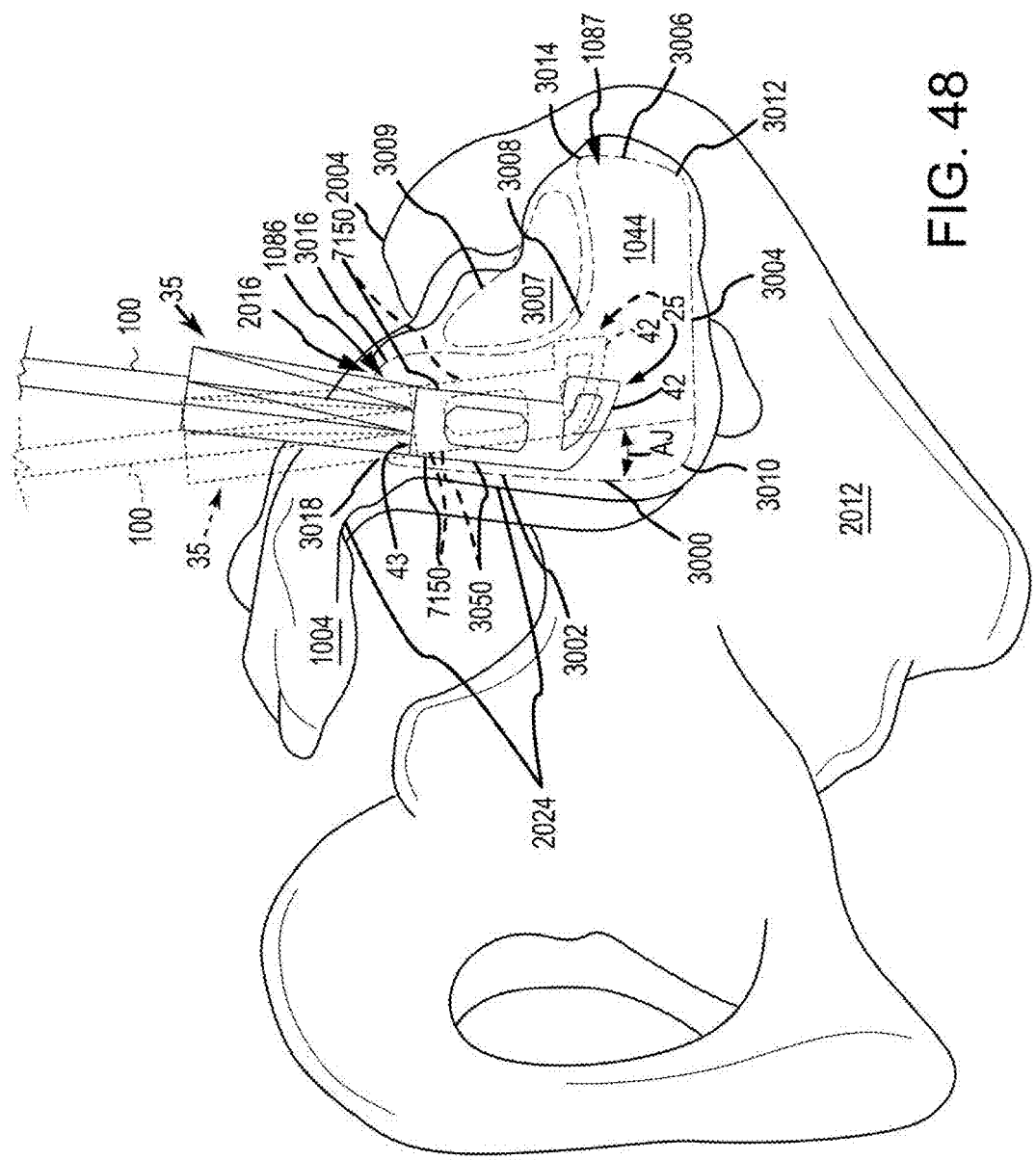
FIG. 48 is generally the same view as FIG. 46, except the ilium is removed to show the sacroiliac joint space boundary defined along the sacrum and the implant positioned for implantation within the joint space.

FIG. 48 is generally the same view as FIG. 46, except the ilium 1005 is removed to show the sacroiliac joint space boundary 3000 defined along the sacrum 1004 and outlining the sacroiliac joint articular region 1044, the implant 25 positioned for implantation within the sacroiliac joint articular region 1044. As shown in FIG. 48, the sacroiliac joint space boundary includes an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

As shown in FIG. 48, the implant 25 is inserted via the distal end 35 of the shaft 100 of the delivery tool 20 into the caudal region 1086 of the sacroiliac joint articular region 1044. As shown via the implant 25 and shaft 100 shown in solid lines, in one embodiment, the implant 25 enters the posterior inferior access region 2016, and is further advanced into the caudal region 1086 of the sacroiliac joint articular region 1044, in an orientation such that the shaft 100 and side edge faces 7150 of the implant body 45 face in a direction that extends along the joint plane 1030 (see, for example, FIGS. 42I-42J and FIGS. 45C and 45D) and the longitudinally extending side edge face 7150 of the implant body 45 next to the inferior boundary segment 3002 is generally parallel to, and immediately adjacent to, the inferior boundary segment 3002. Thus, the distal end 42 of the implant is heading generally perpendicular to, and towards, the anterior boundary segment 3004.

As shown in FIG. 48 via the implant 25 and delivery tool shaft 100 shown in dashed lines, in one embodiment, the implant 25 enters the posterior inferior access region 2016, and is further advanced into the caudal region 1086 of the sacroiliac joint articular region 1044, in an orientation such that the delivery tool shaft 100 and side edge faces 7150 of the implant body 45 face in a direction that extends along the joint plane 1030 (see, for example, FIGS. 42I-42J and FIGS. 45C and 45D) and the longitudinally extending side edge face 7150 of the implant body 45 next to the inferior boundary segment 3002 is somewhere between being generally parallel to the inferior boundary segment 3002 (as illustrated by the solid-lined implant 25 in FIG. 48) or forming an angle AJ with the inferior boundary segment 3002 of up to approximately 50 degrees. Thus, the distal end 42 of the implant shown in dashed lines can be said to head anywhere from generally perpendicular to, and towards, the anterior boundary segment 3004 to heading generally towards the superior-anterior corner 3012, or points in between.

In one embodiment, the implant 25 may be first directed into the joint space as illustrated by the solid-lined implant 25 in FIG. 48 after which the implant 25 is rotated within the joint space to be positioned somewhere between, and including, angled position depicted by the dashed-lined implant 25. In other embodiments, the implant 25 may be first directed into the joint space as illustrated by the dashed-lined implant 25 in FIG. 48 after which the implant 25 is rotated within the joint space to be positioned somewhere between, and including, the parallel position depicted by the solid-lined implant 25.

As can be understood from FIGS. 4A-15, 45 and 48 where the implant 25 has a body 45 that is configured to have a shape that generally mimics and even substantially fills a sacroiliac joint space, depending on the needs of the patient and the treatment plan devised by the physician, generally the entirety of both the long portion 7100 and short portion 7101 of the implant body 45 may reside substantially in the caudal portion 1086 of the sacroiliac joint space (as indicated in FIG. 48). Alternatively, the long portion 7100 of the implant body 45 may reside in the caudal portion 1086 of the sacroiliac joint space and the short portion 7101 may extend into the cranial portion 1087 of the sacroiliac joint space (as indicated in FIG. 45), the small radius 7102 and large radius of the implant body 45 being generally located at the generally right-angled intersection between the cranial portion 1087 and the caudal portion 1086 of the sacroiliac joint.

As can be understood from FIG. 42K, with the delivery tool 20 still coupled to the implant and the implant 25 located within the sacroiliac joint space as shown in FIG. 45A-45D or 48, the anchor members 30 are positioned in the guide lumens 132 of the delivery tool distal end 35 (see FIGS. 17C and 21) in preparation for driving the anchors 30 through the respective bores 40 of the implant body 45.

As can be understood from FIGS. 22-24 and 45B-45D, a distal end of a driving tool (e.g., screw driver) is engaged in turn with a proximal end of the anchor member 30 (e.g., screw) residing in the respective guide lumen 132 to drive the anchor 30 through the implant bores 40 and into the adjacent bone of the sacrum and ilium as reflected in FIG. 42L. Specifically, the driving tool is used to drive (e.g., a screw) each anchor 30 through its respective guide lumen 132 and into the respective implant anchor bore 40 aligned with the respective guide lumen 132 such that the distal region of the anchor 30 extends both distally and laterally from the respective side face 7060 of the implant body 45 into the respective bone (i.e., ilium and sacrum) bordering the sacroiliac joint space as depicted in FIG. 42L.

Prior to anchor member implantation, guide lumen 132 may be further configured with a needle guide sleeve to allow for guided advancement of a needle into the bone of a sacrum or ilium for aspiration of bone marrow which may be used in subsequent steps during the course of the procedure or for administration into the patient at a later date after the procedure has been completed (e.g., the aspirate may be manipulated and stem cells isolated and cultured for administration into the patient to treat a medical condition).

Figure 42M:
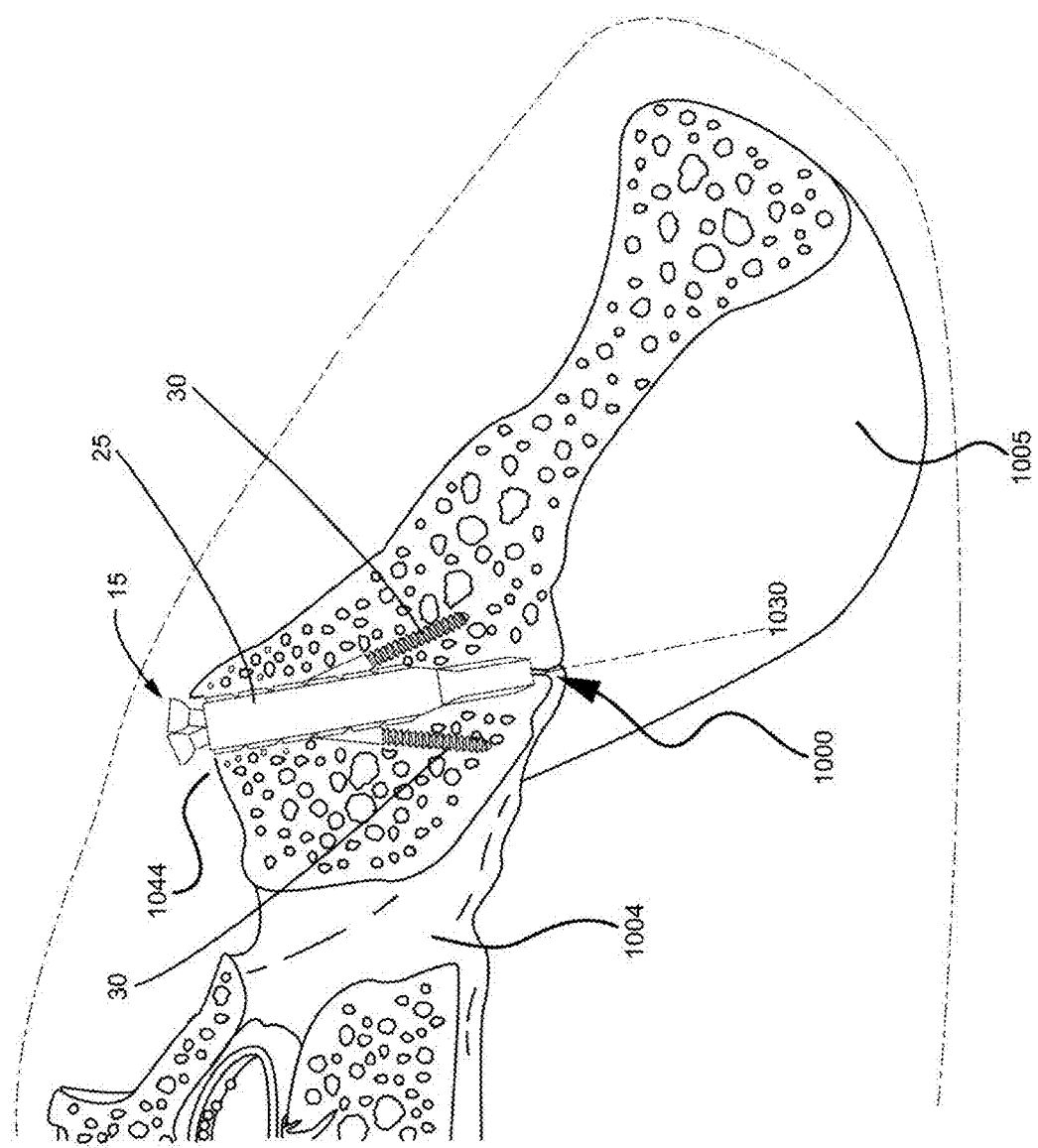

As shown in FIG. 42M, once the implant assembly formed of the implant 25 and anchor members 30 is secured at the implantation site such that the implant 25 is located in the prepared space 1029 of the sacroiliac joint space and the anchor members 30 extend from the implant body bores 45 into the bone of the ilium 1005 and sacrum 1004, the distal end 35 of the delivery tool 20 can be decoupled from the implant proximal end 43, e.g., by unthreading the retainer distal end 220 from the implant threaded bore 70 (see FIG. 20). The incision through which the delivery tool distal end 35 entered the patient can then be closed.

The anchor members 30 prevent migration of the implant 25 within the joint space. The anchor members 30 also can draw the ilium and sacrum together about the implant 25, increasing the sturdiness of the fixation of the implant in the joint space. The anchor members extending through the implant bores and into the bone of both the sacrum and ilium allow the anchor members 30 to be used to drawn the articular surfaces 1016 of the sacroiliac joint 1000 against the external surfaces of the sacroiliac joint implant 25. With the implant implanted in the sacroiliac joint, the body will cause the joint surfaces to fuse together about the implant 25.

Figure 42N:
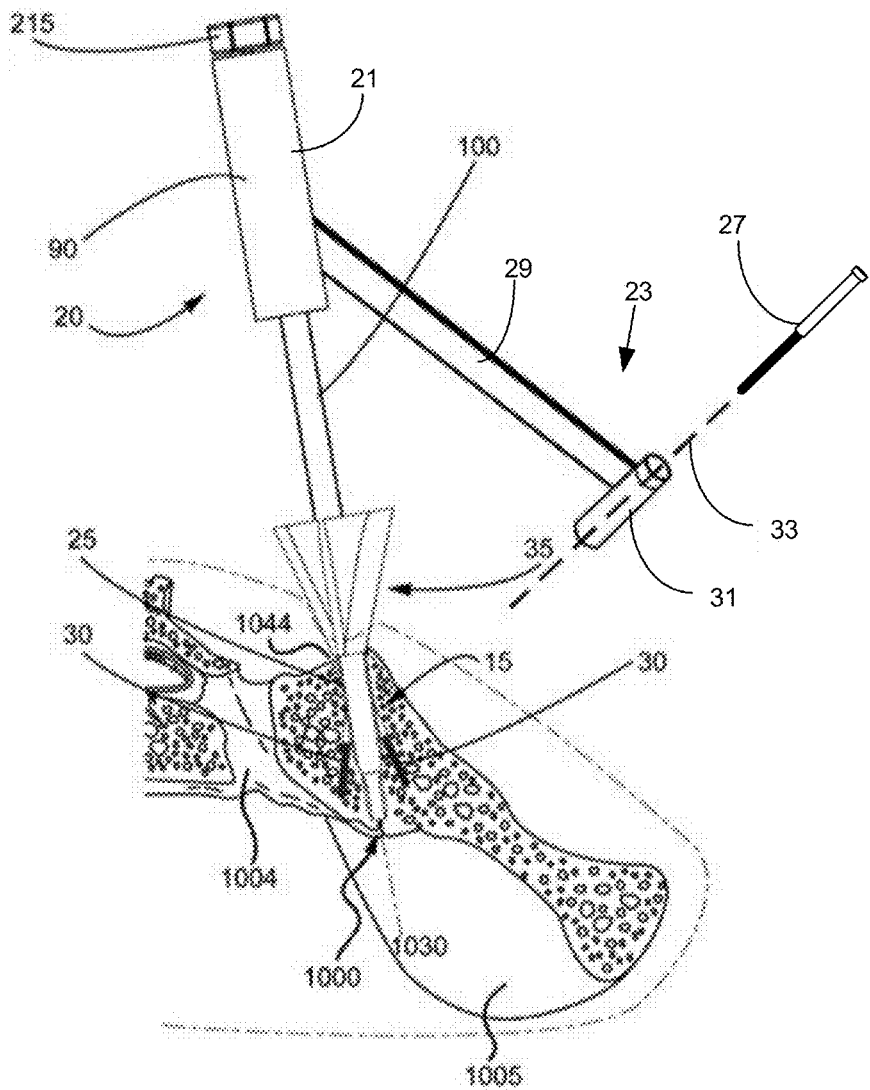
FIG. 42N is a similar view to FIG. 42L, except the delivery tool in FIG. 42N includes an anchor arm extending off of the delivery tool to position an anchor transversely in relation to the implant assembly.

As shown in FIG. 42N, another embodiment of the delivery tool 20 may include an implant arm 21 and an anchor arm 23 adapted to guide the delivery of an anchor 27 into the sacrum 1004, ilium 1005, or both the sacrum 1004 and ilium 1005 in transverse relation to the sacroiliac joint and the implant 25. The implant arm 21 may include a distal region and a proximal region and may releasably couple with or be fixedly attached to the delivery tool 20. The anchor arm 23 may extend from and be supported off of the implant arm 21. The anchor arm 23 may include an extension member 29 and an anchor guide 31, which may be a sleeve, collar, or other guide mechanism configured to guide an anchor 27 or anchor delivery tool (not shown) coupled with an anchor 27 along a trajectory 33 that is transverse (i.e., across) to a longitudinal axis of the implant 25. As seen in the figure, the anchor arm 23 may be fixed and non-adjustable relative to the implant arm 21 and the delivery tool 20 such that the anchor 27 will be delivered in a pre-determined angular orientation relative to the implant 25 when the implant 25 is coupled with the distal end of the delivery tool 20 and when the anchor 27 is guided along the trajectory 33 via the anchor arm 23.

Figure 49A:
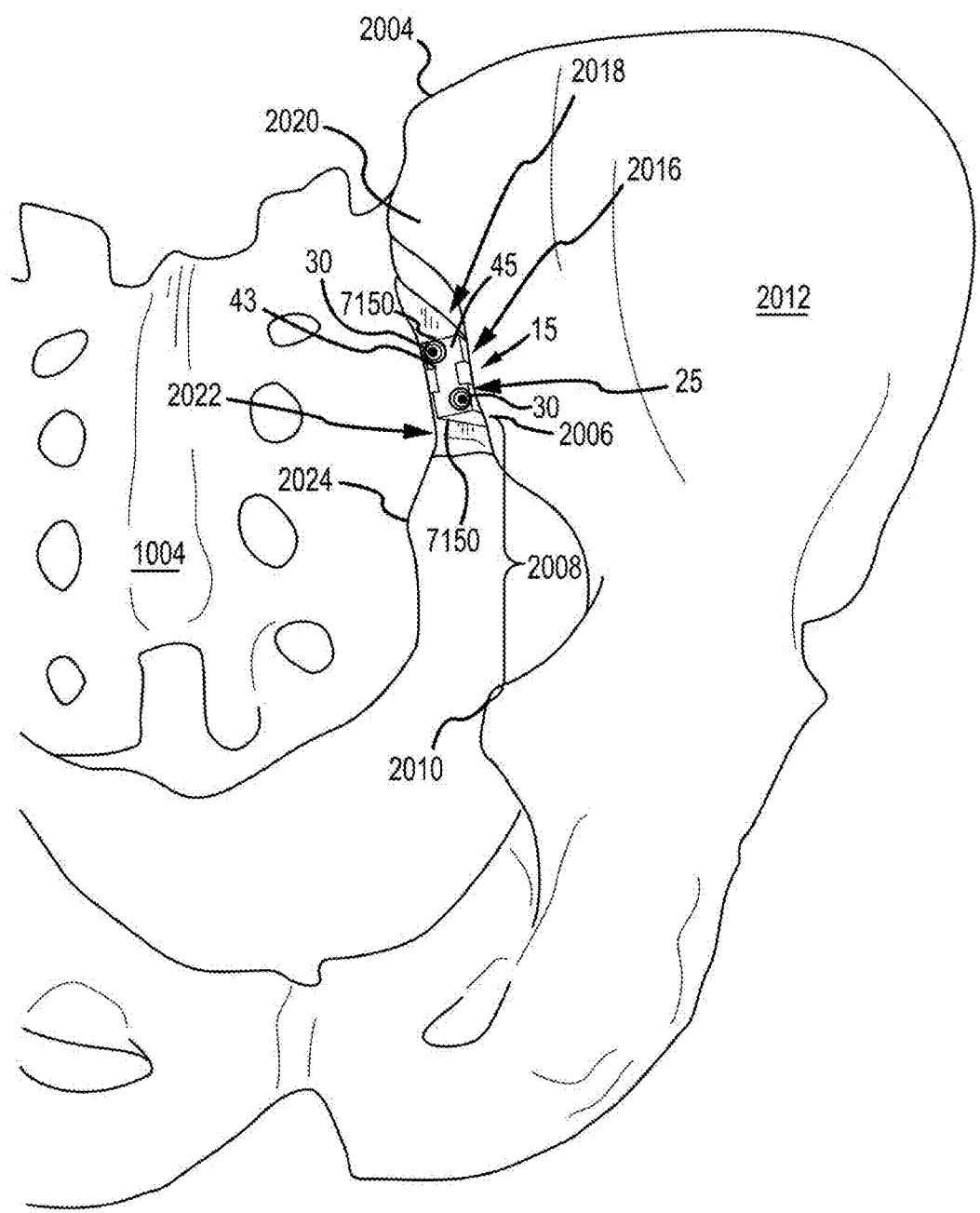
FIGS. 49A and 49B are, respectively, posterior and posterior-lateral views of the implantation area and the implant assembly implanted there.
Figure 49B:
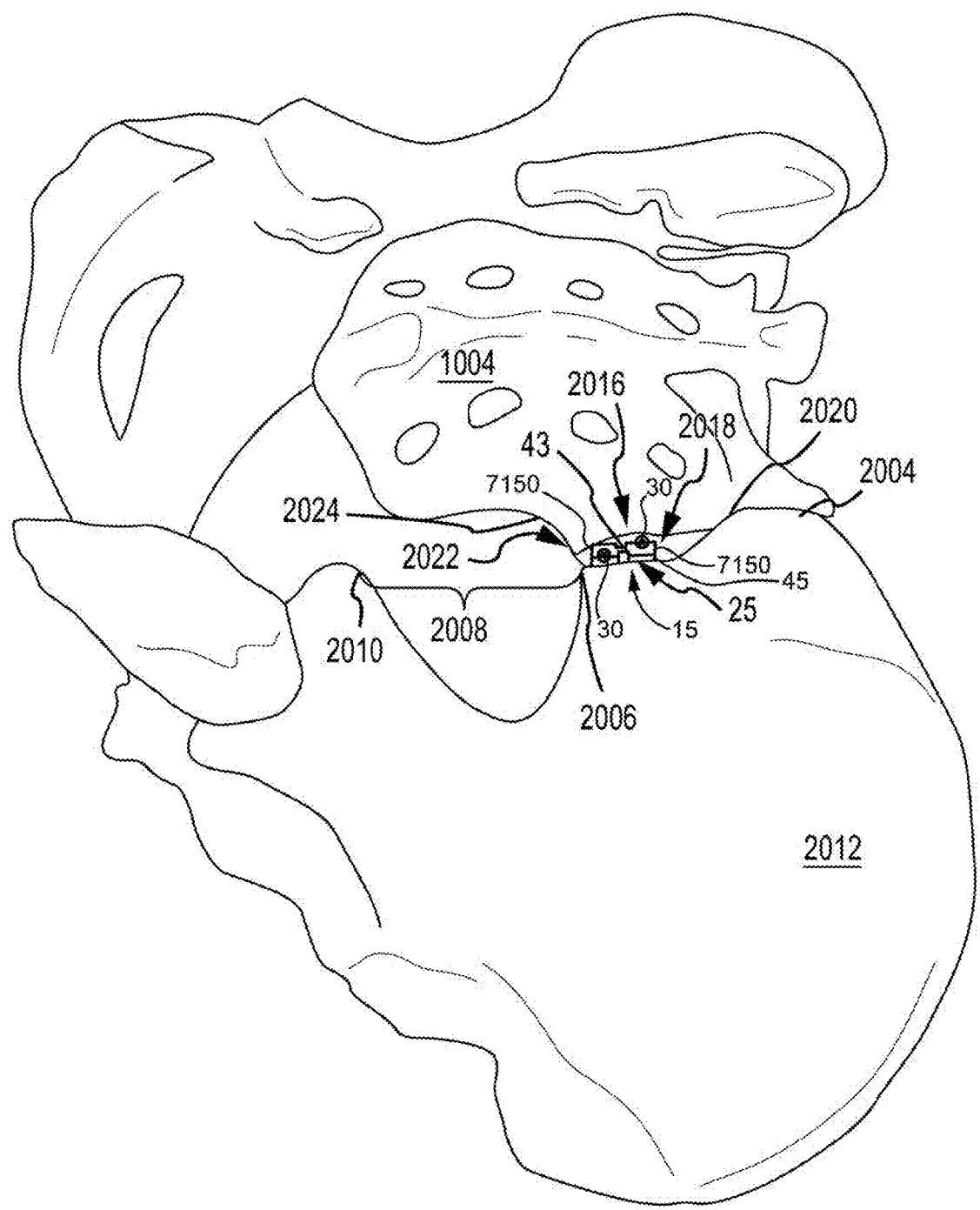

As can be understood from FIGS. 49A and 49B, which are, respectively, posterior and posterior-lateral views the implantation area and the implant assembly implanted there, proximal end 43 of the implant 25 can be seen positioned in the posterior inferior access region 2016, the implant being implanted in the caudal area of the sacroiliac joint space. The anchor member 30 can be understood to have been driven into the implant bore 40 transversely to the joint plane 1030 via a route in the ilium 1005 that avoids contact with vascular and neurological structures, thereby avoiding potentially life threatening injury to such structures. The ability to blindly, yet safely, drive the anchor members 30 into the respective implant bores 40 and adjacent bones while the implant 25 is hidden in the joint space is made possible by the cooperating configurations of the implant 25 and the delivery tool 20. Specifically, the guide lumens 132 of the delivery tool distal end 35 being axially aligned with the respective implant bores 40 when the proximal end 43 of the implant 25 is supported off of the distal end 35 of the delivery tool 20 makes it possible to safely drive the anchor members 30 through the implant bores 40 and into the ilium 1005 and sacrum 1004 when the implant is hidden in the joint space on account of being delivered to the joint space via the delivery tool 20.

While the delivery tool 20 may be employed to deliver the implant 25 to the caudal portion 1086 of the sacroiliac joint space via the caudal approach discussed above with respect to FIGS. 42A-49B, in other embodiments the other approaches and implant locations may be employed. For example, the implant 25 may be implanted in cranial portion 1087 of the sacroiliac joint space via a cranial approach as discussed in U.S. patent application Ser. No. 13/475,695 ("the '695 application"), which is incorporated herein by reference in its entirety. Alternatively, as described in the '695 application, the implant 25 may be implanted in the extra-articular space, as opposed to the sacroiliac joint articular region 1044, the extra-articular space being accessed via the extra-articular recess access region.

Figure 50:
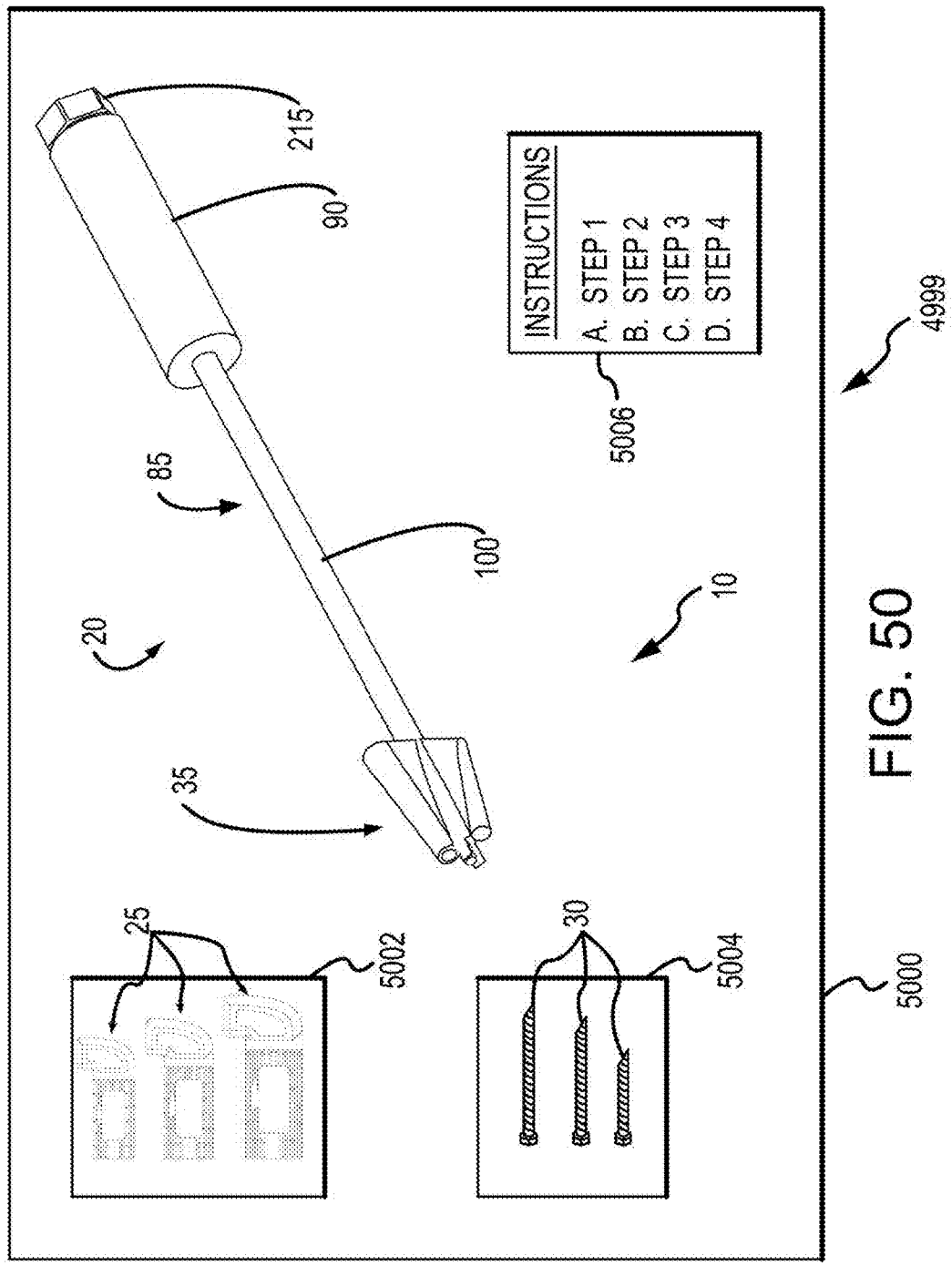
FIG. 50 is a plan view of a medical kit containing the components of the system, namely, the delivery tool, multiple implants of different sizes, and multiple anchor members of different sizes, wherein the system components are sealed within one or more sterile packages and provided with instructions for using the system.

In some embodiments, the system 10 may be provided in the form of a kit 4999. Such a kit 4999 is shown in FIG. 50. The kit 4999 may include the system 10 enclosed in a sterile main package 5000. For example, the delivery tool 20, the implant 25 and anchor members 30 may be sealed within the sterile main package 5000. The delivery tool 20 may be any of the tool embodiments disclosed herein and may include all of its components. Also, the implant 25 may be any of the implant embodiments disclosed herein.

As illustrated in FIG. 113, in some embodiments, the kit 4999 may include multiple sizes of the implant 25 and/or multiple sizes of the anchor members 30. The multiple implants 25 may be contained in a sterile individual package 5002 within the sterile main package 5000, and the multiple anchor members 30 may be contained in another sterile individual package 5004 within the sterile main package 5000. By providing the multiple sizes of implants 25 and anchor members 30, the implants and anchor members can be used as trials during certain steps of the procedure to determine appropriate implant sizes and to allow a physician, who is presented with the kit 4999 containing the delivery system 20 and multiple sizes and configurations of the implant and anchor members, to evaluate particular embodiments of an implant and anchor member as described herein that would be best suited to a particular patient, application or implant receiving space. The kit 4999 may also or alternatively contain multiple implants 25 with different angles of bores 40 to provide various desirable trajectories for anchor members 30 and multiple delivery systems 20 with as-manufactured angular relations corresponding to the different angles of the bores. The kit 4999 may also include color coded, numeric or other indicators corresponding between delivery systems 20 and the corresponding implants 25.

In some embodiments, the kit 4999 may include instructions 5006 that lay out the steps of using the system 10. The instructions 5006 may be contained within one of the sterile packages such as, for example, the sterile main package 5000. Alternatively, the instructions 5006 may be adhered or otherwise attached to an exterior surface of one of the sterile packages such as, for example, the sterile main package 5000. Alternatively, the instructions 5006 may be simply provided separately such as, for example, via simply shipped loose with the rest of the kit 4999, emailed, available for download at a manufacturer website, or provided via a manufacture offered training seminar program.

In some embodiments, the kit 4999 may have any one or more of the tool 20, implants 25 and anchor members 30 contained in individual sterile packages that are not held within a sterile main package. Alternatively, the tool 20, implants 25 and anchor members 30 may be contained in a single common package or in any combination of packages and combination of tool, implants and anchor members.

Figure 51:
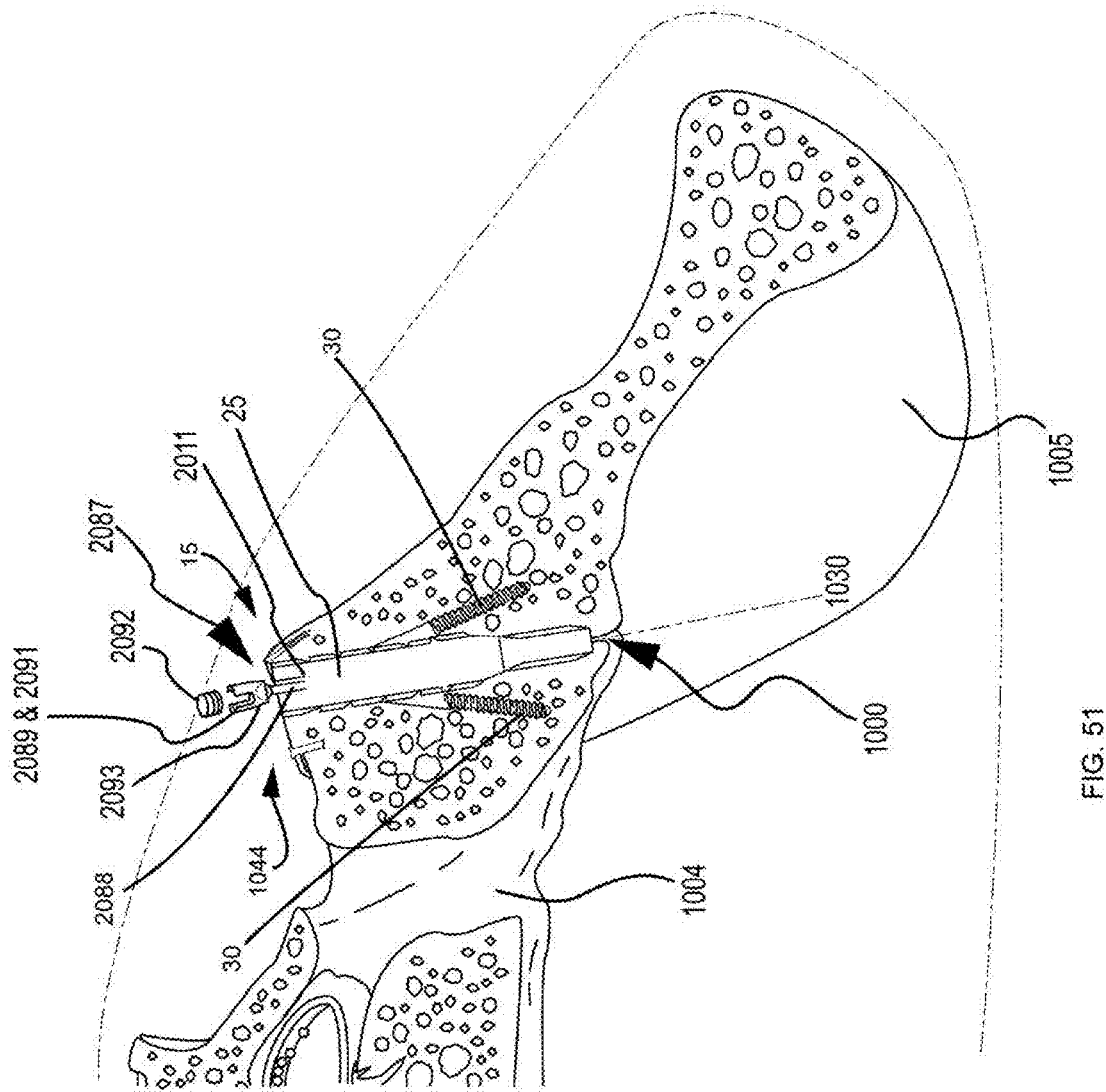
FIG. 51 is the same transverse cross sectional view of the patient's hip as shown in FIG. 42M, except showing the implant having structure attached thereto that will allow the implant to serve as an attachment point for structural components of a spinal support system configured to support across the patient's hip structure and/or to support along the patient's spinal column.

As can be understood from FIG. 51, which is the same transverse cross sectional view of the patient's hip as shown in FIG. 42M, once the implant 25 and anchors 30 are secured at the sacroiliac joint 1000 in the manner depicted in FIG. 42M, the implant 25 can be used as an attachment point for structural components of a spinal support system configured to support across the patient's hip structure and/or to support along the patient's spinal column. To serve as an attachment point for structural components of a spinal support system, a coupling element 2087 is connected to the proximal end 2011 of the sacroiliac joint implant 25. As a non-limiting example, the coupling element 2087 can be disposed in fixed relation to the proximal end 2011 of the sacroiliac joint implant 25 by threaded engagement of a fastener portion 2088; however, the invention is not so limited and the fastener portion 2088 can be connected to the first end 2011 of the sacroiliac joint implant 25 by any method such as welding, spin welding, adhesive, or the like. The coupling element 2087 can further provide a coupling portion 2089 configured to join with a numerous and wide variety of cross sectional geometries of spanning members 2090. As a non-limiting example, the coupling portion 2089 can be configured as cylindrical cup 2091 pivotally coupled to the fastener portion 2088. A spiral thread can be coupled to the internal surface of the cylindrical cup 2091 to rotationally receive a spirally threaded body 2092. The side wall 2093 of the cylindrical cup 2091 can include a pass through element 2094 in which part of a spanning member 2090 can be received. The part of the spanning member 2090 received within the pass through element 2094 can be placed in fixed relation to the cylindrical cup 2091 by rotational engagement of the spirally threaded body 2092.

Figure 52:
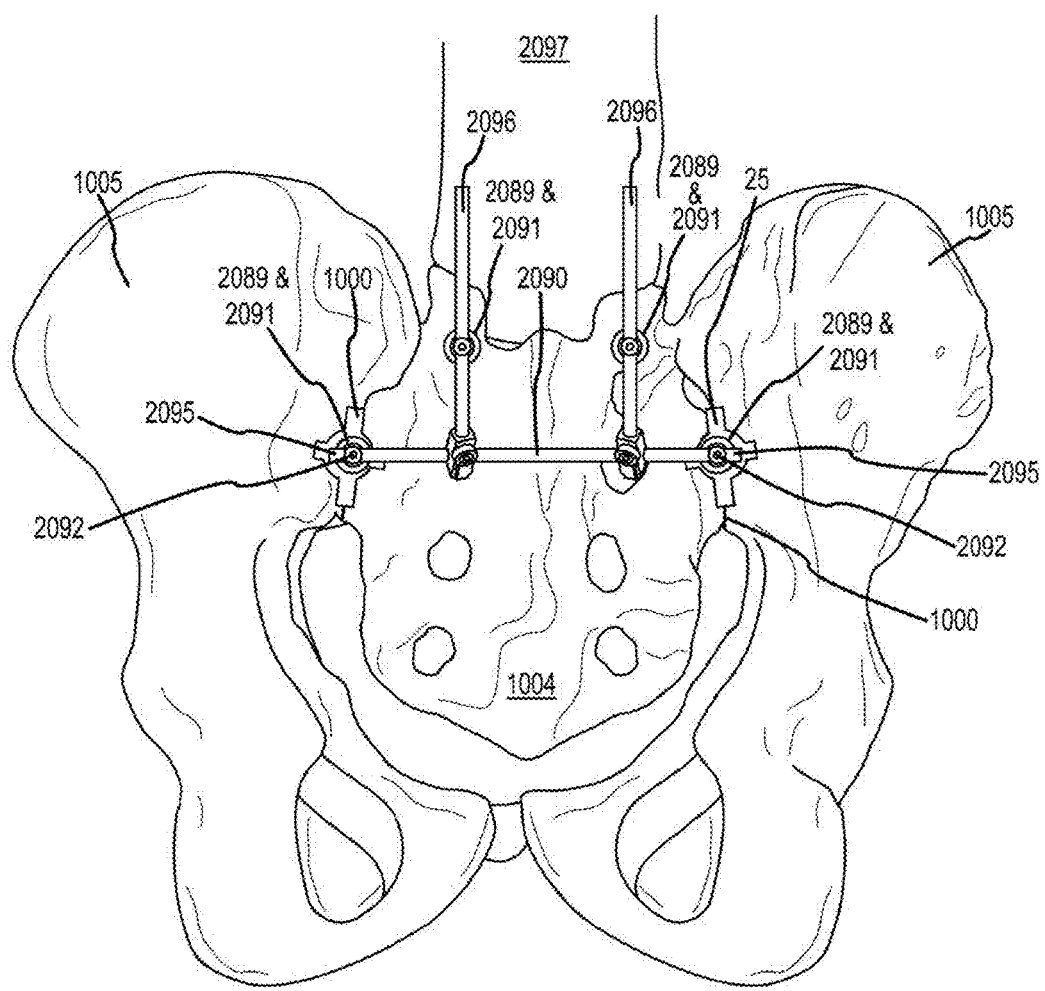
FIG. 52 is a posterior view of the patient's sacrum and ilia, wherein structural components of a spinal support system extend medial-lateral across the patient's hip structure and superiorly to support along the patient's spinal column.

FIG. 52 is a posterior view of the patient's sacrum 1004 and iliums 1005, wherein structural components of a spinal support system extend medial-lateral across the patient's hip structure and superiorly to support along the patient's spinal column. As shown in FIG. 52, in one embodiment, each of a pair of sacroiliac joints 1000 can receive an embodiment of the sacroiliac joint implants 25, disclosed herein, each having a coupling element 2087 coupled to the first end 2011. Each of the coupling elements 2087 can receive the opposed ends 2095 of a spanning member 2090. Additionally, the spanning member 2090 in fixed relation to the sacroiliac joint implants 25 can be connected to a plurality of additional spanning members 2096 which can as a non-limiting example be placed in positional relation to the vertebral column 2097 to allow support of additional implants which can be anchored between vertebrae.

Figure 53:
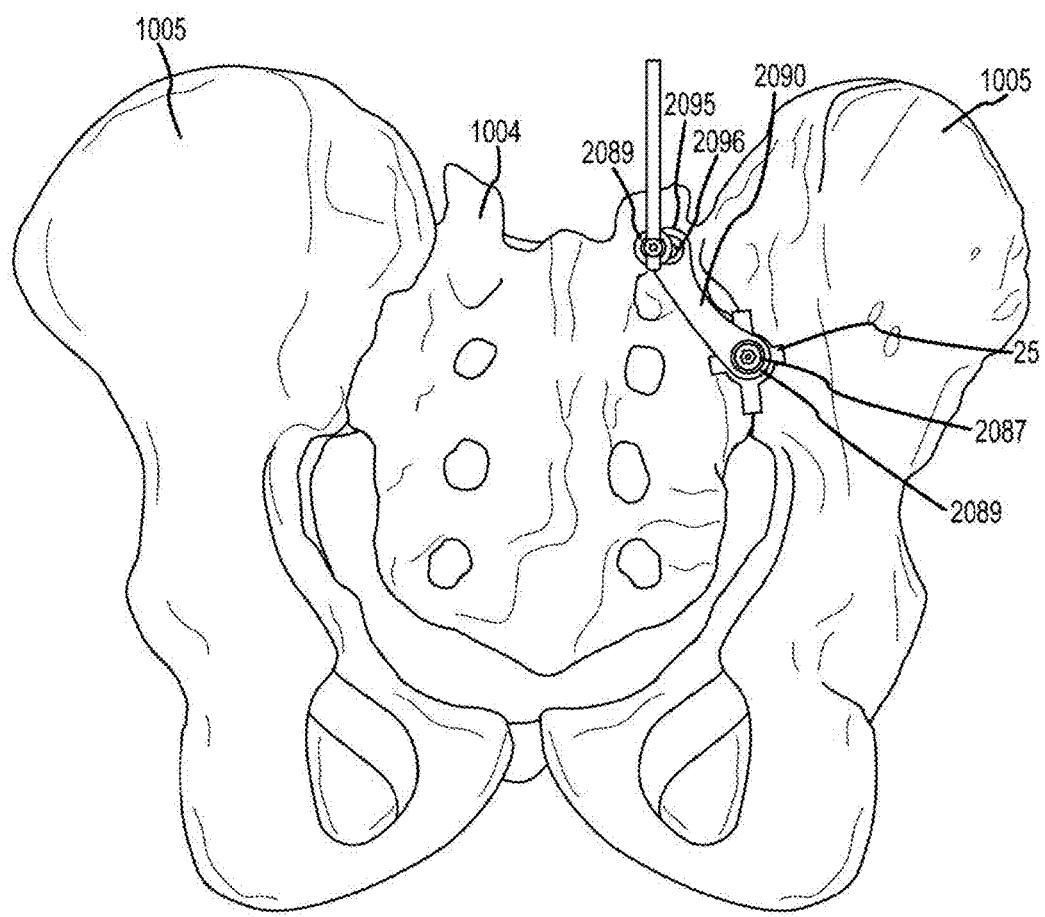
FIG. 53 is the same view as FIG. 52, except having a different spanning member structure.

FIG. 53 is the same view as FIG. 52, except having a different spanning member structure. As illustrated in FIG. 53, a first coupling element 2087 can be joined to the first end 2011 of an embodiment of a sacroiliac joint implant 25 as disclose herein and the fastener portion 2088 of a second coupling element 2087 can be disposed directly into the bone of the sacrum 1004 or the ilium 1005, or both. The opposed ends 2095 of a spanning element 2090 in the form of a flat plate can provide apertures 2096 through which the fastener portion 2088 of the coupling element 2087 can pass. The corresponding parts of the external surface of the coupling portion 2089 and the spanning member 2090 can be engaged to fix the location of the spanning member 2090 allowing for coupling of the lumbar spine to the stabilized pelvis by a plurality of fixation elements to further increase stability. As an example, fastener 2088 can be a pedicle screw and may be implanted in the S1 pedicle and angled generally anteriorly and generally parallel to the S1 endplate. Alternatively or additionally, fastener 2088 can be a S2AI screw and may be implanted in the sacrum, across the sacroiliac joint, and terminate in or through the ilium.

In one embodiment, the implant 25 and spanning element 2090 of FIG. 52 are a multi-piece arrangement as illustrated in FIG. 52 and assembled during the surgery. In another embodiment, the implant 25 and spanning element 2090 of FIG. 52 are in the form of an integral, unitary construction that is provided to the physician by a manufacturer in such an integral, unitary construction with the spanning element 2090 simply being an extension of a proximal region of the implant 25.

Similarly, in one embodiment, the implant 25 and spanning element 2090 of FIG. 53 are a multi-piece arrangement as illustrated in FIG. 53 and assembled during the surgery. In another embodiment, the implant 25 and spanning element 2090 of FIG. 53 are in the form of an integral, unitary construction that is provided to the physician by a manufacturer in such an integral, unitary construction with the spanning element 2090 simply being an extension of a proximal region of the implant 25.

Figure 54:
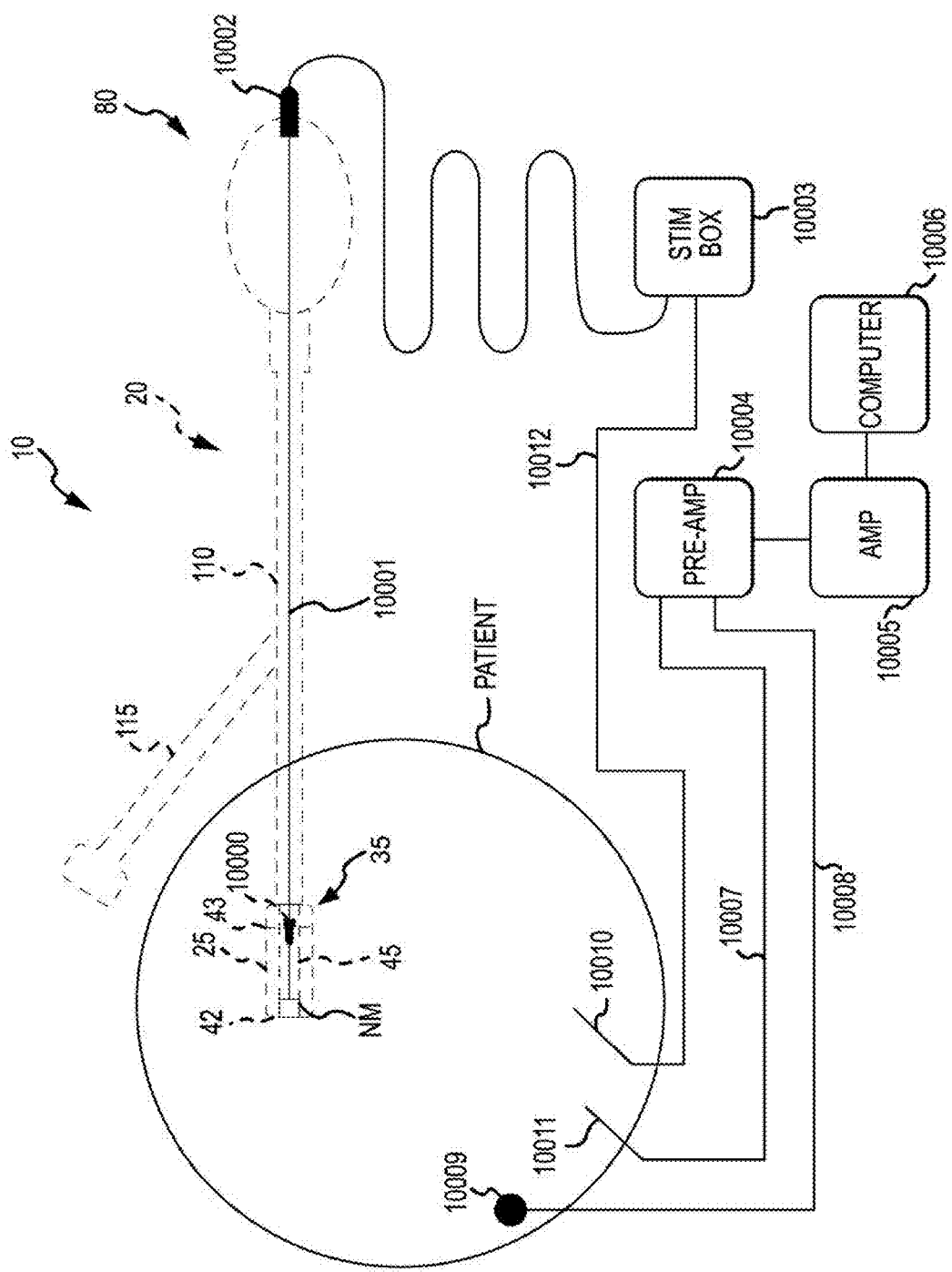
FIG. 54 is a schematic depiction of a system for fusing a joint, wherein the joint implant includes an electrode in electrical communication with a nerve sensing system.

In one embodiment, as schematically depicted in FIG. 54, the implant 25 may be configured to include a stimulating electrode (NM) connected to an internal controllable power source or external controllable power source. For example, the external controllable power sources may be either in the delivery system instrumentation 20 itself or a separate controller unit located in the operating suite and electrically coupled to the implant supported electrode NM via electrical conductors extending through the implant body and the shaft 100 of the delivery system 20 to electrically couple to the separate controller unit via a cable extending proximally from the delivery system 20 to the separate controller. With the exception of the electrode (NM) itself, the entirety of the rest of the implant surfaces may be electrically insulated so as to prevent current shunting into surrounding tissues or the operator.

In one embodiment, the stimulating electrode (NM) during navigation can have an amperage of about 8 milliamps (mA) or, nearing final placement, an amperage of about 1-4 mA and, in certain cases, up to 5 mA. The electrode (NM) may be attached to or at least partially imbedded in implant 25 (either permanently or retrievable/removable after implantation) (or according to particular embodiments, located within, near or on the anchor 30, probe 1054, on or within a trial, broach, drill or other tools of system 10) to reduce the risk to the patient of iatrogenic damage to the nervous system by using intraoperative neurophysiological monitoring, for example electromyography (EMG), which is able to alert the surgeon or technician reliably and in real-time of implant 25 advancing beyond, for example, inferior boundary segment 3002 or beyond anterior-inferior corner 3010.

As illustrated in FIG. 54, which is a schematic depiction of a joint implantation system 10 configured for nerve stimulating and sensing, in one embodiment, the system 10 includes a joint implant 25, a delivery tool 20, a nerve stimulating system 10003, a pre-amplifier unit 10004, an amplifier unit 10005, a computer 10006, and an electrical conductor pathway 10001. The joint implant 25 includes an electrode NM and a body 45 including a distal end 42 and a proximal end 43 opposite the distal end. The electrode NM is supported on the implant 25. The delivery tool 20 includes an implant arm 110 with a distal end 35 configured to releasably couple to the proximal end 43 of the body 45 of the joint implant 25. The nerve stimulating system 10003 is configured to stimulate electrode NM in order to sense nerve contact made with the electrode NM or when NM is approaching and near a nerve. The electrical conductor pathway 10001 extends from the electrode NM along the implant 25 and implant arm 110 to the nerve stimulating system 10003. The electrical conductor pathway 10001 places the electrode NM and nerve stimulating system 10003 in electrical communication.

A sensing (or recording) electrode 10011 can be placed in, for example, a quadriceps femoris, tibialis anterior, gastrocnemius, or abductor hallucis muscle and may be coupled to an electrical conductor pathway 10007 that extends to the pre-amplifier 10004. A reference electrode 10010 can also be placed in, for example, a quadriceps femoris, tibialis anterior, gastrocnemius, or abductor hallucis muscle, but in a location between the area subject to stimulation from the stimulating electrode (NM) and the sensing (or recording) electrode 10011; and may be coupled to an electrical conductor pathway 10012 that extends to the nerve stimulating system 10003. An additional needle 10009 can be placed in proximity to the aforementioned needles (i.e., electrodes 10010, 10011) within a muscle (or when the electrode is in the form of a patch it may be applied to the skin of the patient) and may be coupled to an electrical conductor pathway 10008 that extends to the pre-amplifier 10004 and a ground.

The pre-amplifier 10004 may be connected to the amplifier 10005 that itself may be connected to the computer unit 10006. The computer unit 10006 may process or interpret the signal from the amplifier 10005 and display or otherwise alert (e.g., auditory signals with varying amplitude or frequency) or convey to an observer or operator in an operating suite or to a monitoring physician in a remote location (e.g., by employing computer software and processing and networking hardware) the state of the various electrical connections and pathways (e.g., connected versus disconnected) and electrical activity caused by the stimulating electrode NM.

In one embodiment, the proximal end 43 of the implant 25 and the distal end 35 of the implant arm include a cooperatively mating electrical connection 10000 that form a segment of the electrical conductor pathway 10001. An example of such a cooperatively mating electrical connection includes a male-female pin contact assembly 10000. The proximal end 80 of the delivery tool 20 and a distal end of an electrical conductor segment of the pathway 10001 between the sensing system 10003 and the proximal end 80 include a cooperatively mating electrical connection 10002 that form a segment of the electrical conductor pathway 10001. The electrical conductor pathway 10001 may be in the form of one or more multi-filar cables, one or more solid core wires, etc. The electrode NM is at or near the distal end 42 of the implant 25 and the rest of the implant (or only an area directly surrounding the electrode NM) has an electrically insulative coating or is formed of an electrically nonconductive material.

Figure 55A:
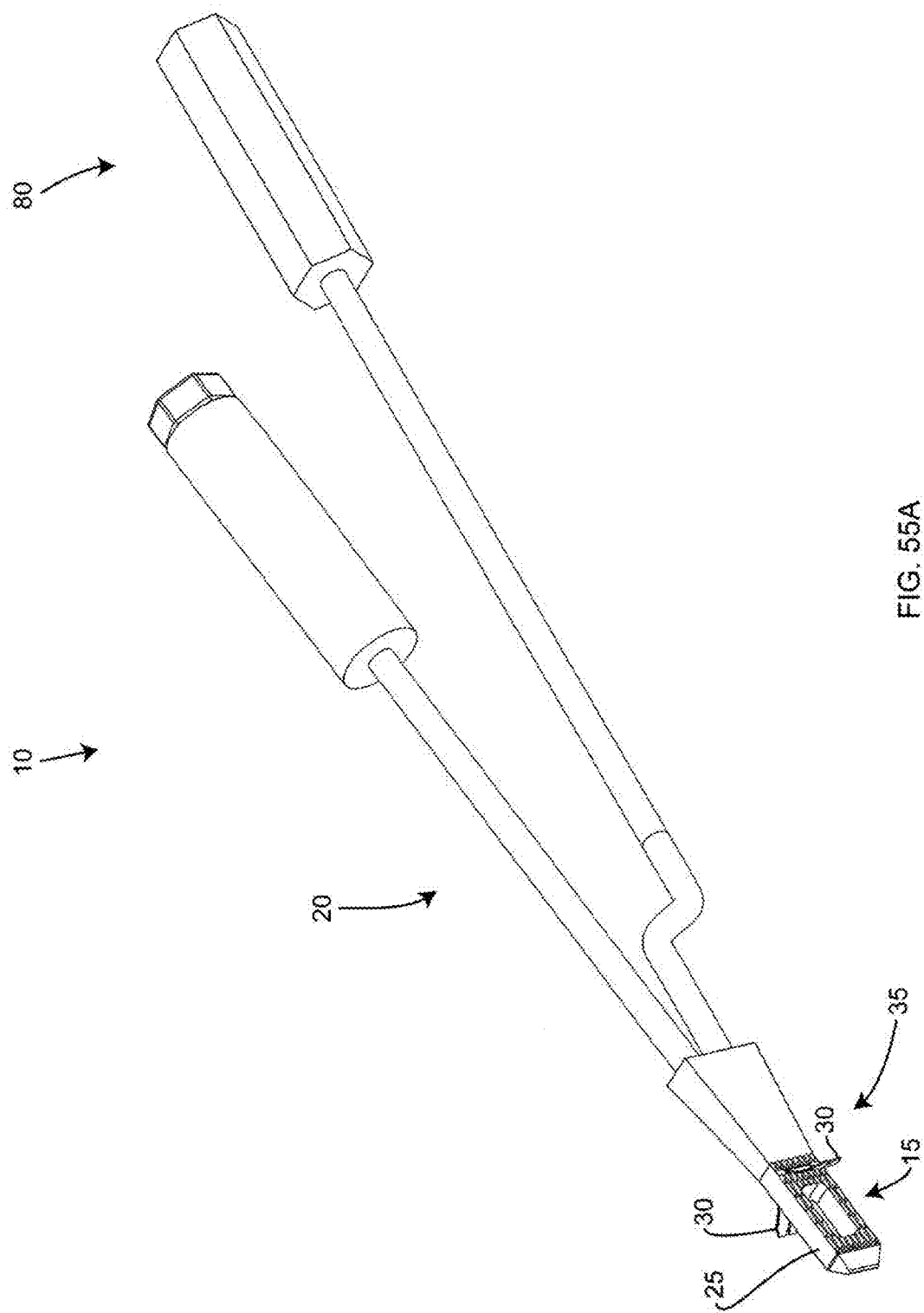
FIG. 55A is an isometric view of a second embodiment of a system for fusing a sacroiliac joint.
Figure 55B:
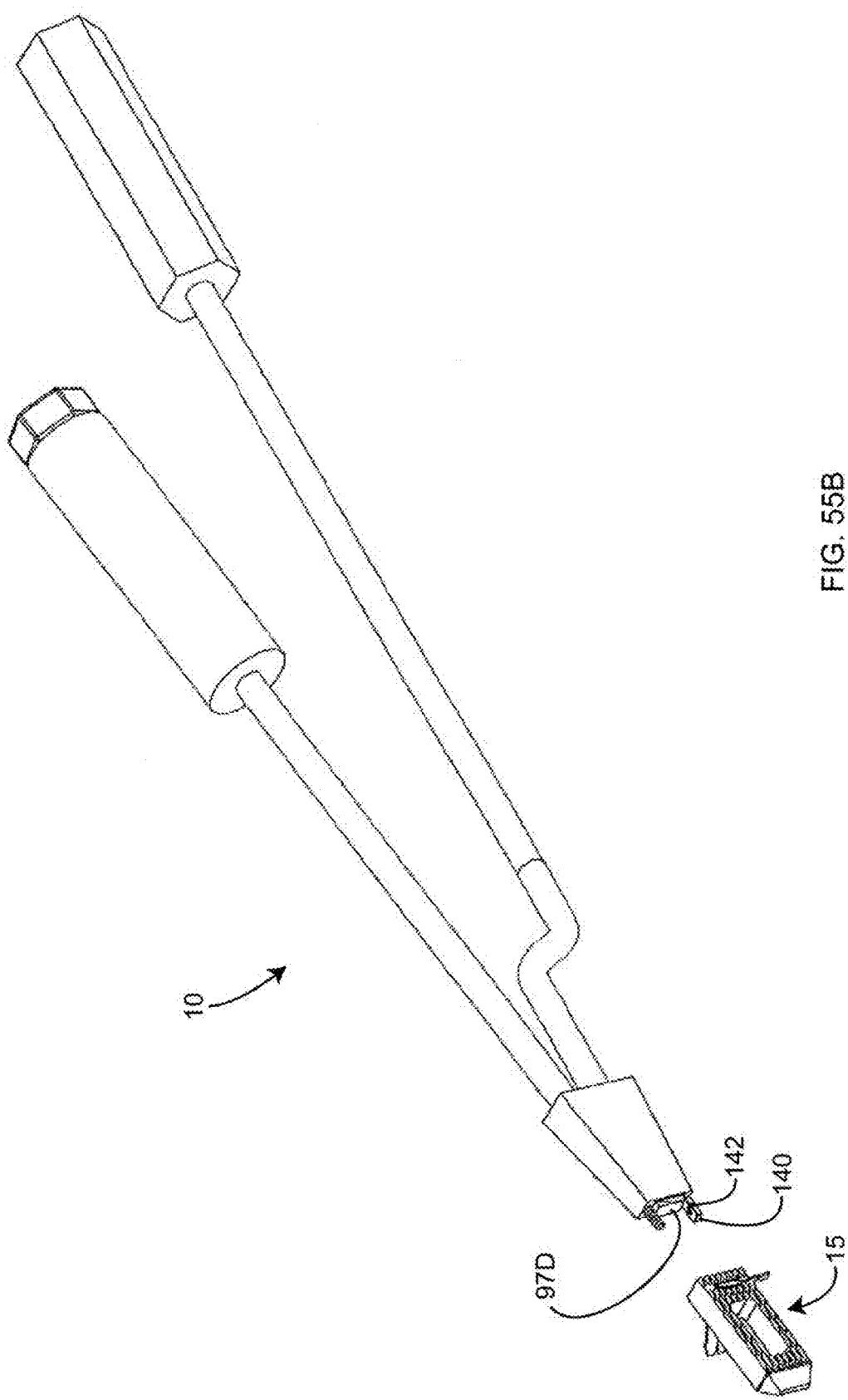
FIG. 55B is the same view as FIG. 55A, except the delivery tool and implant assembly are decoupled from each other.
Figure 56:
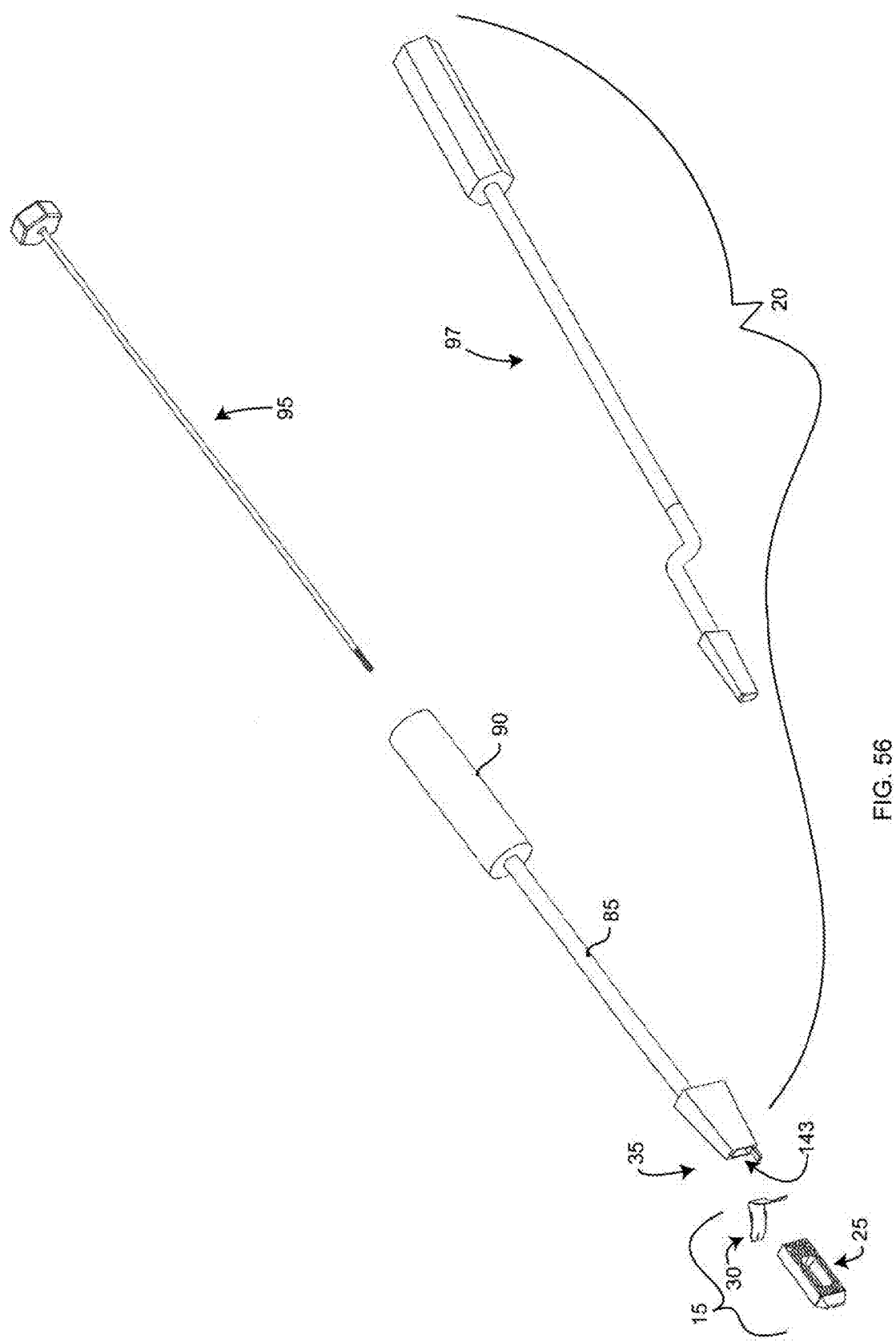
FIG. 56 is the same view as FIG. 55A, except the system is exploded to better illustrate its components.
Figure 57A:
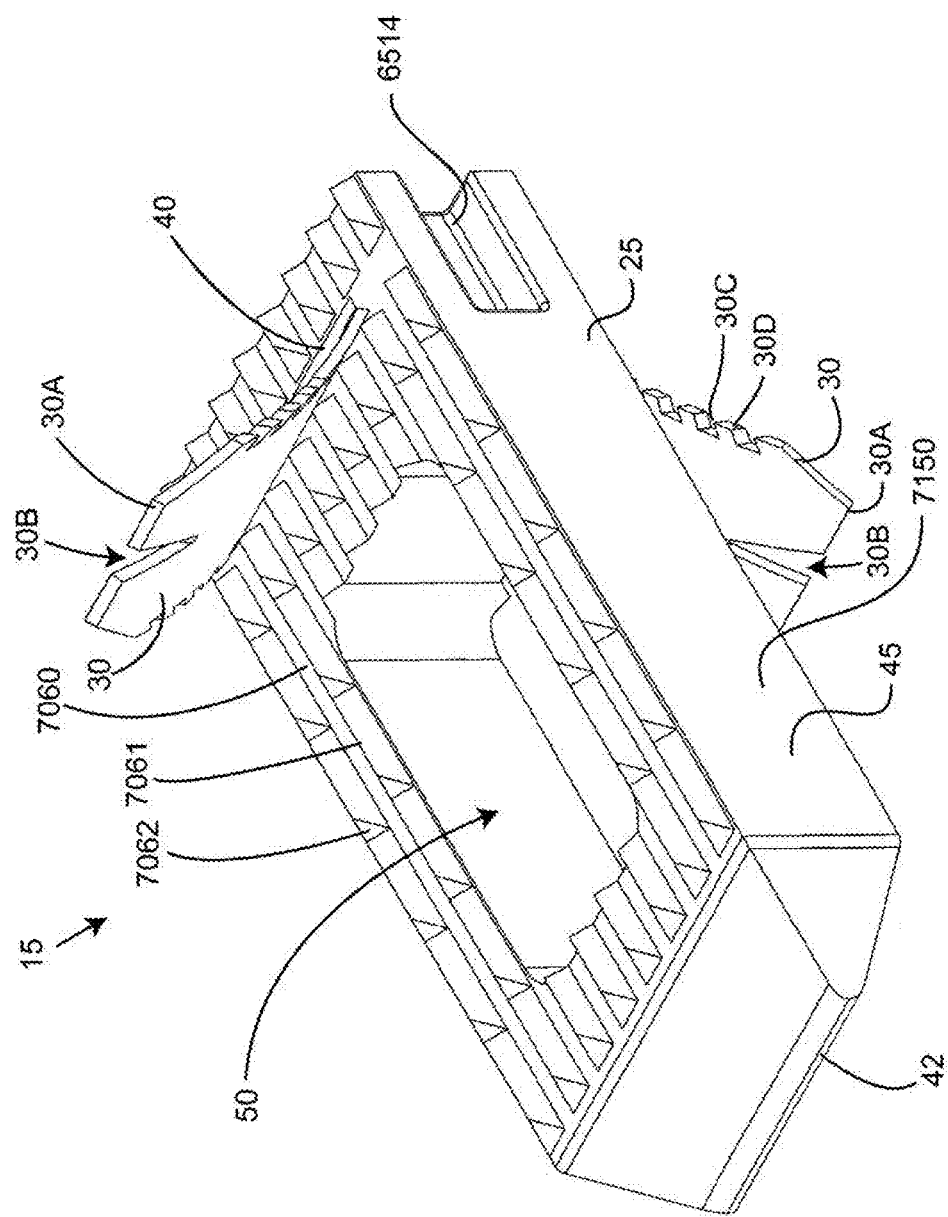
FIGS. 57A-57F are, respectively, distal isometric, proximal end elevation, first side elevation, second side elevation opposite the first side elevation, plan and distal end elevation views of the implant assembly, which has a body that is generally rectangular.
Figure 57B:
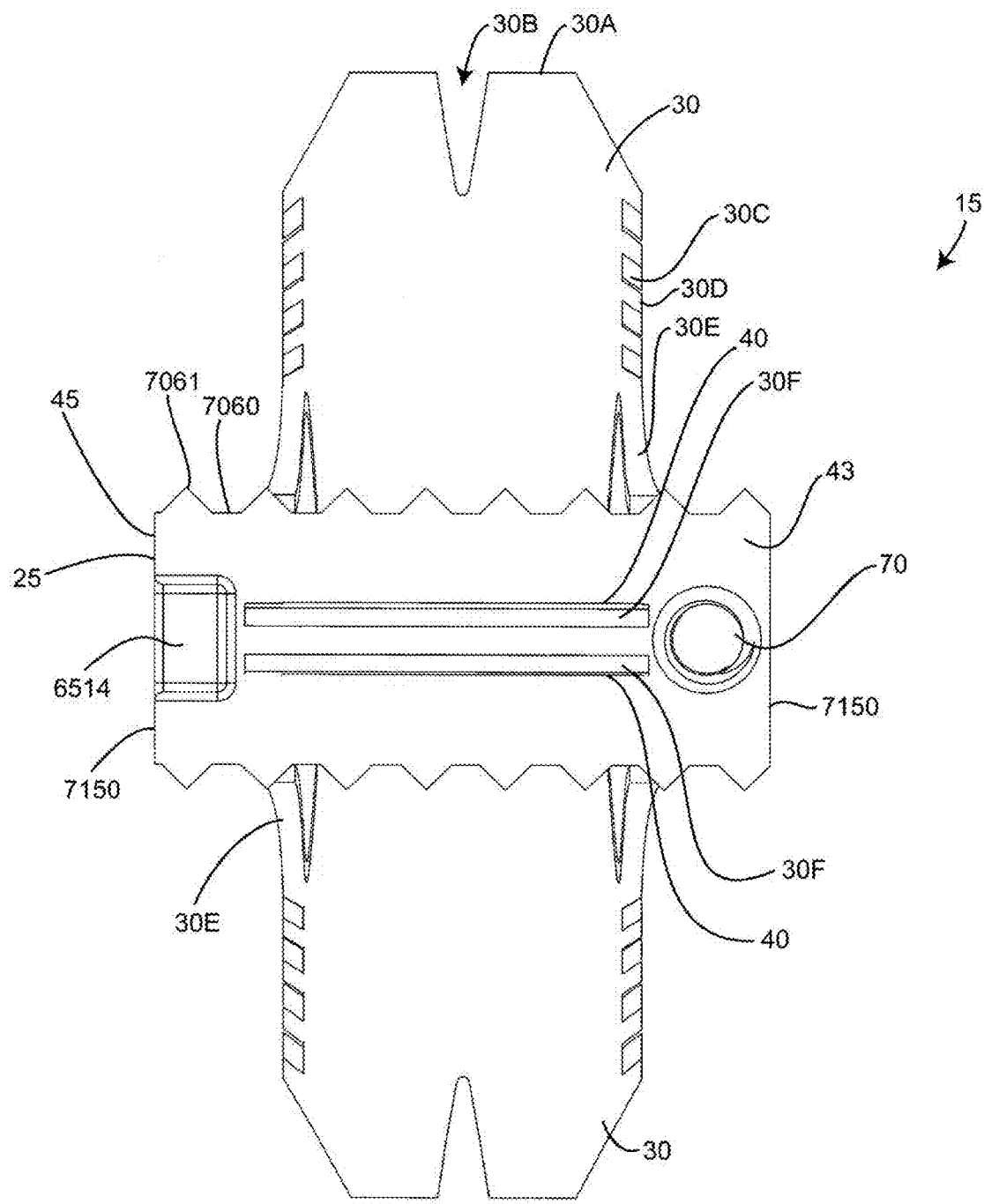
Figure 57C:
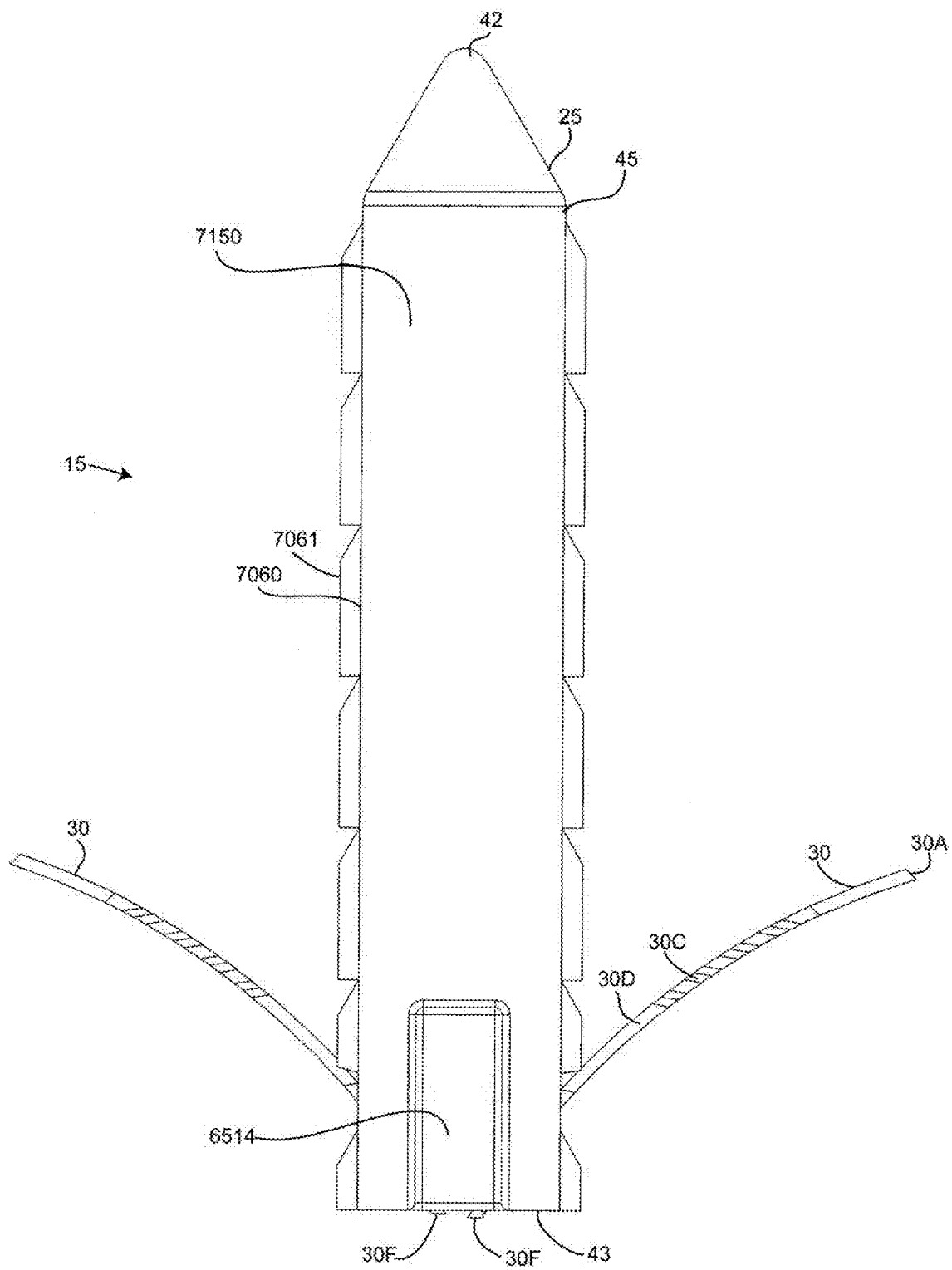
Figure 57D:
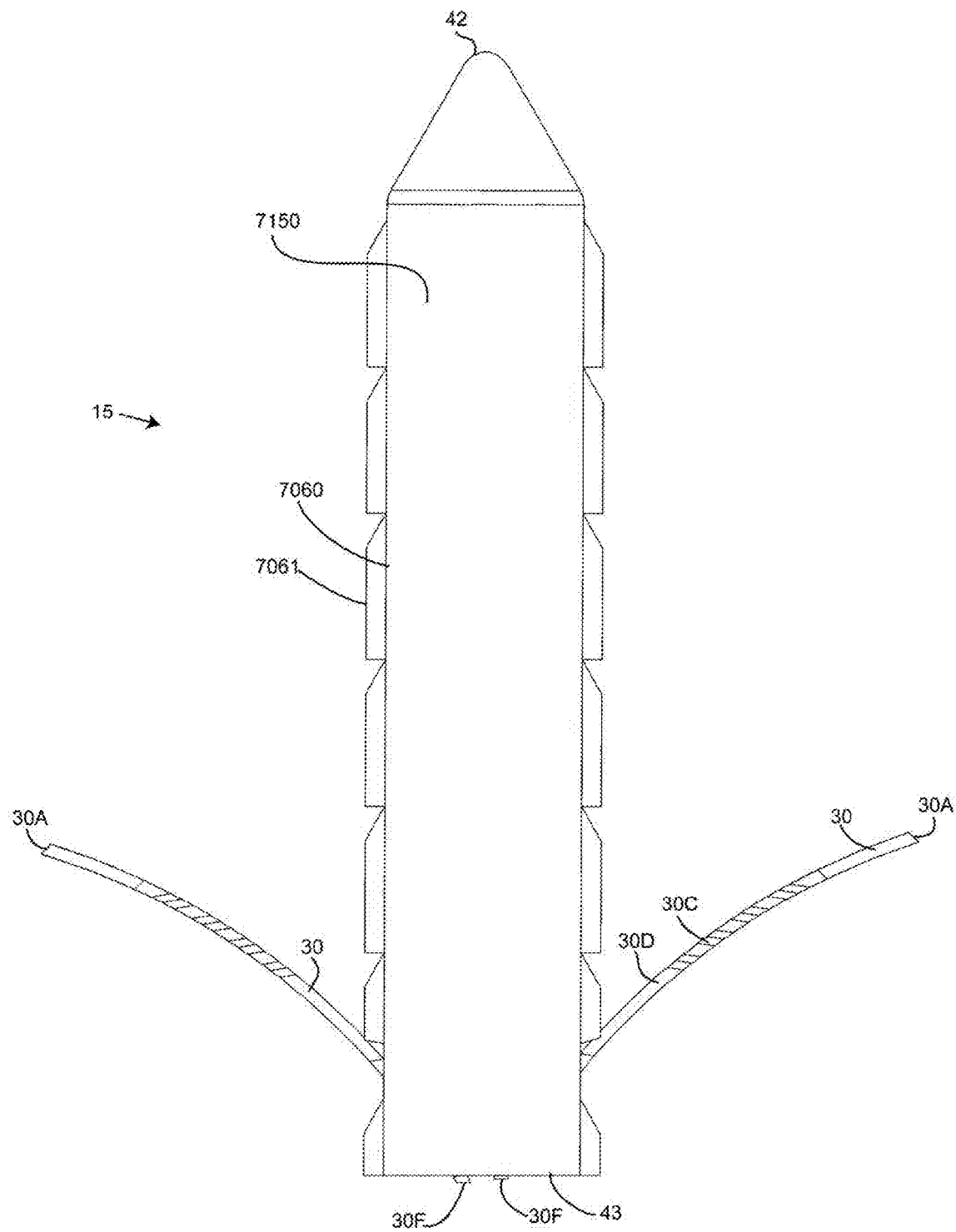
Figure 57E:
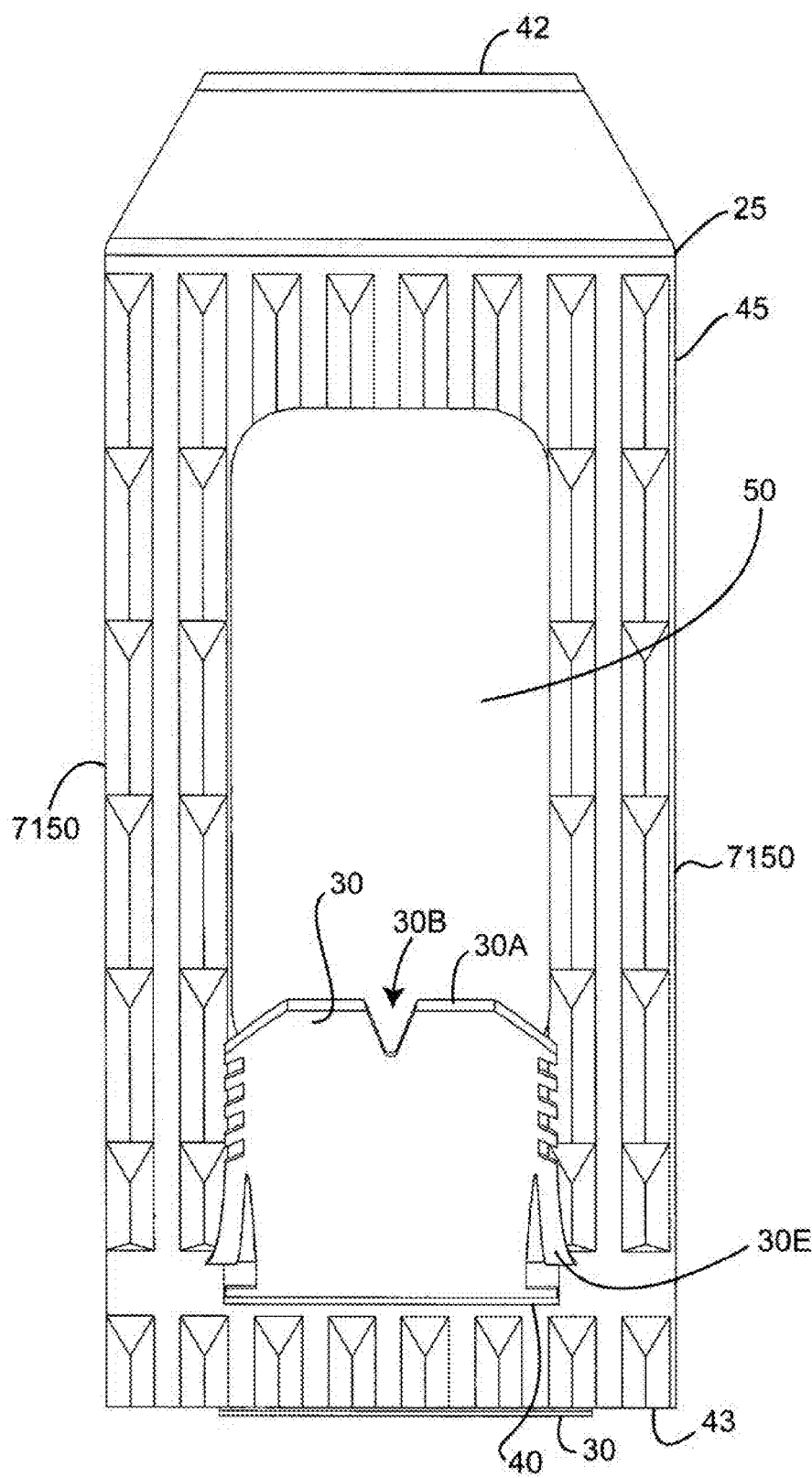
Figure 57F:
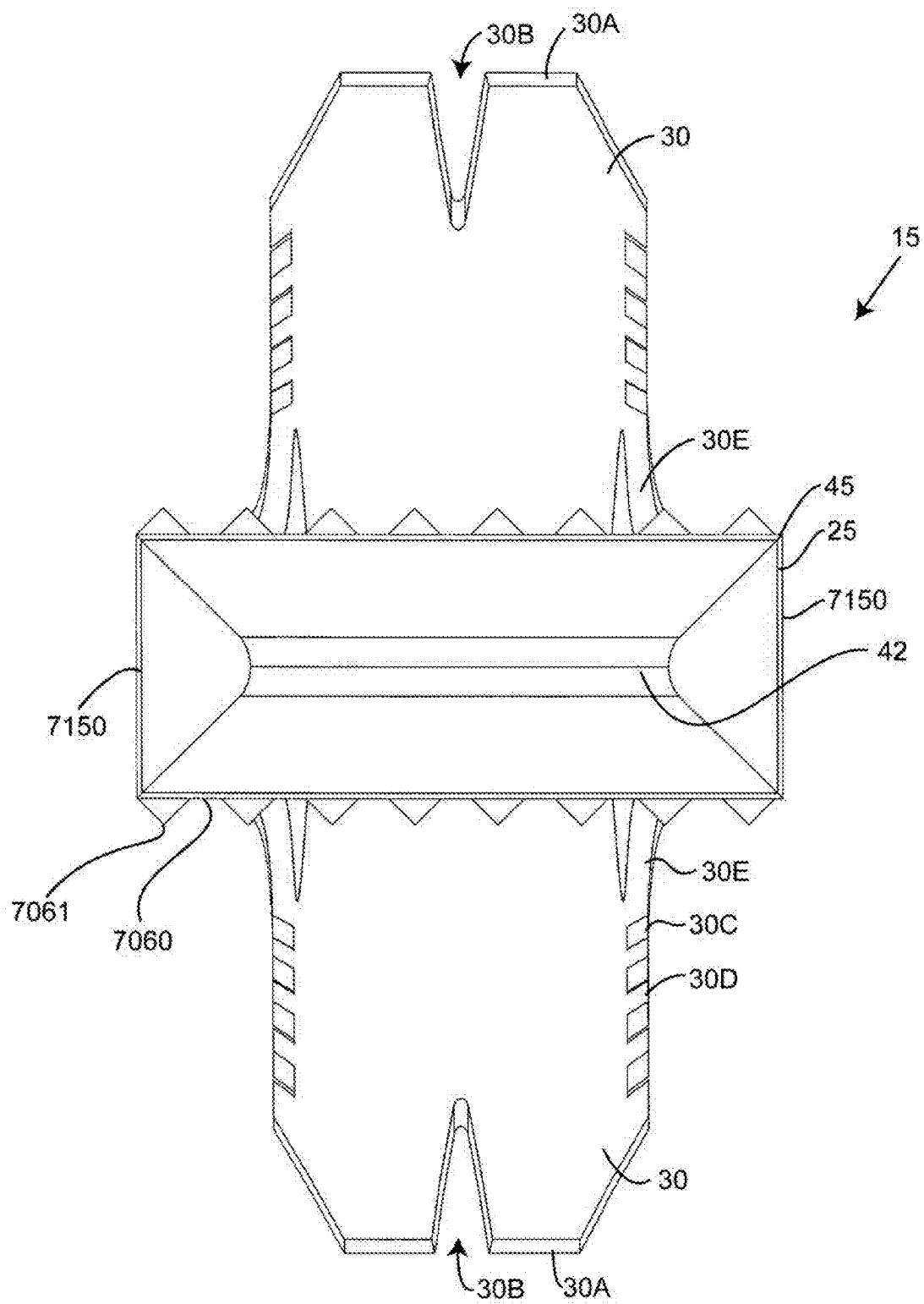

To begin a detailed discussion of a second embodiment of the system 10, reference is made to FIGS. 55A-56. FIG. 55A is an isometric view of the system 10. FIG. 55B is the same view as FIG. 55A, except an implant assembly 15 of the system 10 is separated from a delivery tool 20 of the system 10. FIG. 56 is the same view as FIG. 55A, except the system 10 is shown exploded to better illustrate the components of the system 10.

As can be understood from FIGS. 55A and 55B, the system 10 includes a delivery tool 20 and an implant assembly 15 for implanting at the sacroiliac joint via the delivery tool 20, the implant assembly 15 being for fusing the sacroiliac joint. As indicated in FIG. 56, the implant assembly 15 includes an implant 25 and anchor elements 30 (e.g., self-locking blades or other elongated bodies slidably extendable from the implant body). As discussed below in greater detail, during the implantation of the implant assembly 15 at the sacroiliac joint, the implant 25 and anchor element 30 are supported by a distal end 35 of the delivery tool 20, as illustrated in FIG. 55A. In one embodiment, the distal end 35 may be fixed or non-removable from the rest of the delivery tool 20. In other embodiments, the distal end 35 of the delivery tool 20 may be removable so as to allow interchanging of different sized or shaped distal ends 35 to allow matching to particular implant embodiments without requiring the use of a different delivery tool 20. The delivery tool 20 is used to deliver the implant 25 into the sacroiliac joint space. The delivery tool 20 is then used to cause the anchor elements 30 to deploy or otherwise extend from the sides of the implant 25 and into the bone of the ilium and sacrum defining the sacroiliac joint. The delivery tool 20 is then decoupled from the implanted implant assembly 15, as can be understood from FIG. 55B.

To begin a detailed discussion of components of an embodiment of the implant assembly 15, reference is made to FIGS. 57A-57F, which are various isometric, end elevation, side elevation, and plan views of the implant assembly 15. As shown in FIGS. 57A-57F, the implant assembly 15 includes an implant 25 and anchor elements 30. In one embodiment, the anchor elements 30 may be in the form of an self-locking blades 30 or other elongated bodies slidably extendable from the implant body.

As indicated in FIGS. 57A-57F, the anchor elements 30 are configured to be received in bores 40 defined through the implant 25. The bores 40 extend through the implant 25 distally and laterally from a proximal end 43 of the implant 25 and are sized such that the anchor elements 30 can at least project both laterally and distally from the sides of the implant 25 as illustrated in FIGS. 57A-57F. In one embodiment, the anchor elements 30 may be generally blade-like members 30 that are substantially wider and longer than thick. Where the anchor elements 30 are blade-like, the bores 40 may then be slots 40 that are shaped to match the blade-like anchor elements 30 received therein. Each blade-like member 30 may have a slight curvature along its length that matches the slight curvature of the slot 40 in which the blade-like member 30 is received, as can be understood from FIG. 61, which is a longitudinal cross section of the implant 25 as taken along section line 61-61 in FIG. 60.

As can be understood from FIGS. 57A-57F, the blade-like anchor members 30 may have a distal or leading edge 30A with a notch 30B defined therein. Serrations or other anti-migration features 30C may be defined in the side edges 30D of the members 30. Locking tabs 30E may extend from the side edges 30D of each member 30 to bias outwardly once free of the confines of the slot 40 after the member 30 has been sufficiently distally displaced out of the slot 40. By biasing outwardly to have an overall width that is greater than the width of the corresponding slot 40, the locking tabs 30E prevent the proximal migration of the member 30 within the slot 40. By applying a distal acting force on the blunt proximal end 30F of a member 30, the member 30 may be caused to slide distally within its slot 40 to cause the distal end 30A of the member 30 to project distally and laterally from the implant body 45, such projection being capable of anchoring the implant assembly 15 into bone defining the sacroiliac joint space.

Figure 58:
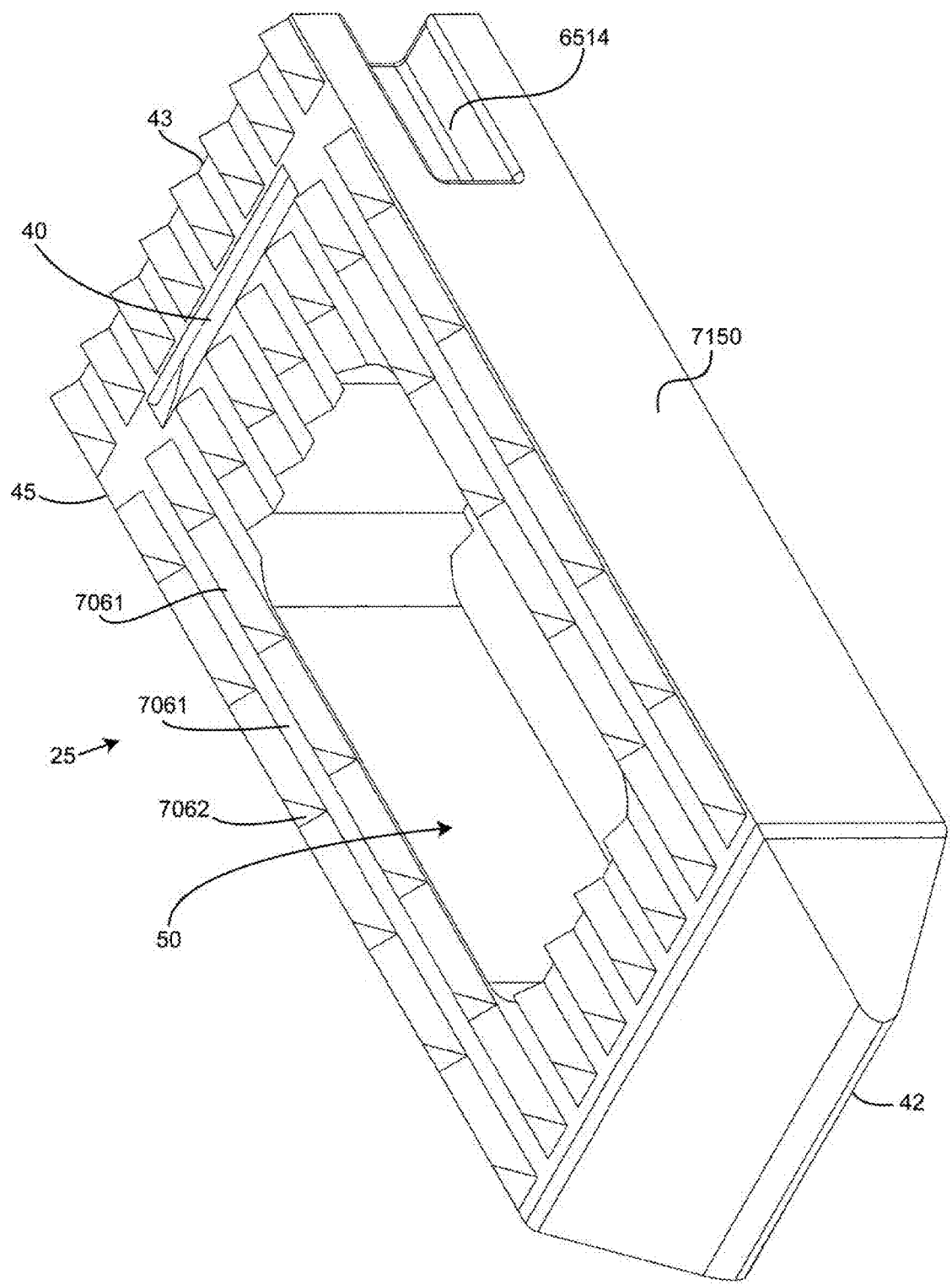
FIG. 58 is a distal end isometric view of the implant of the implant assembly of FIGS. 57A-57F.
Figure 59:
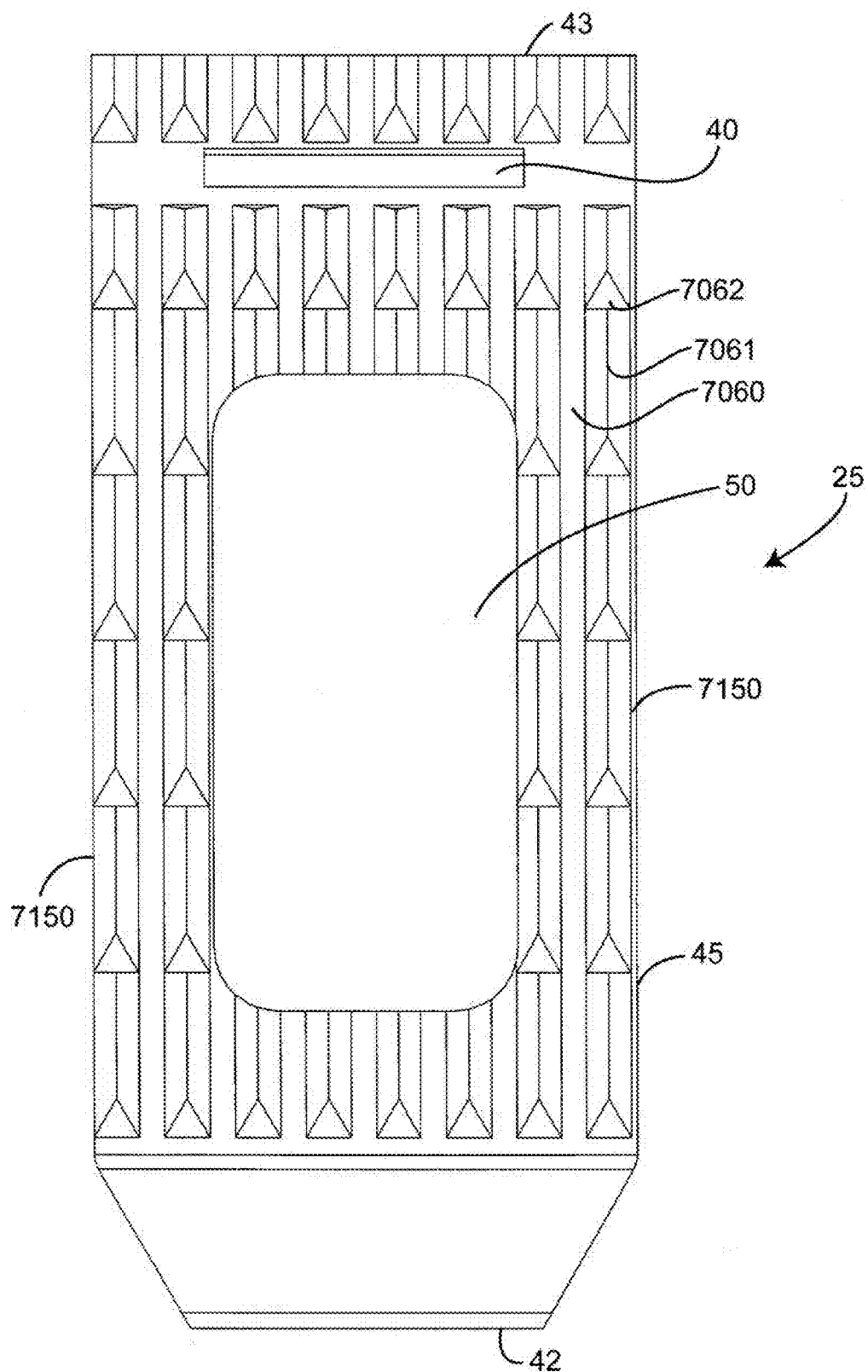
FIG. 59 is a lateral side plan view of the implant of the implant assembly of FIGS. 57A-57F.
Figure 60:
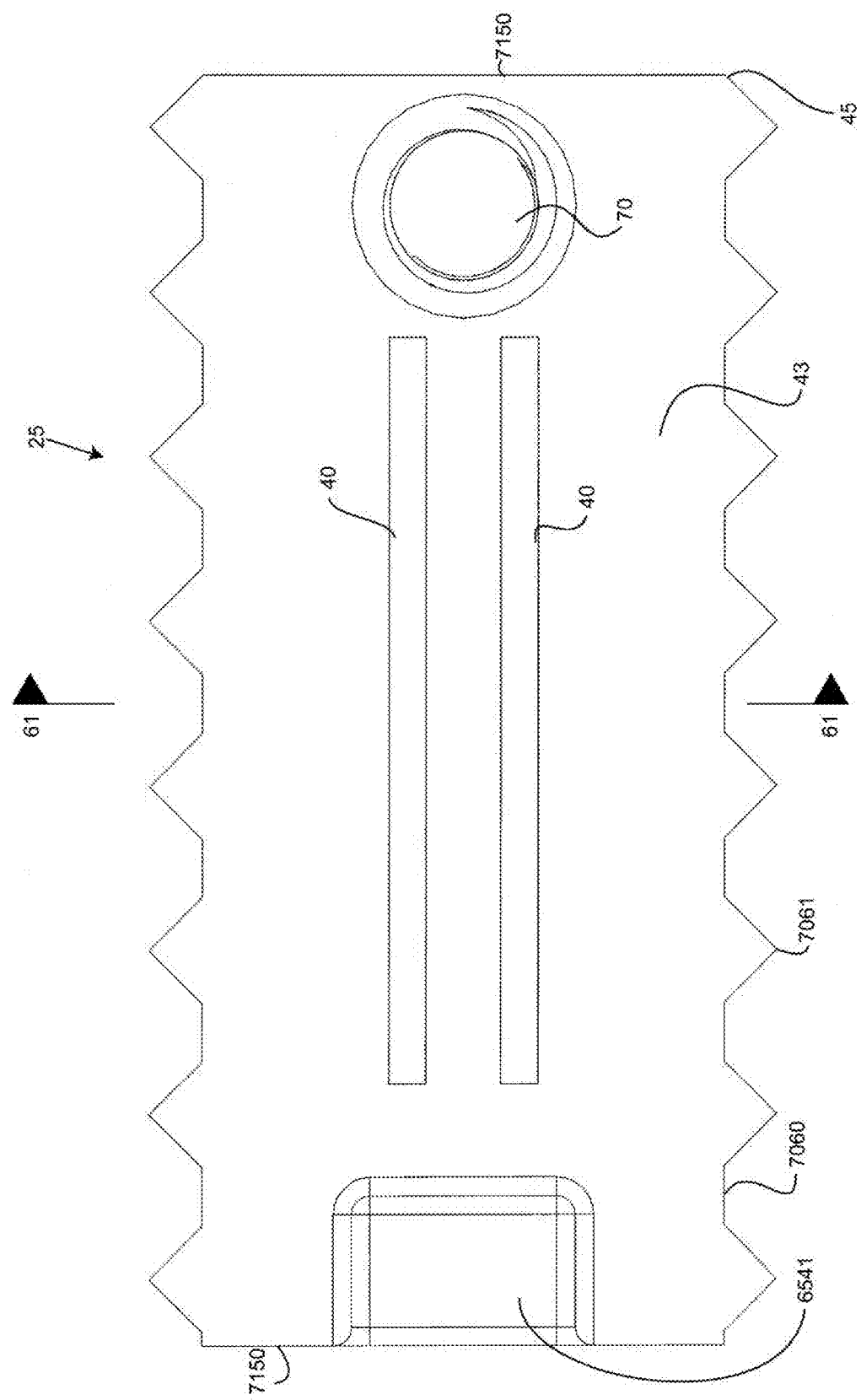
FIG. 60 is a proximal end elevation of the implant of the assembly of FIGS. 57A-57F.
Figure 61:
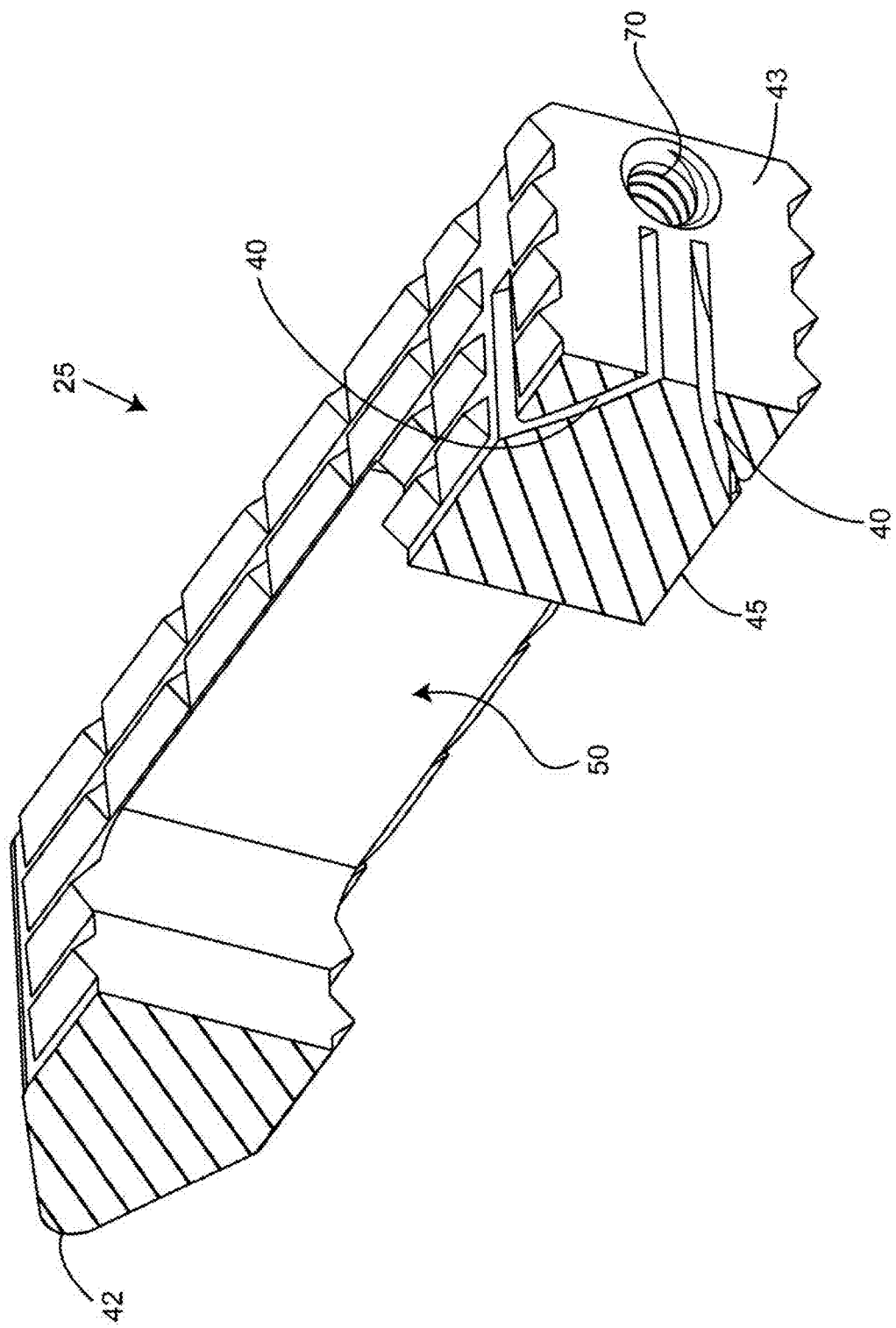
FIG. 61 is a longitudinal cross section of the implant as taken along section lines 61-61 in FIG. 60.

For a detailed discussion of the implant 25 of the implant assembly 15 discussed above with respect to FIGS. 57A-57F, reference is made to FIGS. 58-61. FIG. 58 is an isometric view of the implant 25. FIGS. 59 and 60 are, respectively, plan and proximal end elevation views of the implant 25. FIG. 61 is an isometric longitudinal cross section of the implant 25 as taken along section lines 61-61 in FIG. 60.

As shown in FIGS. 58-61, in one embodiment, the implant 25 includes a distal or leading end 42, a proximal or trailing end 43, a longitudinally extending body 45, slots 40 extending distally and laterally through the body from the proximal end 43, an attachment bore 70, and an opening 50. In one embodiment, as reflected in FIGS. 58-61, the implant body 45 has a generally rectangular box shape. However, in other embodiments similar to that discussed above with respect to FIGS. 5-15, the implant body 45 may be configured to have a shape that generally mimics and even substantially fills a sacroiliac joint space.

As illustrated in FIG. 60, the implant 25 includes a proximal end 43 for being removably coupled to the extreme distal end 35 of the delivery tool 20. Specifically, in one embodiment, the implant proximal end 43 includes an attachment bore 70 that extends distally through the implant from the proximal end 43. The attachment bore 70 may be a blind hole in that it only has a single opening, which is at the proximal end 43. Alternatively, the attachment bore 70 may be configured as a hole that communicates between the implant proximal end 43 and implant opening 50. The attachment bore 70 may be threaded or otherwise configured so as to allow mechanical engagement with a distal end 220 of a retainer member 95 of the delivery tool 20, the retainer member 95 being used to secure the implant 25 off of the distal end 35 of the delivery tool 20, as described in detail below. In one embodiment, the attachment bore 70 has a diameter of between approximately 2 mm and approximately 10 mm, with one embodiment having a diameter of approximately 5 mm.

In one embodiment, the implant 25 can be configured such that the body 45 of the implant is a generally continuous solid surface with the exception of the slots 40 and bore 70 extending through portions of the body 45. However, as illustrated in FIGS. 58 and 60, in other embodiments, the body 45 of the implant 25 may have one or more openings or voids defined in the body 45. For example, an opening or void 50 may be defined in the implant body 45. The void 50 may be packed with bone growth material prior to the implant 25 being delivered into the sacroiliac joint space.

As indicated in FIGS. 58-60, the implant body 45 includes side edge surfaces 7150 that extend between the proximal end 43 and the distal end 42. These side edge surfaces 7150 and the similar side edge surfaces associated with the distal end 42 and proximal end 43 combine to define side edge surface boundary that extends unbroken and unitary through all of the above-mentioned regions of the implant, thereby forming an outer boundary that may at least somewhat resemble a rectangle. In other embodiments, the outer boundary formed by the side edge surfaces may resemble other shapes including, for example, a circle, an oval or etc. In one embodiment, the outer boundary formed by the side edge surfaces may even resemble the sacroiliac joint space as discussed above with respect to FIGS. 5-15, thereby allowing the implant 25 to more fully occupy the joint space than more linearly shaped rectangle and cylindrical implant embodiments.

As illustrated in FIGS. 58-61, in one embodiment, the implant body 45 includes generally planar lateral side surfaces 7060. In some embodiments, the lateral side surfaces 7060 may be generally spaced apart by a distance or body thickness that is generally continuous over the entirety of the surfaces 7060. However, in some embodiments, the distance or body thickness may taper from a greater thickness in some regions of the body to a lesser thickness in other regions of the body.

In one embodiment, the planar lateral side surfaces 7060 may be substantially smooth. However, in other embodiments, as indicated in FIGS. 58-61, the planar lateral side surfaces 7060 may have multiple parallel ridges 7061 that extend longitudinally along the long portion 7100 and may be serrated with notches 7062 oriented so as to prevent proximal migration of the implant 25 once implanted in the sacroiliac joint. The anti-migration features 7062 are generally evenly distributed along the planar surfaces 7060. While the anti-migration features 7062 are depicted as being notches 7062 defined in the longitudinally extending ribs or ridges 7061, in other embodiments the anti-migration features 7062 may be in the form of other types of surface texturing or protrusions in the form of cylinders, trapezoids, squares, rectangles, etc. Further, although the anti-migration features 7062 are depicted in the form of unidirectional serrated notches 7062 in ridges 7061 on the planar lateral side surfaces 7060 the implant 25, the invention is not so limited and, as to particular embodiments, can be configured to have said features 7062 arranged in multiple directions, unidirectional, or a combination of multiple direction on some surfaces of the implant and unidirectional on other surfaces of the implant. Accordingly, the features 7062 can be so arranged on the various surfaces of the implant so as to prevent undesired migration in particular directions due to the forces present at the sacroiliac joint 1000.

As indicated in FIGS. 58 and 60, a longitudinally extending rectangular notch 6514 may be defined in a side edge surface 7150. As described below, such a notch 6514 may interact with a member 140 forming part of the delivery tool distal end 35 so as to help retain the implant 25 on the distal end 35 and to prevent the implant from rotating relative to the distal end 35 when the retaining rod threaded distal end 220 is being threaded into or out of the attachment bore 70.

As can be understood from FIGS. 58-61, in one embodiment, the slots 40 extend distally and laterally from a proximal end 43 of the implant 25 to daylight distally in the planar lateral side surfaces 7060, thereby exiting the implant body 45 laterally as slots 40 defined in the planar lateral side surface 7060. Since the slots 40 are oriented so as to extend distally and laterally from the proximal end 43 and, further, since the blade-like anchors 30 have sufficient length, the anchors 30 project both laterally and distally from the planar lateral side surfaces 7060 of the implant 25, as illustrated in FIGS. 57A-57F.

In one embodiment, the implant 25 may be machined, molded, formed, or otherwise manufactured from stainless steel, titanium, ceramic, polymer, composite, bone or other biocompatible materials. The anchor member 30 may be machined, molded, formed or otherwise manufactured from similar biocompatible materials.

As to particular embodiments as shown in FIGS. 57A-61, and in other embodiments as disclosed throughout, the implants described herein can be configured to be used as trials during certain steps of the procedure to determine appropriate implant sizes and to allow a physician, who is presented with a kit containing the delivery system 20 and multiple sizes and configurations of the implant 15, to evaluate particular embodiments of an implant as described herein that would be best suited to a particular patient, application or implant receiving space.

The particular embodiments of FIGS. 57A-61 depict implant assemblies 15 having an implant 25 with a generally planar body 45 such that the width and length of the body 45 are substantially greater than the thickness of the body 45 and the planar body 45 is generally free of any substantial features of the body extending away from the planar lateral side surfaces 7060. However, in other embodiments, the implant body 45 of the present disclosure may have the anchoring arrangement illustrated in FIGS. 57A-61 and further be configured to have a shape and/or radially extending wings as described with respect to any of the many implant body embodiments described in U.S. patent application Ser. No. 13/475,695, which was filed May 18, 2012 and is hereby incorporated by reference in its entirety.

To begin a detailed discussion of components of an embodiment of the delivery tool 20, reference is again made to FIGS. 55A-56. As shown in FIG. 55A, the delivery tool 20 includes a distal end 35 and a proximal end 80. The distal end 35 supports the components 25, 30 of the implant assembly 15, and the proximal end 80 is configured to be grasped and manipulated to facilitate the implantation of the implant assembly 15 in the sacroiliac joint.

Figure 62A:
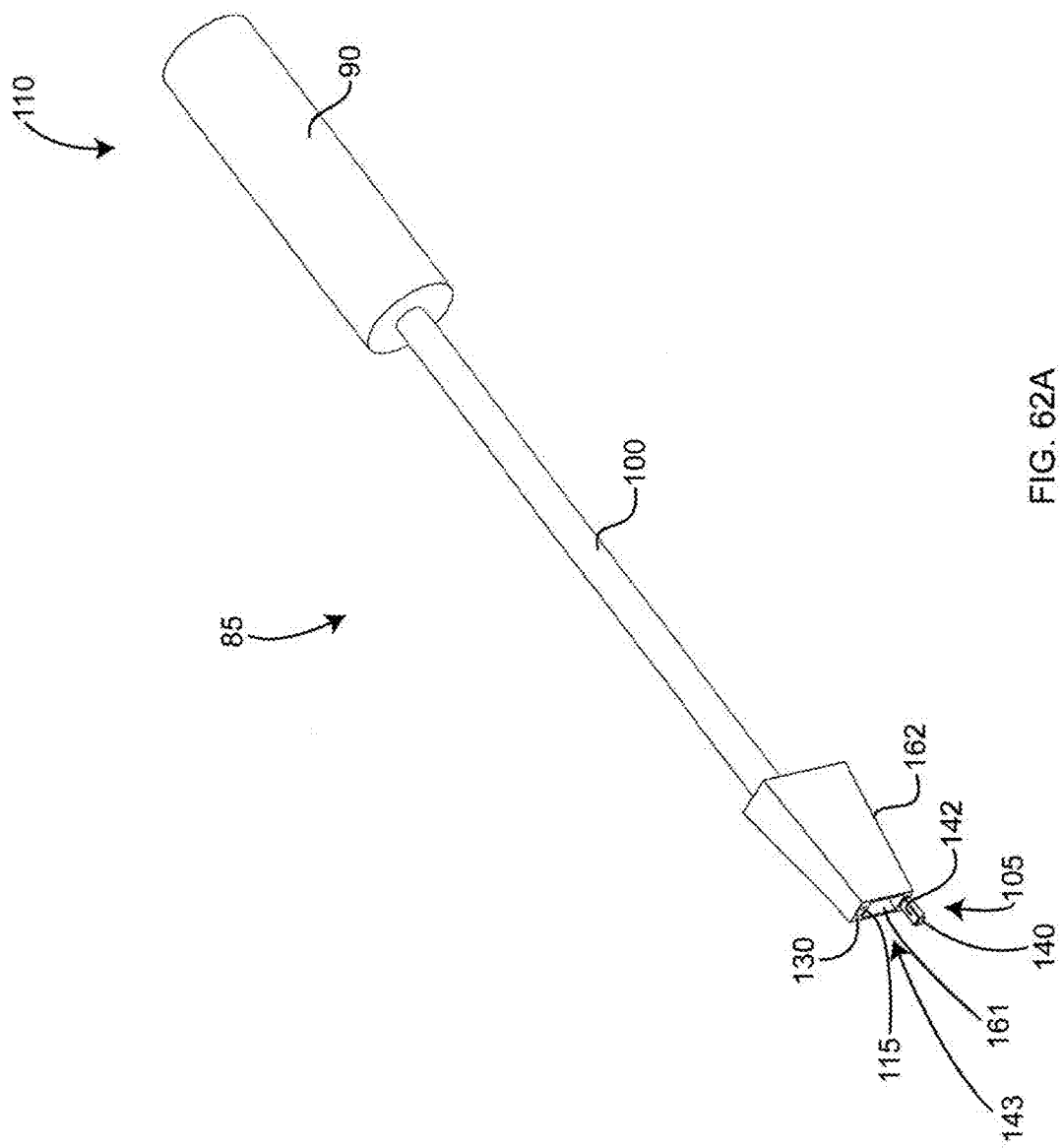
FIGS. 62A and 62B are, respectively, distal and proximal isometric views of the shaft assembly of the delivery tool of FIGS. 55A-56.
Figure 62B:
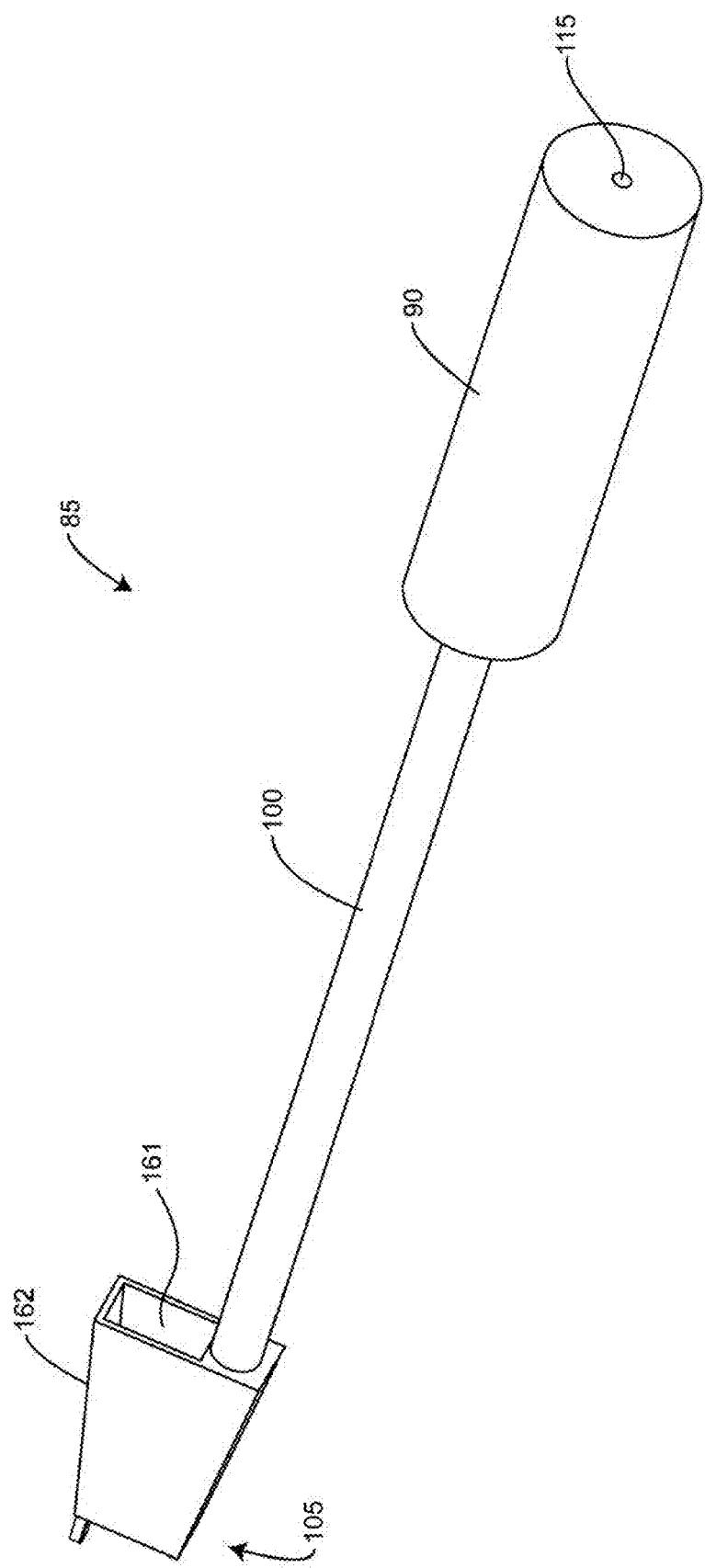

As illustrated in FIG. 56, the delivery tool 20 further includes a shaft assembly 85, a handle 90, an implant retainer 95, and an impactor 97. As shown in FIGS. 62A and 62B, which are, respectively, distal and proximal isometric views of the shaft assembly 85, the shaft assembly 85 includes the handle 90, a tubular elongated body 100, a distal implant engagement end 105, and an impactor guide 161. The handle 90 is coupled on a proximal end 110 of the tubular elongated body 100. The tubular elongated body 100 includes a lumen 115 through which the implant retainer 95 extends, as described below. The impactor guide 161 is a rectangular opening longitudinally extending through a guide head 162 of the distal implant engagement end 105.

Figure 63:
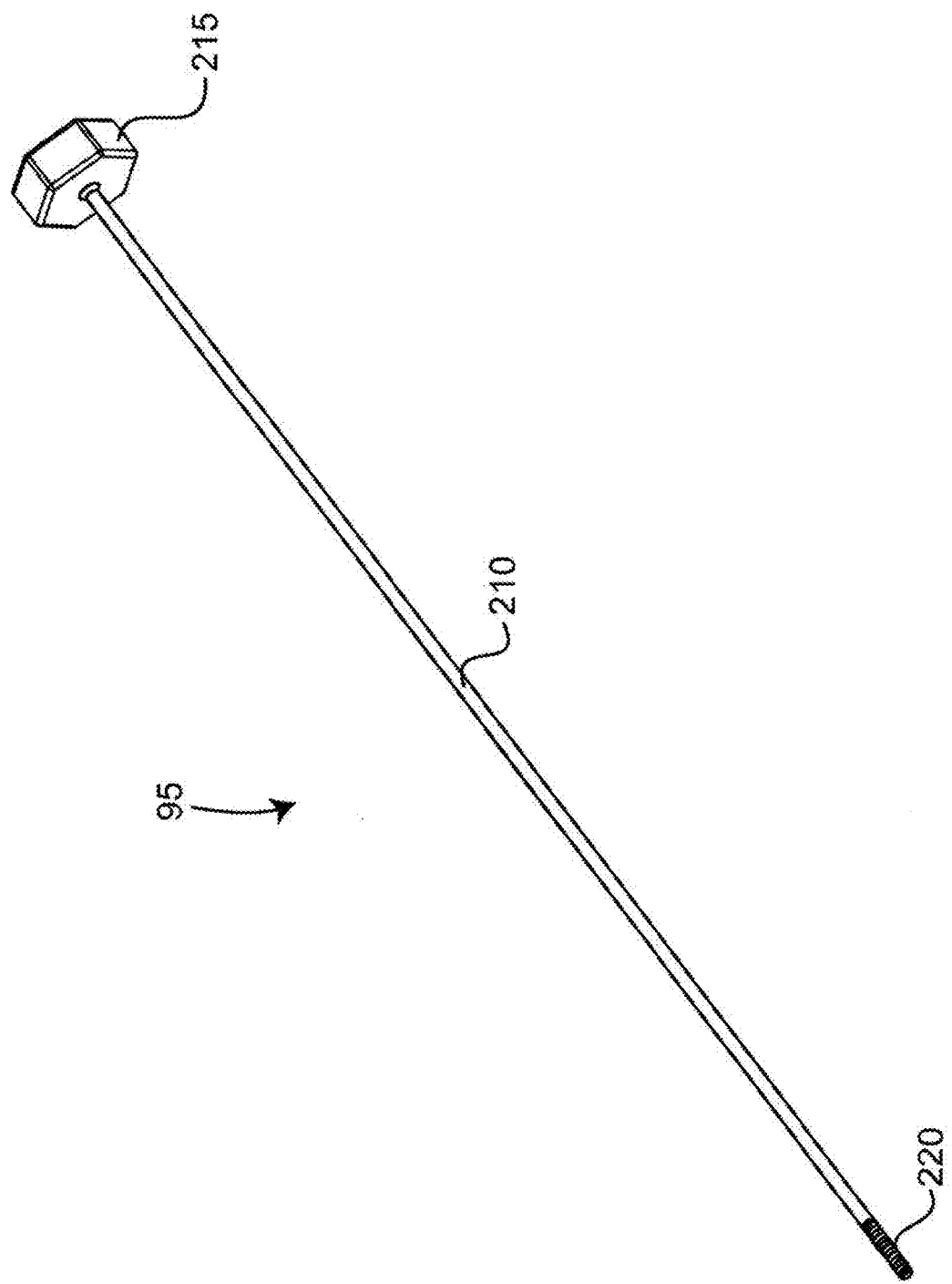
FIG. 63 is a distal isometric view of the implant retainer of the delivery tool of FIGS. 55A-56.
Figure 65:
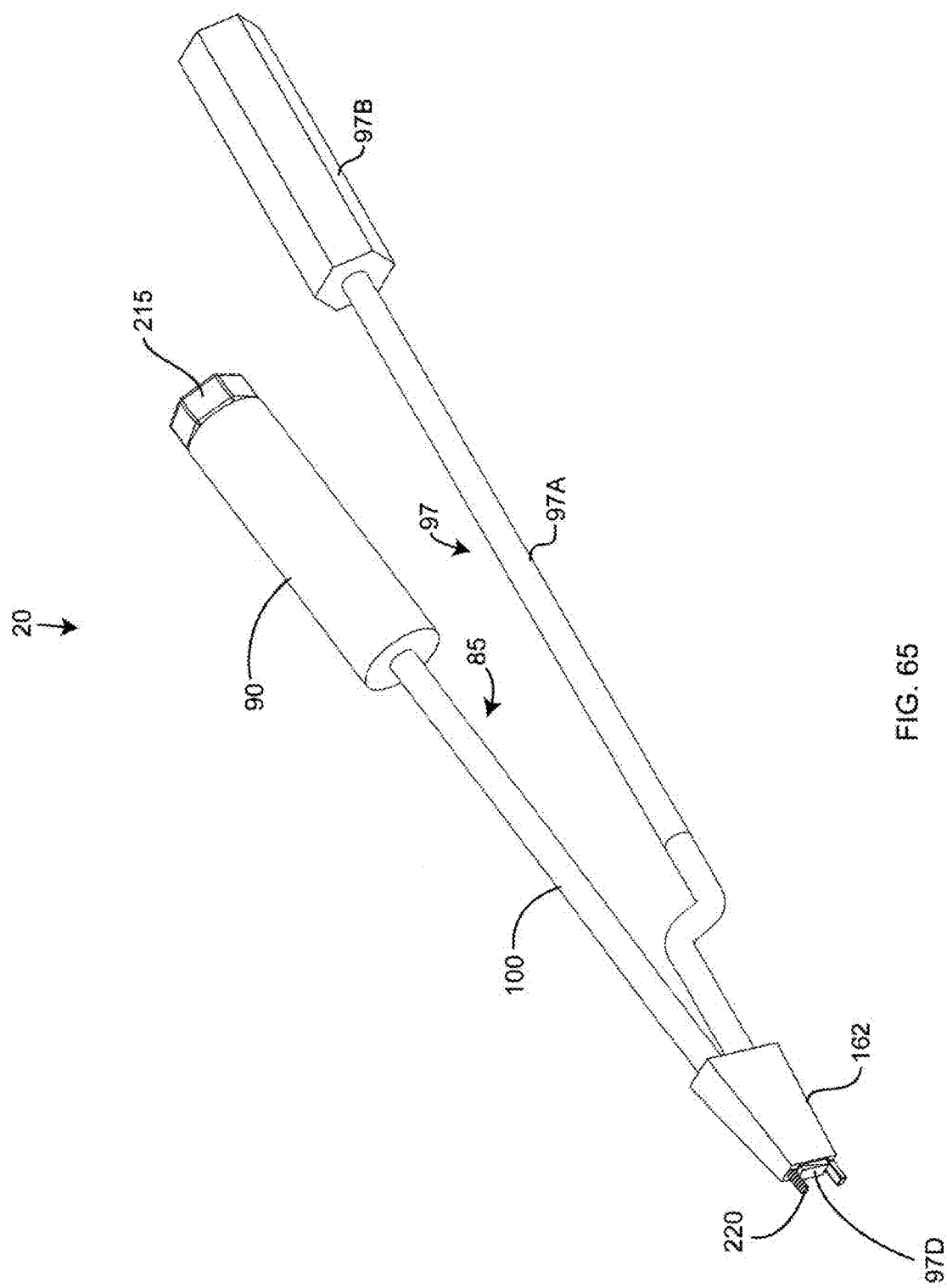
FIG. 65 is a distal isometric view of the delivery tool.

As illustrated in FIG. 63, which is a distal isometric view of the implant retainer 95, the implant retainer 95 includes a longitudinal cylindrical member 210, a handle 215 on a proximal end of the longitudinal cylindrical member 210, and an implant engagement feature 220 on a distal end the longitudinal cylindrical member 210. As can be understood from FIG. 65, which is a distal isometric view of the delivery tool 20, the member 210 of the implant retainer 95 extends through the lumen 115 of the body 100, the engagement feature 220 distally extending from the lumen 115 when a distal face of the retainer handle 215 is abutting against a proximal face of the shaft assembly handle 90.

Figure 64:
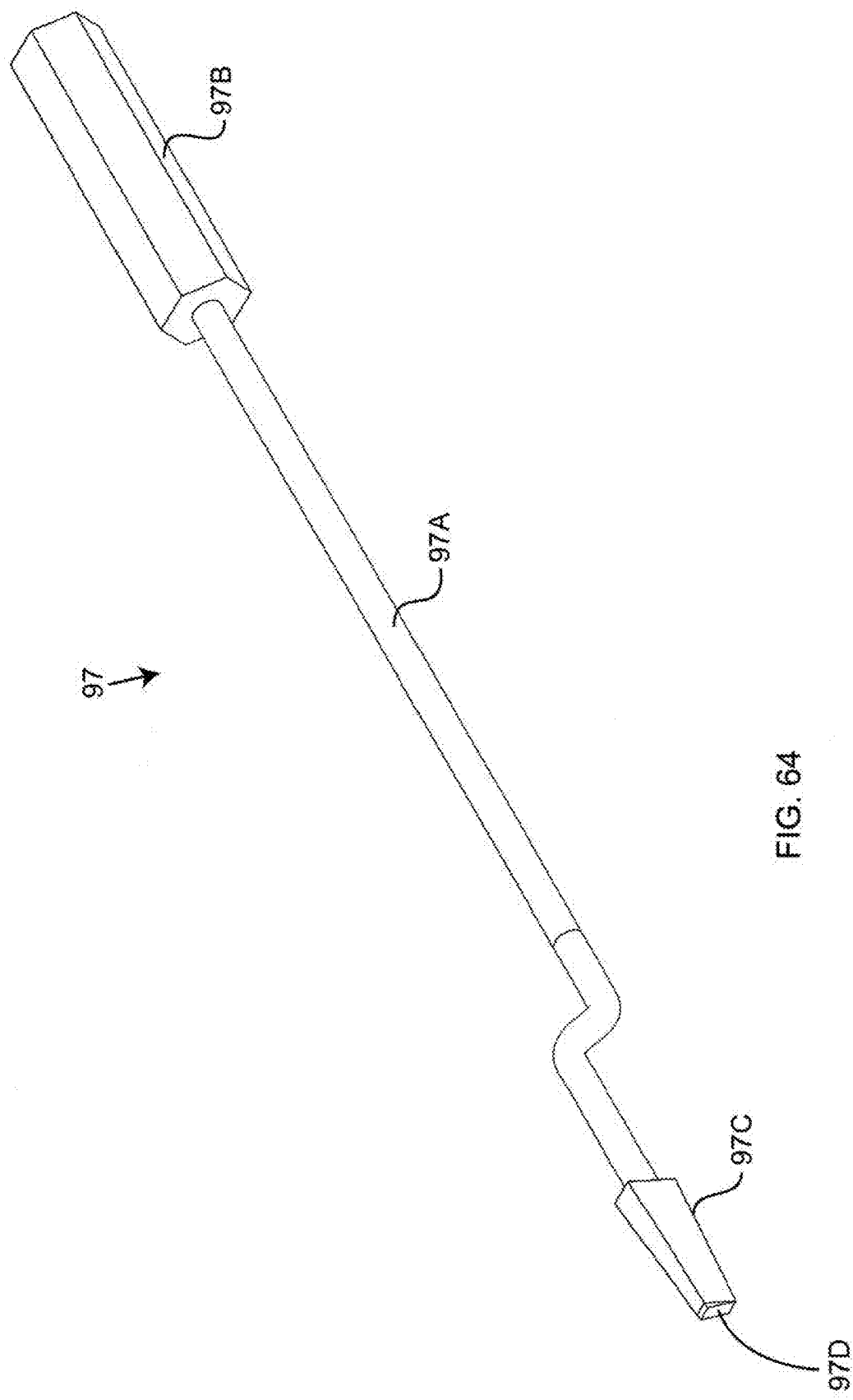
FIG. 64 is a distal isometric view of the impactor of the delivery tool of FIGS. 55A-56.

As illustrated in FIG. 64, which is a distal isometric view of the impactor 97, the impactor 97 includes a shaft 97A, a handle 97B on a proximal end of the shaft 97A, and an impactor head 97C on a distal end of the shaft 97A. The impactor head 97C includes planar lateral sides that taper slightly as the planar lateral sides extend distally to a blunt distal end 97D of the impactor head 97C. As can be understood from FIGS. 62A-62B, the impactor guide 161 is in the form of a tapered rectangular hole 161 that generally matches the shape of the impactor head 97C. Thus, the impactor guide hole 161 includes planar lateral sides that taper slightly as the planar lateral sides extend distally to the distal daylight opening of the hole 161 in the guide head 162. As can be understood from FIG. 65, the interaction of the tapered configurations of the impactor head 97C and the impactor guide hole 161 allow the impactor head 97C to displace distal-proximal within impactor guide hole 161, but limits the maximum distal displacement of the impactor head 97C within the impactor guide hole 161 such that the blunt distal end 97D can protrude from the distal end of the guide head 162 only a small distance.

As shown in FIG. 62A, the distal implant engagement end 105 includes a distal face 130 that surrounds the distal opening of the anchor guide hole 161 and from which a distally extending member 140 distally projects. The member 140 has a planar face 142 that is configured to be matingly received by the notch 6514 of the implant 25 when the proximal end 43 of the implant 25 is received in an implant receiving space 143 (shown in FIG. 56) defined by the distal face 130 and planar face 142 (shown in FIG. 62A). The implant 25 so coupled to the distal implant engagement end 105 of the delivery tool 20 is illustrated in FIG. 67, which is an enlarged distal isometric view of the system 10.

Figure 66:
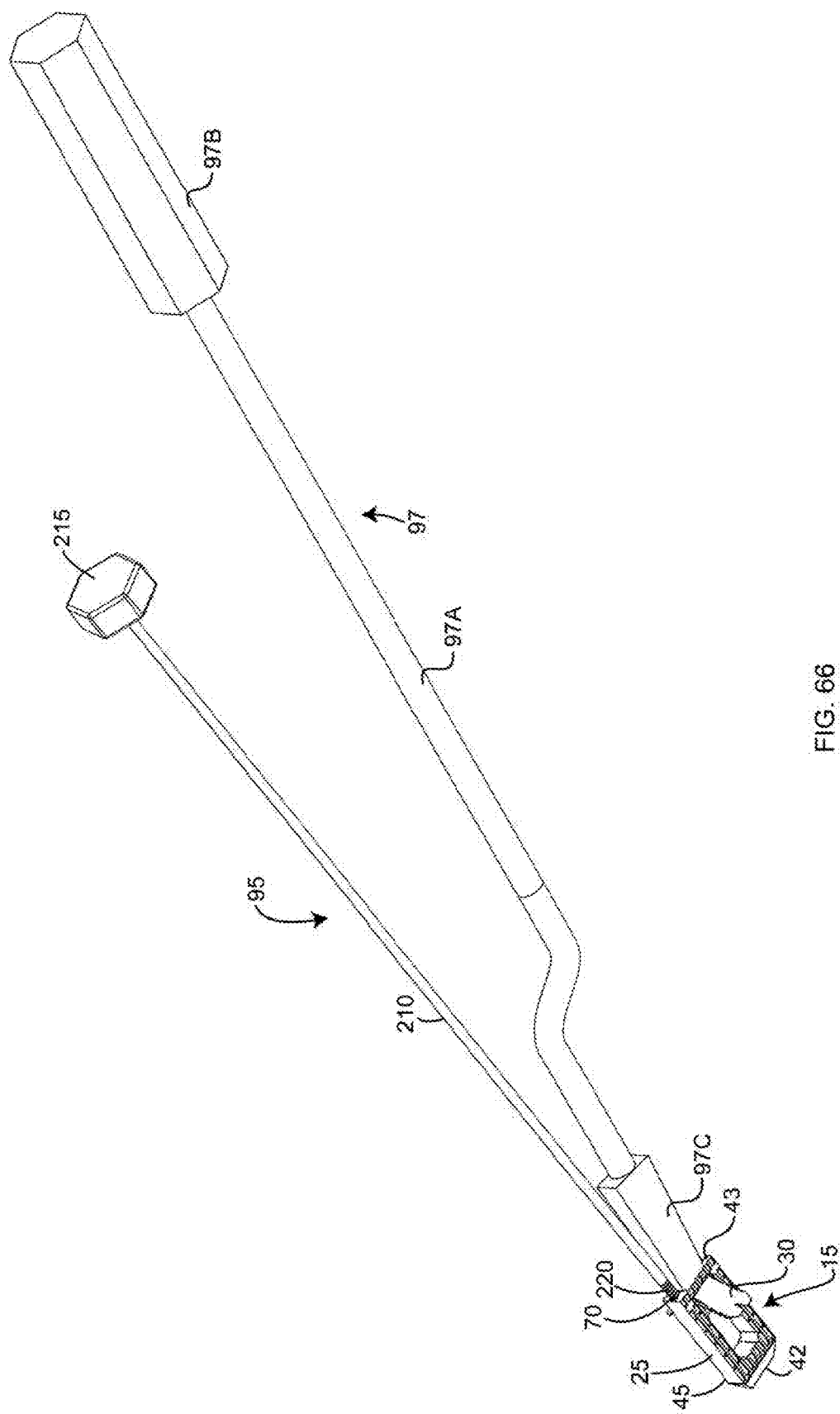
FIG. 66 is a distal isometric view of the implant assembly coupled to the implant retainer, the impactor positioned as if having driven the anchor blades fully distal in the implant slots, and the rest of the delivery tool hidden for clarity purposes.
Figure 67:
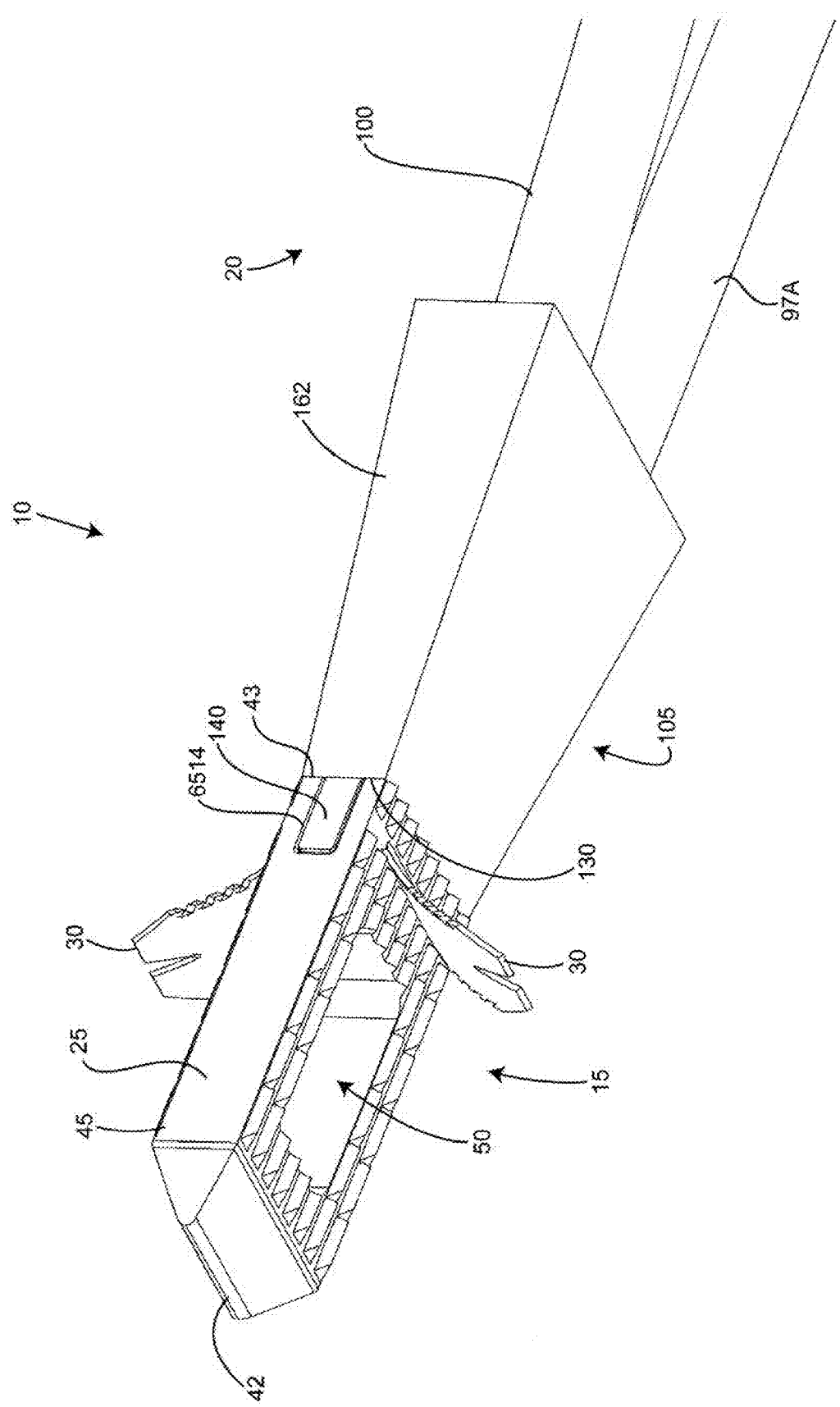
FIG. 67 is an enlarged isometric view of a distal end of the system of FIGS. 55A-56.

As can be understood from FIG. 66, which is an isometric view of the implant assembly 15 coupled to the implant retainer 95, the impactor 97 positioned as having fully distally driven the anchors 30, and the rest of the delivery tool 20 hidden for clarity purposes, in one embodiment, the implant engagement feature 220 is in the form of a threaded shaft for engaging complementary threads in the attachment bore 70, thereby securing the implant proximal face 43 against the distal face 130 of the distal implant engagement end 105, the member 140 being received in the notch 6514, as can be understood from FIGS. 55A and 67. The blunt distal end 97D of the impactor head 97C is abutting against the implant proximal face 43 after having been displaced sufficiently distal so as to impact the blades proximal ends 30F to drive the anchor blades 30 fully distal in their respective slots 40 such that the blade tabs 30E have exited the distal openings of the respective slots 40 and biased wide to prevent the proximal migration of the anchor blades 30 within the slots 40.

Figure 68:
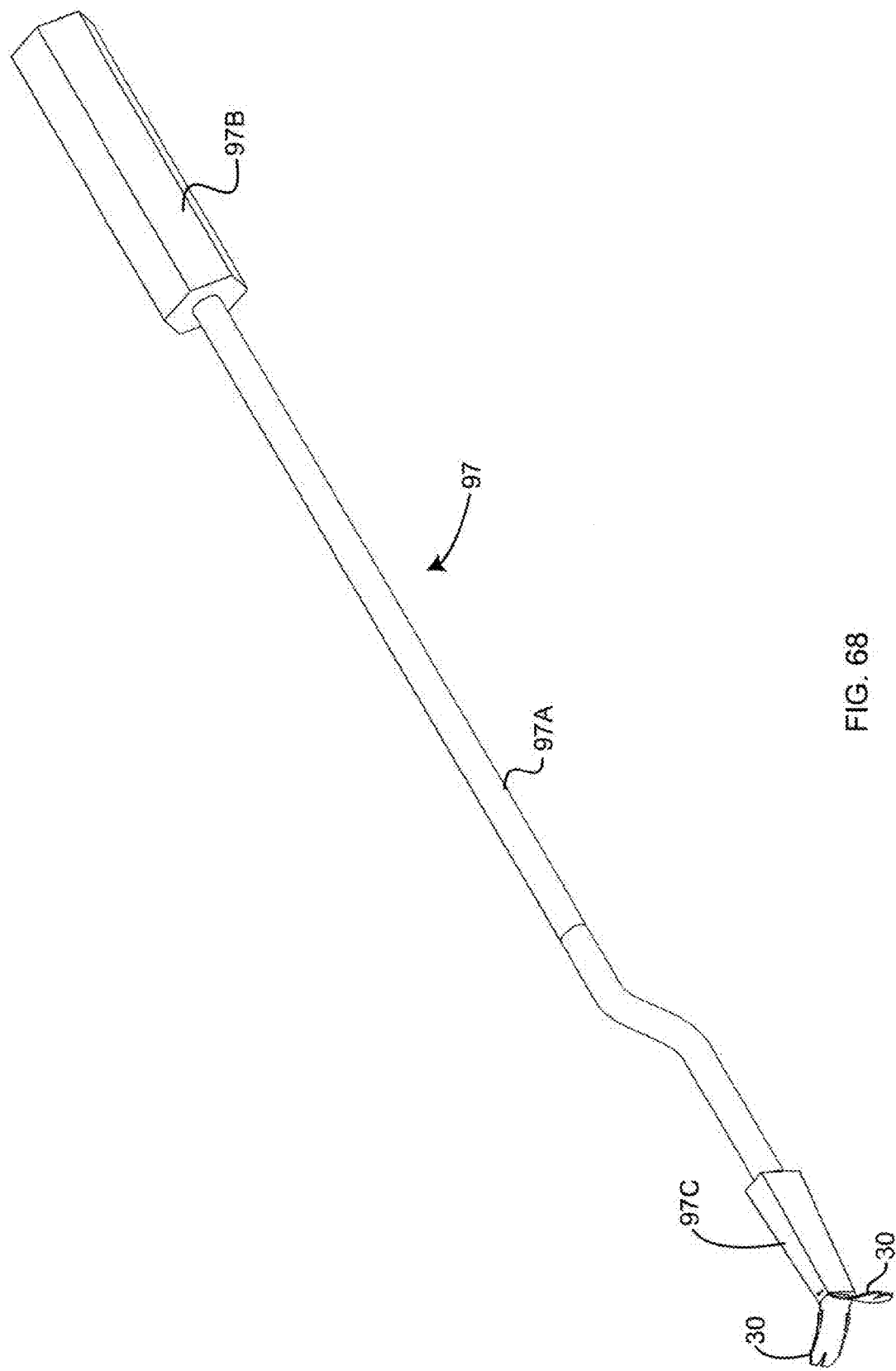
FIG. 68 is a distal isometric view of the impactor abutting against the proximal ends of the blade anchors, the rest of the implant assembly and delivery tool being hidden for clarity purposes.

As illustrated in FIG. 68, which is a distal isometric view of the impactor 97 abutting against the proximal ends of the anchors 30, the rest of the delivery tool and implant being hidden for clarity purposes, the blunt distal end 97D can be brought into impacting contact with the proximal ends 30F of the blade anchors 30. As can be understood from FIGS. 65-66, the threaded distal end 220 of the retainer 95 is threadably received in the attachment bore 70 of the implant 25 to retain the implant 25 in the implant receiving area 143 (see FIG. 56) of the tool attachment end 105. Also, the impactor head 97C is guided in its distal-proximal displacement against the anchor proximal ends 30F by the guide head hole 161.

Prior to being distally driven through the slots 40 by the impactor 97, the implant 25 may be secured to the distal end of the tool 10 via the mechanical interaction of the retainer distal end 220 in the implant attachment hole 70. The blades 30 may be staged in the slots 40 by inserting just the blade distal ends 30A in the proximal openings of the slots 40 when the implant is supported off of the distal end of the delivery tool 10. With the blades so positioned and the implant so supported, the implant can be delivered into the sacroiliac joint via the delivery tool, and once the implant is positioned within the sacroiliac joint as desired, the impactor 97 can then be used to drive the blades 30 from being substantially in the guide hole 161 and only partially in the slots 40 to being fully out of the guide hole 161 and into the implant slots 40 such that the distal ends 30A of the blades 30 distally and laterally project from the lateral faces of 7060 of the implant 25 a substantial distance.

It should be noted that the delivery methods described above with respect to FIGS. 25-53 are readily adaptable to the implant system 15 and delivery tool 20 discussed with respect to FIGS. 55A-68, the main difference being that the anchor blades 30 of the implant 25 of FIGS. 57A-57F are impacted through the implant 25 and into the adjacent sacrum and ilium bone, as opposed to being screwed through the implant 25 and into the adjacent bone as is the case with the screw anchors 30 of the implant 25 of FIGS. 4A-4C.

The systems 10 disclosed herein may be further configured, as disclosed in U.S. patent application Ser. No. 13/475,695, which was filed May 18, 2012 and is incorporated herein in its entirety, to allow placement of an anchor 30 near the implant or through a part of the implant 25 from a generally medial or, in some embodiments, a lateral approach as guided by the delivery tool.

Figure 69:
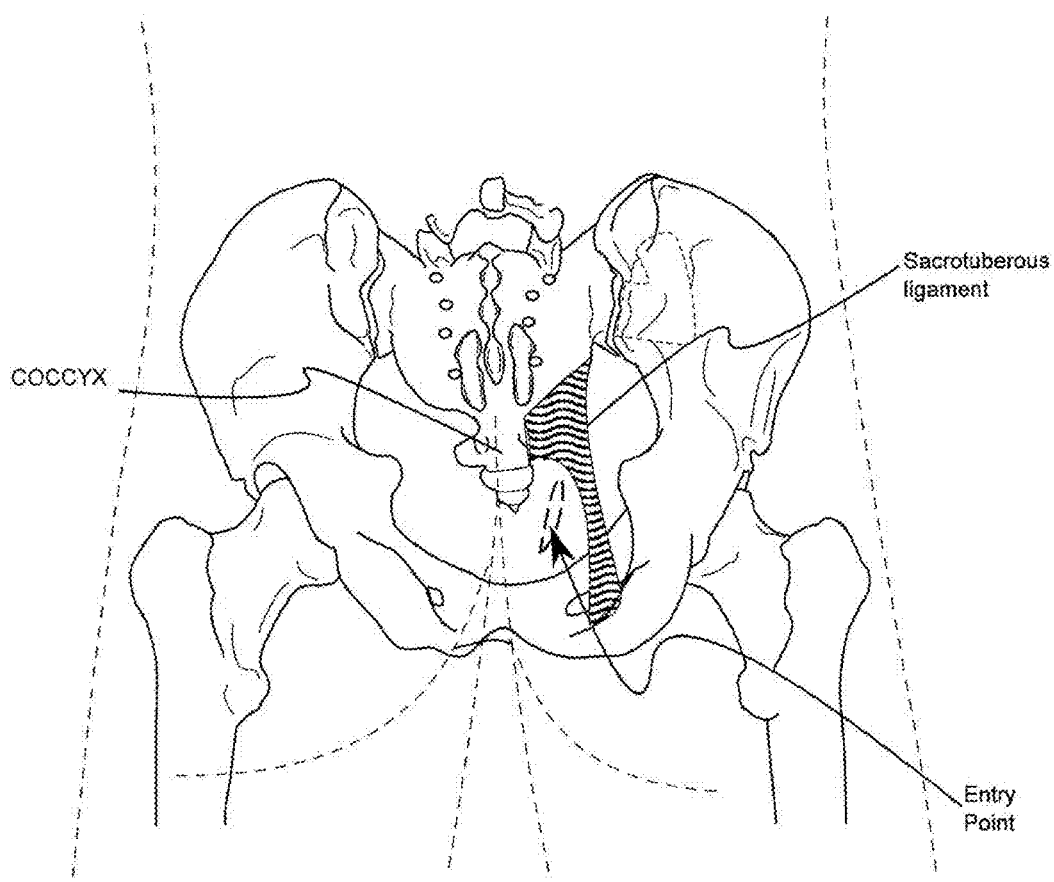
FIGS. 69 and 70 are, respectively, posterior and lateral views of a patient hip region illustrating a surgical approach employing an entry point near the coccyx and the sacrotuberous ligament.
Figure 70:
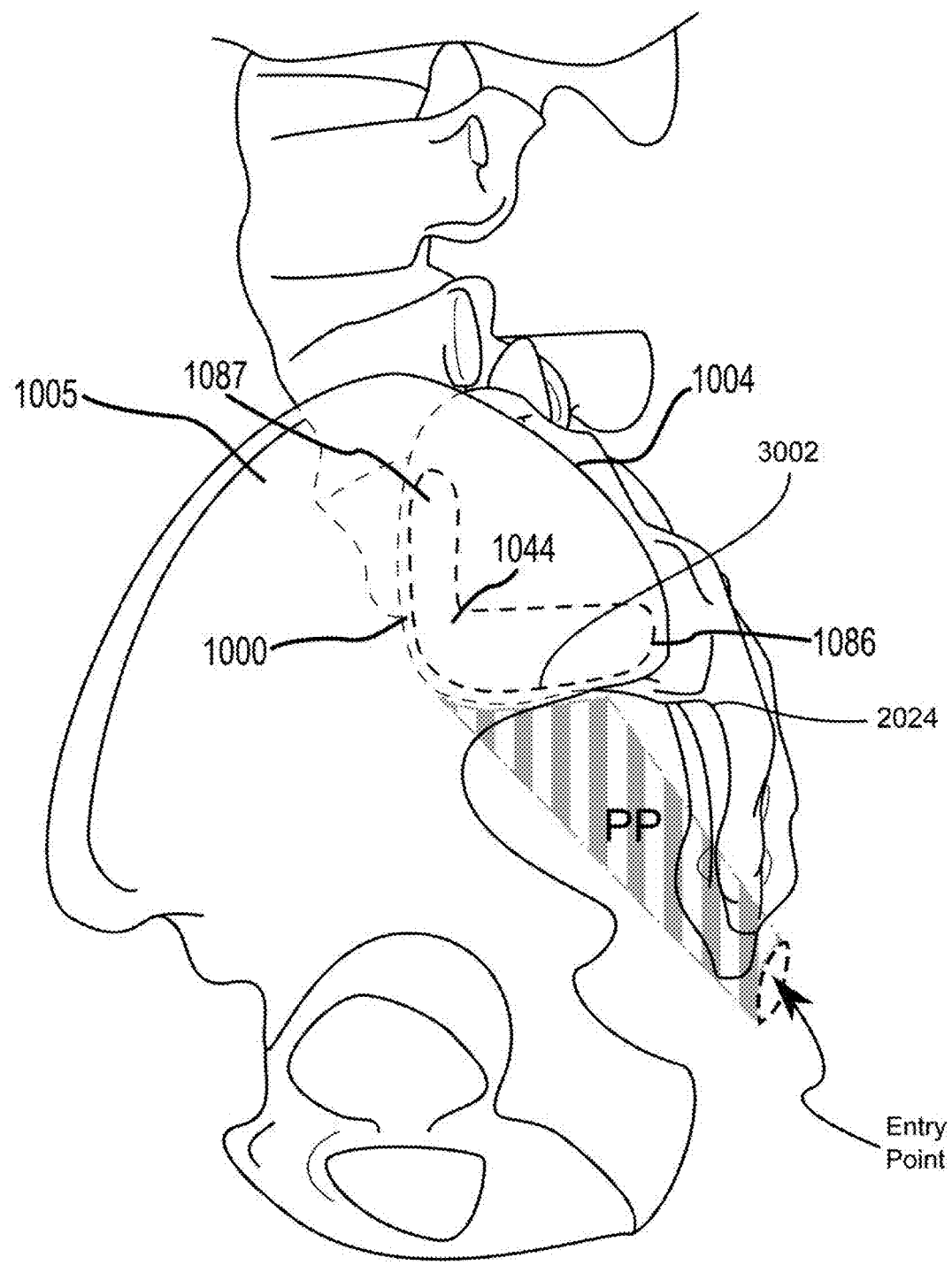
Figure 71:
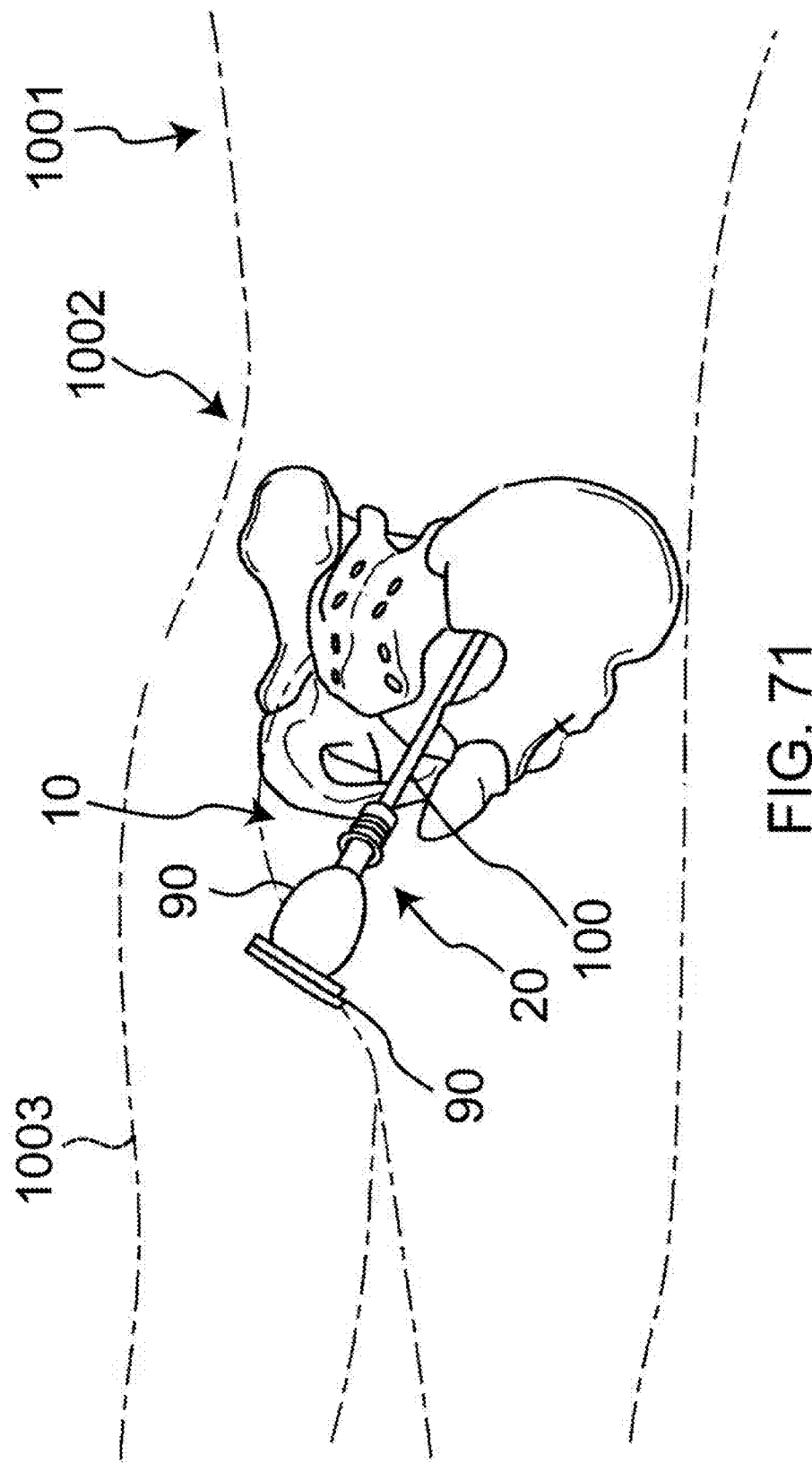
FIG. 71 is a posterior-lateral view of the patient hip region illustrating the delivery tool extending along the surgical approach of FIGS. 69 and 70.

To begin a detailed discussion of another method of accessing a sacroiliac joint space to treat a musculoskeletal condition, reference is made to FIGS. 69-71. To begin and as can be understood from FIGS. 69 and 70, a stab incision is made in the patient's skin to create an entry point near the coccyx and the sacrotuberous ligament. A cannulated blunt dissecting tool for deflecting soft tissue away from the sacrum may be advanced through the entry point and advanced while following the sacrum up to a sacroiliac joint inferior boundary 3002 which is immediately adjacent, and extends along, the sciatic notch 2024. A guide wire may then be placed through the cannulation in the dissecting tool and advanced into the sacroiliac joint. Optionally, after the dissecting tool has been removed an inflatable bowel retractor may be advanced over the guide wire and, once in place, inflated to provide a protected passageway for access to a sacroiliac joint. A working cannula may then be advanced over the guide wire to further protect the soft tissues from subsequent use of tools during the remainder of the procedure. The guide wire may then be removed or alternatively left in place to be used to guide an implant delivery tool up to the sacroiliac joint. Regardless, as can be understood from FIG. 71, any of the tools 20 disclosed herein can be used along the surgical pathway depicted in FIGS. 69 and 70 to deliver corresponding implants 15 into the sacroiliac joint space.

To begin a discussion regarding an embodiment of an implant 15 including an integral rotating anchor arrangement, reference is made to FIGS. 72-76, which are various isometric, side, and end views of such an implant 15. As shown in FIGS. 72-76, the implant 25 includes a distal or leading end 42, a proximal or trailing end 43, a longitudinally extending body 45, bores 70 for coupling the implant to a delivery tool, a center opening 50, and an anchor 30 pivotably supported in the center opening 50. In one embodiment, the implant 25 is configured to have a shape that generally mimics and even substantially fills a sacroiliac joint space. However, as indicated in FIGS. 72-76, in one embodiment, the implant 50 is generally rectangular in shape and includes large opposed radial members 7149 terminating in edge faces 7150 and small opposed radial members terminating 7153 in edge faces 7151, the small opposed radial members 7153 being generally perpendicular to the large opposed radial members 7149.

As illustrated in FIG. 76, the implant 25 includes a proximal end 43 for being removably coupled to the extreme distal end 35 of the delivery tool 20. Specifically, in one embodiment, the implant proximal end 43 includes a bores 70 that extends distally into the implant from the proximal end 43. The bores 70 may be blind holes in that they each only have a single opening, which is at the proximal end 43. Alternatively, the bores 70 may be configured as holes that communicate between the implant proximal end 43 and implant center opening 50. The bores 70 may be threaded or otherwise configured so as to allow mechanical engagement with a distal end of a retainer feature of the delivery tool 20, the retainer feature being used to secure the implant 25 off of the distal end 35 of the delivery tool 20, as described in detail below.

As indicated in FIGS. 72-76, the implant body 45 includes side edge surfaces 7150 of the large radial members and side edge surfaces 7151 of the small radial members that extend between the proximal end 43 and the distal end 42. The center opening 50 is defined in the body 45 so as to extend through an inner region of the large radial members 7149 and through the entirety of the small radial members 7153 such that side edge surfaces 7151 of the small radial members 7153 are not continuous distal to proximal but instead from a distal region and a proximal region separated by center opening 50.

As illustrated in FIGS. 72-76, in one embodiment, the implant body 45 includes generally planar lateral side surfaces 7060 of the large radial members 7149. In some embodiments, the lateral side surfaces 7060 may be generally spaced apart by a distance or body thickness that is generally continuous over the entirety of the surfaces 7060. However, as can be understood from FIGS. 13 and 14, in some embodiments, the distance or body thickness may vary along the length of the implant body 45

In one embodiment, the planar lateral side surfaces 7060 may be substantially smooth. However, in other embodiments, as indicated in FIGS. 72-76, the planar lateral side surfaces 7060 may have multiple serrated features 7061 configurations and spacing 7062 oriented so as to prevent proximal migration of the implant 25 once implanted in the sacroiliac joint. The anti-migration features 7061 are generally evenly distributed along the planar surfaces 7060. Anti-migration features may also be defined in the outer surface faces 7151 of the small radial members 7153 in the form of notches 7063. While the anti-migration features are depicted as being serrated features 7061 or notches 7063, in other embodiments the anti-migration features may be in the form of other types of surface texturing or protrusions in the form of cylinders, trapezoids, squares, rectangles, etc. Further, although the anti-migration features are depicted in the form of unidirectional serrated features or notches on large and small radial members of the implant 25, the invention is not so limited and, as to particular embodiments, can be configured to have of the anti-migration features arranged in multiple directions, unidirectional, or a combination of multiple direction on some surfaces of the implant and unidirectional on other surfaces of the implant. Accordingly, the anti-migration features can be so arranged on the various surfaces of the implant so as to prevent undesired migration in particular directions due to the forces present at the sacroiliac joint 1000.

As can be understood from FIGS. 72-76, the anchor 30 includes bone engagement features 30A radially extending from a center axle 30B about which the anchor 30 is pivotally coupled to the implant body 45 so as to be capable of rotating or pivoting within the confines of the center opening 50. The center axle 30B is generally coaxially arranged with a longitudinal center axis of the implant body 45, as can be understood from FIG. 77, which is an isometric view of another version of the implant having a rotating integral anchor.

Figure 77:
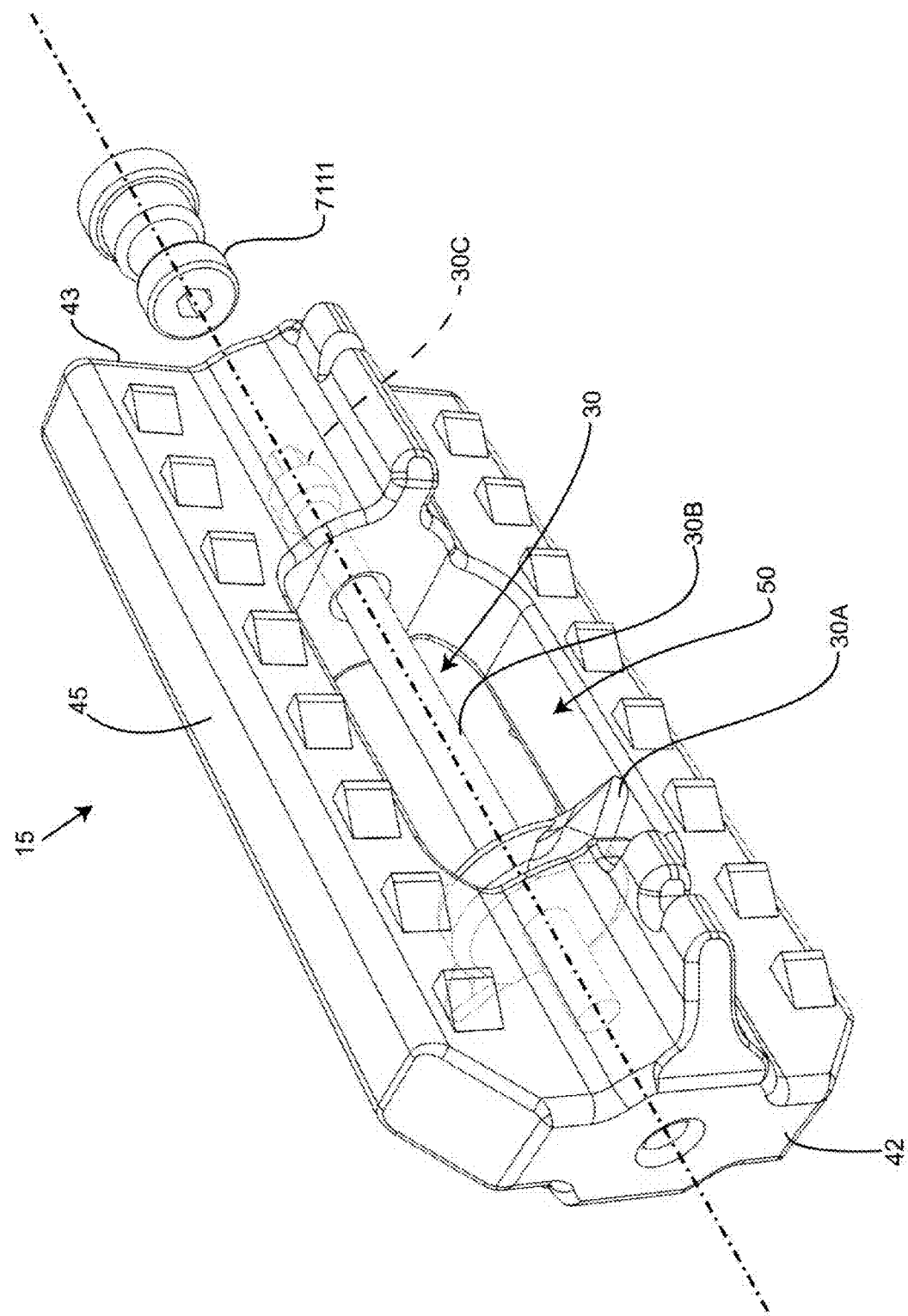
FIG. 77 is an isometric view of an implant similar to that of FIG. 72, except employing a different anchor configuration.

As illustrated in FIG. 77, the proximal end 30C of the anchor 30 may include an engagement feature (e.g., hex-head) for engagement by a complementarily shaped distal end 7111 of a tool (e.g. hex-head wrench or screwdriver) extending through the delivery tool 20 to cause the anchor 30 to rotate about its axle 30B within the center opening 50 defined in the implant body 45 so as to bring the engagement features 30A of the anchor 30 into anchoring engagement with the sacrum and ilium bordering the sacroiliac joint space. When the implant 15 is delivered into the sacroiliac joint space via the delivery tool, the anchor 30 is rotationally positioned in the opening 50 such that the engagement features 30A are each in alignment with the small radial members 7153 or, alternatively, in alignment with the large radial members 7149. Thus, the engagement features 30A are protected from interaction with the bone of the sacrum or ilium by being so aligned with the one set of the radial members. Once the implant 15 is positioned as desired in the sacroiliac joint space, the anchor 30 can be caused to rotate about its axle 30B so as to cause its engagement members 30A to engage the sacrum and ilium in an anchoring fashion. The anchor 30 may have a locking mechanism such as, for example, a pawl tooth or ratchet arrangement, a setscrew, or etc., to prevent the anchor 30 from reverse rotating such that the engagement members 30A ceasing to anchor within the bone of the sacrum and ilium.

Figure 72:
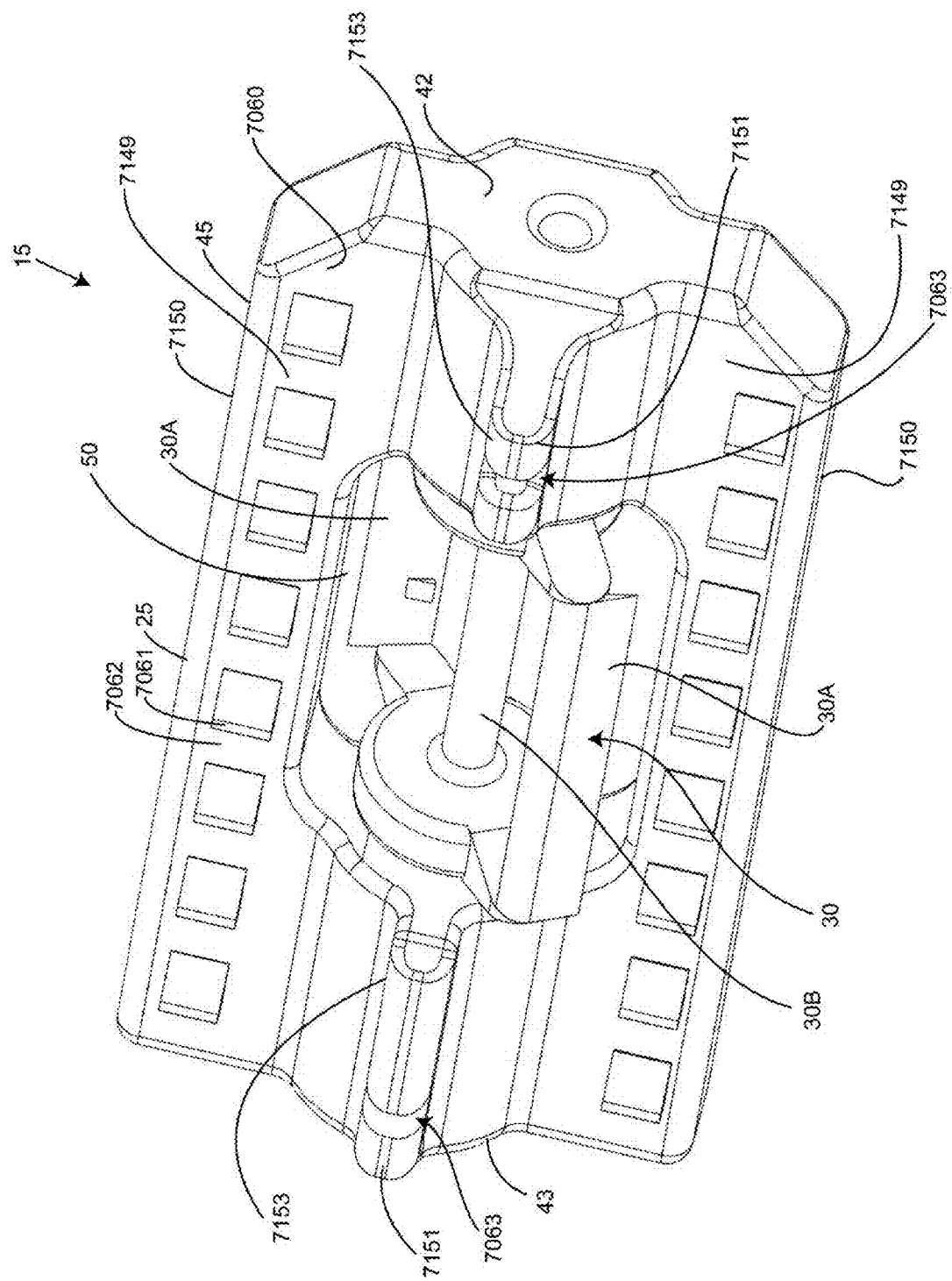
FIG. 72 is an isometric view of an implant employing a rotatable or pivotable integral anchor.
Figure 79:
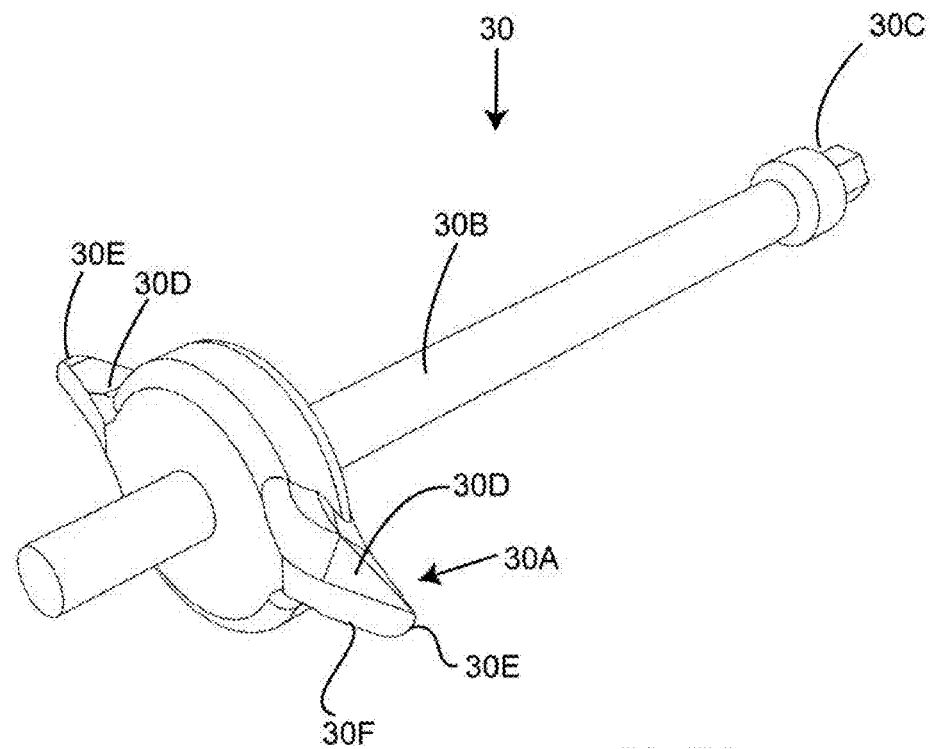
FIGS. 78 and 79 are isometric views of the anchors employed in the implants of FIGS. 72 and 77, respectively.
Figure 78:
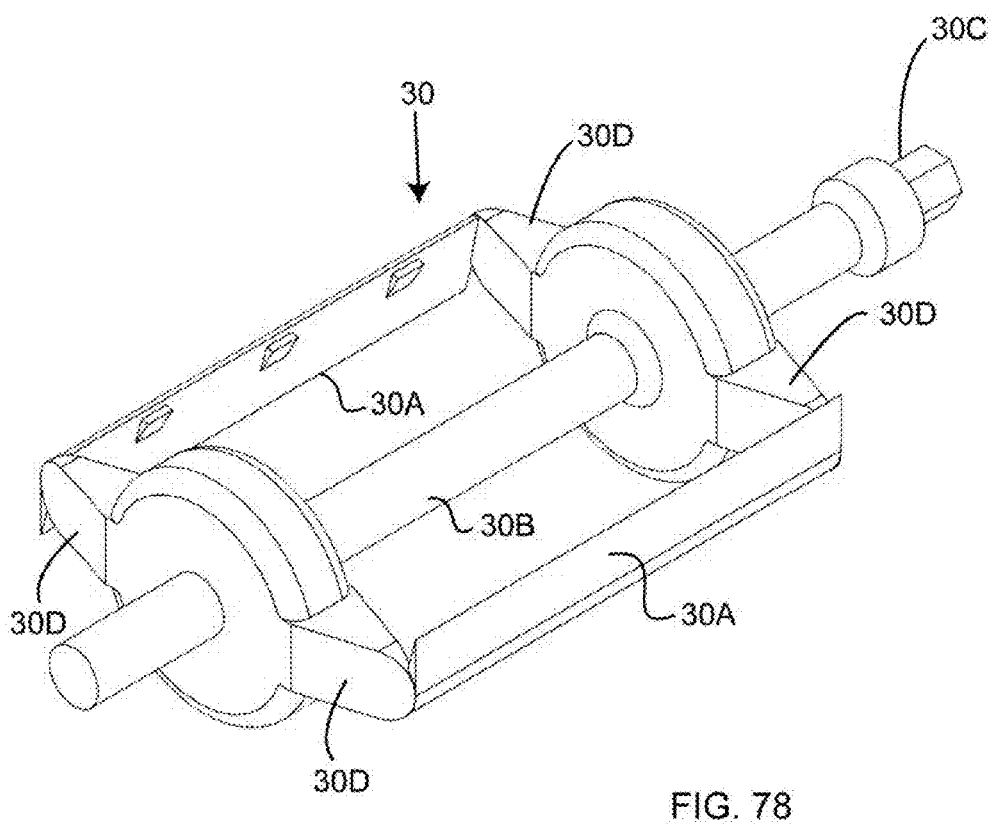
Figure 80:
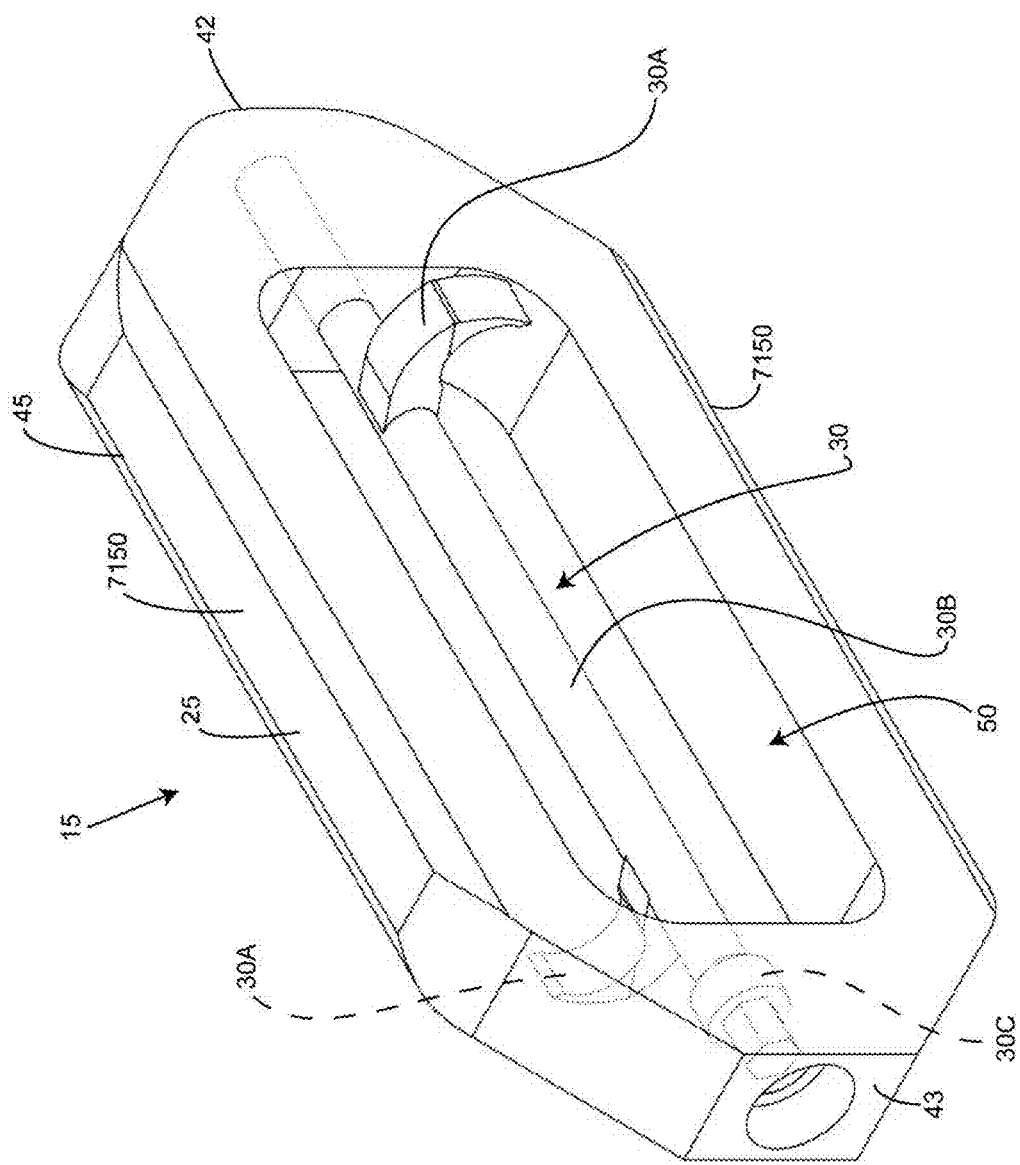
FIG. 80 is an isometric view of an implant employing a rotatable or pivotable integral anchor.

As can be understood from a comparison of the anchors 30 of the embodiments of FIGS. 72 and 77 and further as can be understood from the same respective anchors shown alone in FIGS. 78 and 79, the engagement features 30A may vary. For example, as shown in FIGS. 72 and 78, in one embodiment, the engagement features 30A may be in the form of longitudinally extending blades 30A supported off of radially extending pairs of arms 30D from the axle 30B. In another embodiment, as depicted in FIGS. 77 and 79, the engagement features 30A may be in the form of radially extending arms 30D terminating in tapered points 30E with an optional radially extending edge 30F.

In one embodiment, as illustrated in FIGS. 80-84, which are various isometric, side and end views of another implant 15, the implant 15 may be free of radially extending members and simply have a body 45 with the opening 50 and the anchor 30 pivotably supported therein. The rest of the feature of the implant 15 may be generally the same as already described, the implant body 15 having a generally rectangular shape with tapered distal end 42 and tapered proximal end 43. As can be understood from FIGS. 80-84, the engagement feature 30A of the anchor 30 may be in the form of a hook. Such an anchor embodiment may be employed with the implants of FIGS. 72-79 or the anchors embodiments of those figures may be employed with the implant of FIGS. 80-84.

In one embodiment, the implants 25 of FIGS. 72-84 may be machined, molded, formed, or otherwise manufactured from stainless steel, titanium, ceramic, polymer, composite, bone or other biocompatible materials. The anchor member 30 may be machined, molded, formed or otherwise manufactured from similar biocompatible materials.

Figure 85:
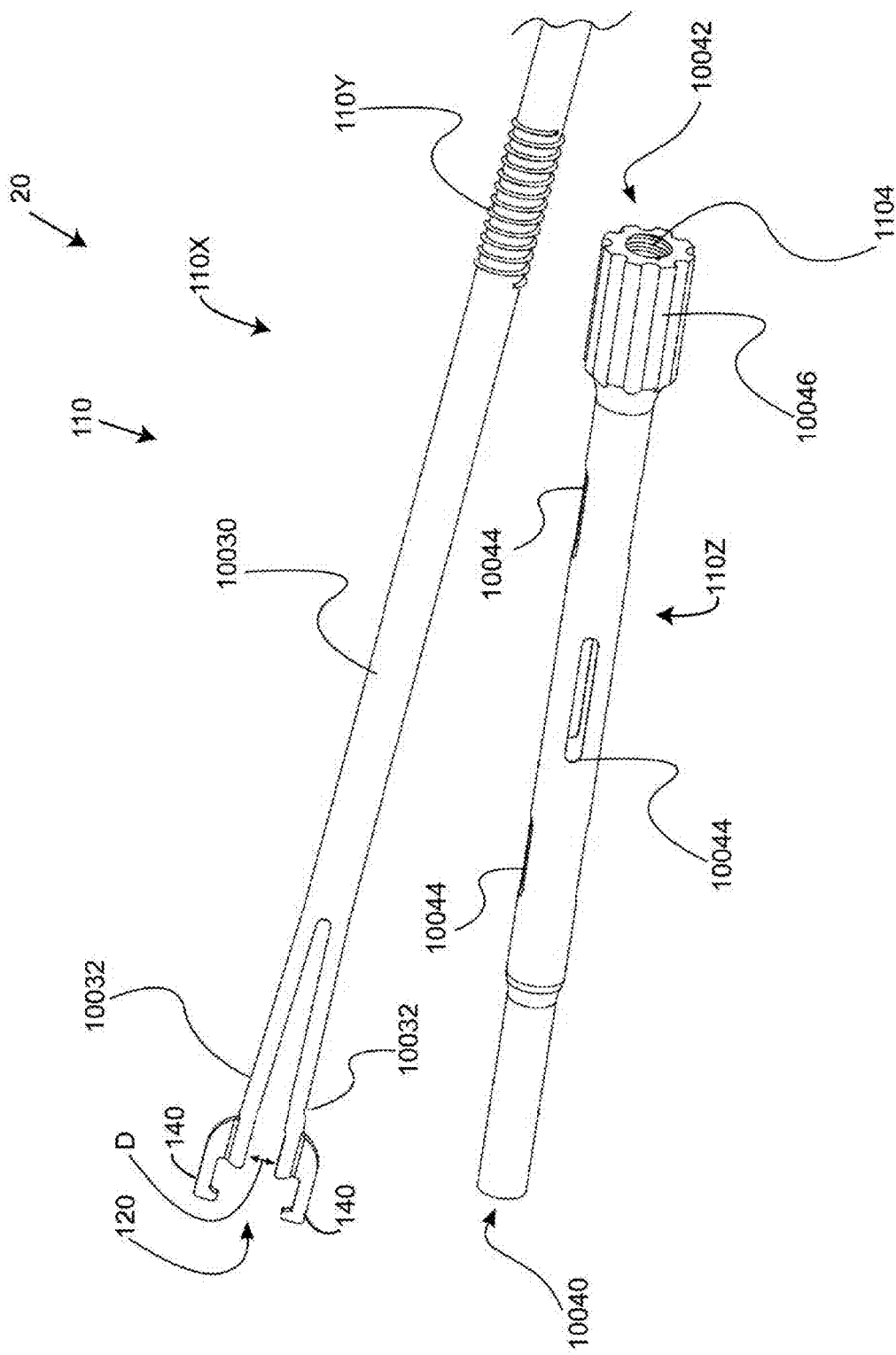
FIG. 85 is an isometric view of an implant delivery tool for use with the implants of FIGS. 72-84.

In one embodiment, a delivery tool 20 for use with the implant embodiments of the FIGS. 72-84 may be configured as illustrated in FIG. 85. Such a tool 20 may have an implant arm 110 formed mainly of a sleeve 110Z and a retainer rod 110X. The retainer rod 110X may be received coaxially within the sleeve 110Z.

The retainer rod 110X includes a shaft 10030 that distally terminates in opposed arms 10032, which in turn terminate in retainer arms or prong arms 140. As shown in FIG. 85, when the rod 110X is free of the sleeve 110Z, the opposed arms 10032 are biased apart, resulting in a space-apart distance indicated by arrow D that is sufficiently wide to allow the implant 25 to be received between the prong arms 140 at the rod distal end 120.

As indicated in FIG. 85, the sleeve 110Z includes a distal end 10040, a proximal end 10042, and slots 10044 that extend into the hollow interior of the shaft of the sleeve 110Z. The slots 10044 provide opening into the hollow interior to facilitate sterilization of the sleeve 110Z via an autoclave. A knurled gripping surface 10046 is defined near the sleeve proximal end 10042 so as to facilitate rotation of the sleeve relative to the rod when the threads 110Y are being threadably engaged.

As can be understood from a comparison of FIG. 85, when the sleeve 110Z is advanced distally over the retainer rod 110X, complementary threads 110Y on both the sleeve 110Z and retainer rod 110X can be engaged and the sleeve can be rotatably driven distally by said thread engagement. Alternatively, a lever or other mechanical arrangement may be provided to cause the sleeve to be driven distally. The sleeve 110Z advancing distally causes prong arms 140 of the retainer rod 110X to draw toward one another and in turn cause the portion of the retainer rod which couples to the implant 25 to grasp the implant. The complementary threads when engaged may prevent proximal movement of the sleeve 110Z relative to the rod 110X and allow the coupling of implant and retainer rod to continue throughout the course of the procedure. While the tool 20 is coupled to the implant 15, a hex-head wrench or screwdriver 7111 may be extended down a central lumen of the shaft 10030 to engage the hex-head end 30C (see FIG. 77) of the anchor 30 of the implant to cause its engagement features 30A to rotate into anchoring engagement with the sacrum and ilium. After implantation the sleeve 110Z may be caused to move proximally along the retainer rod 110X in order to decouple the aforementioned tool and implant arrangement.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of implanting an implant in a sacroiliac joint defined between a sacrum and an ilium, the method comprising:

positioning the implant in the sacroiliac joint such that a first lateral side of the implant faces and contacts a sacrum surface of the sacroiliac joint and a second lateral side of the implant faces and contacts an ilium surface of the sacroiliac joint, the first and second lateral sides being opposite the implant from each other;

acting at a proximal end of the implant to cause an anchor to transition from a recessed condition to a deployed condition, the deployed condition being when a bone engagement portion of the anchor extends from an outer surface of the implant into bone defining at least a portion of the sacroiliac joint, the recessed condition being when the bone engagement portion does not extend from the outer surface of the implant; and using the implanted implant as an attachment point for structural components of a spinal support system.

2. The method of claim 1, wherein the anchor is configured to displace within a passage extending distal-lateral from a proximal opening of the passage when the anchor transitions from the recessed condition to the deployed condition.

3. The method of claim 2, wherein the displacement includes sliding.

4. The method of claim 3, wherein the anchor is a nail.

5. The method of claim 3, wherein the anchor has blade-like configuration and the passage has a slot-like configuration.

6. The method of claim 3, wherein acting at the proximal end of the implant to cause the anchor to transition from the recessed condition to the deployed condition includes pushing or impacting on a proximal end of the anchor.

7. The method of claim 6, further comprising selectively releasably coupling the proximal end of the implant to a distal end of an insertion tool and then employing the insertion tool to deliver the implant into and position the implant in the sacroiliac joint.

8. The method of claim 7, further comprising displacing a member of the insertion tool relative to the rest of the insertion tool and against the proximal end of the implant to cause the anchor to transition from the recessed condition to the deployed condition.

9. The method of claim 8, wherein the displacing of the member of the insertion tool is sliding displacement.

10. The method of claim 1, wherein the anchor is configured to displace within a passage extending generally distal from a proximal opening of the passage when the anchor transitions from the recessed condition to the deployed condition.

11. The method of claim 1, wherein the anchor is configured to displace within a passage extending generally lateral from a proximal opening of the passage when the anchor transitions from the recessed condition to the deployed condition.

12. The method of claim 11, wherein the displacement includes rotation.

13. The method of claim 12, wherein the anchor is a screw.

14. The method of claim 13, wherein the passage has a bore-like configuration.

15. The method of claim 13, wherein acting at the proximal end of the implant to cause the anchor to transition from the recessed condition to the deployed condition includes applying a rotational force to a proximal end of the anchor.

16. The method of claim 15, further comprising selectively releasably coupling the proximal end of the implant to a distal end of an insertion tool and then employing the insertion tool to deliver the implant into and position the implant in the sacroiliac joint.

17. The method of claim 1, wherein the first and second lateral sides are offset from each other by a thickness of the implant that is less than a width of at least one of the first or second lateral sides.

18. The method of claim 1, wherein the first and second lateral sides are generally planar.

19. The method of claim 18, further comprising selectively releasably coupling the proximal end of the implant to a distal end of an insertion tool and then employing the insertion tool to deliver the implant into and position the implant in the sacroiliac joint.

20. The method of claim 1, wherein when in the deployed condition the bone engagement portion of the anchor extends from at least one of the first or second lateral sides.

21. The method of claim 1, wherein the anchor is pivotally supported about a pivot axis in the implant, and the anchor is configured to pivot about the pivot axis when the anchor transitions from the recessed condition to the deployed condition.

22. The method of claim 21, wherein the pivot axis extends proximal-distal between the proximal end of the implant and a distal end of the implant.

23. The method of claim 21, wherein the bone engagement portion of the anchor includes a blade-like edge extending generally parallel to the pivot axis.

24. The method of claim 21, wherein the bone engagement portion of the anchor terminates in a tip extending radially outwardly from the pivot axis.

25. The method of claim 21, wherein acting at the proximal end of the implant to cause the anchor to transition from the recessed condition to the deployed condition includes applying at the proximal end of the implant a torque to the anchor.

26. The method of claim 1, wherein the spinal support system is configured to support across a patient hip structure.

27. The method of claim 1, wherein the spinal support system is configured to support along a patient spinal column.

28. The method of claim 1, wherein the implant enters the sacroiliac joint via a caudal access into the sacroiliac joint.

29. The method of claim 1, wherein the implant enters the sacroiliac joint via a cranial access into the sacroiliac joint.

30. The method of claim 1, wherein the implant enters the sacroiliac joint via an extra-articular access into the sacroiliac joint.

31. The method of claim 1, wherein the implant enters the sacroiliac joint via crossing a sacroiliac joint inferior boundary.

32. The method of claim 31, wherein the implant enters the sacroiliac joint via a patient entry point near a coccyx and a sacrotuberous ligament.

33. The method of claim 1, wherein the implant comprises a coupling element at the proximal end of the implant.

34. The method of claim 33, wherein the coupling element comprises a fastener portion at a distal end thereof and a coupling portion at a proximal end thereof, the fastener portion threadably received in the proximal end of the implant.

35. The method of claim 33, further comprising joining a spanning member to the coupling element.

36. The method of claim 35, wherein the spanning member comprises a rod.

37. The method of claim 35, wherein joining the spanning member to the coupling element comprises engaging a spirally threaded body with the coupling element such that the spanning member is sandwiched between the spirally threaded body and the coupling element.

38. The method of claim 35, further comprising implanting a device into at least one of a bone and a joint proximate the sacroiliac joint.

39. The method of claim 38, further comprising joining the spanning member to the device.

40. The method of claim 38, wherein the bone comprises at least one of the sacrum and the ilium.

41. The method of claim 38, wherein the bone comprises a vertebra.

42. The method of claim 38, wherein the joint proximate the sacroiliac joint comprises another sacroiliac joint spaced apart from the sacroiliac joint by the sacrum.

43. The method of claim 35, wherein the spanning member comprises a plate.

44. The method of claim 43, wherein the plate comprises at least one aperture through which a fastener portion of the coupling element is passable.

45. The method of claim 43, wherein the plate comprises at least one aperture through which a screw is passable and the method further comprising delivering the screw through the at least one aperture generally anteriorly and via an S1 pedicle location.

46. The method of claim 45, wherein the plate comprises a second aperture of the at least one aperture through which a second screw is passable and the method further comprising delivering the screw through the second aperture and into the sacrum, across the sacroiliac joint, and terminating in or through the ilium.

47. The method of claim 33, further comprising joining the coupling element to the proximal end of the implant.

48. The method of claim 33, wherein the coupling element comprises a coupling portion configured to join with a spanning member.

49. The method of claim 48, wherein the coupling portion comprises a cup coupled to the implant and having a pass-through element in which at least part of a spanning member is receivable therethrough.

50. The method of claim 49, wherein the cup is pivotally coupled to the implant.

51. The method of claim 49, wherein the cup is a generally cylindrical body.

52. The method of claim 49, wherein a locking body is engageable with the cup allowing the spanning member to be selectively placed in fixed relation to the cup.

53. The method of claim 1, wherein the implant is coupled to a spanning member in a multi-piece arrangement.

54. The method of claim 53, wherein the implant and spanning member are assembled during a surgery at the sacroiliac joint.

55. The method of claim 54, further comprising coupling the spanning member to the proximal end of the implant.

56. The method of claim 53, wherein the multi-piece arrangement is provided from a manufacturer with the spanning member being an extension of a proximal region of the implant.

57. The method of claim 53, wherein the spanning member comprises a rod.

58. The method of claim 53, wherein the spanning member comprises a plate.

59. The method of claim 58, wherein the plate comprises at least one aperture through which a fastener is passable.

60. The method of claim 59, further comprising delivering the fastener through the at least one aperture and into an S1 body of the sacrum.

61. The method of claim 59, further comprising delivering the fastener through the at least one aperture and into an S2 body of the sacrum, through the sacroiliac joint, and further into the ilium.

62. The method of claim 59, wherein the at least one aperture comprises a first and second aperture through which a first and second fastener, respectively, are passable, and the method further comprising delivering the first fastener through the first aperture and into an S1 body of the sacrum, and delivering the second fastener through the second aperture and into an S2 body of the sacrum, through the sacroiliac joint, and further into the ilium.

63. The method of claim 1, wherein the implant and a spanning member are coupled to each other and form of an integral, unitary construction.

64. The method of claim 63, wherein the spanning member comprises a rod.

65. The method of claim 63, wherein the spanning member comprises a plate.

66. The method of claim 65, wherein the plate comprises at least one aperture through which a fastener is passable.

67. The method of claim 66, further comprising delivering the fastener through the at least one aperture and into an S1 body of the sacrum.

68. The method of claim 66, further comprising delivering the fastener through the at least one aperture and into an S2 body of the sacrum, through the sacroiliac joint, and further into the ilium.

69. The method of claim 66, wherein the at least one aperture comprises a first and second aperture through which a first and second fastener, respectively, are passable, and the method further comprising delivering the first fastener through the first aperture and into an S1 body of the sacrum, and delivering the second fastener through the second aperture and into an S2 body of the sacrum, through the sacroiliac joint, and further into the ilium.

* * * * *